(12) United States Patent
Li et al.

(10) Patent No.: US 8,680,108 B2
(45) Date of Patent: Mar. 25, 2014

(54) SUBSTITUTED FUSED ARYL AND HETEROARYL DERIVATIVES AS PI3K INHIBITORS

(75) Inventors: Yun-Long Li, Chadds Ford, PA (US); Andrew P. Combs, Kennett Square, PA (US); Eddy W. Yue, Landenberg, PA (US); Hui-Yin Li, Hockessin (DE)

(73) Assignee: Incyte Corporation, Wilmington, DE (US)

( * ) Notice: Subject to any disclaimer, the term of this patent is extended or adjusted under 35 U.S.C. 154(b) by 324 days.

(21) Appl. No.: 12/972,155

(22) Filed: Dec. 17, 2010

(65) Prior Publication Data

US 2011/0183985 A1    Jul. 28, 2011

Related U.S. Application Data

(60) Provisional application No. 61/287,904, filed on Dec. 18, 2009, provisional application No. 61/358,775, filed on Jun. 25, 2010.

(51) Int. Cl.

| A61K 31/52 | (2006.01) |
|---|---|
| A61P 13/12 | (2006.01) |
| A61P 11/06 | (2006.01) |
| A61P 37/08 | (2006.01) |
| A61P 19/02 | (2006.01) |
| A61P 17/06 | (2006.01) |
| A61P 35/02 | (2006.01) |
| A61P 35/00 | (2006.01) |
| C12N 9/99 | (2006.01) |
| C07D 473/00 | (2006.01) |

(52) U.S. Cl.
USPC .............. 514/263.1; 514/263.2; 514/263.3; 435/184; 544/235; 544/265; 544/277

(58) Field of Classification Search
USPC ......... 514/119, 252.16, 263.2, 263.22, 263.4; 544/235, 265, 277
See application file for complete search history.

(56) References Cited

U.S. PATENT DOCUMENTS

| 3,037,980 A | 6/1962 | Hitchings et al. |
|---|---|---|
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,612,114 B2 | 11/2009 | Hamaoka et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |

(Continued)

FOREIGN PATENT DOCUMENTS

| AT | 388372 | 6/1989 |
|---|---|---|
| CA | 1066701 | 11/1979 |

(Continued)

OTHER PUBLICATIONS

Xu. Z., Activation of the PI3K/AKT/mTOR pathway in diffuse large B cell lymphoma: clinical significance and inhibitory effect of rituximab, Ann. Hematol. (2013) 92: 1351-1358.*

Uddin, S., Role of phosphatidylinositol 3¢-kinase/AKT pathway in diffuse largeB-cell lymphoma survival, Blood (2006) 108: 4178-4186.*

DeBerardinis, R. J., The Biology of Cancer: Metabolic Reprogramming Fuels Cell Growth and Proliferation, Cell Metabolism 7, Jan. 2008, Cell Press, Elsevier: 11-20.*

Ali, et al., Nature. 2004, 431(7011):1007-11.

(Continued)

Primary Examiner — Kortney L Klinkel
Assistant Examiner — John Mauro
(74) Attorney, Agent, or Firm — Fish & Richardson P.C.

(57) ABSTRACT

The present invention provides fused aryl and heteroaryl derivatives of Formula I:

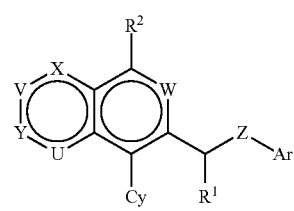

wherein X, V, Y, U, W, Z, $R^1$, $R^2$, Cy, and Ar are defined herein, that modulate the activity of phosphoinositide 3-kinases (PI3Ks) and are useful in the treatment of diseases related to the activity of PI3Ks including, for example, inflammatory disorders, immune-based disorders, cancer, and other diseases.

28 Claims, 3 Drawing Sheets

(56) References Cited

U.S. PATENT DOCUMENTS

| | | | |
|---|---|---|---|
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikian et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1* | 11/2008 | Diacovo et al. ......... 514/263.21 |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1* | 5/2009 | Chen et al. ................ 514/234.2 |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0098248 A1 | 4/2011 | Halcomb et al. |
| 2011/0105508 A1* | 5/2011 | Allen et al. ................... 514/245 |
| 2011/0190319 A1 | 8/2011 | Combs |
| 2011/0224155 A1 | 9/2011 | Tachdjian et al. |
| 2011/0281884 A1 | 11/2011 | Combs et al. |
| 2011/0312979 A1 | 12/2011 | Li et al. |
| 2012/0157430 A1 | 6/2012 | Li et al. |
| 2013/0029982 A1 | 1/2013 | Castro et al. |
| 2013/0059835 A1 | 3/2013 | Li et al. |
| 2013/0261101 A1 | 10/2013 | Combs et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 01250316 | 10/1989 |
| JP | 04190232 | 7/1992 |
| JP | 09087282 | 3/1997 |
| JP | 09176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011136925 | 7/2011 |
| RU | 2233842 | 8/2004 |
| SU | 1712359 | 2/1992 |
| WO | WO 93/16076 | 8/1993 |
| WO | WO 93/25524 | 12/1993 |
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |

(56) References Cited

FOREIGN PATENT DOCUMENTS

| WO | WO2007/042806 | 4/2007 |
|---|---|---|
| WO | WO 2007/076092 | 7/2007 |
| WO | WO 2007/087548 | 8/2007 |
| WO | WO 2007/102392 | 9/2007 |
| WO | WO 2007/126841 | 11/2007 |
| WO | WO 2008/002490 | 1/2008 |
| WO | WO 2008/025821 | 3/2008 |
| WO | WO2008/032033 | 3/2008 |
| WO | WO 2008/064018 | 5/2008 |
| WO | WO 2008/082490 | 7/2008 |
| WO | WO 2008/097991 | 8/2008 |
| WO | WO 2008/100867 | 8/2008 |
| WO | WO 2008/118454 | 10/2008 |
| WO | WO 2008/118468 | 10/2008 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/086123 | 7/2009 |
| WO | WO 2009/097446 | 8/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010129816 A2 * | 11/2010 |
| WO | WO 2010/151735 | 12/2010 |
| WO | WO 2010/151740 | 12/2010 |
| WO | WO 2011/008302 | 1/2011 |
| WO | WO2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO2011/092198 | 8/2011 |
| WO | WO 2011/117711 | 9/2011 |
| WO | WO 2011/123751 | 10/2011 |
| WO | WO2011/130342 | 10/2011 |
| WO | WO 2011/146882 | 11/2011 |
| WO | WO 2011/156759 | 12/2011 |
| WO | WO2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO2012/087881 | 6/2012 |
| WO | WO 2012/097000 | 7/2012 |
| WO | WO2012/125629 | 9/2012 |
| WO | WO2012/135009 | 10/2012 |
| WO | WO2013/033569 | 3/2013 |

OTHER PUBLICATIONS

Allen, et al., "Synthesis of C-6 substituted pyrazolo[1,5-a]pyridines with potent activity against herpesviruses," *Bioorganic & Medicinal Chemistry* (2006), 14(4), 944-954.

Bader, et al., Proc Natl Acad Sci U S A. 2006, 103(5):1475-9.

Barber, et al., Nat Med. 2005, 11(9):933-5.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Benistant, et al., Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Bergman, et al., "Synthesis of indolocarbazole quinones; potent aryl hydrocarbon receptor ligands," *Tetrahedron* (2002), 58(7), 1443-1452.

Bhovi, et al., "1,3-dipolar cycloaddition reaction: Synthesis and anti-microbial activity of some new 3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.

Billottet, et al., Oncogene. 2006, 25(50):6648-59.

Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.

Blom et al., Preparative LC-MS Purification: Improved Compound Specific Method Optimization, J. Combi. Chem. 2004, 6(6), 874-883.

Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.

Brock et al., J Cell Biol., 2003, 160(1):89-99.

Brown, et al., "Small molecule inhibitors of IgE synthesis," *Bioorganic & Medicinal Chemistry Letters* (2006), 16(17), 4697-4699.

Camps, et al., Nat Med. 2005, 11(9):936-43.

Cantley, Science, (2002) 296 (5573):1655-7.

Chai, et al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.

Clayton, et al., J Exp Med. 2002, 196(6):753-63.

Dolezal et al., "Preparation, biological activity and endogenous occurrence of N6- benzyladenosines," *Bioorganic & Medicinal Chemistry* (2007), 15(11), 3737-3747.

Dolezal et al., "Preparation and biological activity of 6-benzylaminopurine derivatives in plants and human cancer cells," *Bioorganic & Medicinal Chemistry* (2006), 14(3), 875-884.

Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.

Fadeyeva, et al., "Inhibitors of early virus-cell interaction stages among 3-ethoxycarbonyl-5-hydroxy-bromoindole derivatives," *Khimiko-Farmatsevticheskii Zhurnal* (1992), 26(9-10), 17-20 (with English abstract).

Floberg et al., "Extractive alkylation of 6-mercaptopurine and determination in plasma by gas chromatography-mass spectrometry," *Journal of Chromatography, Biomedical Applications*, (1981), 225(1), 73-81.

Gati et al., "(125I)Iodohydroxynitrobenzylthioinosine: a new high-affinity nucleoside transporter probe," *Biochemistry and Cell Biology* (1987), 65(5), 467-73.

Geng, et al., "Exploring 9-benzyl purines as inhibitors of glutamate racemase (MurI) in Gram-positive bacteria", Bioorganic & Medicinal Chemistry Letters (2008),18(15), 4368-4372.

Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.

Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).

Hickey, et al., J Biol Chem. 2006, 281(5):2441-50.

(56) References Cited

OTHER PUBLICATIONS

Hirose, et al., "Pyridone-carboxylic acids as antibacterial agents. I. Synthesis and antibacterial activity of 1-alkyl-1,4-dihydro-4-oxo-1,8- and -1,6-naphthyridine-3-carboxylic acids", Chemical & Pharmaceutical Bulletin (1982), 30(7), 2399-409.

Hirota, "Efficient synthesis of 2,9-disubstituted 8-hydroxyadenine derivatives", Organic & Biomolecular Chemistry (2003), 1(8), 1354-1365.

Huang et al., "Design and synthesis of a pyrido[2,3-d]pyrimidin-5-one class of anti-inflammatory FMS inhibitors,", Bioorganic & Medicinal Chemistry Letters (2008), 18(7), 2355-2361.

Huang et al., "Synthesis and bioassay of a fluorine-containing cytokinin, N6-pentafluoro-benzyladenosine," Youji Huaxue (1988), 8(2), 147-8 (with English abstract).

Irie, et al., "Discovery of selective and nonpeptidic cathepsin S inhibitors," Bioorganic & Medicinal Chemistry Letters (2008), 18(14), 3959-3962.

Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.

Itaya, et al., "Synthesis and structure of the marine ascidian 8-oxoadenine aplidiamine," Chemical & Pharmaceutical Bulletin (1999), 47(9), 1297-1300.

Itaya, et al., "Syntheses of the marine ascidian purine aplidiamine and its 9-β-D-ribofuranoside," Tetrahedron Letters (1998), 39(26), 4695-4696.

Jager, et al., "Molecular recognition analyzed by EPR, ENDOR, and NMR spectroscopy," Angewandte Chemie, International Edition in English (1996), 35(16), 1815-1818.

Jager et al., "Molecular recognition. II Discrimination of specific and non-specific intermolecular interactions by means of magnetic resonance spectroscopy," Magnetic Resonance in Chemistry (1998), 36(3), 205-210, CODEN: MRCHEG; ISSN: 0749-1581.

Jimenez, et al., J Biol Chem., 2002, 277(44):41556-62.

Jou, et al., Mol Cell Biol. 2002, 22(24):8580-91.

Journal of Pharmaceutical Science, 66, 2 (1977).

Kang, et al., Proc Natl Acad Sci U S A. 2005, 102(3):802-7.

Kang et al., "Aplidiamine, a unique zwitterionic benzyl hydroxyadenine from the Western Australian marine ascidian Aplidiopsis sp.," Tetrahedron Letters (1997), 38(6), 941-944.

Kasibhatla, "Rationally Designed High-Affinity 2-Amino-6-halopurine Heat Shock Protein 90 Inhibitors That Exhibit Potent Antitumor Activity",Journal of Medicinal Chemistry (2007), 50(12),2767-2778.

Katritzky, et al., "Facile Synthesis of 2-Substituted Indoles and Indolo[3,2-b]carbazoles from 2-(Benzotriazol-1-ylmethyl)indole," Journal of Organic Chemistry (1995), 60(11), 3401-4.

Kim, et al., "A new structural class of S-adenosylhomocysteine hydrolase inhibitors", Bioorganic & Medicinal Chemistry (2009), 17(18), 6707-6714.

Kim, et al., "Synthesis and evaluation of antitumor activity of novel 1,4-naphthoquinone derivatives," Archives of Pharmacal Research (2006), 29(2), 123-130 CODEN: APHRDQ; ISSN: 0253-6269.

Knobbe, et al., Neuropathol Appl Neurobiol. 2005, 31(5):486-90.

Kolasa, et al., "Synthesis of indolylalkoxyiminoalkylcarboxylates as leukotriene biosynthesis inhibitors," Bioorganic & Medicinal Chemistry (1997), 5(3), 507-514.

Kuduk et al., "Heterocyclic fused pyridone carboxylic acid M1 positive allosteric modulators," Bioorganic & Medicinal Chemistry Letters (2010), 20(8), 2533-2537.

Kurimoto, et al., "Synthesis and Biological Evaluation of 8-Oxoadenine Derivatives as Toll-like Receptor 7 Agonists Introducing the Antedrug Concept", Journal of Medicinal Chemistry (2010), 53(7),2964-2972.

Kutney, et al., "Dihydropyridines in synthesis and biosynthesis. IV. Dehydrosecodine, in vitro precursor of indole alkaloids," Canadian Journal of Chemistry (1982), 60(11), 1269-78.

Lee, et al., FASEB J. 2006, 20(3):455-65.

Li et al., "Design, synthesis and antitumor activities of novel 4-anilino-5H-pyridazino[4,5-b]indoles," Zhongguo Yaoxue (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," Zhongguo Yaowu Huaxue Zazhi (2007), 17(6), 339-343, CODEN: ZYHZEF; ISSN: 1005-0108 (with English abstract within the article).

Li, et al., "Synthesis and anti-tumor activities of a novel series of tricyclic 1-anilino-5H-pyridazino[4,5-b]indoles," Archiv der Pharmazie (Weinheim, Germany) (2007), 340(8), 424-428 CODEN: ARPMAS; ISSN: 0365-6233.

Li, et al., "Optimization of the heterocyclic core of the quinazolinone-derived CXCR3 antagonists," Bioorganic & Medicinal Chemistry Letters (2008), 18(2), 688-693.

Lindsay, et al., "SmI2-Promoted Radical Addition Reactions with N-(2-Indolylacyl)oxazolidinones: Synthesis of Bisindole Compounds," Journal of Organic Chemistry (2007), 72(11), 4181-4188, CODEN: JOCEACH; ISSN: 0022-3263.

Link, J. T., "The intramolecular Heck reaction," Organic Reactions (Hoboken, NJ, United States) (2002), 60, No pp. given CODEN: ORHNBA URL: http://www3.interscience.wiley.com/cgi-bin/mrwhome/107610747/HOME.

Lucas, et al., "Rauwolfia alkaloids. XXXI. The synthesis and activity of some reserpine analogs," Journal of the American Chemical Society (1959), 81, 1928-32.

Ma, et al., "Two new constituents from Artemisia capillaris Thunb", Molecules (2008), 13(2), 267-271.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5), 1002-1018.

Matsumoto, et al., "Pyrido[2,3-d]pyrimidine antibacterial agents. 3. 8-Alkyl- and 8-vinyl-5,8-dihydro-5-oxo-2-(1-piperazinyl)pyrido[2,3-d]pyrimidine-6-carboxylic acids and their derivatives", Journal of Medicinal Chemistry (1975), 18(1), 74-9.

McLean, et al., "Discovery of covalent inhibitors for MIF tautomerase via cocrystal structures with phantom hits from virtual screening ," Bioorganic & Medicinal Chemistry Letters (2009), 19(23), 6717-6720.

Meade, et al., "Anxiolytic activity of analogs of 4-benzylamino-2-methyl-7H-pyrrolo[2,3-d]pyrimidines," European Journal of Medicinal Chemistry (1998), 33(5), 363-374.

Miki, et al., "Reaction of 1-benzylindole-2,3-dicarboxylic anhydride with 3-bromo-4-lithiopyridine: formal synthesis of ellipticine," Heterocycles (1998), 48(8), 1593-1597.

Miki, et al., "Synthesis of caulersin and its isomers by reaction of indole-2,3-dicarboxylic anhydrides with methyl indoleacetates," Tetrahedron Letters (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," Journal of the Chemical Society, Perkin Transactions 1 (2001), (18), 2213-2216.

Miki, et al., "Reaction of indole-2,3-dicarboxylic anhydride with (3-bromo-4-pyridyl)triisopropoxytitanium: synthesis of ellipticine," Tetrahedron Letters (1996), 37(43), 7753-7754.

Mishra et al., "Decanuclear Copper Framework Supported by a Tripodal Adenine Ligand," Inorganic Chemistry (Washington, Dc, United States), (2010), 49(8), 3691-3693.

Mizoguchi, et al., Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," Helvetica Chimica Acta (2010), 93(1), 153-157.

Morrison, et al., "Pyrimido[4,5-c]pyridazines. 1. Cyclizations with α-keto esters", Journal of Organic Chemistry (1978), 43(25), 4844-9.

Mukhopadhyay, et al., "An ionic liquid {[secbmim]+ Br-} as a "dual reagent catalyst" for the multicomponent synthesis of (quinolinyl-

(56) References Cited

OTHER PUBLICATIONS and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., Generation and behavior of naphthoyloxyl radicals in photocleavage of 1-(naphthoyloxy)-2-pyridones, *Chemistry Letters* (2001), (10), 1064-1065.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Nettekoven, M., "A combinatorial approach towards 2-acyl-3-amino-indole derivatives," *Tetrahedron Letters* (2000), 41(43), 8251-8254.

Oki, et al., "Reactivities of Stable Rotamers. XLII. Generation and Fates of Rotameric [1-(9-Fluorenyl)-2-naphthyl]methyl Radicals," *Bulletin of the Chemical Society of Japan* (1999), 72(10), 2327-2336.

Okkenhaug, et al., Science, 2002, 297(5583):1031-4).

Phillips, et al., "The reaction of anils with 8-quinolinol," *Journal of Organic Chemistry* (1954), 19, 907-9 CODEN: JOCEACH; ISSN: 0022-3263.

Platts, et al., "A concise synthesis of HIV integrase inhibitors bearing the dipyridone acid motif," *Tetrahedron Letters* (2011), 52(4), 512-514.

Portnaya, et al., "Azomethine dyes. IV. Indoaniline dyes derived from heterocyclic N-substituted 1-hydroxy-2-naphthamides," *Ts. Vses. Nauchn.-Issled. Kinofotoinst.* (1960), (No. 40), 106-18 (with English abstract).

Prezent, et al., STN Abstract, Accession No. 2004:358794, "Boron chelates as intermediates in the synthesis of new functionalized pyridines and pyrimidines from α,α-dioxoketene aminals," *Boron Chemistry at the Beginning of the 21st Century*, [*Proceedings of the International Conference on the Chemistry of Boron*], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.

Randis, et al., Eur. J. Immunol , 2008, 38(5):1215-24.

Reich, et al., "Preparation of a,b-unsaturated carbonyl compounds and nitriles by selenoxide elimination ," *Organic Reactions* (Hoboken, NJ, United States) (1993), 44, No pp. given.

Roxas-Duncan, et al., "Identification and biochemical characterization of small-molecule inhibitors of Clostridium botulinum neurotoxin serotype A," *Antimicrobial Agents and Chemotherapy* (2009), 53(8), 3478-3486.

Sahoo, et al., "Antispasmodic compounds. IV," Journal of the Indian Chemical Society (1959), 36, 421-4.

Sako, M., "Product class 19: pyridopyrimidines," *Science of Synthesis* (2004), 16, 1155-1267.

Samuels, et al., Science, 2004, 304(5670):554.

Samuels, et al., Curr Opin Oncol. 2006, 18(1):77-82.

Sasaki, et al., Science, 2000, 287(5455):1040-6.

Saxena, et al., "Pharmacophore-based virtual screening and docking studies on Hsp90 inhibitors", SAR and QSAR in Environmental Research (2010), 21(5-6), 445-462.

Sebell, et al., "Versatile Solid-Phase Synthesis of Trisubstituted 1H-Pyrido[2,3-d]pyrimidin-4-ones and Related Heterocycles," *Journal of Combinatorial Chemistry* (2005), 7(1), 96-98.

Sen, et al., "Reaction of aldehydes and amines with 8-hydroxyquinaldine and 8-quinolinol. II," *Journal of the Indian Chemical Society* (1960), 37, 640-2.

Shi, et al., "Synthesis and preliminary cytotoxic evaluation of substituted indoles as potential anticancer agents," *Chinese Chemical Letters* (2007), 18(8), 899-901, CODEN: CCLEE7; ISSN: 1001-8417.

Singh et al., "Application of Nazarov cyclization to access [6-5-6] and [6-5-5]tricyclic core embedded new heterocycles: an easy entry to structures related to Taiwaniaquinoids," *Organic & Biomolecular Chemistry* (2009), 7(9), 1858-1867, CODEN: OBCRAK; ISSN: 1477-0520.

Steliou, et al., "Does diatomic sulfur(S2) react as a free species?", *Journal of the American Chemical Society* (1992), 114(4), 1456-62.

Sujobert, et al., Blood, 2005, 106(3):1063-6.

Szuecova, et al., "Synthesis, characterization and biological activity of ring-substituted 6-benzylamino-9-tetrahydropyran-2-yl and 9-tetrahydrofuran-2-ylpurine derivatives," *Bioorganic & Medicinal Chemistry* (2009), 17(5), 1938-1947.

Thomas, et al., Eur J Immunol 2005, 35(4):1283-91.

Travnickek, et al., "2-Chloro-6-[(4-hydroxy-3,5-dimethoxybenzyl)amino]-9-isopropylpurine," *Acta Crystallographica, Section E: Structure Reports Online* (2007), E63(2), o728-o730 CODEN: ACSEBH; ISSN: 1600-5368 URL: http://journals.iucr.org/e/issues/2007/02/00/lh2285/lh2285.pdf.

Vanhaesebroeck et al., Trends Biochem Sci., 2005, 30(4):194-204.

Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).

Yahyazadeh, et al., "Synthesis of 9-benzyl-6-aminopurines from 5-amino-l-benzyl-4-cyanoimidazoles", Bulletin of the Korean Chemical Society (2003), 24(12), 1723-1724.

Yahay-Zadeh, "Synthesis of 9-Aryl-6-aminopurines from 5-Amino-l-aryl-1H-imidazole-4-carbonitriles", Russian Journal of Organic Chemistry (Translation of Zhurnal Organicheskoi Khimii) (2003), 39(11),1649-1651.

Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.

Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.

Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.

Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.

Zhao, et al., "Synthesis and in vitro anti-hepatitis B virus activities of some ethyl 5-hydroxy-1H-indole-3-carboxylates," *Bioorganic & Medicinal Chemistry* (2006), 14(8), 2552-2558.

International Search Report for PCT/US2011/041202 dated Sep. 23, 2011 (12 pgs.).

International Search Report for PCT/US2011/032213 dated Jun. 14, 2011 (11 pgs.).

International Search Report for PCT/US2010/060980 dated Mar. 15, 2011 (12 pgs.).

International Search Report for PCT/US2010/061023 dated Feb. 16, 2011 (10 pgs.).

International Search Report for PCT/US2010/040150 dated Nov. 8, 2010 (19 pgs.).

International Preliminary Report on Patentability for PCT/US2010/040150 dated Jul. 5, 2011 (24pgs.).

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/pagel, 5 pgs.

Boger, et al., "First and Second Generation Total Synthesis of the Teicoplanin Aglycon," JACS, 123(9), 1862-1871, 2001.

Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," *The Journal of Pharmacology and Experimental Therapeutics*, 328(3):758-765, 2009.

Flinn et al., "Preliminary evidence of clinical activity in a phase I study of CAL-101, a selective inhibitor of the p110δ isoform of

(56) References Cited

OTHER PUBLICATIONS phosphatidylinositol 3-kinase (PI3K), in patients with select hematologic malignancies," *Journal of Clinical Oncology*, (abstract), 27(15S):3543, 2009.
Harris et al., "Alkyl 4-Chlorobenzoyloxycarbamates as Highly Effective Nitrogen Source Reagents for the Base-Free, Intermolecular Aminohydroxylation Reaction," *J. Org.Chem.*, 76, 358-372, 2011.
Hauser et al., "B-Cell Depletion with Rituximab in Relapsing—Remitting Multiple Sclerosis," *The New England Journal of Medicine*, 358(7):676-688, 2008.
Ihle et al , "Inhibitors of phosphatidylinositol-3-kinase in cancer therapy", *Molecular Aspects of Medicine*, 31(2): 135- 144, 2010.
Kong and Yamori, "Advances in Development of Phosphatidylinositol 3-Kinase Inhibitors," *Current Medicinal Chemistry*, 16:2839-2854, 2009.
Kung et al., "Characterization of a Murine Model of Allergic Pulmonary Inflammation," *Int. Arch. Allergy Immunol.*, (abstract), 105(1):83-90, 1994.
McMahon, G., "VEGF Receptor Signaling in Tumor Angiogenesis," *The Oncologist*, 5(1):3-10, 2000.
Meijer et al., "Treatment of primary Sjögren syndrome with rituximab: extended follow-up, safety and efficacy of retreatment," *Ann. Rheum. Dis.*, 68(2):284-285, 2009.
Norman, P., "Selective PI3Kδ inhibitors , a review of the patent literature", *Expert Opinion on Therapeutic Patents, Informa Healthcare*, 21(11):1773-1790, 2011.
Park et al., "Phosphoinositide 3-kinase δ inhibitor as a novel therapeutic agent in asthma," *Respirology*, 13:764-771, 2008.
Pinedo and Slamon, "Translational Research: The Role of VEGF in Tumor Angiogenesis," *The Oncologist*, 5(1):1-2, 2000.
Puri and Gold, "Selective inhibitors of phosphoinositide 3-kinase delta: modulators of B-cell function with potential for treating autoimmune inflammatory diseases and B-cell malignancies," *Frontiers in Immunology*, 3(256):1-16, 2012.
Ramos-Casals et al., "Rituximab in systemic lupus erythematosus; A systematic review of off-label use in 188 cases," *Lupus*, 18:767-776, 2009.
Shuttleworth et al., "Progress in the Preclinical Discovery and Clinical Development of Class 1 and Dual Class I/IV Phosphoinositide 3-Kinase (PI3K) Inhibitors", *Current Medicinal Chemistry*, 18(1):2686-2714, 2011.
Stüve et al., "Long-term B-Lymphocyte Depletion With Rituximab in Patients With Relapsing-Remitting Multiple Sclerosis," *Arch. Neurol.*, 66(2):259-261, 2009.
Zhang et al., "Advances in preclinical small molecules for the treatment of NSCLC", *Expert Opinion on Therapeutic Patents*, 19(6):731-751, 2009.
International Preliminary Report on Patentability dated Jun. 19, 2012 for International Appln. No. PCT/US2010/060980 (8 pgs.).
International Preliminary Report on Patentability dated Dec. 28, 2012 for International Appln. No. PCT/US2011/041202 (8 pgs.).
International Preliminary Report on Patentability dated Oct. 16, 2012 for International Appln. No. PCT/US2011/032213 (6 pgs.).
International Preliminary Report on Patentability dated Jun. 19, 2012 for International Appln. No. PCT/US2010/061023 (6 pgs.).
International Search Report dated Feb. 28, 2012 for International Appln. No. PCT/US2011/065743 (13 pgs.).
International Search Report dated May 31, 2012 for International Appln. No. PCT/US2012/028915 (11 pgs.).
International Search Report dated May 11, 2012 for International Appln. No. PCT/US2012/030310 (11 pgs.).
International Search Report dated Dec. 21, 2012 for International Appln. No. PCT/US2012/053398 (11 pgs.).
Results from STN Search Report, conducted Dec. 1, 2010, 132 pages.
Results from STN Search Report, conducted Dec. 16, 2009, 72 pages.
Results from STN Search Report, conducted prior to Jun. 21, 2011, 224 pages.
Results from STN Search Report, conducted Apr. 5, 2010, 513 pages.
Results from STN Search Report, conducted Apr. 24, 2009, 43 pages.
Results from STN Search Report, conducted Dec. 7, 2010, 213 pages.
Results from STN Search Report, conducted Aug. 29, 2011, 181 pages.
Results from STN Search Report, conducted May 27, 2009, 2 pages.
Results from STN Search Report, conducted May 28, 2009, 81 pages.
Results from STN Search Report, conducted Apr. 2, 2010, 141 pages.
Results from STN Search Report, conducted Aug. 30, 2011, 61 pages.
Barragan et al., "Protein Kinases in the Regulation of Apoptosis in B-cell Chronic Lymphocytic Leukemia," *Leukemia and Lymphoma*, 2003, 44(11):1865-1870.
Fruman and Bismuth, "Fine Tuning the Immune Response with PI3K," *Immunological Revs.*, 2006, 228:253-272.
Ringshausen et al., "Constitutively Actived phosphatidylinositol-3-kinase (PI-3K) is involved in the defect of apoptosis is B-CLL: assocaite with protein kinase C delta," *Blood*, 2002, 100:3741-3748.
Venet et al., "Lymphocytes in the Development of Lung Inflammation: A role of Regulatory CD4+ T Cells in Indirect Pulmonary Lung Injury," *J Immunol.*, 2009, 183:6472-3480.
Yaguchi et al., "Antitumor Activity of ZSTK474, a new Phosphatidinylinositol 3-Kinase Inhibitor," *J Natl. Cancer Inst.*, 2006, 98(8):545-556.
International Preliminary Report on Patentability dated Jul. 4, 2013 for International Appln. No. PCT/US2011/065743 (8 pgs).
International Search Report dated Jul. 11, 2013 for International Appln. No. PCT/US2013/034803 (15 pgs.).

* cited by examiner

SUBSTITUTED FUSED ARYL AND HETEROARYL DERIVATIVES AS PI3K INHIBITORS

This application claims the benefit of priority of U.S. Provisional Appl. No. 61/287,904, filed Dec. 18, 2009, and U.S. Provisional Appl. No. 61/358,775, filed Jun. 25, 2010, each of which is incorporated herein by reference in its entirety.

FIELD OF THE INVENTION

The present invention provides substituted aryl and heteroaryl fused derivatives that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate ($PIP_2$) giving rise to phosphatidylinosito-3,4,5-trisphosphate ($PIP_3$). $PIP_3$ functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4): 194-204).

The differential tissue distribution of the PI3K isoforms factors in their distinct biological functions. Genetic ablation of either PI3Kα or PI3Kμ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et at, Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005). Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3): 802-7; Bader, et al., Proc Natl Acad Sci USA. 2006, 103(5): 1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3): 1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44): 5083-90; Mizoguchi, et al., Brain Pathol. 2004, 14(4):372-7; Knobbe, et al., Neuropathol Appl Neurobiol. 2005, 31(5): 486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and others.

SUMMARY

The present invention provides, inter alfa, compounds of Formula I:

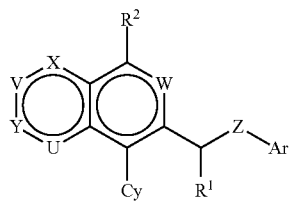

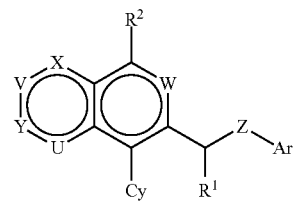

and pharmaceutically acceptable salts thereof; wherein the variables X, V, Y, U, W, Z, $R^1$, $R^2$, Cy, and Ar are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

DETAILED DESCRIPTION

Figure 1:
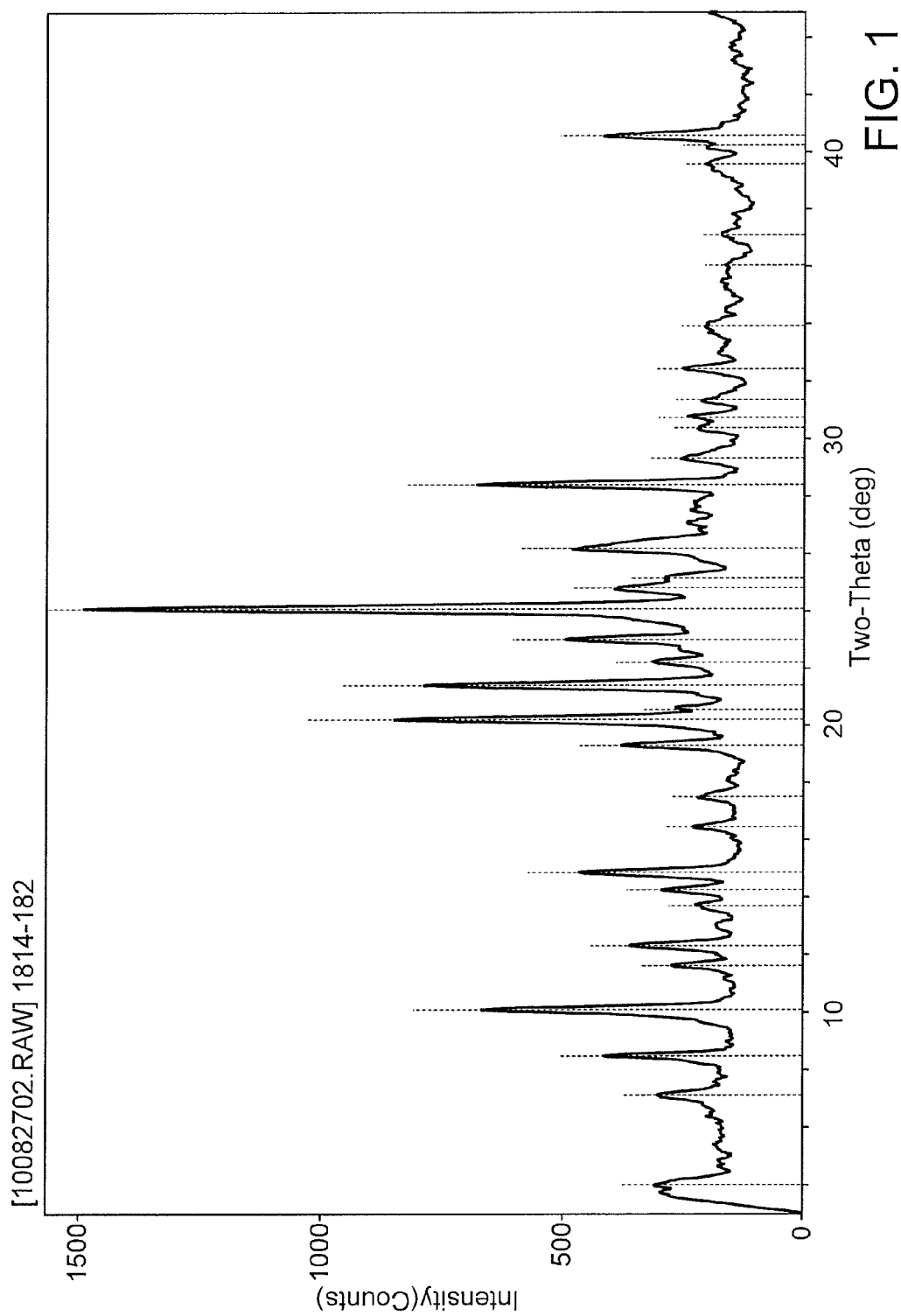
FIG. 1 depicts the XRPD pattern for the product of Example 108.

The present invention provides, inter alia, a compound of Formula I:

or a pharmaceutically acceptable salt thereof; wherein:
the sumbol

indicates that the ring is aromatic;

Z is O, S, or $NR^A$;

Cy is cycloalkyl, heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^c$ $R^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^c$-$S(O)R^b$, $NR^cS(O)_2R^b$, $NR^cS(O)_2NR^cR^d$, $S(O)R^b$, $S(O)NR^c$ $R^d$, $S(O)_2R^b$, and $S(O)_2NR^cR^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $Cy^1$, $NO_2$, $OR^a$, $SR^a$, $C(O)R^b$, $C(O)NR^c$ $R^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^c$ $R^d$, $S(O)R^b$, $S(O)NR^cR^d$, $S(O)_2R^b$, and $S(O)_2NR^cR^d$;

W is $CR^3$ or N; V is $CR^4$ or N; X is $CR^5$; Y is $CR^6$ or N; and U is $CR^7$ or N; or W is $CR^3$ or N; V is $CR^4$ or N; X is O or S; Y is absent; and U is $CR^7$ or N; or W is $CR^3$ or N; V is N; X is $CR^5$; Y is absent; and U is $NR^{41}$; or W is $CR^3$ or N; V is O or S; X is $CR^5$; Y is absent; and U is $CR^7$ or N;

provided that when Y is present, then at least one of V, Y, and U is other than N;

$R^1$ is independently selected from H, $C_{1-6}$ alkyl, $C_{1-6}$ haloalkyl, $C_{2-6}$ alkenyl, and $C_{2-6}$ alkynyl; wherein said $C_{1-6}$ alkyl, $C_{1-6}$ haloalkyl, $C_{2-6}$ alkenyl, and $C_{2-6}$ alkynyl are each optionally substituted with 1, 2, 3 or 4 substituents independently selected from halo, OH, CN, $NR^{1\dagger}tR^{2\dagger}$, $C_{1-6}$ alkoxy, $C_{1-6}$haloalkoxy, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl) carbamyl, carboxy, $C_{1-6}$ alkylcarbonyl, $C_{1-6}$ alkoxycarbonyl, and $C_{1-6}$ alkylcarbonylamino;

each $R^{1\dagger}$ and $R^{2\dagger}$ is independently selected from H and $C_{1-6}$ alkyl;

or any $R^{1\dagger}$ and $R^{2\dagger}$ together with the N atom to which they are attached form a 3-, 4-, 5-, 6-, or 7-membered heterocycloalkyl group, which is optionally substituted with 1, 2, 3, or 4 substituents independently selected from $C_{1-6}$ alkyl;

$R^2$, $R^3$, $R^4$, $R^5$, $R^6$ and $R^7$ are each independently selected from H, OH, $NO_2$, CN, halo, $C_{1-6}$ alkyl, $C_{2-6}$ alkynyl, $C_{3-7}$ cycloalkyl, $C_{1-6}$ haloalkyl, $C_{1-6}$ alkoxy, $C_{1-6}$haloalkoxy, amino, $C_{1-6}$ alkylamino, di($C_{1-6}$ alkyl)amino, thio, $C_{1-6}$ alkylthio, $C_{1-6}$alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$alkylcarbonyl, and $C_{1-6}$ alkoxycarbonyl;

Ar is heteroaryl, substituted with 1, 2, 3, 4, or 5 independently selected $R^D$ groups;

each $R^D$ is independently selected from H, —($C_{1-4}$ alkyl)$_r$-$Cy^1$, halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^A$ is selected from H, $C_{1-6}$ alkyl, $C_{2-6}$ alkenyl, and $C_{2-6}$ alkynyl;

$R^{A1}$ is selected from H, $C_{1-6}$ alkyl, $C_{2-6}$ alkenyl, and $C_{2-6}$ alkynyl;

each $Cy^1$ is, independently, aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^e)NR^{c1}R^{d1}$, $NR^{c1}C(=NR^e)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $R^a$, $R^b$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5\,Rd5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^e$ and $R^f$ is independently selected from H, $C_{1-6}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$haloalkoxy;

or any $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$haloalkoxy; and r is 0 or 1.

In some embodiments:

W is $CR^3$ or N;

V is $CR^4$ or N;

X is $CR^5$; and Y is $CR^6$ or N; or

X is O or S; and Y is absent;

U is $CR^7$ or N; and each $R^C$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^eS(O)R^b$, $NR^eS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, the compound is other than:

2-((1-(9H-fluoren-9-yl)naphthalen-2-yp methylthio)pyridine; and

7'-((1H-benzo[d]imidazol-6-ylamino)methyl)-N-methyl-6,8'-biquinazolin-2-amine; or a pharmaceutically acceptable salt thereof.

In some embodiments, Ar is other than a benzo[d]imidazole ring.

In some embodiments, Z is $NR^A$.

In some embodiments, Cy is heterocycloalkyl, aryl or heteroaryl, each optionally substituted with 1, 2, 3, 4, or 5 independently selected $R^C$ groups.

In some embodiments, Cy is aryl, optionally substituted with 1, 2, 3, 4, or 5 substituents independently selected $R^C$ groups.

In some embodiments, Cy is heterocycloalkyl, optionally substituted with 1, 2, 3, 4, or 5 independently selected $R^C$ groups.

In some embodiments, Cy is heteroaryl, optionally substituted with 1, 2, 3, 4, or 5 independently selected $R^C$ groups.

In some embodiments, Cy is a phenyl ring, a pyrrolidine ring, a piperazine ring, or a pyridine ring, each of which is optionally substituted with 1, 2, 3, 4, or 5 independently selected $R^C$ groups.

In some embodiments, Cy is a phenyl ring, a pyrrolidine ring, a piperidine ring, a piperazine ring, or a pyridine ring, each of which is optionally substituted with 1, 2, 3, 4, or 5 independently selected $R^C$ groups.

In some embodiments, each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^1$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, $C_{1-6}$ haloalkoxy.

In some embodiments, each $R^c$ is independently selected from halo, $C_{1-6}$ alkyl, $C_{1-6}$ haloalkyl, CN, $OR^A$, and $NR^cC(O)R^b$; wherein said $C_{1-6}$ alkyl is optionally substituted with 1, 2, 3, 4, or 5 substituents independently selected from hydroxy, $C_{1-6}$ alkoxy, $C_{1-6}$ haloalkoxy.

In some embodiments, each $R^C$ is independently selected from $C_{1-6}$ alkyl, halo, $OR^a$, and $NR^cC(O)R^b$, wherein said $C_{1-6}$ alkyl is optionally substituted with hydroxyl or $C_{1-4}$ alkoxy.

In some embodiments, each $R^C$ is independently halo.

In som embodiments, each $R^C$ is independently selected from halo, $C_{1-6}$ alkyl, aryl, cycloalkyl, heteroaryl, heterocycloalkyl, CN, $OR^a$, $C(O)R^b$, $C(O)NR^cR^d$, $C(O)OR^a$, $NR^cC(O)R^b$, $NR^c(O)OR^a$, or $NR^cS(O)_2R^b$; wherein said $C_{1-6}$ alkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C1_{-6}$ haloalkyl, halosulfanyl, CN, $NO_2$, $OR^a$, $SR^a$, $C(O)R^b$, $C(O)NR^aR^d$, $C(O)OR^a$, $OC(O)R^b$, $OC(O)NR^cR^d$, $C(=NR^e)NR^cR^d$, $NRC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2R^cR^d$.

In some embodiments, each $R^C$ is independently selected from halo, $C_{1-6}$ alkyl, aryl, cycloalkyl, heteroaryl, heterocycloalkyl, CN, $OR^a$, $C(O)R^b$, $C(O)NR^cR^d$, $C(O)OR^a$, $NR^c$, $C(O)R^b$, $NR^cC(O)OR^a$, or $NR^cS(O)_2R^b$; wherein said $C_{1-6}$ alkyl, aryl, cycloalkyl, heteroaryl, and heterocycloalkyl are each optionally substituted with 1, 2, 3, 4, or 5 substituents independently selected from halo, $C_{1-6}$ alkyl, CN, $OR^a$, and $NR^cC(O)R^b$.

In some embodiments, Ar is a bicyclic azaheteroaryl group, substituted with 1, 2, 3, 4, or 5 independently selected $R^D$ groups.

In some embodiments, Ar is a purine ring, substituted with 1, 2, 3, 4, or 5 independently selected $R^D$ groups.

In some embodiments, Ar is a moiety of formula:

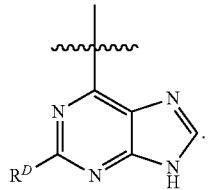

In some embodiments, each $R^D$ is independently selected from H, $C_{1-6}$ alkyl, and $NR^{c1}R^{d1}$.

In some embodiments, each $R^D$ is independently selected from H, methyl, amino, $C_{1-6}$ alkylamino, and di-$C_{1-6}$-alkylamino.

In some embodiments, each $R^D$ is independently selected from H, methyl, and amino.

In some embodiments, each $R^D$ is H.

In some embodiments, $R^1$ is selected from H and $C_{1-6}$ alkyl.

In some embodiments, $R^1$ is methyl.

In some embodiments, $R^1$ is H, methyl, or ethyl.

In some embodiments, $R^2$, $R^3$, $R^4$, $R^5$, $R^6$, and $R^7$ are independently selected from H, CN, halo, $C_{1-6}$ alkyl, and $C_{1-6}$ haloalkyl.

In some embodiments, $R^2$ is H, CN, halo, $C_{1-3}$ alkyl, or $C_{1-3}$ haloalkyl; and $R^3$, $R^4$, $R^5$, $R^6$, and $R^7$ are each independently H or C1.3 alkyl.

In some embodiments, $R^4$ is selected from H and $C_{1-6}$ alkyl.

In some embodiments, $R^4$ is H.

In some embodiments, each $R^a$, $R^b$, $R^c$, and $R^d$ is independently selected from H and $C_{1-6}$ alkyl, wherein said $C_{1-6}$ alkyl is optionally substituted with 1, 2, 3, 4, or 5 substituents independently selected from $C_{1-6}$ alkyl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, each $R^a$, $R^b$, $R^c$, and $R^d$ is independently selected from H, $C_{1-6}$ alkyl, aryl, cycloalkyl, heteroaryl, and heterocycloalkyl; wherein said $C_{1-6}$ alkyl, aryl, cycloalkyl, heteroaryl, and heterocycloalkyl are each optionally substituted with 1, 2, 3, 4, or 5 substituents independently selected from $C_{1-6}$ alkyl, halo, CN, and $OR^{a5}$.

In some embodiments, each $R^{a1}$, $R^{b1}$, $R^{c1}$, and $R^{d1}$ is independently selected from H and $C_{1-6}$ alkyl, wherein said $C_{1-6}$ alkyl is optionally substituted with 1, 2, 3, 4, or 5 substituents independently selected from $C_{1-6}$ alkyl, $C_{1-6}$ haloalkyl, halo, CN, $OR^{15}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$.

In some embodiments, each $R^{a5}$, $R^{b5}$, le, and $R^{d5}$ is independently selected from H and $C_{1-6}$ alkyl, wherein said $C_{1-6}$ alkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$alkyl)amino, $C_{1-6}$ haloalkyl, and $C_{1-6}$ haloalkoxy.

In some embodiments, each $R^{a5}$, $R^{b5}$, $R^{c5}$, and $R^{d5}$ is independently selected from H and $C_{1-6}$ alkyl.

In some embodiments, each $R^e$ and $R^f$ is H.

In some embodiments, each $R^a$, $R^b$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^c$ and $R^d$ together with the N atom to which they are attached form a 3-, 4-, 5-, 6-, or 7-membered heterocycloalkyl group, each optionally substituted with 1, 2, or 3 substituents independently selected from $C_{1-6}$ alkyl, $C_{1-6}$haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^cR^{d5}$, $NR^{c5}C(O)R^{b5}$, $NR^{c5}C(O)NR^{c5}R^{d5}$, $NR^{c5}(O)IR^{a5}$, $C(=NR^f)NR^{c5}R^{d5}$, $NR_{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^e$ and $R^f$ is independently selected from H, $C_{1-6}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

$R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C2_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{ds}$ together with the N atom to which they are attached form a 3-, 4-, 5-, 6-, or 7-membered heterocycloalkyl group, each optionally substituted with 1, 2, or 3 substituents independently selected from $C_{1-6}$ alkyl, $C_{1-6}$haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^f)NR^{c5}R^{d5}$, $NR^{c5}C(=NR^f)NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NH^{c5}R^{d5}$; and each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C2_6$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$haloalkyl, and $C_{i-6}$haloalkoxy;

or any $R^{c5}$ and $R^{d5}$ together with the N atom to which they are attached form a 3-, 4-, 5-, 6-, or 7-membered heterocycloalkyl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$haloalkyl, and $C_{1-6}$haloalkoxy.

In some embodiments, W is $CR^3$.
In some embodiments, W is N.
In some embodiments, V is $CR^4$.
In some embodiments, U is $CR^7$.
In some embodiments, U is N.
In some embodiments, Y is $CR^6$.
In some embodiments, Y is N.
In some embodiments, Y is absent.
In some embodiments, X is $CR^5$.
In some embodiments, X is S.
In some embodiments, X is $CR^5$.
In some embodiments, V is O.
In some embodiments, U is N.
In some embodiments, V is N.
In some embodiments, U is $NR^{A1}$
In some embodiments, $R^{A1}$ is H or $C_{1-4}$ alkyl.
In some embodiments:
Z is $NR^4$;
Cy is heterocycloalkyl, aryl or heteroaryl, each optionally substituted with 1, 2, 3, 4, or 5 independently selected $R^C$ groups;
each $R^C$ is independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
Ar is a bicyclic azaheteroaryl group, substituted with 1, 2, 3, 4, or 5 independently selected $R^D$ groups;
each $R^D$ is independently selected from H, $C_{1-6}$ alkyl, and $NR^{c1}R^{d1}$;
$R^1$ is independently selected from H and $C_{1-6}$ alkyl;
$R^4$ is selected from H and $C_{1-6}$ alkyl; and
$R^2$, $R^3$, $R^4$, $R^5$, $R^6$, and $R^7$ are independently selected from halo, CN, hydroxyl, $C_{1-4}$ alkoxy, $C_{1-4}$ haloalkoxy, amino, $C_{1-4}$ alkylamino, di-$C_{1-4}$-alkylamino, carboxy, $C_{1-4}$ alkylcarbonyl, $C_{1-4}$ alkoxycarbonyl, carbamyl, $C_{1-4}$alkylcarbamyl, di-$C_{1-4}$-alkylcarbamyl, $C_{n-m}$ alkylcarbonylamino, $C_{1-4}$ alkylthio, $C_{1-4}$ alkylsulfinyl, and $C_{1-4}$ alkylsulfonyl.
In some embodiments:
Z is $NR^4$;
Cy is heterocycloalkyl, aryl or heteroaryl, each optionally substituted with 1, 2, 3, 4, or 5 independently selected $R^C$ groups;
each $R^C$ is independently selected from halo, $C_{1-6}$ alkyl, $C_{2-6}$ alkenyl, $C_{2-6}$ alkynyl, $C_{1-6}$ haloalkyl, CN, $NO_2$, $OR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $S(O)R^b$, $S(O)NR^cR^d$, $S(O)_2R^b$, and $S(O)_2NR^cR^d$; wherein said $C_{1-6}$ alkyl is optionally substituted with 1, 2, 3, 4, or 5 substituents independently selected from hydroxy, $C_{1-6}$ alkoxy, $C_{1-6}$ haloalkoxy;
Ar is a bicyclic azaheteroaryl group, substituted with 1, 2, 3, 4, or 5 independently selected $R^D$ groups;
each $R^D$ is independently selected from H, $C_{1-6}$ alkyl, and $NR^{c1}R^{d1}$;
$R^1$ is independently selected from H and $C_{1-6}$ alkyl;
$R^4$ is selected from H and $C_{1-6}$ alkyl; and $R^2$, $R^3$, $R^4$, $R^5$, $R^6$, and $R^7$ are each independently selected from H, halo, CN, $C_{1-6}$ alkyl, and $C_{1-6}$ haloalkyl.

In some embodiments:

Z is $NR^A$;

Cy is heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, $C_{1-6}$ haloalkyl, CN, $OR^a$, and $NR^cC(O)R^b$; wherein said $C_{1-6}$ alkyl is optionally substituted with 1, 2, 3, 4, or 5 substituents independently selected from hydroxy, $C_{1-6}$ alkoxy, and $C_{1-6}$haloalkoxy;

Ar is a purine ring, substituted with 1, 2, 3, 4, or 5 independently selected $R^D$ groups;

each $R^D$ is independently selected from H, $C_{1-6}$ alkyl, and $NR^{c1}R^{d1}$;

$R^1$ is independently selected from H and $C_{1-6}$ alkyl;

$R^A$ is selected from H and $C_{1-6}$ alkyl; and $R^2$, $R^3$, $R^4$, $R^5$, $R^6$, and $R^7$ are each independently selected from H, halo, CN, $C_{1-6}$ alkyl, and $C_{1-6}$haloalkyl.

In some embodiments:

Z is $NR^A$;

Cy is heterocycloalkyl, aryl or heteroaryl, each optionally substituted with 1, 2, 3, 4, or 5 independently selected $R^c$ groups;

each $R^C$ is independently selected from $C_{1-6}$ alkyl, halo, $OR^a$, and $NR^cC(O)R^b$, wherein said $C_{1-6}$ alkyl is optionally substituted with hydroxyl or $C_{1-4}$ alkoxy;

each $R^a$, $R^b$, and $R^c$ is independently selected from H and $C_{1-4}$ alkyl;

Ar is a moiety of formula:

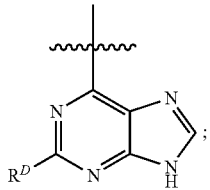

each $R^D$ is independently selected from H, methyl and amino.

$R^1$ is methyl;

$R^A$ is H;

$R^2$ is H or halo; and $R^3$, $R^4$, $R^5$, $R^6$, and $R^7$ are each independently H or methyl.

In some embodiments:

Z is $NR^A$;

Cy is heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, aryl, cycloalkyl, heteroaryl, heterocycloalkyl, CN, $OR^a$, $C(O)R^b$, $C(O)NR^cR^d$, $C(O)OR^a$, $NR^cC(O)R^b$, $NR^cC(O)OR^a$, or $NR^cS(O)_2R^b$; wherein said $C_{1-6}$ alkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

Ar is a moiety of formula:

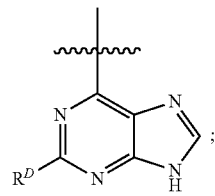

$R^1$ is independently selected from H and $C_{1-6}$ alkyl;

$R^A$ is selected from H and $C_{1-6}$ alkyl; and $R^2$, $R^3$, $R^4$, $R^5$, $R^6$, and $R^7$ are each independently selected from H, halo, CN, $C_{1-6}$ alkyl, and $C_{1-6}$ haloalkyl.

In some embodiments:

Z is $NR^A$;

Cy is heterocycloalkyl, aryl or heteroaryl, each optionally substituted with 1, 2, 3, 4, or 5 independently selected $R^C$ groups;

each $R^C$ is independently selected from halo, $C_{1-6}$ alkyl, aryl, cycloalkyl, heteroaryl, heterocycloalkyl, CN, $OR^a$, $C(O)R^b$, $C(O)NR^cR^d$, $C(O)OR^a$, $NR^cC(O)R^b$, $NR^cC(O)OR^a$, or $NR^cS(O)_2R^b$; wherein said $C_{1-6}$ alkyl, aryl, cycloalkyl, heteroaryl, and heterocycloalkyl are each optionally substituted with 1, 2, 3, 4, or 5 substituents independently selected from halo, $C_{1-6}$ alkyl, CN, $OR^a$, and $NR^cC(O)R^b$;

Ar is a moiety of formula:

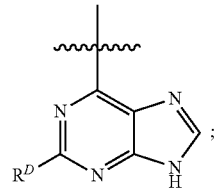

$R^1$ is independently selected from H and $C_{1-6}$ alkyl;

$R^A$ is selected from H and $C_{1-6}$ alkyl; and $R^2$, $R^3$, $R^4$, $R^5$, $R^6$, and $R^7$ are each independently selected from H, halo, CN, $C_{1-6}$ alkyl, and $C_{1-6}$haloalkyl.

In some embodiments, the compound is a compound of Formula Ia:

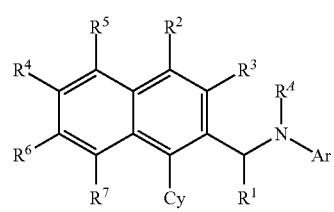

or a pharmaceutically acceptable salt thereof.

In some embodiments, the compound is a compound of Formula Ib:

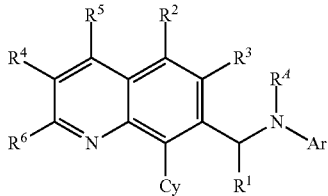

Ib or a pharmaceutically acceptable salt thereof.

In some embodiments, the compound is a compound of Formula Ic:

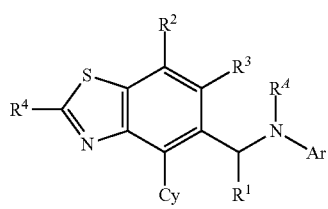

Ic or a pharmaceutically acceptable salt thereof.

In some embodiments, the compound is a compound of Formula Id:

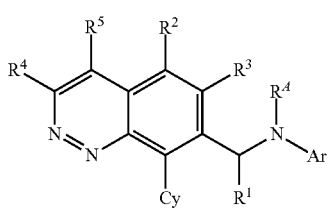

Id or a pharmaceutically acceptable salt thereof.

In some embodiments, the compound is a compound of Formula Ie:

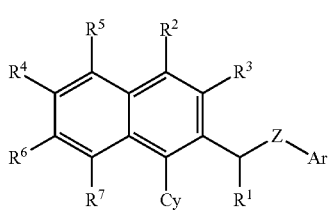

Ie or a pharmaceutically acceptable salt thereof.

In some embodiments, the compound is a compound of Formula If:

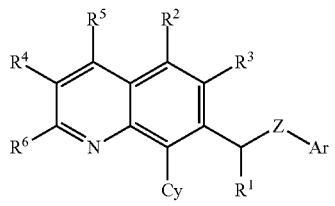

If or a pharmaceutically acceptable salt thereof.

In some embodiments, the compound is a compound of Formula Ig:

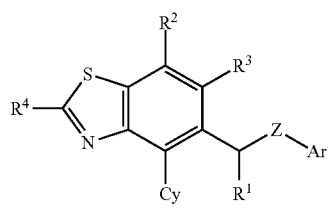

Ig or a pharmaceutically acceptable salt thereof.

In some embodiments, the compound is a compound of Formula Ih:

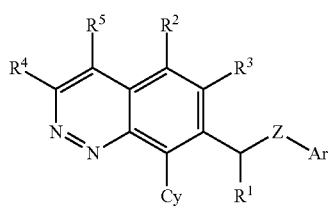

Ih or a pharmaceutically acceptable salt thereof.

In some embodiments, the compound is a compound of Formula IIe, IIf, IIg, or IIh:

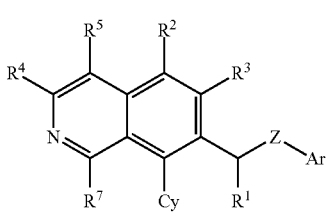

IIe

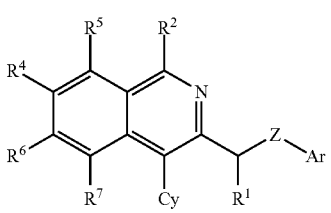

IIf

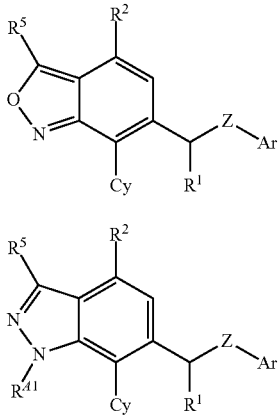

or a pharmaceutically acceptable salt thereof.

In some embodiments, the compound is selected from:
N-{1-[1-(3-fluorophenyl)-2-naphthyl]ethyl}-9H-purin-6-amine;
N-{1-[4-(3-fluorophenyl)-2-methyl-1,3-benzothiazol-5-yl]ethyl}-9H-purin-6-amine;
N(6)-{1-[1-(5-fluoropyridin-3-yl)-2-naphthyl]ethyl}-9H-purine-2,6-diamine;
N(6)-{1-[1-(3-fluorophenyl)-2-naphthyl]ethyl}-9H-purine-2,6-diamine;
N-{1-[1-(5-fluoropyridin-3-yl)-2-naphthyl]ethyl}-9H-purin-6-amine;
N-{1-[8-(3,5-difluorophenyl)quinolin-7-yl]ethyl}-9H-purin-6-amine;
N-{1-[8-(2-fluorophenyl)quinolin-7-yl]ethyl}-9H-purin-6-amine;
N-{1-[8-(3-fluorophenyl)quinolin-7-yl]ethyl}-9H-purin-6-amine;
N-{1-[8-(5-fluoropyridin-3-yl)quinolin-7-yl]ethyl}-9H-purin-6-amine;
N-{1-[5-chloro-8-(2-fluorophenyl)quinolin-7-yl]ethyl}-9H-purin-6-amine;
N-(1-{5-chloro-8-[4-(2-methoxyethyl)piperazin-1-yl]quinolin-7-yl}ethyl)-9H-purin-6-amine;
(3R)-1-{5-chloro-7-[1-(9H-purin-6-ylamino)ethyl]quinolin-8-yl}pyrrolidin-3-ol;
N-((3S)-1-{5-chloro-7-[1-(9H-purin-6-ylamino)ethyl]quinolin-8-yl}pyrrolidin-3-yl)acetamide;
N-(1-{5-chloro-8-[(2R)-2-(methoxymethyl)pyrrolidin-1-yl]quinolin-1-yl}ethyl)-9H-purin-6-amine; and
N-{1-[5-chloro-8-(3-fluorophenyl)quinolin-7-yl]ethyl}-9H-purin-6-amine;
or a pharmaceutically acceptable salt thereof.

In some embodiments, the compound is selected from:
N-{1-[5-Chloro-8-(3-fluorophenyl)cinnolin-7-yl]ethyl}-9H-purin-6-amine;
N-{1-[5-Fluoro-8-(3-fluorophenyl)cinnolin-7-yl]ethyl}-9H-purin-6-amine;
N(6)-{1-[5-Fluoro-8-(3-fluorophenypcinnolin-7-yl]ethyl}-9H-purine-2,6-diamine;
N-{1-[5-Chloro-8-(3,5-difluorophenypcinnolin-7-yl]ethyl}-9H-purin-6-amine; and
N-{1-[5-Chloro-8-(2-fluorophenyl)cinnolin-7-yl]ethyl}-9H-purin-6-amine;
or a pharmaceutically acceptable salt thereof.

In some embodiments, the compound is selected from:
N-{1-[8-(3,5-difluorophenyl)-5-fluorocinnolin-7-yl]ethyl}-9H-purin-6-amine;
N-{[5-Chloro-8-(3-fluorophenypcinnolin-7-yl]methyl}-9H-purin-6-amine;
N-{1-[5-chloro-8-(3-fluorophenyl)cinnolin-7-yl]propyl}-9H-purin-6-amine;
N-{1-[5-chloro-8-(5-fluoropyridin-3-yl)cinnolin-7-yl]ethyl}-9H-purin-6-amine;
N-{1-[8-(3-fluorophenyl)-5-methylcinnolin-7-yl]ethyl}-9H-purin-6-amine;
N-{1-[8-(3,5-difluorophenyl)-5-methylcinnolin-7-yl]ethyl}-9H-purin-6-amine;
3-{5-Chloro-7-[1-(9H-purin-6-ylamino)ethyl]cinnolin-8-yl}-5-fluoro-N-methylbenzamide;
N-{1-[5-Chloro-8-(3-fluoro-4-methoxyphenyl)cinnolin-7-yl]ethyl}-9H-purin-6-amine;
N-{1-[5-Chloro-8-(2-fluoropyridin-4-yl)cinnolin-7-yl]ethyl}-9H-purin-6-amine;
1-{5-Chloro-7-[1-(9H-purin-6-ylamino)ethyl]quinolin-8-yl}piperidin-4-ol;
N-{1-[4-(3-Fluorophenyl)-1-methylisoquinolin-3-yl]ethyl}-9H-purin-6-amine;
1-{4-Chloro-2-[1-(9H-purin-6-ylamino)ethyl]-1-naphthyl}piperidin-4-ol;
N-{1-[4-Chloro-1-(3-fluorophenyl)-2-naphthyl]ethyl}-9H-purin-6-amine;
N-{1-[5-Chloro-8-(4,4-difluoropiperidin-1-yl)quinolin-7-yl]ethyl}-9H-purin-6-amine;
(3S)-1-{5-Chloro-7-[1-(9H-purin-6-ylamino)ethyl]quinolin-8-yl}piperidin-3-ol;
1-{5-Chloro-7-[1-(9H-purin-6-ylamino)ethyl]quinolin-8-yl}-4-phenylpiperidin-4-ol;
N-{1-[8-(3-Fluorophenyl)-5-methylquinolin-7-yl]ethyl}-9H-purin-6-amine;
N-{1-[5-Ethyl-8-(3-fluorophenyl)quinolin-7-yl]ethyl}-9H-purin-6-amine;
8-(3-fluorophenyl)-7-[1-(9H-purin-6-ylamino)ethyl]quinoline-5-carbonitrile;
(3R)-1-{5-fluoro-7-[1-(9H-purin-6-ylamino)ethyl]quinolin-8-yl}pyrrolidin-3-ol;
4-(3-fluorophenyl)-3-[1-(9H-purin-6-ylamino)ethyl]isoquinoline-1-carbonitrile;
N-{1-[8-(4-Cyclobutylpiperazin-1-yl)-5-fluoroquinolin-7-yl]ethyl}-9H-purin-6-amine;
N-{1-[5-Chloro-8-(3-fluorophenyl)isoquinolin-7-yl]ethyl}-9H-purin-6-amine;
N-(1-{5-Chloro-8-[(3S)-3-fluoropyrrolidin-l-yl]quinolin-7-yl}ethyl)-9H-purin-6-amine;
2-(4-{5-Chloro-7-[1-(9H-purin-6-ylamino)ethyl]quinolin-8-yl}piperazin-1-yl)ethanol;
1-{5-Chloro-7-[1-(9H-purin-6-ylamino)ethyl]quinolin-8-yl}piperidine-4-carbonitrile;
1-{5-Chloro-7-[1-(9H-purin-6-ylamino)ethyl]quinolin-8-yl}pyrrolidine-3-carbonitrile;
N-{1-[5-Chloro-8-(3-fluoropiperidin-1-yl)quinolin-7-yl]ethyl}-9H-purin-6-amine;
N-{1-[5-Chloro-8-(4-fluoropiperidin-1-yl)quinolin-7-yl]ethyl}-9H-purin-6-amine;
(1-{5-Chloro-7-[1-(9H-purin-6-ylamino)ethyl]quinolin-8-yl}piperidin-3-yl)methanol;
(1-{5-Chloro-7-[1-(9H-purin-6-ylamino)ethyl]quinolin-8-yl}piperidin-4-yl)methanol;
N-{1-[5-Chloro-8-(4-cyclohexylpiperazin-1-yl)quinolin-7-yl]ethyl}-9H-purin-6-amine;
N-{1-[5-Chloro-8-(4-cyclopropylpiperazin-1-yl)quinolin-7-yl]ethyl}-9H-purin-6-amine;

-{1-[5-Chloro-8-(3-methoxypiperidin-1-yl)quinolin-7-yl]ethyl}-9H-purin-6-amine;
N-{1-[5-Chloro-8-(3-methoxypyrrolidin-1-yl)quinolin-7-yl]ethyl}-9H-purin-6-amine;
N-{1-[5-Chloro-8-(4-cyclobutylpiperazin-1-yl)quinolin-7-yl]ethyl}-9H-purin-6-amine;
N-{1-[8-(1,4'-Bipiperidin-1'-yl)-5-chloroquinolin-7-yl]ethyl}-9H-purin-6-amine;
N-{1-[5-Chloro-8-(4-methoxypiperidin-1-yl)quinolin-7-yl]ethyl}-9H-purin-6-amine;
N-{1-[5-Chloro-8-(4-phenylpiperidin-1-yl)quinolin-7-yl]ethyl}-9H-purin-6-amine;
2-(1-{5-Chloro-7-[1-(9H-purin-6-ylamino)ethyl]quinolin-8-yl}piperidin-4-yl)ethanol;
N-(1-{5-Chloro-8-[4-(pyridin-4-ylmethyl)piperazin-1-yl]quinolin-7-yl}ethyl)-9H-purin-6-amine;
N-{1-[5-Chloro-8-(4-phenoxypiperidin-1-yl)quinolin-7-yl]ethyl}-9H-purin-6-amine;
N-{1-[5-Chloro-8-(3-phenylpyrrolidin-1-yl)quinolin-7-yl]ethyl}-9H-purin-6-amine;
N-((3S)-1-{5-Chloro-7-[1-(9H-purin-6-ylamino)ethyl]quinolin-8-yl}pyrrolidin-3-yl)propanamide;
N-((3S)-1-{5-Chloro-7-[1-(9H-purin-6-ylamino)ethyl]quinolin-8-yl}pyrrolidin-3-yl)-2-methylpropanamide;
Methyl ((3S)-1-{5-Chloro-7-[1-(9H-purin-6-ylamino)ethyl]quinolin-8-yl}pyrrolidin-3-yl)carbamate;
N-((3S)-1-{5-Chloro-7-[1-(9H-purin-6-ylamino)ethyl]quinolin-8-yl}pyrrolidin-3-yl)methanesulfonamide;
N-(1-{5-Chloro-7-[1-(9H-purin-6-ylamino)ethyl]quinolin-8-yl}piperidin-4-yl)methanesulfonamide;
N-(1-{5-Chloro-7-[1-(9H-purin-6-ylamino)ethyl]quinolin-8-yl}piperidin-4-yl)acetamide;
Methyl (1-{5-Chloro-7-[1-(9H-purin-6-ylamino)ethyl]quinolin-8-yl}piperidin-4-yl)carbamate;
N-(1-{5-Chloro-8-[4-(cyclopropylcarbonyl)piperazin-1-yl]quinolin-7-yl}ethyl)-9H-purin-6-amine;
Methyl 4-{5-Chloro-7-[1-(9H-purin-6-ylamino)ethyl]quinolin-8-yl}piperazine-1-carboxylate;
N-(1-{5-Chloro-8-[4-(cyclobutylcarbonyl)piperazin-1-yl]quinolin-7-yl}ethyl)-9H-purin-6-amine;
N-(1-{5-Chloro-8-[4-(methoxyacetyl)piperazin-1-yl]quinolin-7-yl}ethyl)-9H-purin-6-amine;
4-{5-Chloro-7-[1-(9H-purin-6-ylamino)ethyl]quinolin-8-yl}-N,N-dimethylpiperazine-1-carboxamide;
N-{1-[8-(4-Benzoylpiperazin-1-yl)-5-chloroquinolin-7-yl]ethyl}-9H-purin-6-amine;
2-(4-{5-Chloro-7-[1-(9H-purin-6-ylamino)ethyl]quinolin-8-yl}piperazin-1-yl)-N,N-dimethylacetamide;
N-(1-{5-Chloro-8-[4-(4-fluorobenzoyl)piperazin-1-yl]quinolin-7-yl}ethyl)-9H-purin-6-amine;
N-(1-{5-Chloro-8-[4-(3-fluorobenzoyl)piperazin-1-yl]quinolin-7-yl}ethyl)-9H-purin-6-amine;
N-(1-{5-Chloro-8-[4-(2-fluorobenzoyl)piperazin-1-yl]quinolin-7-yl}ethyl)-9H-purin-6-amine;
N-[1-(8-{4-[(1-Acetylpiperidin-4-yl)carbonyl]piperazin-1-yl}-5-chloroquinolin-7-yl)ethyl]-9H-purin-6-amine;
N-(1-{5-Chloro-8-[4-(pyridin-2-ylcarbonyl)piperazin-1-yl]quinolin-7-yl}ethyl)-9H-purin-6-amine;
N-(1-{5-Chloro-8-[4-(pyridin-3-ylcarbonyl)piperazin-1-yl]quinolin-7-yl}ethyl)-9H-purin-6-amine;
N-(1-{5-Chloro-8-[4-(pyrazin-2-ylcarbonyl)piperazin-1-yl]quinolin-7-yl}ethyl)-9H-purin-6-amine;
N-{1-[5-Chloro-8-(4-isonicotinoylpiperazin-1-yl)quinolin-7-yl]ethyl}-9H-purin-6-amine;
N-[1-(5-Chloro-8-{4-[(5-methylisoxazol-3-yl)carbonyl]piperazin-1-yl}quinolin-7-yl)ethyl]-9H-purin-6-amine;
N-[1-(5-Chloro-8-{4-[(3,5-dimethylisoxazol-4-yl)carbonyl]piperazin-1-yl}quinolin-7-yl)ethyl]-9H-purin-6-amine;
N-[1-(5-Chloro-8-{4-[(1-methyl-1H-pyrazol-3-yl)carbonyl]piperazin-1-yl}quinolin-7-yl)ethyl]-9H-purin-6-amine;
N-{1-[5-fluoro-8-(3-fluorophenyl)quinolin-7-yl]ethyl}-9H-purin-6-amine;
N-[1-(5-Fluoro-8-{4-[(1-methyl-1H-pyrazol-4-yl)carbonyl]piperazin-1-yl}quinolin-7-yl)ethyl]-9H-purin-6-amine;
N-{1-[4-Chloro-7-(3-fluorophenyl)-2,1-benzisoxazol-6-yl]ethyl}-9H-purin-6-amine;
N-{1-[4-Chloro-7-(3-fluorophenyl)-1H-indazol-6-yl]ethyl}-9H-purin-6-amine;
N-{1-[4-Chloro-7-(3,5-difluorophenyl)-1H-indazol-6-yl]ethyl}-9H-purin-6-amine;
N-{1-[4-Chloro-7-(3,5-difluorophenyl)-1-methyl-1H-indazol-6-yl]ethyl}-9H-purin-6-amine;
or a pharmaceutically acceptable salt of any of the aforementioned.

In some embodiments, the compound is N-{1-[5-chloro-8-(3-fluorophenyl)cinnolin-7-yl]ethyl}-9H-purin-6-amine, or a pharmaceutically acceptable salt thereof.

In some embodiments, the compound is N-{(1S)-1-[5-chloro-8-(3-fluorophenyl)cinnolin-7-yl]ethyl}-9H-purin-6-amine, or a pharmaceutically acceptable salt thereof.

In some embodiments, the compound is N-{1-[5-chloro-8-(3-fluorophenyl)cinnolin-7-yl]ethyl)-9H-purin-6-amine adipic acid salt.

In some embodiments, the compound is N-{(1S)-1-[5-chloro-8-(3-fluorophenyl)cinnolin-7-yl]ethyl}-9H-purin-6-amine adipic acid salt.

In some embodiments, the salt is a 1:1 free base: adipic acid salt (on a molar basis). In some embodiments, the salt is that described in Example 108.

In some embodiments, the salt is characterized by a melting point of about 182° C.

In some embodiments, the salt has a differential scanning calorimetry thermogram which is characterized by an endothermic peak with an onset temperature of about 179° C.

Figure 2:
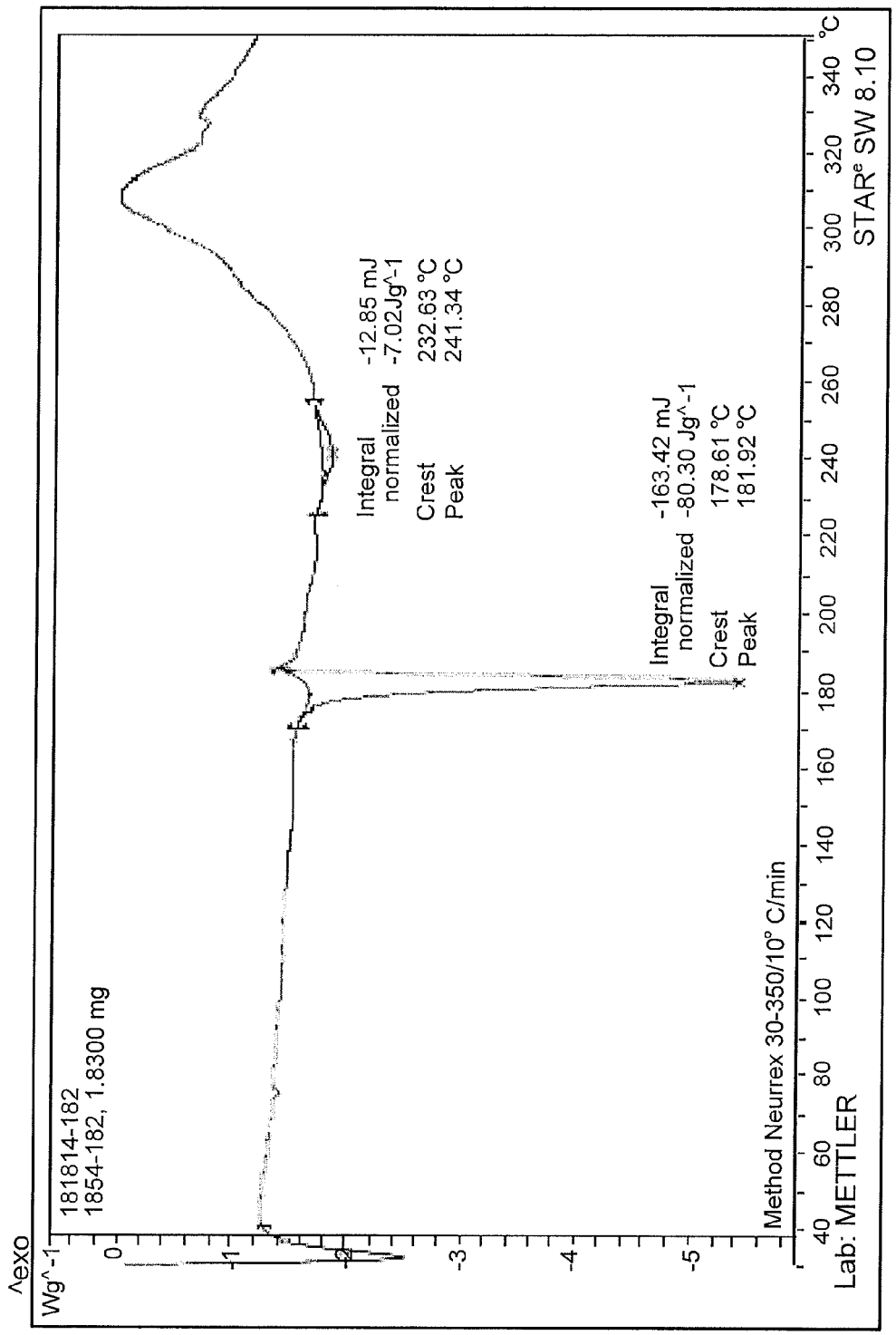
FIG. 2 depicts the DSC thermogram for the product of Example 108.

In some embodiments, the salt has a differential scanning calorimetry thermogram substantially as shown in FIG. 2.

Figure 3:
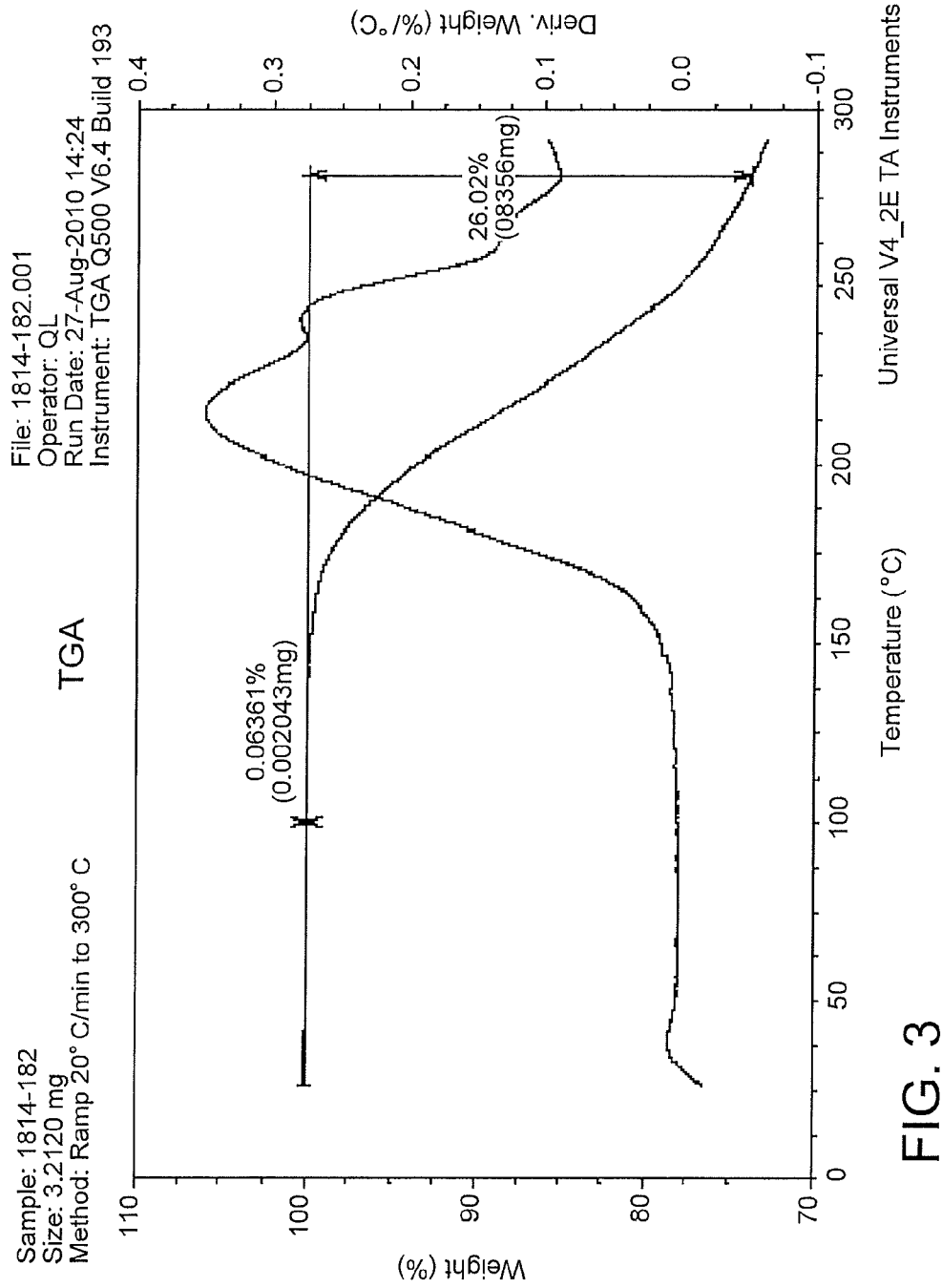
FIG. 3 depicts the TGA thermogram for the product of Example 108.

In some embodiments, the salt has a thermal gravimetric analysis thermogram substantially as shown in FIG. 3.

In some embodiments, the salt has a X-ray powder diffraction pattern substantially as shown in FIG. 1.

In some embodiments, the salt has an X-ray powder diffraction pattern comprising a characteristic peak expressed in degrees 2θ at about 10.1.

In some embodiments, the salt has an X-ray powder diffraction pattern comprising a characteristic peak expressed in degrees 2θ at about 20.2.

In some embodiments, the salt has an X-ray powder diffraction pattern comprising a characteristic peak expressed in degrees 2θ at about 21.4.

In some embodiments, the salt has an X-ray powder diffraction pattern comprising a characteristic peak expressed in degrees 2θ at about 24.1.

In some embodiments, the salt has an X-ray powder diffraction pattern comprising a characteristic peak expressed in degrees 2θ at about 28.4.

In some embodiments, the salt has an X-ray powder diffraction pattern comprising characteristic peaks expressed in degrees 2θ at about 10.1, 20.2, 21.4, 24.1, and 28.4.

In some embodiments, the salt has an X-ray powder diffraction pattern comprising characteristic peaks expressed in degrees 2θ at about 20.2, 21.4, and 24.1.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the machine or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures is understood to accommodate such variation.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and -(CR'R")$_n$NR—. Where the structure clearly requires a divalent linking group, the Markush variables listed for that group are understood to be divalent linking groups. For example, if the structure requires a linking group and the Markush group definition for that variable lists "alkyl" or "aryl" then it is understood that the "alkyl" or "aryl" represents a divalent linking alkylene group or arylene group, respectively.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

Throughout the definitions, the term indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 7 carbon atoms, from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like.

As used herein, the term "alkylene" refers to a divalent alkyl linking group. Examples of alkylene groups include, but are not limited to, ethan-1,2-diyl, propan-1,3-diyl, propan-1, 2-diyl, butan-1,4-diyl, butan-1,3-diyl, butan-1,2-diyl, 2-methyl-propan-1,3-diyl, and the like.

As used herein, "$C_{n-m}$ alkenyl", employed alone or in combination with other terms, refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to an group of formula -O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "$C_{n-m}$ alkylamino" refers to a group of formula -NH(alkyl), wherein the alkyl group has n to m carbon atoms. In some embodiments, the alkyl group has 1 to 6 or 1 to 4 carbon atoms.

As used herein, the term "$C_{n-m}$ alkoxycarbonyl" refers to a group of formula —C(O)O—-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6 or 1 to 4 carbon atoms.

As used herein, the term alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "$C_{n-m}$ aryl" (or "aryl"), employed alone or in combination with other terms, refers to a monocyclic or polycyclic (e.g., having 2, 3 or 4 fused rings) aromatic hydrocarbon having n to m carbons, such as, but not limited to, phenyl, 1-naphthyl, 2-naphthyl, anthracenyl, phenanthrenyl, and the like. In some embodiments, aryl groups have from 6 to 20 carbon atoms, from 6 to 14 carbon atoms, or from 6 to 10 carbon atoms. In some embodiments, the aryl group is phenyl.

As used herein, the term aryl-$C_{n-m}$ alkyl" (or "arylalkyl") refers to a group of formula—alkylene-aryl, wherein the alkylene and aryl portions each has, independently, n to m carbon atoms. As used herein, the term "arylalkyl" refers to a group of formula—alkylene-aryl, wherein the alkylene and aryl portions each has, independently, n to m carbon atoms. In some embodiments, the alkylene portion has 1 to 4, 1 to 3, 1 to 2, or 1 carbon atom(s). In some embodiments, the alkylene portion of the arylalkyl group is methyl or ethyl. In some embodiments, the arylalkyl group is benzyl.

As used herein, the term "carbamyl" refers to a group of formula —C(O)NH$_2$.

As used herein, the term "carbonyl" refers to a —C(O)— group, which is a divalent one-carbon moiety further bonded to an oxygen atom with a double bond.

As used herein, the term "carboxy" refers to a group of formula —C(O)OH.

As used herein, the term "$C_{n-m}$ cycloalkyl" (or "cycloalkyl"), employed alone or in combination with other terms, refers to a non-aromatic cyclic hydrocarbon moiety, which may optionally contain one or more alkenylene or alkynylene groups as part of the ring structure and which has n to m carbons. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. In some embodiments, the cycloalkyl group is monocyclic and has 3 to 14 ring members, 3 to 10 ring members, 3 to 8 ring members, or 3 to 7 ring members. One or more ring-forming carbon atoms of a cycloalkyl group can be oxidized to form carbonyl linkages. Examplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "$C_{n-m}$ cycloalkyl-$C_{n-m}$alkyl" (or "cycloalkylalkyl") refers to a group of formula -alkylenecycloalkyl, wherein the alkylene and cycloalkyl portions each has, independently, n to m carbon atoms. In some embodiments, the alkylene portion has 1 to 4, 1 to 3, 1 to 2, or 1 carbon atom(s). In some embodiments, the cycloalkyl portion has 3 to 7 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "di-$C_{n-m}$-alkylcarbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6 or 1 to 4 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6 or 1 to 4 carbon atoms.

As used herein, the term "fluorinated $C_{n-m}$ haloalkyl" refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl. In some embodiments, the alkyl group has 1 to 6 or 1 to 4 carbon atoms.

As used herein, "halosulfanyl" refers to a sulfur group having one or more halogen substituents. Example halosulfanyl groups include pentahalosulfanyl groups such as SF$_5$.

As used herein, the term "$C_{n-m}$ heteroaryl", "$C_{n-m}$ heteroaryl ring", or "$C_{n-m}$ heteroaryl group" (or "heteroaryl"), employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen, and having n to m carbon atoms. In some embodiments, the heteroaryl group has 1, 2, 3, or 4 heteroatoms. In some embodiments, the heteroaryl group has 1, 2, or 3 heteroatoms. In some embodiments, the heteroaryl group has 1 or 2 heteroatoms. In some embodiments, the heteroaryl group has 1 heteroatom. When the heteroaryl group contains more than one heteroatom ring member, the heteroatoms may be the same or different. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. In some embodiments, the heteroaryl group has 5 to 10 carbon atoms.

As used herein, the term "bicyclic azaheteroaryl" refers to a bicyclic fused heteroaryl group having 1, 2, 3, or 4 nitrogen ring members. The bicyclic azaheteroaryl group may optionally have O or S heteroatom ring members in addition to the nitrogen ring members. In some embodiments, the only heteroatom ring members in the bicyclic azaheteroaryl group are nitrogen heteroatoms.

As used herein, the term "$C_{n-m}$ heteroaryl-$C_{n-m}$alkyl" (or "heteroarylalkyl") refers to a group of formula—alkyleneheteroaryl, wherein the alkylene and heteroaryl portions each has, independently, n to m carbon atoms. In some embodiments, the alkylene portion has 1 to 4, 1 to 3, 1 to 2, or 1 carbon atom(s). In some embodiments, the heteroaryl portion has 1 to 9 carbon atoms.

As used herein, the term "$C_{n-m}$ heterocycloalkyl", "$C_{n-m}$ heterocycloalkyl ring", or "$C_{n-m}$ heterocycloalkyl group" (or "hetereocycloalkyl"), employed alone or in combination with other terms, refers to a non-aromatic ring system, which may optionally contain one or more alkenylene or alkynylene groups as part of the ring structure, and which has at least one heteroatom ring member selected from nitrogen, sulfur and oxygen, and which has n to m carbon atoms. In some embodiments, the heteroaryl group has 1, 2, 3, or 4 heteroatoms. In some embodiments, the heteroaryl group has 1, 2, or 3 heteroatoms. In some embodiments, the heteroaryl group has 1 or 2 heteroatoms. In some embodiments, the heteroaryl group has 1 heteroatom. In some embodiments, the heteroaryl group has 1 or 2 heteroatoms. When the heterocycloalkyl groups contains more than one heteroatom, the heteroatoms may be the same or different. Heterocycloalkyl groups can include mono- or polycyclic (e.g., having 2, 3 or 4 fused rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. In some embodiments, the heterocycloalkyl group has 3 to 20 ring-forming atoms, 3 to 10 ring-forming atoms, or about 3 to 8 ring forming atoms. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, the heterocycloalkyl group is a monocyclic or bicyclic ring. In some embodiments, the heterocycloalkyl group is a monocyclic ring, wherein the ring comprises from 3 to 6 carbon atoms and from 1 to 3 heteroatoms, referred to herein as $C_{3-6}$heterocycloalkyl.

Examples of heterocycloalkyl groups include pyrrolidinyl, pyrrolidino, piperidinyl, piperidino, piperazinyl, piperazino, morpholinyl, morpholino, thiomorpholinyl, thiomorpholino, and pyranyl.

A five-membered ring heteroaryl is a heteroaryl with a ring having five ring atoms wherein one or more (e.g., 1, 2, or 3) ring atoms are independently selected from N, O, and S.

Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "$C_{n-m}$ heterocycloalkyl-$C_{n-m}$ alkyl" (or "heterocycloalkylalkyl") refers to a group of formula -alkylene-heterocycloalkyl, wherein the alkylene and heterocycloalkyl portions each has, independently, n to m carbon atoms. In some embodiments, the alkylene portion of the heterocycloalkylalkyl group is methylene. In some embodiments, the alkylene portion has 1-4, 1-3, 1-2, or 1 carbon atom(s). In some embodiments, the heterocycloalkyl portion has 2 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration at the carbon attached to $R^1$. In some embodiments, the compound has the (S)-configuration at the carbon attached to $R^1$.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H-1- and 4H-1,2,4-triazole, 1H- and 2H-isoindole, and 1H- and 2H-pyrazole. Tautomeric forms can be in equilibrium or sterically locked into one form by appropriate substitution. For example, purine includes the 9H and a 7H tautomeric forms:

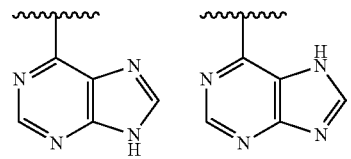

Compounds of the invention can include both the 9H and 7H tautomeric forms.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS) or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Example synthetic methods for preparing compounds of the invention (wherein Cy is aryl or heteroaryl) is provided in Scheme I. An aryl or heteroaryl carboxylic acid compound (i) (wherein $X^1$ is halo (e.g., chloro or bromo)) can be converted to its acid chloride and then reacted with N,O-dimethylhydroxylamine or appropriate derivative (e.g., N,O-dimethylhydroxylamine HCl) to give a N-methoxy-N-methylcarboxamide derivative (ii) or direct activation of the carboxylic acid with a coupling agent (e.g. HBTU, HATU) and then reaction with N,O-dimethylhydroxylamine to give a N-methoxy-N-methylcarboxamide derivative (ii). The carboxamide (ii) may then be reacted with a Grignard reagent of formula $R^1$—MgBr to give a ketone (iii). The ketone (iii) can be reduced to give an alcohol (iv) which can be converted to the mesylate and reacted with sodium azide to give an azide derivative (v). The azide compound (v) can then be reacted with a compound of formula Cy-B(OH)$_2$ in the presence of a palladium(O) catalyst, such as tetrakis(triphenylphosphine)palladium(O) in the presence of a base to give an azide compound (vi). The azide group may then be converted to an amine under appropriate conditions such as catalytic hydrogenation with palladium-on-carbon to give an amine (vii). Finally, the amine (vii) can be reacted with an appropriate alkylating agent $R^4X$ (e.g., MeI) and then a heteroaryl halide compound (e.g., Ar—X) to give a compound of Formula I. The reaction of amine (vii) with $R^4$ can be eliminated to give compounds of Formula I where $R^4$ is H.

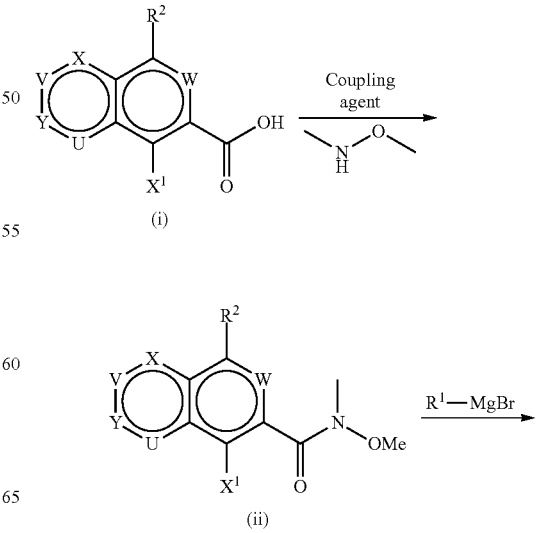

Scheme I

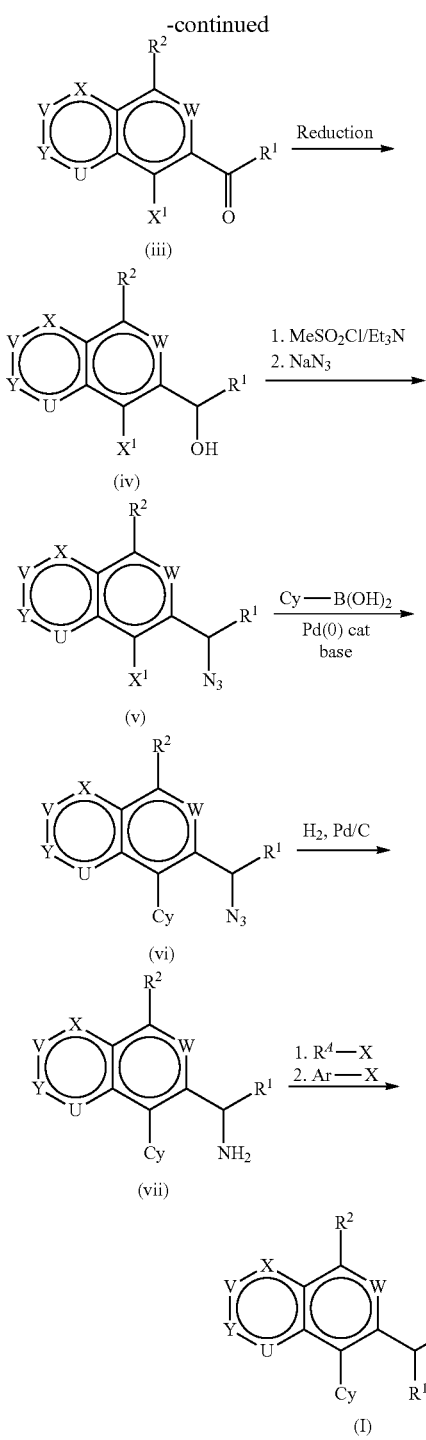

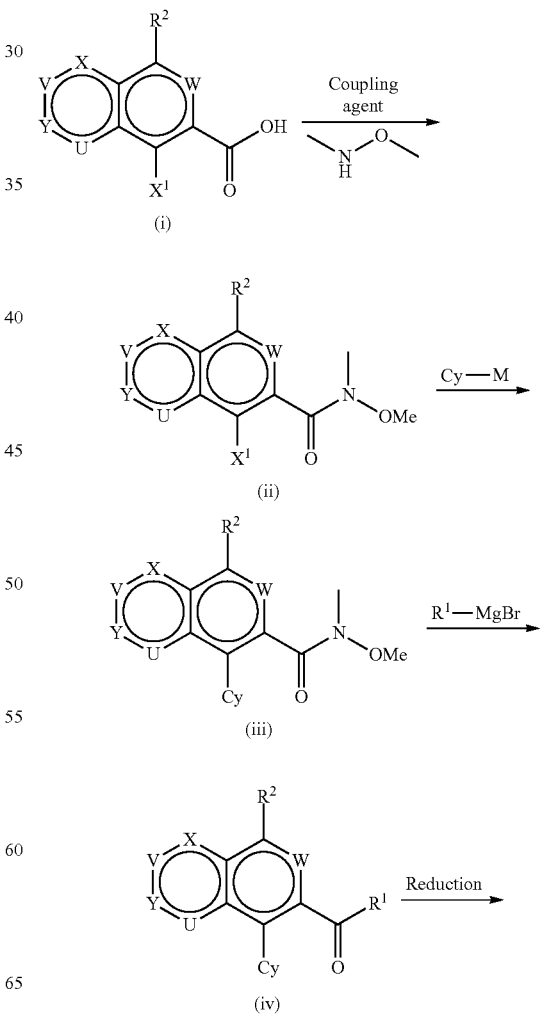

metal (e.g., Cy-M is Cy-B(OH)$_2$ or Cy-Sn(Bu)$_4$), under standard Suzuki conditions or standard Stille conditions (e.g., in the presence of a palladium(O) catalyst, such as tetrakis(triphenylphosphine)palladium(O) and a base (e.g., a bicarbonate or carbonate base)) to afford compound (iii). Alternatively, Cy-M can be a cyclic amine (where M is H and attached to the amine nitrogen) with coupling to compound (ii) being performed by heating in base or under Buchwald conditions (e.g., in the presence of a palladium(O) catalyst, such as tetrakis(triphenylphosphine)palladium(O) and a base (e.g., an alkoxide base)) to afford compound (iii). Amide (iii) may then be reacted with a Grignard reagent of formula $R^1$—MgBr to give a ketone (iv). The ketone (iv) can be reduced to give an alcohol (v) which can be converted to the mesylate and reacted with sodium azide to give an azide derivative (vi). The azide group may then be converted to an amine (vii) under appropriate conditions such as catalytic hydrogenation with palladium-on-carbon. Finally, the amine (vii) can be reacted with an appropriate alkylating agent $R^A X$ (e.g., Met) and then a heteroaryl halide compound (e.g., Ar—X) to give a compound of Formula I. The reaction of amine (vii) with $R^A$ can be eliminated to give compounds of Formula I where $R^A$ is H.

Alternatively, for some compounds, it may be appropriate to carry out the coupling reaction prior to completion of the final steps. Accordingly in Scheme II, an aryl or heteroaryl carboxylic acid compound (i) (wherein $X^1$ is halo (e.g., chloro or bromo)) can be converted to its acid chloride and then reacted with N,O-dimethylhydroxylamine to give a N-methoxy-N-methylcarboxamide derivative (ii) or direct activation of the carboxylic acid (i) with a coupling agent (e.g. HBTU, HATU) and then reaction with N,O-dimethylhydroxylamine to give a N-methoxy-N-methylcarboxamide derivative (ii). The carboxamide (ii) may then be coupled to Cy-M, where M is a boronic acid, boronic ester or an appropriately substituted

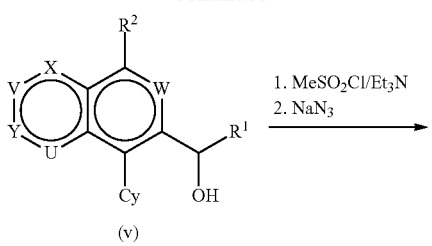

(v)

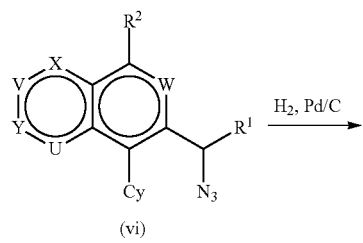

(vi)

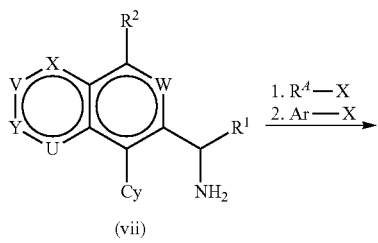

(vii)

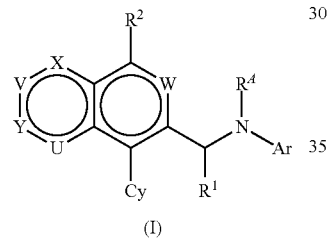

(I)

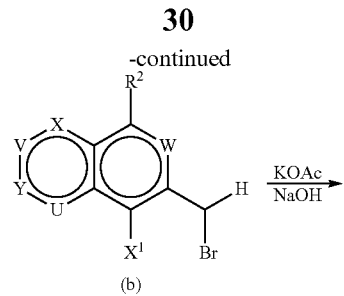

(b)

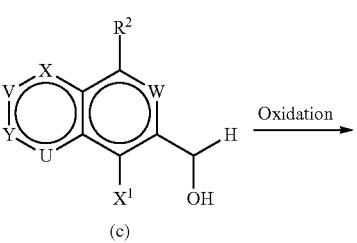

(c)

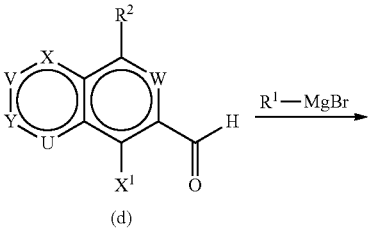

(d)

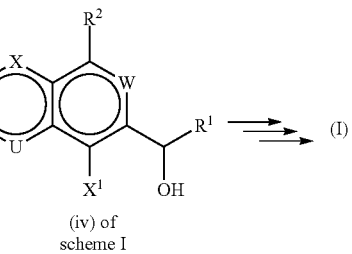

(iv) of scheme I

The alcohol (iv) in Scheme I may be alternatively synthesized by the methods shown in Scheme III. Accordingly, a methyl derivative (a) can be reacted with N-bromosuccinimide to give a bromomethyl compound (b). The bromomethyl compound (b) can then be converted to the hydroxymethyl compound (c) by first converting the bromo group to an acetate group and then reacting with sodium hydroxide in water. The hydroxyl group can then be oxidized to an aldehyde compound (d). Finally, the aldehyde compound (d) can then be reacted with a Grignard reagent of formula $R^1$—MgBr to give the alcohol compound (iv) of scheme I. Scheme I can then be followed to give a compound of Formula I.

Scheme III

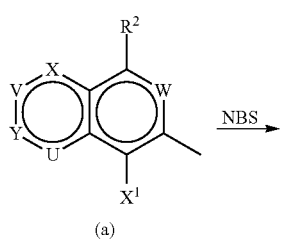

(a)

Alternatively, compounds of Formula I can be synthesized as shown in Scheme IV. Aminomethylation of electron rich aromatic compounds (i) with an imine generated from an aldehyde and an amine gives a secondary amine compound (ii). Removal of the auxiliary group with TFA or certium ammonium nitrate provides a primary amine (iii) which can in turn be protected (e.g. $(Boc)_2O$) in general procedures as known in the art of organic synthesis. The protected compound (iv) can be activated at another position. For instance, the hydroxyl group can be activated through transformation to its trifluoromethanesulfonate (v). The activated compound (v) can then be subjected to various coupling reactions, including Suzuki coupling, Negishi coupling, Stille coupling, or Buchwald-Hartwig cross-coupling, to afford a compound of formula (vi). After deprotection of compound (vi), the amine compound (vii) can be reacted with an appropriate heteroaryl halide compound (e.g., Ar—Br) to give a compound of Formula I, with or without a catalyst. Alternatively, an electron rich aromatic compound of formula (i) can also be subjected to a Friedel-Crafts reaction condition to generate, for example, corresponding acetyl compound (viii). The latter can be reduced to corresponding alcohol and then converted to compounds of Formula I as described in Scheme I or II.

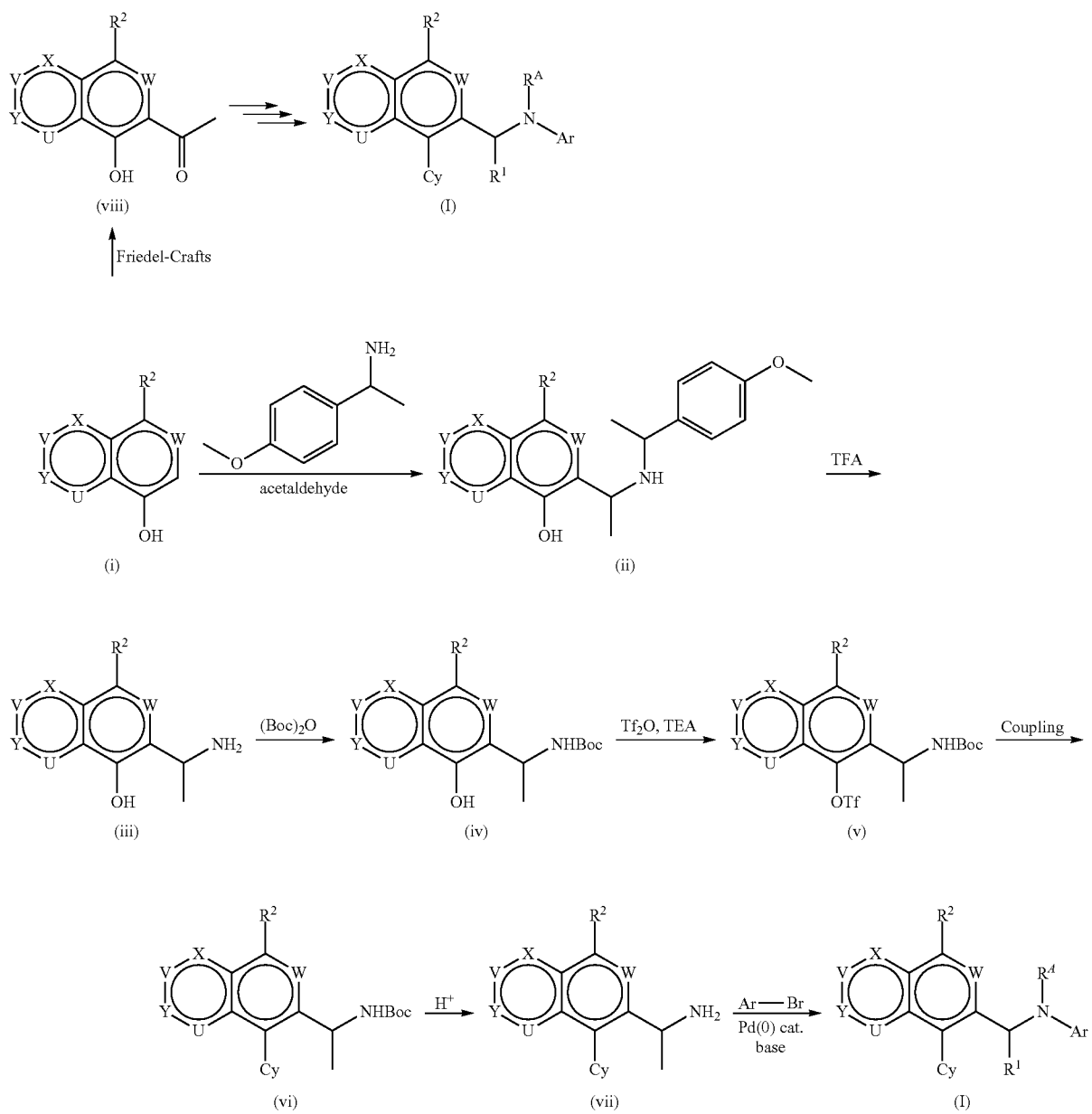

Alternatively, compounds of Formula I can also be prepared starting from a bromide compound (i) or other halide compound as shown in Scheme V. The bromide compound (i) can be reacted with diethylzinc or triethylborane under Negishi conditions to afford the corresponding ethyl compound (ii). The latter can be converted to the triflate intermediate (iii) and coupled to Cy-M as described in Scheme IV to give compound (iv). The coupling product (iv) can be halogenated using for example N-bromosuccinamide or N-chlorosuccinamide to give the halogenated intermediate (v). Further transformation of the halo compound (v) to an amino compound (vi) can be achieved through azide substitution/reduction, or SN₂ substitution with amine or amine derivative (e.g. phthalimide) followed by appropriate functional group manipulations. The amino compound (vi) can then be converted to a compound of Formula I as described in Scheme I.

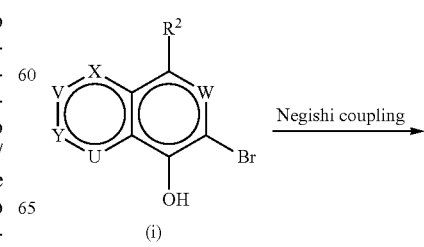

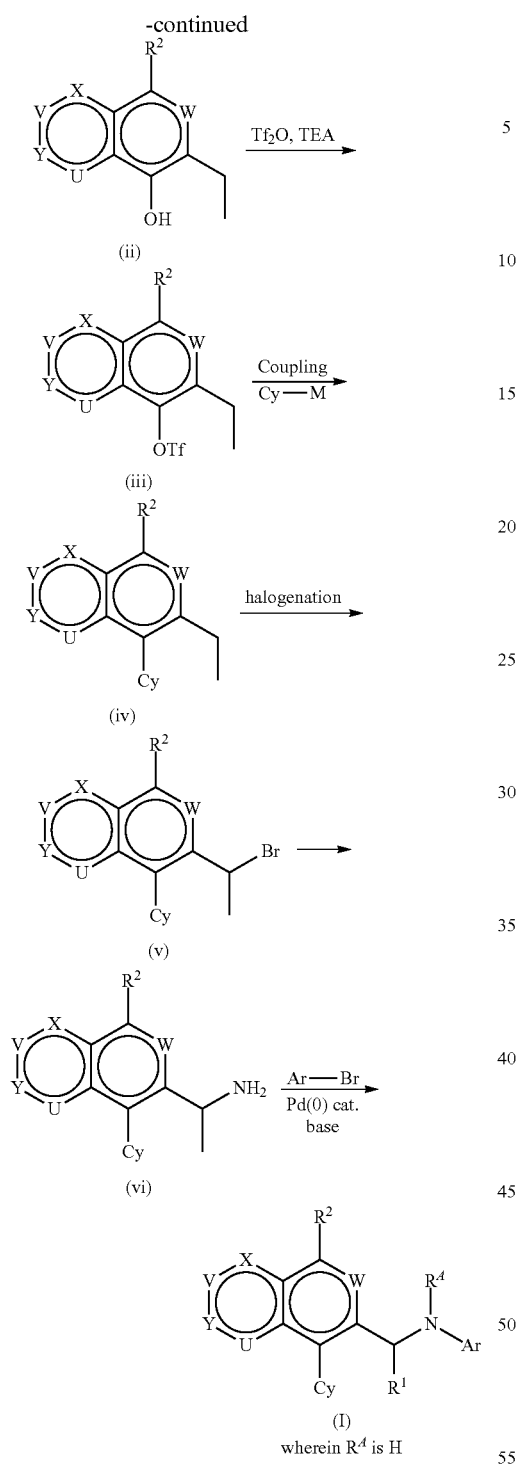

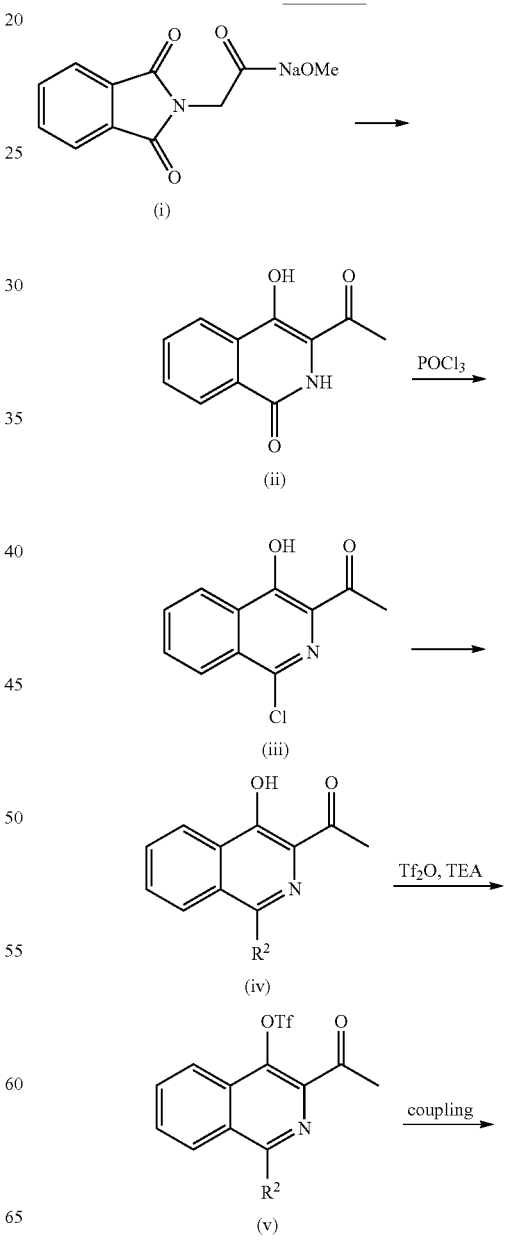

(OH)$_2$ or Cy-Sn(Bu)$_4$), under standard Suzuki conditions or standard Stille conditions (e.g., in the presence of a palladium (O) catalyst, such as tetrakis(triphenylphosphine)palladium (O) and a base (e.g., a bicarbonate or carbonate base)) to afford compound (vi). Alternatively, Cy-M can be a cyclic amine (where M is H and attached to the amine nitrogen) with coupling to compound (ii) being performed by heating in base or under Buchwald conditions (e.g., in the presence of a palladium(O) catalyst, such as tetrakis(triphenylphosphine) palladium(O) and a base (e.g., an alkoxide base)) to afford ketone (vi). Reductive amination of the ketone (vi) can furnish the amine intermediate (vii). The amino compound (vii) can then be converted to compounds of Formula I by similar methods described for conversion of amino compound (vii) into compounds of Formula I in Scheme I.

Isoquinoline compounds of Formula I may be synthesized as shown in Scheme VI. Treatment of commercially available N-acetonylphthalimide (i) with sodium methoxide gives a ketone of formula (ii). The ketone (ii) can be reacted with phosphorous oxychloride to give the chlorinated isoquinoline (iii) which can be reacted under standard Negishi coupling conditions to give compound (iv). Reaction of the hydroxyl group of compound (iv) with triflic anhydride can form the triflate (v) which can be reacted under standard coupling conditions to Cy-M, where M is a boronic acid, boronic ester or an appropriately substituted metal (e.g., Cy-M is Cy-B

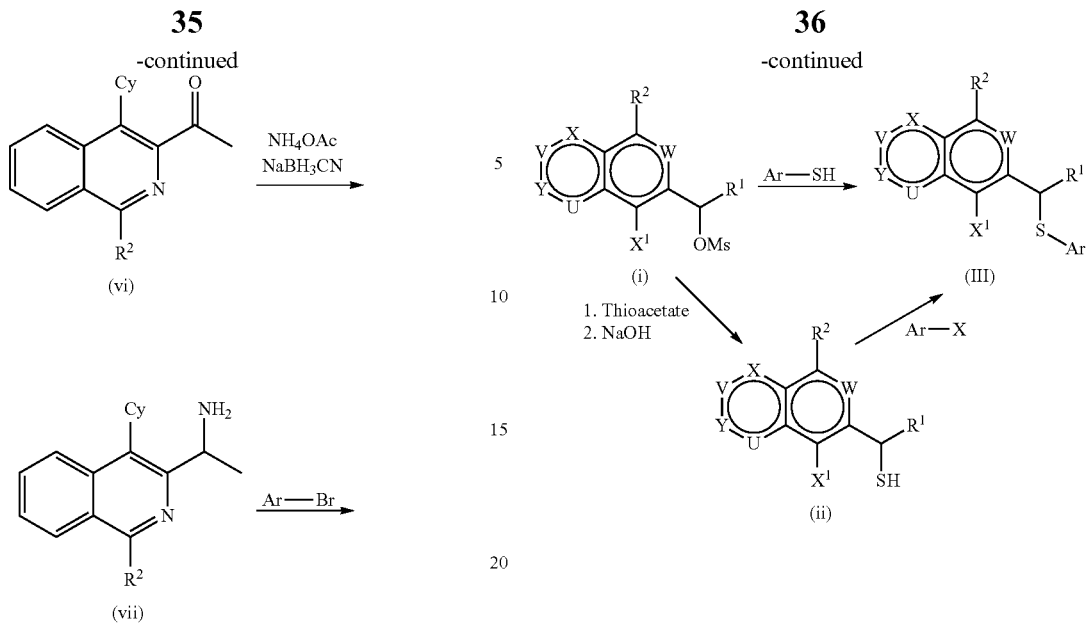

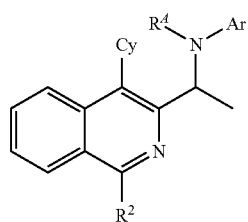

Alternatively, compounds of Formula II and Formula III (infra) can be synthesized as shown in Scheme VI. The hydroxyl group of (iv) from scheme I can be transformed to a thiol group by activation with mesyl chloride, conversion to the thioacetate and cleavage of the acetate to afford (ii). The hydroxyl compound (iv) or the thiol (i) can be reacted with an appropriate heteroaryl halide compound (e.g., Ar—Br) to give a compound of Formula II and III, respectively, with or without a catalyst. Alternatively, mesylate (i) can be reacted with aryl or heteroaryl thiol (e.g., Ar—SH) to give compounds of Formula (III).

Scheme VII

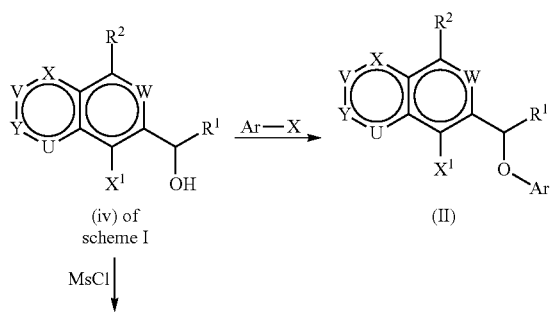

Cinnoline compounds of Formula I can be synthesized starting from a phenol compound (i) as shown in Scheme VIII. The phenol compound (i) can be halogenated with N-bromosuccinamide or N-chlorosuccinamide to give compound (ii). The iodo of compound (ii) can be transformed to the alkyne (iii) under Sonagashira coupling conditions. Compound (iii) can be nitrated to give the nitro compound (iv). The phenol of compound (iv) can be converted to a triflate with triflic anhydride and the triflate can be coupled to Cy-M, where M is a boronic acid, boronic ester or an appropriately substituted metal (e.g., Cy-M is Cy-B(OH)$_2$), under standard Suzuki conditions (e.g., in the presence of a palladium(O) catalyst, such as tetrakis(triphenylphosphine)palladium(O) and a base (e.g., a bicarbonate or carbonate base)) to afford compound (v). Compound (v) can be reduced using iron or zinc to give the amine compound (vi). The aniline in compound (vi) can be diazotized and trapped with an amine such as diethylamine or pyrrolidine to give compound (vii). Hydrolysis of compound (vii) to convert the ester to an acid can also remove the TMS group. The acid can then be activated with a coupling agent (e.g. HBTU, HATU) and then reacted with N,O-dimethylhydroxylamine to give a N-methoxy-N-methylcarboxamide derivative (viii). Amide (viii) may then be reacted with a Grignard reagent of formula $R^1$—MgCl to give a ketone (ix). The ketone (ix) can be reduced to give an alcohol and cyclized to the cinnoline under standard thermal conditions or with microwave irradiation to give compound (x). The alcohol of compound (x) can be converted to the mesylate and reacted with sodium azide to give an azide derivative (xi). The azide group may then be converted to an amine (xii) under appropriate conditions such as trimethylphosphine or trimethylsilyliodide. The amine (xii) can be reacted with an appropriate alkylating agent $R^4X$ (e.g., MeI) or reacted under reductive amination conditions to give compound (xiii). Finally compound (xiii) can be reacted with a heteroaryl halide compound (e.g., Ar—X) to give a compound of Formula I. The reaction of amine (xii) with $R^4X$ can be eliminated to give compounds of Formula I where $R^4$ is H. Alternatively, the compound of formula (x) can be transformed to compounds of Formula (I) by processes analogous to those shown in Scheme VII and the surrounding text.

Scheme VIII

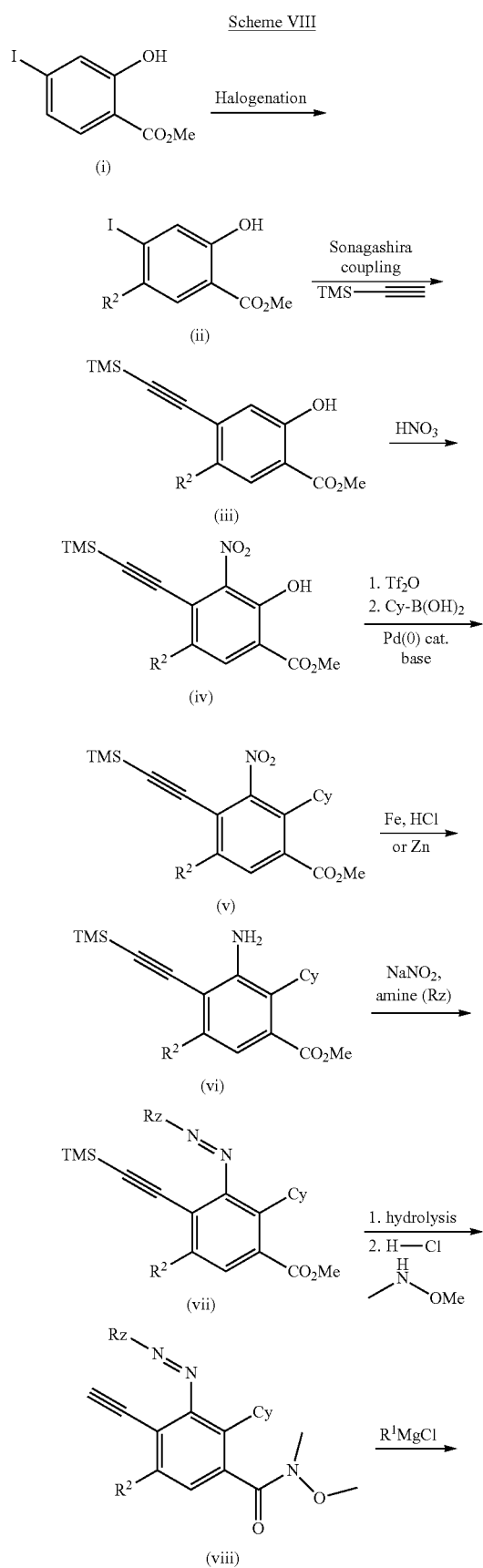

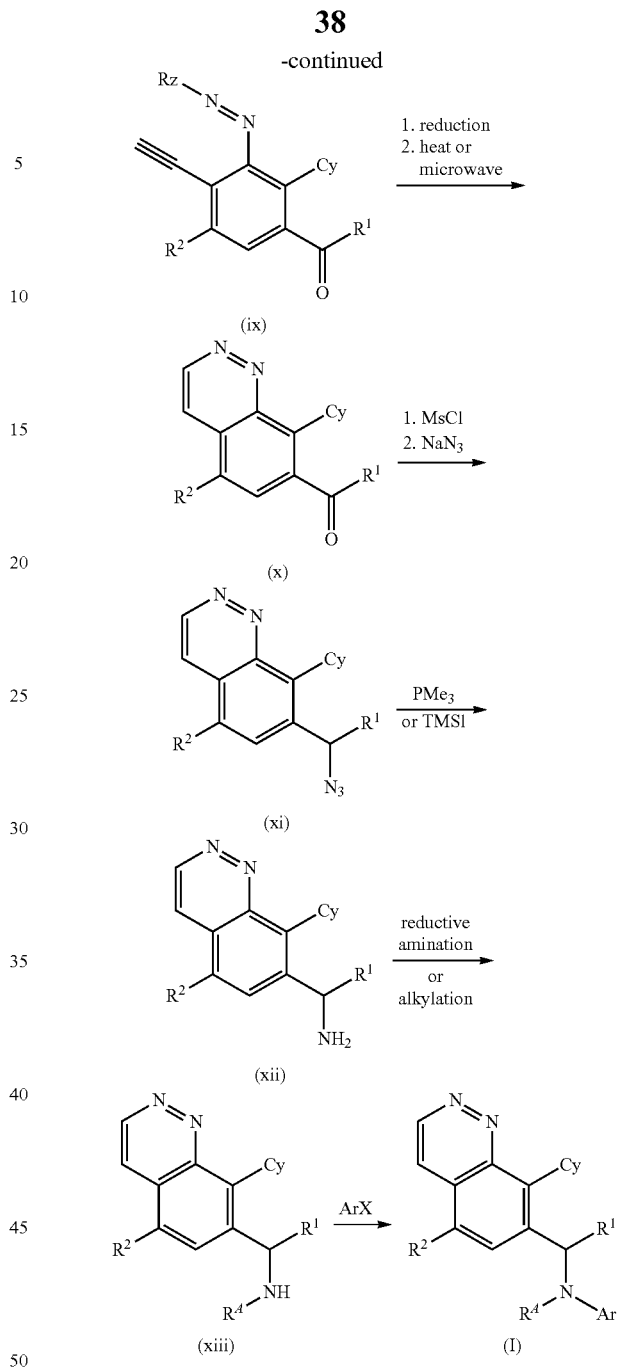

Alternatively, cinnoline compounds of Formula I can also be synthesized starting from phenol compound (i) as shown in Scheme IX. The phenol compound (i) can be acetylated with a reagent such as acetyl chloride and rearranged to give compound (ii). The bromo of compound (ii) can be transformed to the alkyne (iii) under Sonagashira coupling conditions. Compound (iii) can be nitrated to give the nitro compound (iv). The phenol of compound (iv) can be converted to a triflate with triflic anhydride and the triflate can be coupled to Cy-M, where M is a boronic acid, boronic ester or an appropriately substituted metal (e.g., Cy-M is Cy-B(OH)$_2$), under standard Suzuki conditions (e.g., in the presence of a palladium(O) catalyst, such as tetrakis(triphenylphosphine)palladium(O) and a base (e.g., a bicarbonate or carbonate base)) to afford compound (v). Compound (v) can be reduced using iron to give the amine compound (vi). The aniline in compound (vi)

can be diazotized and trapped with diethylamine to give compound (vii). The TMS group of compound (vii) can be removed to give compound (viii). The ketone (viii) can be reduced to give an alcohol and cyclized to the cinnoline in the microwave at 200° C. to give compound (ix). The alcohol of compound (ix) can be converted to the mesylate and reacted with sodium azide to give an azide derivative (x). The azide group may then be converted to an amine (xi) under appropriate conditions such as trimethylphosphine. The amine (xi) can be reacted with an appropriate alkylating agent $R^A X$ (e.g., MeI) or reacted under reductive amination conditions to give compound (xii) Finally compound (xii) can be reacted with a heteroaryl halide compound (e.g., Ar—X) to give a compound of Formula I. The reaction of amine (xi) with $R^A X$ can be eliminated to give compounds of Formula I where $R^A$ is H. Alternatively, the compound of formula (ix) can be transformed to compounds of Formula (I) by processes analogous to those shown in Scheme VII and the surrounding text.

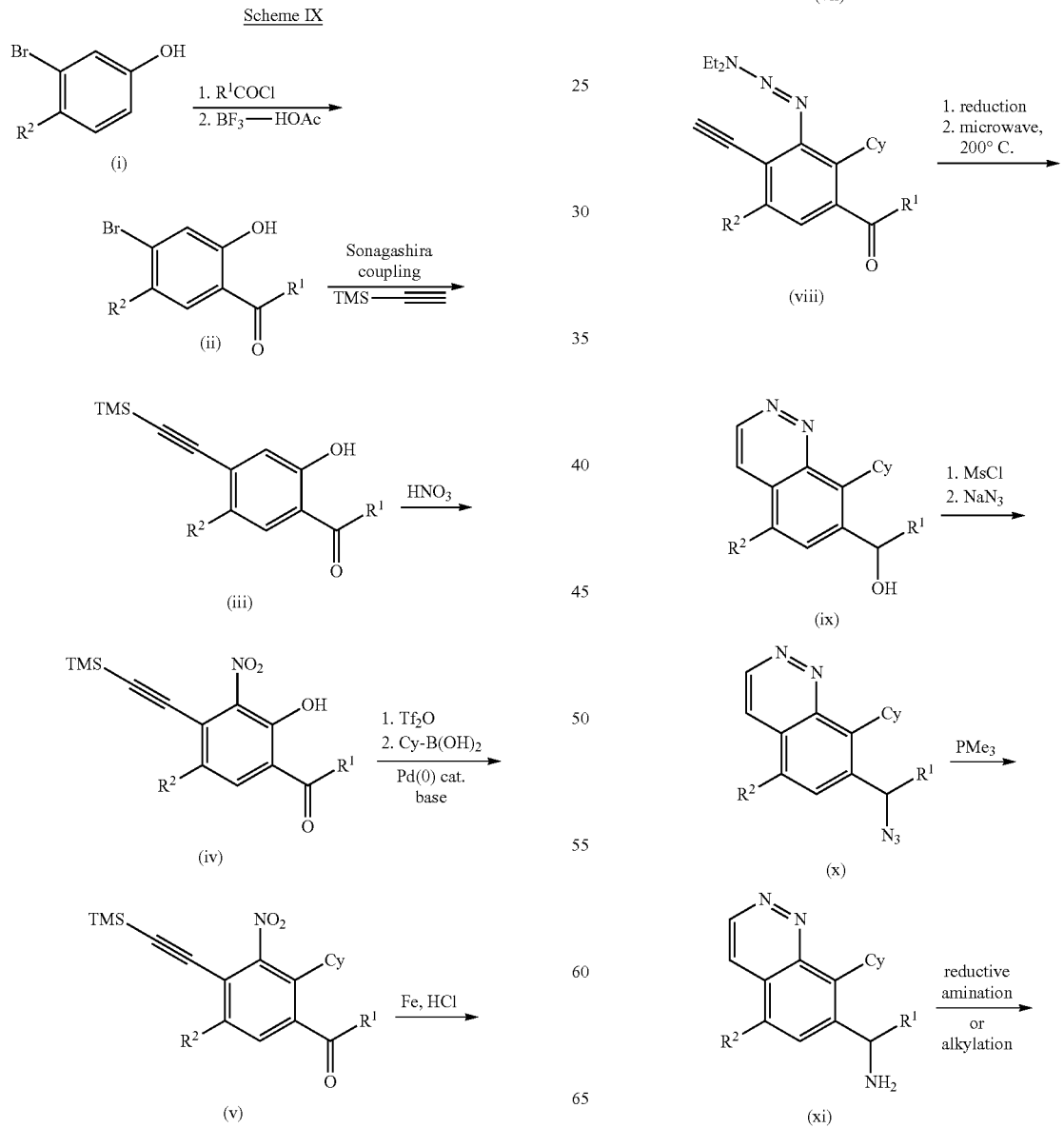
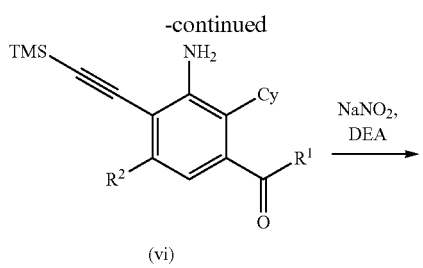
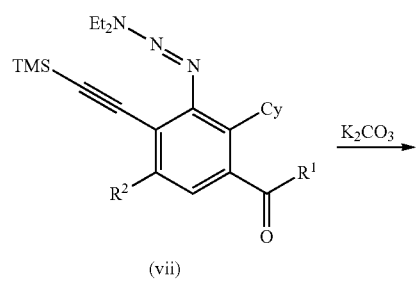
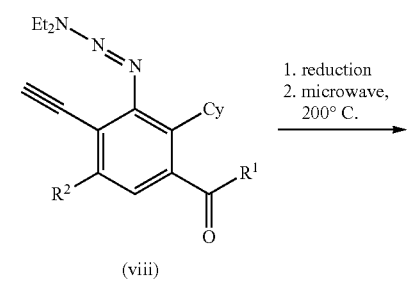
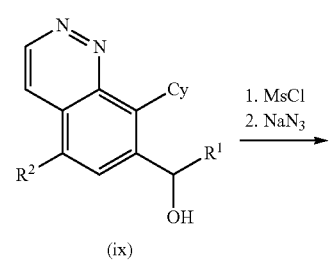
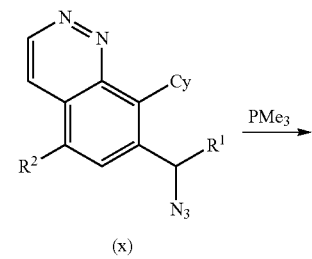
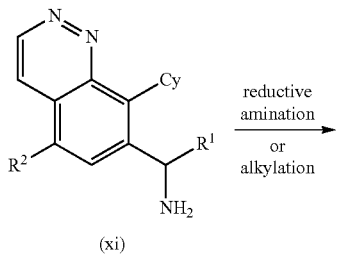

-continued

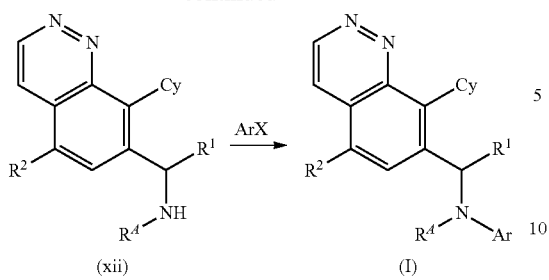

Compounds of Formula I, wherein U is NR$^{AL}$, V is N, X is CH, Y is absent, and W is CR$^3$ can be formed as shown in Scheme X. Treatment of methylether (i) with borontribromide gives a phenol of formula (ii). Reaction of the hydroxyl group of compound (ii) with triflic anhydride can form the triflate (iii) which can be reacted under standard coupling conditions to Cy-M, where M is a boronic acid, boronic ester or an appropriately substituted metal (e.g., Cy-M is Cy-B(OH)$_2$ or Cy-Sn(Bu)$_4$), under standard Suzuki conditions or standard Stille conditions (e.g., in the presence of a palladium (O) catalyst, such as tetrakis(triphenylphosphine)palladium (O) and a base (e.g., a bicarbonate or carbonate base)) to afford compound (iv). Alternatively, Cy-M can be a cyclic amine (where M is H and attached to the amine nitrogen) with coupling to compound (iii) being performed by heating in base or under Buchwald conditions (e.g., in the presence of a palladium(O) catalyst, such as Bis(dibenzylideneacetone) palladium and a base (e.g., an alkoxide base)) to afford nitro derivative (iv). Compound (iv) can be reduced using iron to give the amine compound (v). Treatment of compound (v) with amylnitrate can give an indazole (vi) which can be further derivatised by alkylation of the indazole with R$^{A1}$—X (e.g. alkylhalide, such as MeI, EtI) in the presence of an appropriate base (e.g., NaH, Na$_2$CO$_3$) to give compounds of formula (vii). Reductive amination of the ketone (vii) can furnish the amine intermediate (viii). The amino compound (viii) can then be converted to compounds of Formula I by similar methods described for conversion of amino compound (vii) into compounds of Formula I in Scheme I.

Scheme X

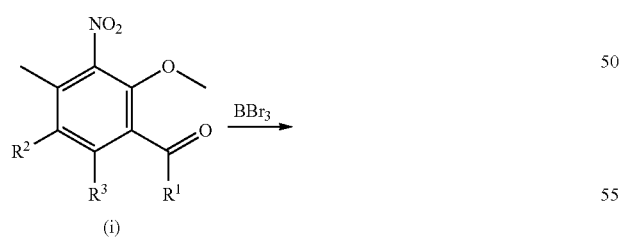

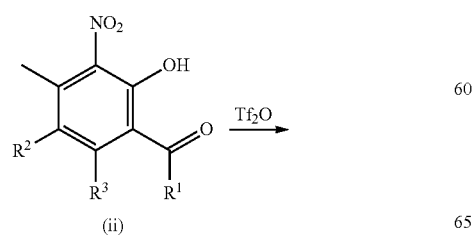

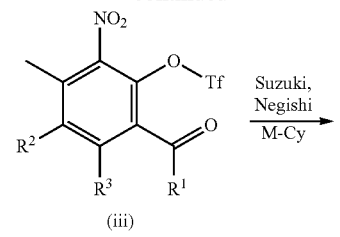

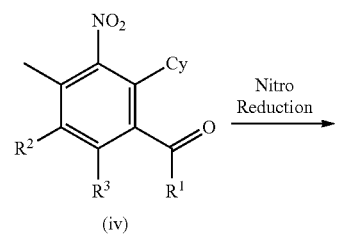

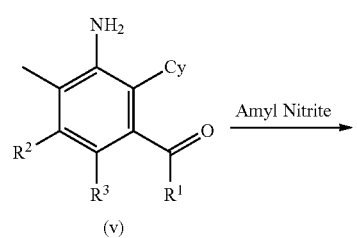

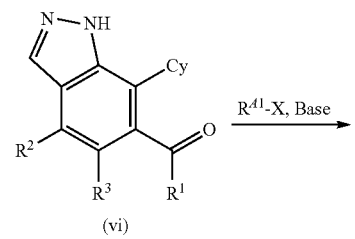

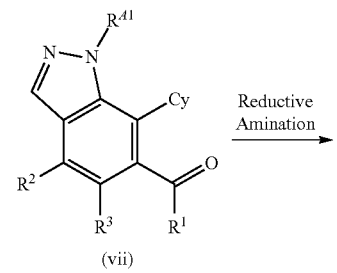

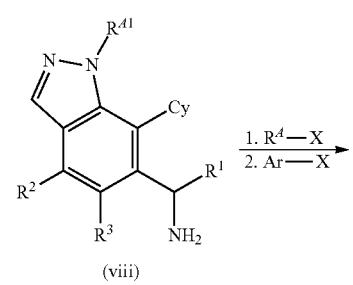

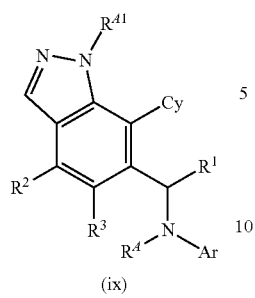

(ix)

Compounds of Formula I, wherein U is CH, V is CH, X is CH, Y is N and W is CR³ can be formed as shown in Scheme XI. The phenol compound (i) can be halogenated with N-chlorosuccinamide, N-bromosuccinamide or N-iodosuccinamide to give compound (ii) where X=Cl, Br, I. The halogenated compound (ii) can be reacted with CuCN to give the cyano compound (iii). The hydroxyl group of (iii) can be converted to a triflate with triflic anhydride and the triflate (iv) can be coupled to Cy-M, where M is a boronic acid, boronic ester or an appropriately substituted metal (e.g., Cy-M is Cy-B(OH)₂), under standard Suzuki conditions (e.g., in the presence of a palladium(O) catalyst, such as tetrakis(triphenylphosphine)palladium(O) and a base (e.g., a bicarbonate or carbonate base)) to afford compound (v). Compound (v) can be halogenated (e.g., NBS) to give bromide (vi) which can then be treated with sodium cyanide to give a cyano compound (vii). Reduction of the cyano with an appropriate reducing agent (e.g., DIBAL) can give the di-aldehyde (viii) which can be cyclized under condensation conditions to give the isoquinoline (ix). The alcohol of compound (ix) can be converted to the mesylate and reacted with sodium azide to give an azide (x) which may then be converted to an amine (xi) under appropriate reducing conditions, such as trimethylphosphine. The amine (xi) can be reacted with an appropriate alkylating agent R⁴X (e.g., MeI) or reacted under reductive amination conditions to give compound (xii). Finally compound (xii) can be reacted with a heteroaryl halide compound (e.g., Ar—X) to give a compound of Formula I, wherein U is CH, V is CH, X is CH, Y is N and W is CR³. The reaction of amine (xi) with R⁴ can be eliminated to give compounds of Formula I, wherein U is CH, V is CH, X is CH, Y is N and W is CR³ and R⁴ is H. Alternatively, the compound of formula (ix) can be transformed to compounds of Formula I, wherein U is CH, V is CH, X is CH, Y is N and W is CR³, by processes analogous to those shown in Scheme VII and the surrounding text.

Scheme XI

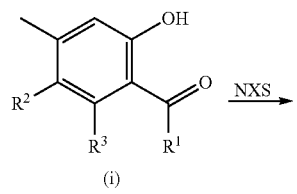

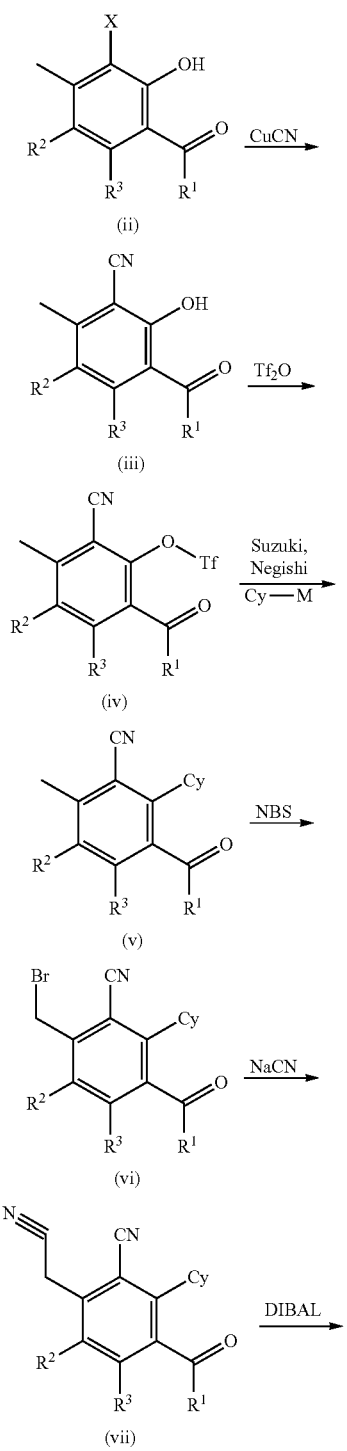

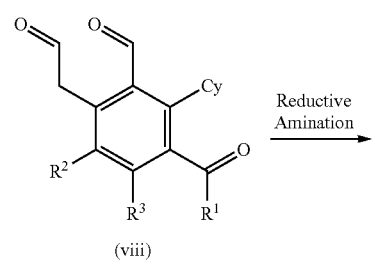

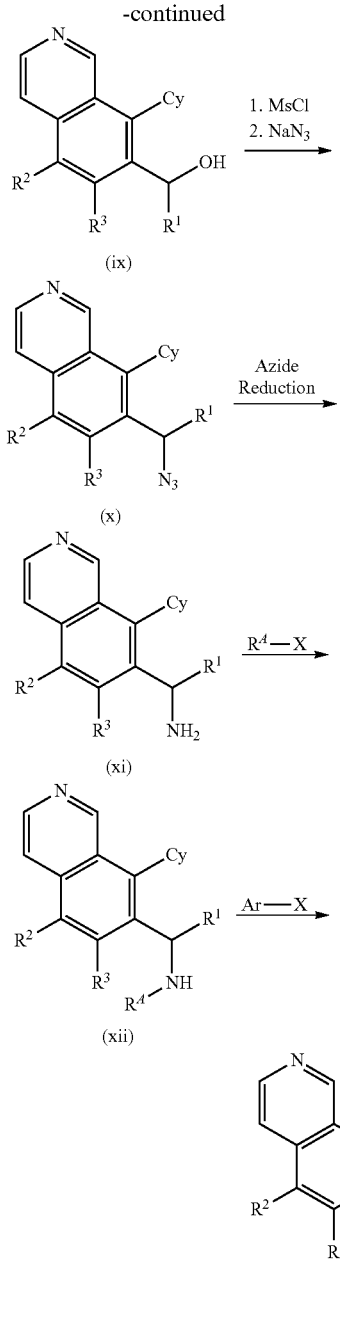

MgBr R[1] where R[1]=alkyl). Reductive amination of the ketone (vii) can furnish the amine intermediate (viii) which can then be converted to compounds of Formula I by similar methods described for conversion of amino compound (vii) into compounds of Formula I in Scheme I.

Compounds of Formula I, wherein X is CR[5], V is CR[4], Y is CR[6], U is CR[7], and W is N can be formed as shown in Scheme XII. The halogenated compound (i) can be reacted under standard Stille, Suzuki or Negishi conditions to give derivative (ii). The hydroxyl group of (ii) can be converted to a triflate with triflic anhydride and the triflate (iii) can be coupled to Cy-M, where M is a boronic acid, boronic ester or an appropriately substituted metal (e.g., Cy-M is Cy-B(OH)$_2$), under standard Suzuki conditions (e.g., in the presence of a palladium(O) catalyst, such as tetrakis(triphenylphosphine)palladium(O) and a base (e.g., a bicarbonate or carbonate base)) to afford compound (iv). The ester of compound (iv) can be hydrolyzed (e.g., LiOH, NaOH) to give acid (v) which can be activated with a suitable coupling agent (e.g., HBTU, HATU, EDC) and reacted with N,O-dimethylhydroxylamine to give amide (vi), which can be further converted to a ketone (vii) by the addition of an alkyl metal (e.g.

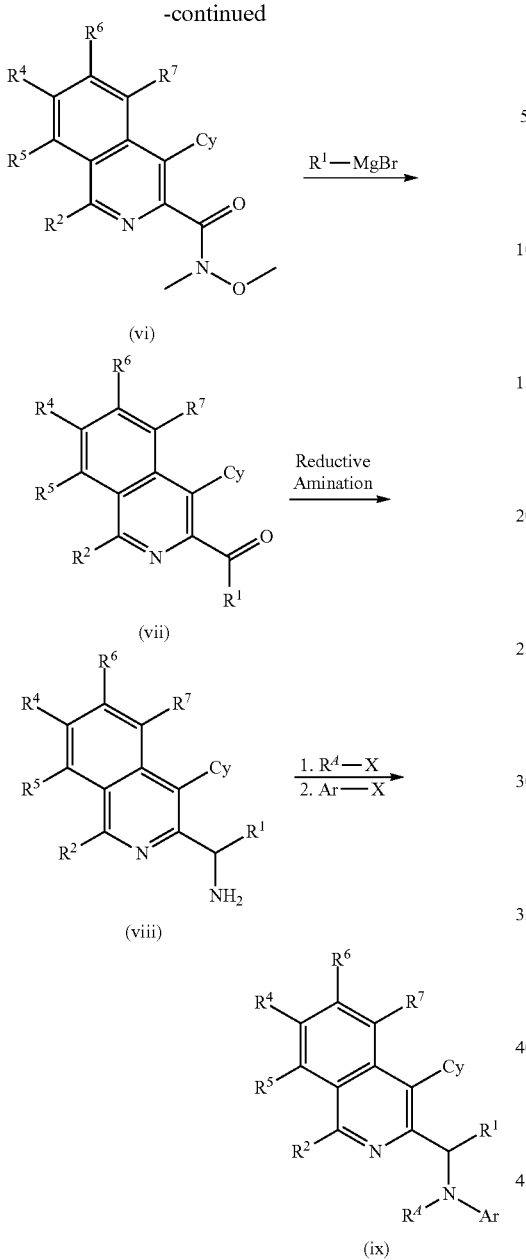

with Pd/C) to give the nitroso intermediate which can cyclize to afford benzooxazole (viii). Oxidation of the alcohol of compound (viii) under appropriate oxidazing conditions (e.g. Swern oxidation or Dess-Martin oxidation) can give the aldehyde (ix) which can be converted to a secondary alcohol (x) by the addition of a alkyl metal (e.g. MgBr $R^1$ where $R^1$=alkyl, such as Me). The alcohol of compound (x) can be converted to the mesylate and reacted with sodium azide to give an azide (xi) which may then be converted to an amine (xii) under appropriate reducing conditions, such as trimethylphosphine. The amine (xii) can be reacted with an appropriate alkylating agent $R^A X$ (e.g., MeI) or reacted under reductive amination conditions to give an intermediate secondary amine that can be reacted with a heteroaryl halide compound (e.g., Ar—X) to give benzooxazole compounds (xiii). The reaction of amine (xii) with $R^A$ can be eliminated to give benzooxazole compounds (xiii) where $R^A$ is H. Alternatively, the compound of formula (x) can be transformed to compounds of Formula I by processes analogous to those shown in Scheme VII and the surrounding text.

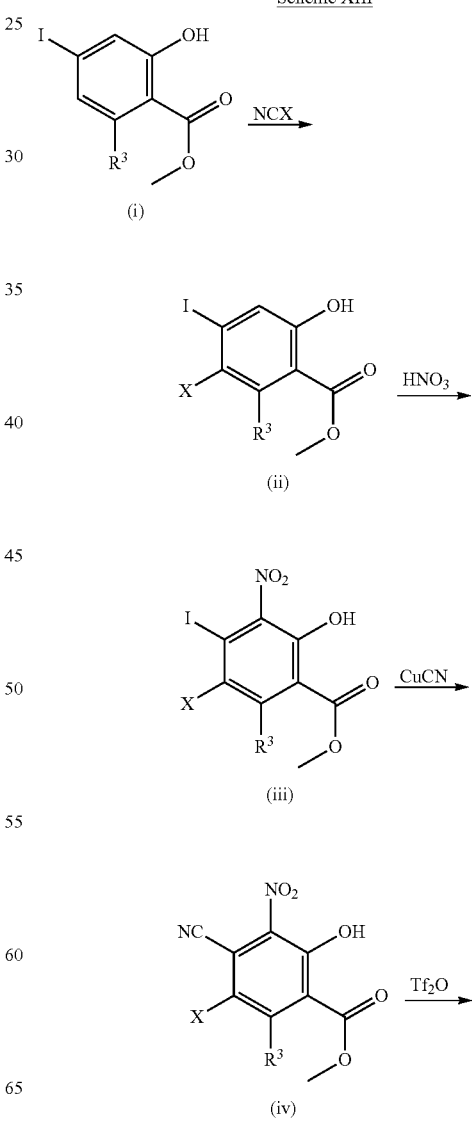

Scheme XIII

Compounds of Formula I, wherein X is CH, V is O, Y is absent, U is N, and W is $CR^3$ can be formed as shown in Scheme XIII. The phenol compound (i) can be halogenated with N-chlorosuccinamide, N-bromosuccinamide to give compound (ii) where $R^2$=Cl, Br. The halogenated compound (ii) can be nitrated with $HNO_3$ to give the nitro compound (iii) which can be further reacted with CuCN to give the cyano derivative (iv). The hydroxyl group of (iv) can be converted to a triflate with triflic anhydride and the triflate (v) can be coupled to Cy-M, where M is a boronic acid, boronic ester or an appropriately substituted metal (e.g., Cy-M is Cy-B $(OH)_2$), under standard Suzuki conditions (e.g., in the presence of a palladium(0) catalyst, such as tetrakis(triphenylphosphine)palladium(0) and a base (e.g., a bicarbonate or carbonate base)) to afford compound (vi). The nitrile group of compound (vi) can be reduced (e.g. DIBAL) to give aldehyde (vii). The nitro of compound (vii) can be reduced (e.g. Fe, $H_2$

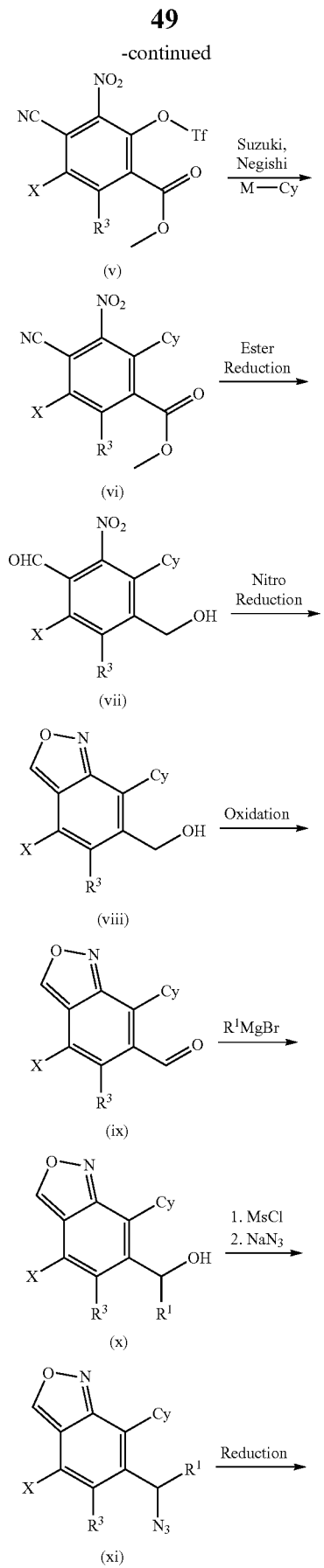

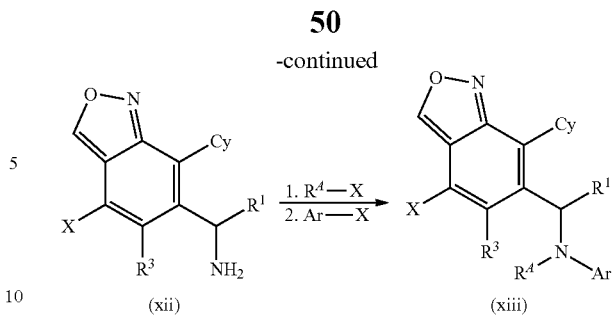

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e.g., inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3δ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjogren's syndrome, and the like. As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK, c-MET, VEGFR, PDGFR, cKit, IGF-1R, RAF and FAK kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH66336, R115777, L778,123, BMS 214662, Iressa®, Tarceva®, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin®, herceptin, Bexxar®, Velcade®, Zevalin®, Trisenox®, Xeloda®, Vinorelbine, Porfimer, Erbitux®, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, and bendamustine (Treanda®).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 pg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radiolabeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PI3K labeling and competition assays, compounds that incorporate $^{3}H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (L e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. Where the procedures refer to peak 1 or peak 2, "peak 1" refers to the compound which eluted first, whereas "peak 2" refers to the compound which eluted second. At points throughout the Examples, the stereochemistry at the carbon attached to $R^1$ has been indicated, as currently understood.

Example 1

N-{1-[1-(3-fluorophenyl)-2-naphthyl]ethyl}-9H-purin-6-amine trifluoroacetate

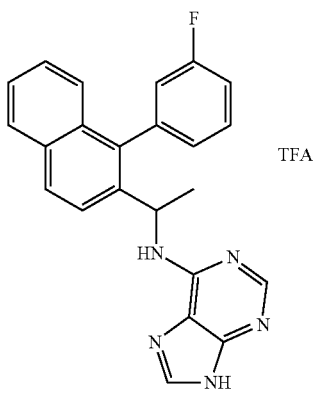 [SMILES: CC(Nc1ncnc2[nH]cnc12)c1ccc2ccccc2c1-c1cccc(F)c1]

Step 1.
1-bromo-N-methoxy-N-methyl-2-naphthamide

To a mixture of 1-bromo-2-naphthoic acid (1.04 g, 4.14 mmol, TCI America) and N,O-dimethylhydroxylamine hydrochloride (0.465 g, 4.76 mmol) in N,N-dimethylformamide (10 mL,) was added benzotriazol-1-yloxytris(dimethylamino)phosphonium hexafluorophosphate (2.11 g, 4.76 mmol). After stirred at room temperature for 10 minutes, N,N-diisopropylethylamine (2.16 mL, 12.4 mmol) was added to the resulting mixture. The reaction was stirred at room temperature for 2 h, quenched with water, and extracted with EtOAc. The combined organic layers were washed with water, brine, dried over sodium sulfate, and concentrated under reduced pressure. The residue was concentrated and the residue was purified on silica gel, eluting with 0% to 50% ethyl acetate in hexane, to give the desired product (1.08 g, 88%). LCMS calculated for $C_{13}H_{13}BrNO_2(M+H)^+$: m/z=294.0; found: 294.2.

Step 2. 1-(1-bromo-2-naphthyl)ethanone

To a mixture of 1-bromo-N-methoxy-N-methyl-2-naphthamide (0.708 g, 0.00241 mol) in tetrahydrofuran (10 mL) was added 3.00 M of methylmagnesium bromide in ether (8.19 mL, 0.0246 mol). The reaction was stirred at room temperature for 2 h, quenched with water at 0° C., then acidified with 1 N HCl, and extracted with EtOAc. The combined organic layers were washed with saturated sodium bicarbonate and brine, dried over magnesium sulfate, and evaporated to dryness under reduced pressure. The residue was used directly in next step (488 mg, 81%). LCMS calculated for $C_{12}H_{10}BrO(M+H)^+$: m/z=249.0.; found: 249.2.

Step 3. 1-(1-bromo-2-naphthyl)ethanol

To a mixture of 1-(1-bromo-2-naphthyl)ethanone (0.488 g, 1.96 mmol) in methanol (10 mL) was added sodium tetrahydroborate (0.0741 g, 1.96 mmol). The reaction was stirred at room temperature for 30 minutes, quenched with water, extracted with ethyl acetate. The combined organic layers were washed with brine, dried over magnesium sulfate, and concentrated to dryness under reduced pressure. The residue was used directly in next step (467 mg, 94%). LCMS calculated for $C_{12}H_{10}Br(M-OH)^+$: m/z=233.0; found: 233.2.

Step 4. 2-(1-azidoethyl)-1-bromonaphthalene

To a mixture of 1-(1-bromo-2-naphthyl)ethanol (0.467 g, 1.86 mmol) and triethylamine (0.389 mL, 2.79 mmol) in dichloromethane (10 mL) was added methanesulfonyl chloride (0.180 mL, 2.32 mmol). The reaction was stirred at room temperature for 1 hour, quenched with water, and extracted with dichloromethane. The combined organic layers were washed with brine, dried over magnesium sulfate, and evaporated to dryness under reduced pressure to yield corresponding mesylate. LCMS (M−MsO) 233.2. To the crude mesylate in N,N-dimethylformamide (5 mL, 60 mmol) was added sodium azide (0.604 g, 9.30 mmol). The reaction was stirred at room temperature for 2 h, quenched with water, and extracted with ethyl acetate. The combined organic layers were washed with water, brine, dried over magnesium sulfate, and concentrated to dryness under reduced pressure. The residue was used directly in next step (386 mg, 75.17%). LCMS calculated for $C_{12}H_{10}Br(M-N3)^+$: m/z=233.0.; found: 233.1.

Step 5. 2-(1-azidoethyl)-1-(3-fluorophenyl)naphthalene

To a mixture of 2-(1-azidoethyl)-1-bromonaphthalene (0.080 g, 0.29 mmol) and (3-fluorophenyl)boronic acid (48.6 mg, 0.348 mmol) in 1,4-dioxane (2 mL) was added a 1 M solution of sodium carbonate in water (0.34 mL, 19 mmol) and tetrakis(triphenylphosphine)palladium(0) (16.7 mg, 0.0145 mmol). The reaction mixture was heated at 100° C. overnight. After cool to room temperature, the mixture was diluted with ethyl acetate, washed with water, brine, dried over $MgSO_4$, and then concentrated. The residue was purified on silica gel, eluting with 0 to 20% EtOAc in hexane, to give the desired product (35 mg, 41.5%). LCMS calculated for $C_{18}H_{14}FN3Na(M+Na)^+$: m/z=314.1; found: 314.3.

Step 6. 1-[1-(3-fluorophenyl)-2-naphthyl]ethanamine

A mixture of 2-(1-azidoethyl)-1-(3-fluorophenyl)naphthalene (0.035 g, 0.12 mmol) in 1 mL of methanol was hydrogenated in the presence of 5% Pd/C, under balloon pressure of hydrogen, for 1 hour. After filtering off the catalyst, the filtrate was concentrated under reduced pressure and the resulting residue was used directly in next step. LCMS calculated for $C_{18}H_{14}F(M-NH_2)^+$: m/z=249.1; found: 249.3.

Step 7. N-{1-[1-(3-fluorophenyl)-2-naphthyl]ethyl}-9H-purin-6-amine

A mixture of 6-bromo-9H-purine (0.02696 g, 0.1355 mmol), 1-[1-(3-fluorophenyl)-2-naphthyl]ethanamine (0.030 g, 0.11 mmol), and N,N-diisopropylethylamine (0.024 mL, 0.14 mmol) in ethanol (0.9 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a TFA salt. LCMS calculated for $C_{23}H_{19}FN_5(M+H)^+$: m/z=384.2; found: 384.3. $^1$H NMR (DMSO-$d_6$, 400 MHz) δ 8.92 (1H, br s), 8.30 (2H, m), 7.97 (1H, d, J=9.2 Hz), 7.90 (1H, d, J=7.6 Hz), 7.79 (1H, m), 7.57 (1H, m), 7.47 (1H, m), 7.40 (2H, m), 7.31 (1H, m), 7.19 (2H, m), 5.23 (1H, m), 1.49 (3H, m) ppm. $^{19}$F NMR (DMSO-d$_6$, 376.28 MHz) δ −74.6 ppm.

Example 2

N-{1-[4-(3-fluorophenyl)-2-methyl-1,3-benzothiazol-5-yl]ethyl}-9H-purin-6-amine trifluoroacetate

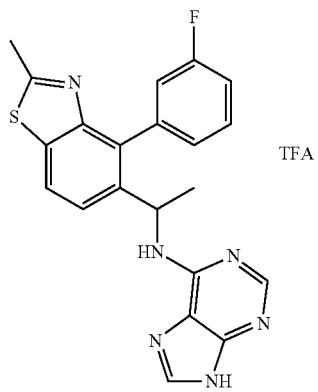 [SMILES: Cc1nc2c(-c3cccc(F)c3)c(C(C)Nc3ncnc4[nH]cnc34)ccc2s1]

Step 1. 4-bromo-2,5-dimethyl-1,3-benzothiazole

A mixture of 2,5-dimethyl-1,3-benzothiazole (10.00 g, 61.26 mmol, Aldrich) and bromine (6.94 mL, 134.8 mmol) in chloroform (200 mL) was heated at reflux overnight. After cooling to room temperature, the mixture was washed with 1 N NaOH, followed by saturated sodium thiosulfate and brine, then dried over sodium sulfate and evaporated to dryness. The residue was purified on silica gel, eluting with 0 to 50% EtOAc in hexane. The first peak had a retention time of 2.51 minutes, LCMS calculated for C$_9$H$_9$BrNS(M+H)$^+$: m/z=242.0; found: 241.9. $^1$H NMR shown to be the desired product B (980 mg, 6.61%). $^1$H NMR (CDCl3, 400 MHz) 7.63 (1H, d, J=8.4 Hz), 7.22 (1H, d, J=8.4 Hz), 2.87 (3H, s), 2.55 (3H, s) ppm. The second peak had a retention time of 2.758 minutes, LCMS (M+H)$^+$m/z=241.9; found: 242. $^1$H NMR showed no coupling for the two phenyl hydrogens confirming the 6-bromo isomer.

Step 2. 4-bromo-5-(bromomethyl)-2-methyl-1,3-benzothiazole

A mixture of 4-bromo-2,5-dimethyl-1,3-benzothiazole (5.8 g, 24 mmol), N-bromosuccinimide (5.12 g, 28.7 mmol), and benzoyl peroxide (0.580 g, 2.40 mmol) in carbon tetrachloride (100 mL) was heated at reflux overnight. The mixture was diluted with dichloromethane, washed with 1 N NaOH, brine and dried over sodium sulfate, then concentrated under reduced pressure. The residue was purified on silica gel, eluting with 0% to 50% EtOAc in hexane, to give the desired product (5.70 g, 74%). LCMS calculated for C$_9$H$_8$Br$_2$NS(M+H)$^+$: m/z=319.9; found: 319.8.

Step 3. (4-bromo-2-methyl-1,3-benzothiazol-5-yl)methanol

A mixture of 4-bromo-5-(bromomethyl)-2-methyl-1,3-benzothiazole (2.85 g, 8.88 mmol) and potassium acetate (1.74 g, 17.8 mmol) in N,N-dimethylformamide (20 mL) was heated at 80° C. overnight. After cooling, the mixture was diluted with ethyl acetate, and washed with water and brine. The resulting EtOAc solution was dried then over Mg$_2$SO$_4$, filtered and solvent removed under reduced pressure to afford the acetate intermediate. LCMS (M+H)$^+$m/z=299.9. The crude acetate was dissolved in tetrahydrofuran (30 mL) and treated with 1.00 M of sodium hydroxide in water (17.8 mL, 17.8 mmol) at room temperature for 1 hour. After neutralization with HCl, the mixture was extracted with ethyl acetate. The combined organic layers were washed with brine, dried over sodium sulfate, and then concentrated to dryness under reduced pressure. The resulting residue was purified on silica gel, eluting with 0 to 100% ethyl acetate in hexane, to give the desired product (2.07 g, 90%). LCMS calculated for C$_9$H$_9$BrNOS(M+H)$^+$: m/z=258.0; found: 257.9. NOE between methylene hydrogen and H-6 confirmed that phenyl methyl was brominated in step 2 and subsequently converted to hydroxyl in this step.

Step 4. 4-bromo-2-methyl-1,3-benzothiazole-5-carbaldehyde

Dimethyl sulfoxide (1.13 mL, 0.016 mol) was added to oxalyl chloride (0.84 mL, 0.0099 mol) in methylene chloride (37.10 mL) at −78° C. After 10 minutes, (4-bromo-2-methyl-1,3-benzothiazol-5-yl)methanol (1.71 g, 0.00662 mol) in methylene chloride (74 mL) was added and the resultant mixture was stirred at −78° C. for 30 minutes. Triethylamine (4.62 mL, 0.0331 mol) was then added and the mixture was stirred for 5 h and the temperature allowed to gradually warm up to room temperature. After quenching with water, the mixture was extracted with methylene chloride. The organic layers were combined, washed with brine, dried over magnesium sulfate and evaporated to dryness. The resultant solid was used directly in next step (1.70 g, 100%). LCMS calculated for C$_9$H$_7$BrNOS(M+H)$^+$: m/z=255.9; found: 255.9.

Step 5. 1-(4-bromo-2-methyl-1,3-benzothiazol-5-yl)ethanol

To a mixture of 4-bromo-2-methyl-1,3-benzothiazole-5-carbaldehyde (1.70 g, 6.64 mmol) in tetrahydrofuran (30 mL) was added 1.40 M methylmagnesium bromide in tetrahydrofuran (9.48 mL) at 0° C. The reaction was stirred at room temperature for 30 minutes, quenched with water, and extracted with EtOAc. The combined organic layers were washed with brine, dried over magnesium sulfate, and then concentrated to dryness under reduced pressure. The crude residue was used directly in next step (1.81 g, 100%). LCMS calculated for C$_{10}$H$_{11}$BrNOS(M+H)$^+$: m/z=272.0; found: 271.9.

Step 6. 5-(1-azidoethyl)-4-bromo-2-methyl-1,3-benzothiazole

To a mixture of 1-(4-bromo-2-methyl-1,3-benzothiazol-5-yl)ethanol (1.81 g, 6.65 mmol) in methylene chloride (40 mL) was added triethylamine (1.39 mL, 9.98 mmol), followed by methanesulfonyl chloride (0.643 mL, 8.31 mmol). After stirring at room temperature for 30 minutes, the resultant mixture was diluted with dichloromethane, washed with saturated sodium bicarbonate and brine, dried over magnesium sulfate, and then concentrated to dryness under reduced pressure. The crude mesylate was dissolved in N,N-dimethylformamide (20 mL) and treated with sodium azide (2.16 g, 33.2 mmol) at room temperature overnight. After diluting with ethyl acetate, the mixture was washed with water and brine, dried over magnesium sulfate, and evaporated to dryness. The crude product was used in next step (1.90 g, 96%). LCMS calculated for $C_{10}H_{10}BrI\T4S(M+H)^+$: m/z=297.0; found: 297.0.

Step 7. 5-(1-azidoethyl)-4-(3-fluorophenyl)-2-methyl-1,3-benzothiazole

To a mixture of 5-(1-azidoethyl)-4-bromo-2-methyl-1,3-benzothiazole (0.100 g, 0.336 mmol) and (3-fluorophenyl) boronic acid (56.5 mg, 0.404 mmol) in 1,4-dioxane (2 mL) was added a 1 M solution of sodium carbonate in water (0.40 mL, 22 mmol) and tetrakis(triphenylphosphine)palladium(0) (19.4 mg, 0.0168 mmol). The reaction mixture was heated at 100° C. overnight. After cooling to room temperature, the mixture was diluted with ethyl acetate, washed with water and brine, dried over $MgSO_4$, and then concentrated. The crude mixture was purified on silica gel, eluting with 0 to 40% EtOAc in hexane, to give the desired product (88 mg, 83%). LCMS calculated for $C_{16}H_{14}FN_4S(M+H)^+$: m/z=313.1; found: 313.0.

Step 8. 1-[4-(3-fluorophenyl)-2-methyl-1,3-benzothiazol-5-yl]ethanamine

To a stirred solution of 5-(1-azidoethyl)-4-(3-fluorophenyl)-2-methyl-1,3-benzothiazole (0.088 g, 0.28 mmol) in tetrahydrofuran (0.8 mL) and water (0.203 mL) was added 1.00 M of trimethylphosphine in tetrahydrofuran (0.338 mL, 0.338 mmol) at room temperature and the mixture was stirred at room temperature for 1 hour. To the mixture was added EtOAc and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The residue, showing two peaks with the same desired mass, was used directly in next step (74 mg, 91%). LCMS calculated for $C_{16}H_{16}FN2S(M+H)^+$: m/z=287.1; found: 287.1.

Step 9. N-{1-[4-(3-fluorophenyl)-2-methyl-1,3-benzothiazol-5-yl]ethyl}-9H-purin-6-amine A mixture of 6-bromo-9H-purine (0.1028 g, 0.52 mmol), 144-(3-fluorophenyl)-2-methyl-1,3-benzothiazol-5-yl]ethanamine (0.074 g, 0.26 mmol), and N,N-diisopropylethylamine (0.05401 mL, 0.31 mmol) in ethanol (0.9 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a TFA salt. LCMS calculated for $C_{21}H_{18}FN_6S(M+H)^+$: m/z=405.1; found: 404.9. $^1H$ NMR (DMSO-$d_6$, 400 MHz) δ 9.11 (1H, br s), 8.38 (2H, m), 8.03 (1H, d, J=8.4 Hz), 7.64 (1H, d, J=8.4 Hz), 7.45 (2H, m), 7.25~7.00 (3H, m), 5.34 (1H, m), 2.68 (3H, s), 1.47 (3H, d, J=6.8 Hz) ppm. $^{19}F$ NMR (DMSO-d6, 376.28 MHz) δ −74.4 ppm.

Example 3

N(6)-{1-[1-(5-fluoropyridin-3-yl)-2-naphthyl]ethyl}-9H-purine-2,6-diamine bis-trifluoroacetate

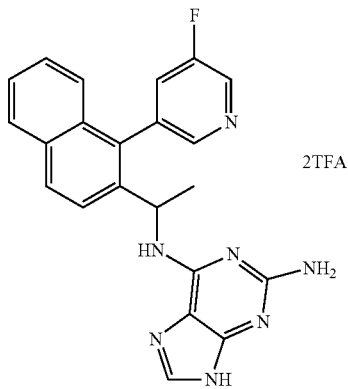 [SMILES: CC(Nc1nc(N)nc2[nH]cnc12)c1ccc2ccccc2c1-c1cncc(F)c1]

Step 1. 3-[2-(1-azidoethyl)-1-naphthyl]-5-fluoropyridine

To a mixture of 2(1-azidoethyl)-1-bromonaphthalene (0.080 g, 0.29 mmol) and (5-fluoropyridin-3-yl)boronic acid (49.0 mg, 0.348 mmol) in 1,4-dioxane (2 mL) was added a 1 M solution of sodium carbonate in water (0.34 mL) and tetrakis(triphenylphosphine)palladium(0) (16.7 mg, 0.0145 mmol). The reaction mixture was heated at 100° C. overnight. After cooling to room temperature, the mixture was diluted with ethyl acetate, washed with water and brine, dried over $MgSO_4$, and then concentrated. The residue was purified on silica gel, eluting with 0 to 50% EtOAc in hexane, to give the desired product. LCMS calculated for $C_{17}H_{14}FN_4(M+H)^+$: m/z=293.1; found: 293.0.

Step 2. 1-[7-(5-fluoropyridin-3-yl)-2-naphthyl]ethanamine

To a stirred solution of 3-[2-(1-azidoethyl)-1-naphthyl]-5-fluoropyridine (0.085 g, 0.29 mmol) in tetrahydrofuran (0.8 mL) and water (0.210 mL) was added 1.00 M of trimethylphosphine in tetrahydrofuran (0.35 mL, 0.35 mmol) at room temperature and the mixture was stirred at room temperature for 1 hour. To the mixture was added ethyl acetate and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The residue showed two peaks with the same desired mass and was used directly in next step. LCMS calculated for $C_{17}H_{16}FN_2(M+H)^+$: m/z=267.1; found: 267.0.

Step 3. N(6)-{1-[1-(5-fluoropyridin-3-yl)-2-naphthyl]ethyl}-9H-purine-2,6-diamine A mixture of 2-amino-6-bromopurine (0.030 g, 0.14 mmol), 1-[1-(5-fluoropyridin-3-yl)-2-naphthyl]ethanamine (0.019 g, 0.07 mmol), and N,N-diisopropylethylamine (0.01465 mL, 0.084 mmol) in ethanol (0.2 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a mixture of rotomers (bis-TFA salt). LCMS calculated for $C_{22}H_{19}FN_7(M+H)^+$: m/z=400.2; found: 400.0.

Example 4

N(6)-{1-[1-(3-fluorophenyl)-2-napthyl]ethyl}-9H-purine-2,6-diamine

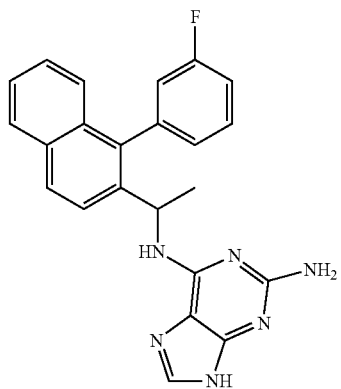 [SMILES: CC(Nc1nc(N)nc2[nH]cnc12)c1ccc2ccccc2c1-c1cccc(F)c1]

A mixture of 2-amino-6-bromopurine (0.1258 g, 0.59 mmol), 1-[1-(3-fluorophenyl)-2-naphthyl]ethanamine (0.078 g, 0.29 mmol), and N,N-diisopropylethylamine (0.06145 mL, 0.35 mmol) in ethanol (1 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a TFA salt. The first peak had a retention time of 1.895 minutes, LCMS calculated for $C_{23}H_{20}FN_6(M+H)^+$: m/z=399.2; found: 399.0. The second peak had a retention time of 1.941 minutes, LCMS calculated for $C_{23}H_{20}FN_6(M+H)^+$: m/z=399.2; found: 399.0. $^1$H NMR (DMSO-$d_6$, 400 MHz) δ 8.88 (1H, m), 8.16 (1H, s), 8.04 (1H, d, J=8.8 Hz), 7.96 (1H, d, J=8.4 Hz), 7.72 (1H, d, J=8.4 Hz), 7.58~7.13 (9H, m), 5.20 (1H, m), 1.46 (3H, d, J=6.8 Hz) ppm. $^{19}$F NMR (DMSO-$d_6$, 376.28 MHz) δ −74.2 ppm.

Example 5

N-{1-[1-(5-fluoropyridin-3-yl)-2-napthyl]ethyl}-9H-purin-6-amine bis-trifluoroacetate

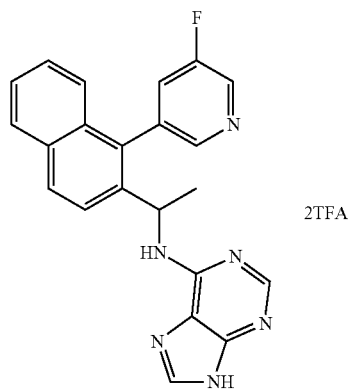 [SMILES: CC(Nc1ncnc2[nH]cnc12)c1ccc2ccccc2c1-c1cncc(F)c1]

A mixture of 6-bromo-9H-purine (0.05829 g, 0.29 mmol), 1-[1-(5-fluoropyridin-3-yl)-2-naphthyl]ethanamine (0.039 g, 0.15 mmol), and N,N-diisopropylethylamine (0.03061 mL, 0.18 mmol) in ethanol (0.5 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a mixture of rotomer (bis-TFA salt). LCMS calculated for $C_{22}H_{18}FN_6(M+H)^+$: m/z=385.2; found: 385.1.

Example 6

N-{1-[8-(3,5-difluorophenyl)quinolin-7-yl]ethyl}-9H-purin-6-amine bis-trifluoroacetate

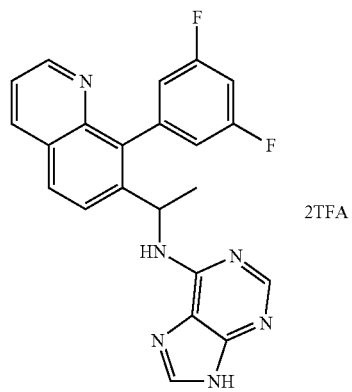 [SMILES: CC(Nc1ncnc2[nH]cnc12)c1ccc2cccnc2c1-c1cc(F)cc(F)c1]

Step 1. 8-hydroxy-N-methoxy-N-methylquinoline-7-carboxamide

To a mixture of 8-hydroxyquinoline-7-carboxylic acid (5.0 g, 26 mmol, TCI America) in methylene chloride (50 mL) was added thionyl chloride (4.24 mL, 58.1 mmol). After stirred at room temperature overnight, the mixture was concentrated to dryness under reduced pressure. The residue was exposed to high vacuum then mixed with tetrahydrofuran (50 mL). To the resultant mixture was added N,O-dimethylhydroxylamine hydrochloride (3.09 g, 31.7 mmol) followed by N,N-diisopropylethylamine (13.8 mL, 79.3 mmol). The reaction was heated at 50° C. overnight, then cooled and quenched with water, and extracted with dichloromethane. The combined organic layers were washed with water, brine and dried over sodium sulfate. After evaporated to dryness, the residue was purified on silica gel, eluting with 0 to 10% methanol in dichloromethane, to give the desired product (4.09 g, 66%). LCMS calculated for $C_{12}H_{13}N_2O_3(M+H)^+$: m/z=233.1; found: 233.0.

Step 2. 7-{[methoxy(methyl)amino]carbonyl}quinolin-8-yl trifluoromethanesulfonate To a solution of 8-hydroxy-N-methoxy-N-methylquinoline-7-carboxamide (3.2 g, 0.014 mol) and triethylamine (5.8 mL, 0.041 mol) in methylene chloride (50 mL) at −78° C. was added trifluoromethanesulfonic anhydride (2.9 mL, 0.017 mol) dropwise. The reaction mixture was stirred at this temperature for 1 hour and then diluted with water. The organic phase was separated, washed with brine, dried over $MgSO_4$, and then concentrated and purified on silica gel, eluting with 0-80% EtOAc in hexane, to give the desired triflate salt (1.54 g, 30%). LCMS calculated for $C_{13}H_{12}F_3N_2O_5S(M+H)^+$:

m/z=365.1; found: 365.0. ¹H NMR (DMSO-d₆, 400 MHz) δ 9.02 (1H, m), 8.20 (1H, m), 7.83 (1H, d, J=8.4 Hz), 7.57 (1H, d, J=8.4 Hz), 7.52 (1H, m), 3.42 (3H, s), 3.39 (3H, s) ppm.

Step 3. 8-(3,5-difluorophenyl)-N-methoxy-N-methylquinoline-7-carboxamide

To a mixture of 7-{[methoxy(methyl)amino]carbonyl}quinolin-8-yl trifluoromethanesulfonate (0.15 g, 0.41 mmol) and (3,5-difluorophenyl)boronic acid (0.078 g, 0.49 mmol) in 1,4-dioxane (2 mL) was added 1 N solution of sodium carbonate in water (0.62 mL, 34 mmol) and tetrakis(triphenylphosphine)palladium(0) (0.024 g, 0.020 mmol). The mixture was heated at 100° C. overnight. After cooling, the mixture was diluted with ethyl acetate, washed with water, dried over MgSO₄, and concentrated. The residue was purified on silica gel (eluting with 0-80% EtOAc in Hexane) to give the desired product (110 mg, 81.4%). LCMS calculated for $C_{18}H_{15}F_2N_2O_2(M+H)^+$: m/z=329.1; found: 329.0.

Step 4. 1-[8-(3,5-difluorophenyl)quinolin-7-yl]ethanone

To a mixture of 8-(3,5-difluorophenyl)-N-methoxy-N-methylquinoline-7-carboxamide (67 mg, 0.20 mmol) in tetrahydrofuran (0.5 mL) was added 1.40 M methylmagnesium bromide in tetrahydrofuran (0.87 mL, 1.2 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was used directly in next step. LCMS calculated for $C_{17}H_{12}F_2NO(M+H)^+$: m/z=284.1; found: 284.0.

Step 5. 1-[8-(3,5-difluorophenyl)quinolin-7-yl]ethanol

To a mixture of 1-[8-(3,5-difluorophenyl)quinolin-7-yl]ethanone (0.057 g, 0.20 mmol) in methanol (0.5 mL) was added sodium tetrahydroborate (0.0076 g, 0.20 mmol). The reaction was stirred at room temperature for 1 hour, quenched with saturated sodium bicarbonate, and extracted with ethyl acetate. The combined organic layers were washed with brine, dried over magnesium sulfate, and then concentrated to dryness under reduced pressure. The resulting residue was used in next step (48 mg, 84.1%). LCMS calculated for $C_{17}H_{14}F_2NO(M+H)^+$: m/z=286.1; found: 286.0.

Step 6. 7-(1-azidoethyl)-8-(3,5-difluorophenyl)quinoline

To a mixture of 1-[8-(3,5-difluorophenyl)quinolin-7-yl]ethanol (0.048 g, 0.17 mmol) in methylene chloride (1 mL) was added triethylamine (0.0352 mL, 0.252 mmol), followed by methanesulfonyl chloride (0.0163 mL, 0.210 mmol). After stirred at room temperature for 30 minutes, the resultant mixture was diluted with dichloromethane, washed with saturated sodium bicarbonate and brine, dried over magnesium sulfate, and then concentrated to dryness under reduced pressure. The crude mesylate was dissolved in N,N-dimethylformamide (0.5 mL) and treated with sodium azide (0.0547 g, 0.841 mmol) at room temperature overnight. After diluted with ethyl acetate, the mixture was washed with water and brine, dried over magnesium sulfate, and evaporated to dryness. The crude product was used in next step (40 mg, 76%). LCMS calculated for $C_{17}H_{13}F_2N_4(M+H)^+$: m/z=311.1; found: 311.0.

Step 7. 1-[8-(3,5-difluorophenyl)quinolin-7-yl]ethanamine

To a stirred solution of 7-(1-azidoethyl)-8-(3,5-difluorophenyl)quinoline (0.040 g, 0.13 mmol) in tetrahydrofuran (0.4 mL) and water (0.093 mL) was added 1.00 M of trimethylphosphine in tetrahydrofuran (0.155 mL, 0.155 mmol) at room temperature and the mixture was stirred at room temperature for 1 hour. To the mixture was added ethyl acetate and the mixture was extracted with 1 N HCl twice. The combined extracts were neutralized with solid sodium bicarbonate, and extracted with dichloromethane. The combined organic layers were washed with brine, dried over magnesium sulfate, and concentrated under reduced pressure. The residue showed two peaks by LCMS with same desired mass and was used directly in next step (30 mg, 81%). LCMS calculated for $C_{17}H_{15}F_2N_2(M+H)^+$: m/z=285.120; found: 285.0.

Step 8. N-{1-[8-(3,5-difluorophenyl)quinolin-7-yl]ethyl}-9H-purin-6-amine

A mixture of 6-bromo-9H-purine (0.06394 g, 0.3213 mmol), 1-[8-(3,5-difluorophenyl)quinolin-7-yl]ethanamine (0.046 g, 0.16 mmol), and N,N-diisopropylethylamine (0.05596 mL, 0.32 mmol) in ethanol (0.5 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired product as a bis-TFA salt. LCMS calculated for $C_{22}H_{17}F_2N_6(M+H)^+$: m/z=403.1; found: 403.1. ¹H NMR (DMSO-d₆, 400 MHz) δ 9.04 (1H, br s), 8.10 (1H, dd, J=4.0 and 1.6 Hz), 8.38 (2H, dd, J=8.0 and 1.6 Hz), 8.32 (1H, m), 8.06 (1H, m), 7.88 (1H, dd, J=8.4 and 3.2 Hz), 7.53 (1H, dd, J=8.0 and 4.4 Hz), 7.27 (2H, m), 7.08 (1H, d, J=8.8 Hz), 7.00 (1H, dd, J=8.4 and 2.4 Hz), 5.30 (1H, m), 1.53 (3H, d, J=6.8 Hz) ppm. ¹⁹F NMR (DMSO-d₆, 376.28 MHz) δ -74.6 ppm.

Example 7

N-{1-[8-(2-fluorophenyl)quinolin-7-yl]ethyl}-9H-purin-6-amine bis-trifluoroacetate

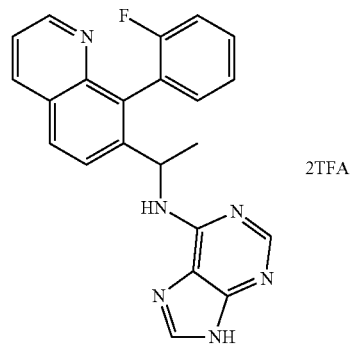 [SMILES: CC(Nc1ncnc2[nH]cnc12)c1ccc2cccnc2c1-c1ccccc1F]

Step 1. 8-(2-fluorophenyl)-N-methoxy-N-methylquinoline-7-carboxamide

To a mixture of 7-{[methoxy(methyl)amino]carbonyl}quinolin-8-yl trifluoromethanesulfonate (0.15 g, 0.41 mmol) and (2-fluorophenyl)boronic acid (0.069 g, 0.49 mmol) in 1,4-dioxane (2 mL) was added 1 N solution of sodium carbonate (0.065 g, 0.62 mmol) in water (0.62 mL, 34 mmol) and tetrakis(triphenylphosphine)palladium(0) (0.024 g, 0.020 mmol). The mixture was heated at 100° C. overnight. After cooling, the mixture was diluted with ethyl acetate, washed with water, dried over MgSO$_4$, and concentrated and purified on silica gel (0-100% EtOAc in Hexane) to give the desired product (100 mg, 78%). LCMS calculated for C$_{18}$H$_{16}$FN$_2$O$_2$(M+H)$^+$: m/z=311.1; found: 311.0.

Step 2. 1-[8-(2-fluorophenyl)quinolin-7-yl]ethanone

To a mixture of 8-(2-fluorophenyl)-N-methoxy-N-methylquinoline-7-carboxamide (63 mg, 0.20 mmol) in tetrahydrofuran (0.5 mL) was added 1.40 M methylmagnesium bromide in tetrahydrofuran (0.87 mL, 1.2 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was used directly in next step. LCMS calculated for C$_{17}$H$_{13}$FNO (M+H)$^+$: m/z=266.1; found: 266.0.

Step 3. 1-[8-(2-fluoropheny)quinolin-7-yl]ethanol

To a mixture of 1-[8-(2-fluorophenyequinolin-7-yl]ethanone (0.053 g, 0.20 mmol) in methanol (0.5 mL) was added sodium tetrahydroborate (0.0076 g, 0.20 mmol). The reaction was stirred at room temperature for 1 hour, quenched with saturated sodium bicarbonate, extracted with ethyl acetate. The combined organic layers were washed with brine, dried over magnesium sulfate, and then concentrated to dryness under reduced pressure. The resulting residue was used in the next step (39 mg, 73%). LCMS calculated for C$_{17}$H$_{15}$FNO (M+H)$^+$: m/z=268.1; found: 268.0.

Step 4. 7-(1-azidoethyl)-8-(2-fluorophenyl)quinoline

To a mixture of 1-[8-(2-fluorophenyl)quinolin-7-yl]ethanol (0.039 g, 0.14 mmol) in methylene chloride (0.9 mL) was added triethylamine (0.0305 mL, 0.22 mmol), followed by methanesulfonyl chloride (0.014 mL, 0.18 mmol). After stirred at room temperature for 30 minutes, the resultant mixture was diluted with dichloromethane, washed with saturated sodium bicarbonate and brine, dried over magnesium sulfate, and then concentrated to dryness under reduced pressure. The crude mesylate was dissolved in N,N-dimethylformamide (0.4 mL) and treated with sodium azide (0.0474 g, 0.73 mmol) at room temperature overnight. After diluting with ethyl acetate, the mixture was washed with water and brine, dried over magnesium sulfate and then evaporated to dryness. The crude product was used in next step (33 mg, 77%). LCMS calculated for C$_{17}$H$_{14}$FN$_4$(M+H)$^+$: m/z=293.1; found: 293.1.

Step 5. 1-[8-(2-fluorophenyl)quinolin-7-yl]ethanamine

To a stirred solution of 7-(1-azidoethyl)-8-(2-fluorophenyl)quinoline (0.033 g, 0.11 mmol) in tetrahydrofuran (0.3 mL) and water (0.0813 mL) was added 1.00 M trimethylphosphine in tetrahydrofuran (0.135 mL, 0.135 mmol) at room temperature and the mixture was stirred at room temperature for 1 hour. To the mixture was added ethyl acetate and the mixture was extracted with 1 N HCl twice. The combined extracts were neutralized with solid sodium bicarbonate, and extracted with dichloromethane. The combined organic layers were washed with brine, dried over magnesium sulfate, and concentrated under reduced pressure. The residue had two peaks with the same desired mass and was used directly in next step (25 mg, 83%). LCMS calculated for C$_{17}$H$_{16}$FN$_2$ (M+H)$^±$: m/z=267.1; found: 267.1.

Step 6. N-{1-[8-(2-fluorophenyl)quinolin-7-yl]ethyl}-9H-purin-6-amine

A mixture of 6-bromo-9H-purine (0.03736 g, 0.19 mmol), 1-[8-(2-fluorophenyl)quinolin-7-yl]ethanamine (0.025 g, 0.094 mmol), and N,N-diisopropylethylamine (0.03270 mL, 0.19 mmol) in ethanol (0.3 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired isomers as bis-TFA salts. The first peak had a retention time of 1.157 minutes, LCMS calculated for C$_{22}$H$_{18}$FN$_6$ (M+H)$^+$: m/z=385.2; found: 385.0. The second peak has a retention time of 1.247 minutes, LCMS calculated for C$_{22}$H$_{18}$FN$_6$(M+H)$^+$: m/z=385.2; found: 385.1. $^1$H NMR (DMSO-d$_6$, 400 MHz) δ 8.76 (1H, m), 8.38 (2H, m), 8.06 (1H, dd, J=8.8 and 7.2 Hz), 7.88 (1H, dd, J=17.6 and 8.8 Hz), 7.67 (1H, m), 7.51 (1H, m), 7.46 (1H, m), 7.31 (3H, m), 5.33 (1H, m), 1.45 (3H, d, J=7.2 Hz) ppm. $^{19}$F NMR (DMSO-d$_6$, 376.28 MHz) δ −74.6 ppm.

Example 8

N-{1-[8-(3-fluorophenyl)quinolin-7-yl]ethyl}-9H-purin-6-amine bis-trifluoroacetate

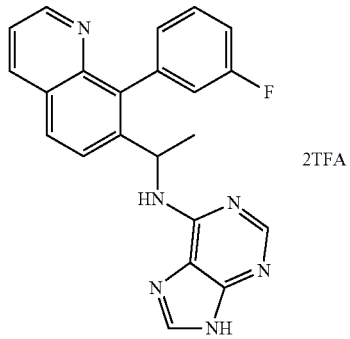 [SMILES: CC(Nc1ncnc2[nH]cnc12)c1ccc2cccnc2c1-c1cccc(F)c1]

Step 1. 7-(1-azidoethyl)-8-(3-fluorophenyl)quinoline

To a mixture of 1-[8-(3-fluorophenyl)quinolin-7-yl]ethanol (0.160 g, 0.598 mmol) (prepared in analogy to Example 7 step 1-4, using (3-fluorophenyl)boronic acid instead of (2-fluorophenyl)boronic acid as starting material) in methylene chloride (4 mL) was added triethylamine (0.125 mL, 0.898 mmol), followed by methanesulfonyl chloride (0.0579 mL, 0.748 mmol). After stirring at room temperature for 30 minutes, the resultant mixture was diluted with dichloromethane, washed with saturated sodium bicarbonate and brine, dried over magnesium sulfate, and then concentrated to dryness under reduced pressure. The crude mesylate was dissolved in N,N-dimethylformamide (2 mL, 20 mmol) and treated with sodium azide (0.194 g, 2.99 mmol) at room temperature overnight. After diluted with ethyl acetate, the mixture was washed with water and brine and then dried over magnesium sulfate and evaporated to dryness. The crude product was used in the next step. LCMS calculated for $C_{17}H_{14}FN_4(M+H)^+$: m/z=293.1; found: 293.0.

Step 3.
1-[8-(3-fluorophenyl)quinolin-7-yl]ethanamine

To a stirred solution of 7-(1-azidoethyl)-8-(3-fluorophenyl)quinoline (0.146 g, 0.500 mmol) in tetrahydrofuran (1 mL) and water (0.360 mL, 20.0 mmol) was added 1.00 M of trimethylphosphine in tetrahydrofuran (0.600 mL, 0.600 mmol) at room temperature and the mixture was stirred at room temperature for 1 hour. To the mixture was added ethyl acetate and the mixture was extracted with 1 N HCl twice. The combined extracts were neutralized with solid sodium bicarbonate, and then extracted with dichloromethane. The combined organic layers were washed with brine, dried over magnesium sulfate, and concentrated under reduced pressure. The residue showed two peaks by LCMS with the same desired mass and was used directly in next step. LCMS calculated for $C_{17}H_{16}FN_2(M+H)^+$: m/z=267.1; found: 267.0.

Step 4. N-{1-[8-(3-fluorophenyl)quinolin-7-yl]ethyl}-9H-purin-6-amine

A mixture of 6-bromo-9H-purine (0.1076 g, 0.5407 mmol), 1-[8-(3-fluorophenyl)quinolin-7-yl]ethanamine (0.072 g, 0.27 mmol), and N,N-diisopropylethylamine (0.05651 mL, 0.3244 mmol) in ethanol (0.9 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired product as a bis-TFA salt. LCMS calculated for $C_{22}H_{18}FN_6(M+H)^+$: m/z=385.2; found: 385.1. $^1$H NMR (DMSO-d$_6$, 400 MHz) δ 9.48 (1H, br s), 8.81 (1H, dd, J=4.4 and 1.6 Hz), 8.53 (1H, s), 8.47 (1H, m), 8.42 (1H, s), 8.08 (1H, d, J=8.8 Hz), 7.87 (1H, m), 7.56 (1H, m), 7.50 (1H, m), 7.39 (1H, m), 7.26~7.13 (3H, m), 5.33 (1H, m), 1.54 (3H, d, J=6.4 Hz) ppm. $^{19}$F NMR (DMSO-d$_5$, 376.28 MHz) δ −74.6 ppm.

Example 9

N-{1-[8-(5-fluoropyridin-3-yl)quinolin-7-yl]ethyl}-9H-purin-6-amine tris-trifluoroacetate

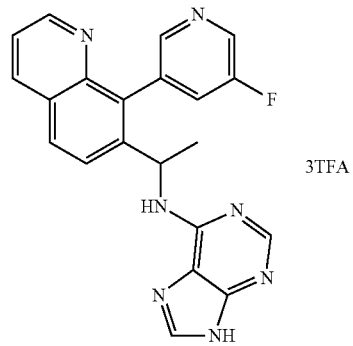 [SMILES: CC(Nc1ncnc2[nH]cnc12)c1ccc2cccnc2c1-c1cncc(F)c1]

3TFA

Step 1. 7-(1-azidoethyl)-8-(5-fluoropyridin-3-yl)quinoline

To a mixture of 1-[8-(5-fluoropyridin-3-yl)quinolin-7-yl]ethanol (0.135 g, 0.503 mmol) (prepared in analogy to Example 7 step 1-4, using 5-fluoropyridin-3-ylboronic acid instead of (2-fluorophenyp)boronic acid as starting material) in methylene chloride (3 mL) was added triethylamine (0.105 mL, 0.755 mmol), followed by methanesulfonyl chloride (0.0487 mL, 0.629 mmol). After stirring at room temperature for 30 minutes, the resultant mixture was diluted with dichloromethane, washed with saturated sodium bicarbonate, brine, dried over magnesium sulfate, then concentrated to dryness under reduced pressure. The crude mesylate was dissolved in N,N-dimethylformamide (2 mL) and treated with sodium azide (0.164 g, 2.52 mmol) at room temperature overnight. After diluting with ethyl acetate, the mixture was washed with water and brine, dried over magnesium sulfate and then evaporated to dryness. The crude product was used in the next step. LCMS calculated for $C_{16}H_{13}FN_5(M+H)^+$: m/z=294.1; found: 294.0.

Step 2. 1-[8-(5-fluoropyridin-3-yl)quinolin-7-yl]ethanamine

To a stirred solution of 7-(1-azidoethyl)-8-(5-fluoropyridin-3-yl)quinoline (0.147 g, 0.500 mmol) in tetrahydrofuran (1 mL) and water (0.360 mL) was added 1.00 M trimethylphosphine in tetrahydrofuran (0.60 mL, 0.60 mmol) at room temperature and the mixture was stirred at room temperature for 1 hour. To the mixture was added ethyl acetate and the mixture was extracted with 1 N HCl twice. The combined extracts were neutralized with solid sodium bicarbonate, and then extracted with dichloromethane. The combined organic layers were washed with brine, dried over magnesium sulfate, and concentrated under reduced pressure. The residue showed two peaks by LCMS with the same desired mass and was used directly in next step (112 mg, 84%). LCMS calculated for $C_{16}H_{15}FN_3(M+H)^+$: m/z=268.1; found: 268.0.

Step 3. N-{1-[8-(5-fluoropyridin-3-yl)quinolin-7-yl]ethyl}-9H-purin-6-amine

A mixture of 6-bromo-9H-purine (0.1072 g, 0.54 mmol), 1-[8-(5-fluoropyridin-3-yl)quinolin-7-yl]ethanamine (0.072 g, 0.27 mmol), and N,N-diisopropylethylamine (0.05630 mL, 0.32) in ethanol (0.9 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired product as a tris-TFA salt. LCMS calculated for $C_{21}H_{17}FN_7(M+H)^+$: m/z=386.2; found: 386.1. $^1$H NMR (DMSO-$d_6$, 400 MHz) δ 9.40 (1H, s), 8.81 (1H, m), 8.65 (1H, s), 8.62 (1H, s), 8.50 (1H, s), 8.41 (2H, m), 8.11 (1H, d, J=8.8 Hz). 7.97~7.84 (2H, m), 7.55 (1H, dd, J=8.4 and 4.4 Hz), 5.25 (1H, m), 1.58 (3H, d, J=6.8 Hz) ppm. $^{19}$F NMR (DMSO-$d_6$, 376.28 MHz) δ −75.0 ppm.

Example 10

N-{1-[5-chloro-8-(2-fluorophenyl)quinolin-7-yl]ethyl}-9H-purin-6-amine bis-trifluoroacetate

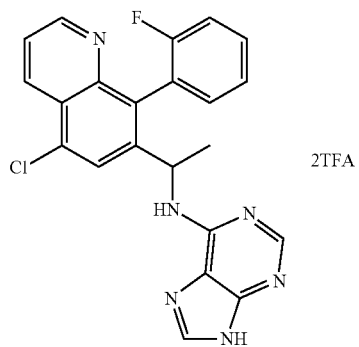 [SMILES: CC(Nc1ncnc2[nH]cnc12)c1cc(Cl)c2cccnc2c1-c1ccccc1F]

Step 1. 5-chloro-8-hydroxy-N-methoxy-N-methylquinoline-7-carboxamide

To a stirred solution of 8-hydroxy-N-methoxy-N-methylquinoline-7-carboxamide (5.00 g, 21.5 mmol) in acetic acid (100 mL) was added N-chlorosuccinimide (3.16 g, 23.7 mmol) and the resulting mixture heated at 100° C. for 18 hours. After allowing the mixture to cool to ambient temperature, the reaction mixture was concentrated in vacuo, then neutralized with saturated sodium bicarbonate, and then extracted with ethyl acetate. The combined organic layers were washed with brine, dried over sodium sulfate, and then concentrated to dryness under reduced pressure. The residue was purified on silica gel, eluting with 0 to 10% methanol in dichloromethane, to give the desired product (4.68 g, 81%). LCMS calculated for $C_{12}H_{12}ClN_2O_3(M+H)^+$: m/z=267.1; found: 267.0. $^1$H NMR (DMSO-$d_6$, 400 MHz) δ 90.4 (1H, dd, J=4.0 and 1.2 Hz), 8.61 (1H, dd, J=8.8 and 1.6 Hz), 7.92 (1H, s), 7.80 (1H, dd, J=8.8 and 4.4 Hz), 3.45 (3H, s), 3.30 (4H, br s) ppm.

Step 2. 5-chloro-7-{[methoxy(methyl)amino]carbonyl}quinolin-8-yl trifluoromethanesulfonate To a mixture of 5-chloro-8-hydroxy-N-methoxy-N-methylquinoline-7-carboxamide (5.30 g, 19.9 mmol) in methylene chloride (100 mL) was added N,N-diisopropylethylamine (5.192 mL, 29.81 mmol), followed by trifluoromethanesulfonic anhydride (4.012 mL, 23.85 mmol) dropwise at −78° C. The reaction was stirred at −78° C. for 30 min and then allowed to warm to 0° C. The mixture was then diluted with dichloromethane and washed with water and brine and dried over sodium sulfate. After evaporating to dryness, the resulting residue was purified on silica gel, eluting with 0 to 80% EtOAc in hexane, to give the desired product (5.36 g, 67%). LCMS calculated for $C_{13}H_{11}ClF_3N_2O_5S(M+H)^+$: m/z=399.0; found: 399.0.

Step 3. 5-chloro-8-(2-fluorophenyl)-N-methoxy-N-methylquinoline-7-carboxamide To a mixture of 5-chloro-7-{[methoxy(methyl)amino]carbonyl}quinolin-8-yl trifluoromethanesulfonate (0.16 g, 0.41 mmol) and (2-fluorophenyl)boronic acid (0.069 g, 0.49 mmol) in 1,4-dioxane (2 mL) was added 1 N solution of sodium carbonate in water (0.62 mL, 34 mmol) and tetrakis(triphenylphosphine)palladium(0) (0.024 g, 0.020 mmol). The mixture was heated at 100° C. overnight. After cooling, the mixture was diluted with ethyl acetate, washed with water, dried over MgSO$_4$, and then concentrated. The residue was purified on silica gel (eluting with 0-60% EtOAc in Hexane) to give the desired compound as a bis-trifluoroacetate salt (42 mg, 29%). LCMS calculated for $C_{18}H_{15}ClFN_2O_2(M+H)^+$: m/z=345.1; found: 345.0.

Step 4. 1-[5-chloro-8-(2-fluorophenyl)quinolin-7-yl]ethanone

To a mixture of 5-chloro-8-(2-fluorophenyl)-N-methoxy-N-methylquinoline-7-carboxamide (40 mg, 0.1 mmol) in tetrahydrofuran (0.2 mL) was added 1.40 M methylmagnesium bromide in tetrahydrofuran (0.50 mL, 0.70 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was used directly in next step (32 mg, 92%). LCMS calculated for $C_{17}H_{12}ClFNO(M+H)$': m/z=300.1; found: 284.0.

Step 5. 1-[5-chloro-8-(2-fluorophenyl)quinolin-7-yl]ethanol

To a mixture of 1-[5-chloro-8-(2-fluorophenyl)quinolin-7-yl]ethanone (0.032 g, 0.11 mmol) in methanol (0.3 mL) was added sodium tetrahydroborate (0.0040 g, 0.11 mmol). The reaction was stirred at room temperature for 1 hour, quenched with saturated sodium bicarbonate and extracted with ethyl acetate. The combined organic layers were washed with brine, dried over magnesium sulfate, and then concentrated to dryness under reduced pressure. The resulting residue was used in next step (33 mg, 100%). LCMS calculated for $C_{17}H_{14}ClFNO(M+H)^+$: m/z=302.1; found: 302.0.

Step 6. 7-(1-azidoethyl)-5-chloro-8-(2-fluorophenyl)quinoline

To a mixture of 1-[5-chloro-8-(2-fluorophenyl)quinolin-7-yl]ethanol (0.044 g, 0.14 mmol) in methylene chloride (0.9 mL) was added triethylamine (0.0305 mL, 0.219 mmol), followed by methanesulfonyl chloride (0.0141 mL, 0.182 mmol). After stirring at room temperature for 30 minutes, the resultant mixture was diluted with dichloromethane, washed with saturated sodium bicarbonate and brine, dried over magnesium sulfate, and then concentrated to dryness under reduced pressure. The resulting residue was used directly in next step. LCMS (M+H)$^+$ m/z=380.0. The crude mesylate was dissolved in N,N-dimethylformamide (0.4 mL) and treated with sodium azide (0.0474 g, 0.730 mmol) at 60° C. for 1 hour. After diluting with ethyl acetate, the mixture was washed with water and brine and then dried over magnesium sulfate and evaporated to dryness. The crude product was used in the next step. LCMS calculated for $C_{17}H_{13}ClFN_4(M+H)^+$: m/z=327.1; found: 327.0.

Step 7. 1-[5-chloro-8-(2-fluorophenyl)quinolin-7-yl]ethanamine

To a stirred solution of 7-(1-azidoethyl)-5-chloro-8-(2-fluorophenyl)quinoline (0.037 g, 0.11 mmol) in tetrahydrofuran (0.3 mL) and water (0.0813 mL) was added 1.00 M trimethylphosphine in tetrahydrofuran (0.135 mL, 0.135 mmol) at room temperature and the mixture was stirred at room temperature for 1 hour. To the mixture was added ethyl acetate and the mixture was extracted with 1 N HCl twice. The combined extracts were neutralized with solid sodium bicarbonate, and extracted with dichloromethane. The combined organic layers were washed with brine, dried over magnesium sulfate, and concentrated under reduced pressure. The residue showed two peaks by LCMS with the same desired mass and was used directly in the next step (28 mg, 82%). LCMS calculated for $C_{17}H_{15}ClFN_2(M+H)^+$: m/z=301.1; found: 301.0.

Step 8. N-{1-[5-chloro-8-(2-fluorophenyl)quinolin-7-yl]ethyl}-9H-purin-6-amine

A mixture of 6-bromo-9H-purine (0.0374 g, 0.188 mmol), 1-[5-chloro-8-(2-fluorophenyl)quinolin-7-yl]ethanamine (0.028 g, 0.094 mmol), and N,N-diisopropylethylamine (0.0327 mL, 0.188 mmol) in ethanol (0.3 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired isomers as bis-TFA salts. The first peak had a retention time of 1.725 minutes, LCMS calculated for $C_{22}H_{17}ClFN_6(M+H)^+$: m/z=419.1; found: 419.0. The second peak had a retention time of 1.831 minutes, LCMS calculated for $C_{22}H_{17}ClFN_6(M+H)^+$: m/z=419.1; found: 419.1. $^1$H NMR (DMSO-d$_6$, 400 MHz) δ 8.87 (1H, m), 8.54 (1H, m), 8.24 (2H, m), 8.10 (1H, s), 7.74 (1H, m), 7.65 (1H, dd, J=8.8 and 4.4 Hz), 7.49 (1H, m), 7.32 (2H, m), 5.34 (1H, m), 1.41 (3H, d, J=7.2 Hz) ppm. $^{19}$F NMR (DMSO-d$_6$, 376.28 MHz) δ -74.2 ppm.

Example 11

N-(1-{5-chloro-8-[4-(2-methoxyethyl)piperazin-1-yl]quinolin-7-yl}ethyl)-9H-purin-6-amine tris-trifluoroacetate

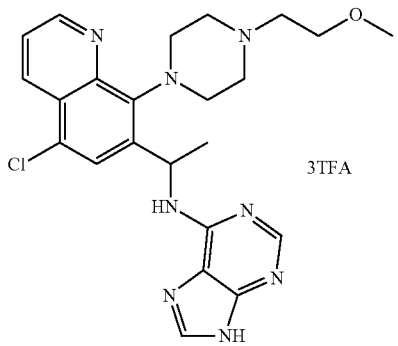 [SMILES: COCCN1CCN(c2c(C(C)Nc3ncnc4[nH]cnc34)cc(Cl)c3cccnc23)CC1]

Step 1. 5-chloro-N-methoxy-8-[4-(2-methoxyethyl)piperazin-1-yl]-N-methylquinoline-7-carboxamide A stirred mixture of 5-chloro-7-{[methoxy(methyl)amino]carbonyl}quinolin-8-yl trifluoromethanesulfonate (0.120 g, 0.301 mmol), 1-(2-methoxyethyl)piperazine (0.0522 g, 0.362 mmol, from Aldrich), palladium acetate (1 mg, 0.006 mmol), 2,2'-bis(diphenylphosphino)-1,1'-binaphthyl (6 mg, 0.009 mmol), and cesium carbonate (0.14 g, 0.42 mmol) in tetrahydrofuran (3 mL) was heated at 65° C. overnight. The mixture was cooled, diluted with dichloromethane, and filtered. The filtrate was washed with brine, dried over sodium sulfate, and evaporated to dryness. The resultant residue was purified on silica gel, eluting with 0 to 10% MeOH in dichloromethane, to give the desired product (63 mg, 53%). LCMS calculated for $C_{19}H_{26}ClN_4O_3(M+H)^+$: m/z=393.2; found: 393.1.

Step 2. 1-{5-chloro-8-[4-(2-methoxyethyl)piperazin-1-yl]quinolin-7-yl}ethanone

To a mixture of 5-chloro-N-methoxy-8-[4-(2-methoxyethyl)piperazin-1-yl]-N-methylquinoline-7-carboxamide (63 mg, 0.16 mmol) in tetrahydrofuran (0.2 mL) was added 1.40 M methylmagnesium bromide in tetrahydrofuran (0.69 mL, 0.96 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was purified on silica gel, eluting with 0 to 10% MeOH in dichloromethane, to give the desired product (22 mg, 39%). LCMS calculated for $C_{18}H_{23}ClN_3O_2(M+H)^+$: m/z=348.1; found: 348.1.

Step 3. 1-{5-chloro-8-[4-(2-methoxyethyl)piperazin-1-yl]quinolin-7-yl}ethanamine A mixture of 1-{5-chloro-8-[4-(2-methoxyethyl)piperazin-1-yl]quinolin-7-yl}ethanone (22 mg, 0.063 mmol) and ammonium acetate (48.8 mg, 0.632 mmol) in methanol (0.36 mL) and acetonitrile (0.36 mL) was heated at 65° C. in a sealed tube for 30 minutes. After cooling, sodium cyanoborohydride (7.95 mg, 0.126 mmol) was added to the resultant mixture. The reaction was heated at 65° C. for another 4 hours, then cooled to room temperature, quenched with saturated sodium bicarbonate, and extracted with dichloromethane. The combined extracts were dried over magnesium sulfate and evaporated to dryness (22 mg, 99%). The residue was used directly in the next step. LCMS calculated for $C_{18}H_{26}ClN_4O(M+H)^+$: m/z=349.2; found: 349.1.

Step 4. N-(1-{5-chloro-8-[4-(2-methoxyethyl)piperazin-1-yl]quinolin-7-yl}ethyl)-9H-purin-6-amine A mixture of 6-bromo-9H-purine (0.0274 g, 0.138 mmol), 1-{5-chloro-8-[4-(2-methoxyethyl)piperazin-1-yl]quinolin-7-yl}ethanamine (0.024 g, 0.069 mmol), and N,N-diisopropylethylamine (0.02396 mL, 0.1376 mmol) in ethanol (0.2 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired product as a tris-TFA salt. LCMS calculated for $C_{23}H_{28}ClN_8O(M+H)^+$: m/z=467.2; found: 467.1. $^1$H NMR (DMSO-d$_6$, 400 MHz) δ 9.70 (1H, br s), 8.98 (1H, s), 8.50 (1H, d, J=8.0 Hz), 8.21 (2H, m), 8.02

(1H, s), 7.66 (1H, dd, J=8.4 and 4.4 Hz), 6.41 (1H, m), 4.42~3.02 (12H, m), 3.33 (3H, s), 1.55 (3H, d, J=6.4 Hz) ppm.

Example 12

(3R)-1-{5-chloro-7-[1-(9H-purin-6-ylamino)ethyl]quinolin-8-yl}pyrrolidin-3-ol bis-trifluoroacetate

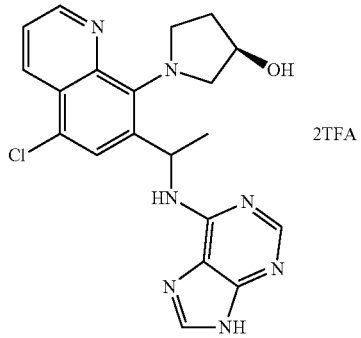 [SMILES: CC(Nc1ncnc2[nH]cnc12)c1cc(Cl)c2cccnc2c1N1CC[C@@H](O)C1]

Step 1. 5-chloro-8-[(3R)-3-hydroxypyrrolidin-1-yl]-N-methoxy-N-methylquinoline-7-carboxamide A stirred mixture of 5-chloro-7-{[methoxy(methyl)amino]carbonyl}quinolin-8-yl trifluoromethanesulfonate (0.150 g, 0.376 mmol), (3R)-pyrrolidin-3-ol (0.0394 g, 0.452 mmol, Aldrich), palladium acetate (2 mg, 0.008 mmol), 2,2'-bis(diphenylphosphino)-1,1'-binaphthyl (7 mg, 0.01 mmol), and cesium carbonate (0.343 g, 1.05 mmol) in tetrahydrofuran (4 mL) was heated at 65° C. overnight. The mixture was cooled, diluted with dichloromethane, washed with brine, dried over sodium sulfate, and evaporated to dryness. The resultant residue was purified on silica gel, eluting with 0 to 10% MeOH in dichloromethane, to give the desired product (115 mg, 91%). LCMS calculated for $C_{16}H_{19}ClN_3O_3(M+H)^+$: m/z=336.1; found: 336.1.

Step 2. 1-{5-chloro-8-[(3R)-3-hydroxypyrrolidin-1-yl]quinolin-7-yl}ethanone

To a mixture of 5-chloro-8-[(3R)-3-hydroxypyrrolidin-1-yl]-N-methoxy-N-methylquinoline-7-carboxamide (115 mg, 0.342 mmol) in tetrahydrofuran (0.5 mL) was added 1.40 M methylmagnesium bromide in tetrahydrofuran (1.5 mL, 2.0 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was purified on silica gel, eluting with 0 to 10% MeOH in dichloromethane, to give the desired product (95 mg, 95%). LCMS calculated for $C_{15}H_{16}ClN_2O_2(M+H)^+$: m/z=291.1; found: 291.1.

Step 3. (3R)-1-[7-(1-aminoethyl)-5-chloroquinolin-8-yl]pyrrolidin-3-ol

A mixture of 1-{5-chloro-8-[(3R)-3-hydroxypyrrolidin-1-yl]quinolin-7-yl}ethanone (95 mg, 0.33 mmol) and ammonium acetate (252 mg, 3.27 mmol) in methanol (1.8 mL) and acetonitrile (1.9 mL) was heated at 65° C. in a sealed tube for 30 minutes. After cooling, sodium cyanoborohydride (41.1 mg, 0.653 mmol) was added to the resultant mixture. The reaction was heated at 65° C. for another 4 hours, then cooled to room temperature and quenched with saturated sodium bicarbonate. The mixture was then extracted with dichloromethane. The combined extracts were dried over magnesium sulfate and evaporated to dryness (58 mg, 60%). The residue was used directly in the next step. LCMS calculated for $C_{15}H_{19}ClN_3O(M+H)^+$: m/z=292.1; found: 292.1.

Step 4. (3R)-1-(5-chloro-7-[1-(9H-purin-6-ylamino)ethyl]quinolin-8-yl}pyrrolidin-3-ol A mixture of 6-bromo-9H-purine (0.0791 g, 0.398 mmol), (3R)-1-[7-(1-aminoethyl)-5-chloroquinolin-8-yl]pyrrolidin-3-ol (0.058 g, 0.20 mmol), and N,N-diisopropylethylamine (0.0693 mL, 0.398 mmol) in ethanol (0.7 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired diastereomers as bis-TFA salts. The first peak has a retention time of 1.303 minutes, LCMS calculated for $C_{20}H_{21}ClN_7O(M+H)^+$: m/z=410.2; found: 410.1. $^1$H NMR (DMSO-d$_6$, 400 MHz) δ 8.95 (1H, dd, J=4.4 and 2.0 Hz), 8.56 (1H, dd, J=8.4 and 1.6 Hz), 8.33 (2H, m), 7.94 (1H, s), 7.68 (1H, dd, J=8.8 and 4.4 Hz), 6.25 (1H, m), 4.52 (1H, m), 3.74~3.38 (5H, m), 2.26 (1H, m), 1.98 (1H, m), 1.59 (3H, d, J=7.2 Hz) ppm. The second peak had a retention time of 1.373 minutes, LCMS calculated for $C_{20}H_{21}ClN_7O(M+H)^+$: m/z=410.2; found: 410.1. $^1$H NMR (DMSO-d$_6$, 400 MHz) δ 8.96 (1H, dd, J=4.0 and 1.6 Hz), 8.55 (1H, dd, J=8.8 and 2.0 Hz), 8.31 (2H, m), 7.95 (1H, s), 7.67 (1H, dd, J=8.4 and 4.4 Hz), 6.25 (1H, m), 4.52 (1H, m), 3.77~3.20 (5H, m), 2.28 (1H, m), 1.98 (1H, m), 1.59 (3H, d, J=7.2 Hz) ppm.

Example 13

N-((3S)-1-{5-chloro-7-[1-(9H-purin-6-ylamino)ethyl]quinolin-8-yl}pyrrolidin-3-yl}acetamide bis-trifluoroacetate

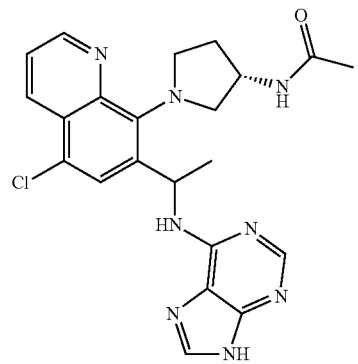 [SMILES: CC(=O)N[C@H]1CCN(c2c(C(C)Nc3ncnc4[nH]cnc34)cc(Cl)c3cccnc23)C1]

Step 1. 8-[(3S)-3-(acetylamino)pyrrolidin-1-yl]-5-chloro-N-methoxy-N-methylquinoline-7-carboxamide A stirred mixture of 5-chloro-7-{[methoxy(methyl)amino]carbonyl}quinolin-8-yl trifluoromethanesulfonate (0.120 g, 0.301 mmol), N-[(3S)-pyrrolidin-3-yl]acetamide (0.0464 g, 0.362 mmol, Lancaster), palladium acetate (1 mg, 0.006 mmol), 2,2'-bis(diphenylphosphino)-1,1'-binaphthyl (6 mg, 0.009 mmol), and cesium carbonate (0.274 g, 0.843 mmol) in tetrahydrofuran (3 mL) was heated at 65° C. overnight. The mixture was cooled, diluted with dichloromethane, and filtered. The filtrate was washed with brine, dried over sodium sulfate, and evaporated to dryness. The resultant residue was purified on silica gel, eluting with 0 to 10% MeOH in dichloromethane, to give the desired product (75 mg, 66%). LCMS calculated for $C_{18}H_{22}ClN_4O_3(M+H)^+$: m/z=377.1; found: 377.1.

Step 2. N-[(3S)-1-(7-acetyl-5-chloroquinolin-8-yl)pyrrolidin-3-yl]acetamide

To a mixture of 8-[(3S)-3-(acetylamino)pyrrolidin-1-yl]-5-chloro-N-methoxy-N-methylquinoline-7-carboxamide (75 mg, 0.20 mmol) in tetrahydrofuran (0.3 mL) was added 1.40 M methylmagnesium bromide in tetrahydrofuran (0.85 mL, 1.2 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was purified on silica gel, eluting with 0 to 10% MeOH in dichloromethane, to give the desired product (22 mg, 33%). LCMS calculated for $C_{17}H_{19}ClN_3O_2(M+H)^+$: m/z=332.1; found: 332.1.

Step 3. N-{(3S)-1-[7-(1-aminoethyl)-5-chloroquinolin-8-yl]pyrrolidin-3-yl}acetamide A mixture of N-[(3S)-1-(7-acetyl-5-chloroquinolin-8-yl)pyrrolidin-3-yl]acetamide (22 mg, 0.066 mmol) and ammonium acetate (51.1 mg, 0.663 mmol) in methanol (0.37 mL) and acetonitrile (0.38 mL) was heated at 65° C. in a sealed tube for 30 minutes. After cooling, sodium cyanoborohydride (8.33 mg, 0.133 mmol) was added to the resultant mixture. The reaction was heated at 65° C. for another 4 hours, then cooled to room temperature, quenched with saturated sodium bicarbonate, and extracted with dichloromethane. The combined extracts were dried over magnesium sulfate and evaporated to dryness (17 mg, 77%). The residue was used directly in the next step. LCMS calculated for $C_{17}H_{22}ClN_4O(M+H)^+$: m/z=333.1; found: 333.1.

Step 4. N-((3S)-1-{5-chloro-7-[7-(9H-purin-6-ylamino)ethyl]quinolin-8-yl}pyrrolidin-3-yl)acetamide A mixture of 6-bromo-9H-purine (0.0203 g, 0.102 mmol), N-{(3S)-1-[7-(1-aminoethyl)-5-chloroquinolin-8-yl]pyrrolidin-3-yl}acetamide (0.017 g, 0.051 mmol), and N,N-diisopropylethylamine (0.01779 mL, 0.1022 mmol) in ethanol (0.2 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the products as a mixture of diastereoisomers (bis-TFA salts). LCMS calculated for $C_{22}H24ClN_8O(M+H)^+$: m/z=451.2; found: 451.1. $^1$H NMR (DMSO-d$_6$, 400 MHz) δ 8.99 (1H, dd, J=4.0 and 1.2 Hz), 8.88 (1H, br s), 8.53 (1H, dd, J=8.4 and 1.2 Hz), 8.31 (2H, m), 7.96 (1H, s), 7.66 (1H, dd, J=8.8 and 4.0 Hz), 6.29 (1H, m), 4.54 (1H, m), 3.78 (3H, m), 3.63 (1H, m), 3.42 (1H, m), 2.31 (1H, m), 1.98 (1H, m), 1.86 and 1.84 (3H, 2 singlet in ratio 1:2), 1.58 (3H, d, J=6.8 Hz) ppm.

Example 14

N-(1-{5-chloro-8-[(2R)-2-(methoxymethyl)pyrrolidin-1-yl]quinolin-7-yl}ethyl)-9H-purin-6-amine bis-trifluoroacetate

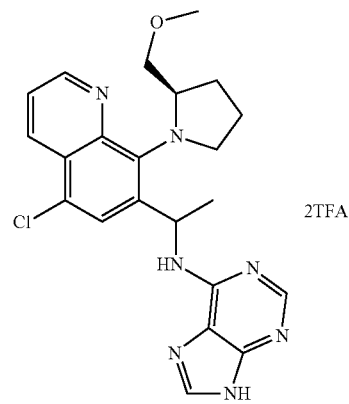 [SMILES: COC[C@H]1CCCN1c1c(C(C)Nc2ncnc3[nH]cnc23)cc(Cl)c2cccnc12]

Step 1. 5-chloro-N-methoxy-8-[(2R)-2-(methoxymethyl)pyrrolidin-1-yl]-N-methylquinoline-7-carboxamide A stirred mixture of 5-chloro-7-{[methoxy(methyl)amino]carbonyl}quinolin-8-yl trifluoromethanesulfonate (0.150 g, 0.376 mmol), (2R)-2-(methoxymethyl)pyrrolidine (0.0521 g, 0.452 mmol, Fluka), palladium acetate (2 mg, 0.008 mmol), 2,2'-bis(diphenylphosphino)-1,1'-binaphthyl (7 mg, 0.01 mmol), and cesium carbonate (0.343 g, 1.05 mmol) in tetrahydrofuran (4 mL) was heated at 65° C. overnight. The mixture was cooled, diluted with dichloromethane, and filtered. The filtrate was washed with brine, dried over sodium sulfate, and evaporated to dryness. The resultant residue was purified on silica gel, eluting with 0 to 10% MeOH in dichloromethane, to give the desired product (132 mg, 96%). LCMS calculated for $C_{18}H_{23}ClN_3O_3(M+H)^+$: m/z=364.1; found: 364.1.

Step 2. 1-{5-chloro-8-[(2R)-2-(methoxymethyl)pyrrolidin-1-yl]quinolin-7-yl}ethanone To a mixture of 5-chloro-N-methoxy-8-[(2R)-2-(methoxymethyl)pyrrolidin-1-yl]-N-methylquinoline-7-carboxamide (132 mg, 0.363 mmol) in tetrahydrofuran (0.5 mL) was added 1.40 M methylmagnesium bromide in tetrahydrofuran (1.6 mL, 2.2 mmol). The reaction was stirred at room temperature overnight, quenched with saturated ammonium chloride, and extracted with ethyl acetate. The combined organic layers were washed with brine, dried over magnesium sulfate, then concentrated to dryness under reduced pressure. The resultant residue was purified on silica gel, eluting with 0 to 10% methanol in dichloromethane, to give the desired product (14 mg, 12%). LCMS calculated for $C_{17}H_{20}ClN_2O_2(M+H)^+$: m/z=319.1; found: 319.1.

Step 3. 1-{5-chloro-8-[(2R)-2-(methoxymethyl)pyrrolidin-1-yl]quinolin-7-yl}ethanamine A mixture of 1-{5-chloro-8-[(2R)-2-(methoxymethyl)pyrrolidin-1-yl]quinolin-7-yl}ethanone (14 mg, 0.044 mmol) and ammonium acetate (33.8 mg, 0.439 mmol) in methanol (0.25 mL,) and acetonitrile (0.25 mL) was heated at 65° C. in a sealed tube for 30 minutes. After cooling, sodium cyanoborohydride (5.52 mg, 0.0878 mmol) was added to the resultant mixture. The reaction was heated at 65° C. for another 4 hours, then cooled to room temperature, quenched with saturated sodium bicarbonate, and extracted with dichloromethane. The combined extracts were dried over magnesium sulfate and evaporated to dryness. The residue was used directly in the next step. LCMS calculated for $C_{17}H_{23}ClN_3O$ $(M+H)^+$: m/z=320.2; found: 302.1.

Step 4. N-(1-{5-chloro-8-[(2R)-2-(methoxymethyl)pyrrolidin-1-yl]quinolin-7-yl}ethyl)-9H-purine-6-amine A mixture of 6-bromo-9H-purine (0.0174 g, 0.0876 mmol), 1-{5-chloro-8-[(2R)-2-(methoxymethyl)pyrrolidin-1-yl]quinolin-7-yl}ethanamine (0.014 g, 0.044 mmol), and N,N-diisopropylethylamine (0.01525 mL, 0.0876 mmol) in ethanol (0.1 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the product as a mixture of diastereoisomers (bis-TFA salts). LCMS calculated for $C_{22}H_{25}ClN_7O(M+H)^+$: m/z=438.2; found: 438.2.

Example 15

N-{1-[5-chloro-8-(3-fluorophenyl)quinolin-7-yl]ethyl}-9H-purin-6-amine bis-trifluoroacetate

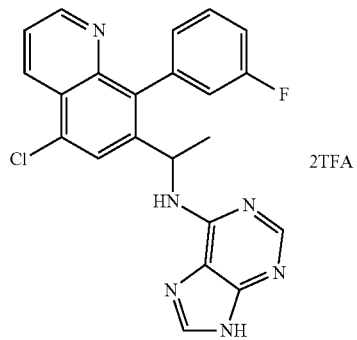 [SMILES: CC(Nc1ncnc2[nH]cnc12)c1cc(Cl)c2cccnc2c1-c1cccc(F)c1]

Step 1. 5-chloro-8-(3-fluorophenyl)-N-methoxy-N-methylquinoline-7-carboxamide To a mixture of 5-chloro-7-{[methoxy(methyl)amino]carbonyl}quinolin-8-yl trifluoromethanesulfonate (0.200 g, 0.502 mmol) in tetrahydrofuran (5 mL) was added 0.50 M (3-fluorophenyl)(iodo)zinc in tetrahydrofuran (1.20 mL, 0.602 mmol) with stirring, followed by addition of tetrakis(triphenylphosphine)palladium(0) (29.0 mg, 0.0251 mmol). The reaction mixture was heated at 60° C. overnight. After cooling to room temperature, the mixture was filtered and concentrated under reduced pressure. The crude mixture was purified on silica gel, eluting with 0 to 60% EtOAc in hexane, to give the desired product (154 mg, 89%). LCMS calculated for $C_{18}H_{15}ClFN_2O_2(M+H)^+$: m/z=345.1; found: 345.0.

Step 2. 1-[5-chloro-8-(3-fluorophenyl)quinolin-7-yl]ethanone

To a mixture of 5-chloro-8-(3-fluorophenyl)-N-methoxy-N-methylquinoline-7-carboxamide (154 mg, 0.447 mmol) and 5-chloro-7-{[methoxy(methyl)amino]carbonyl}quinolin-8-yl trifluoromethanesulfonate (154 mg, 0.386 mmol) in tetrahydrofuran (1 mL) was added 1.40 M methylmagnesium bromide in tetrahydrofuran (3.8 mL, 5.3 mmol). The reaction was stirred at room temperature overnight, quenched with saturated ammonium chloride, and extracted with ethyl acetate. The combined organic layers were washed with brine, dried over magnesium sulfate, and then concentrated to dryness under reduced pressure. The resultant residue was purified on silica gel, eluting with 0 to 50% of EtOAc in hexane, to give the desired product (38 mg, 32%). LCMS calculated for $C_{17}H_{12}ClFNO(M+H)^+$: m/z=300.1; found: 300.0.

Step 3. 1-[5-chloro-8-(3-fluorophenyl)quinolin-7-yl]ethanamine

A mixture of 1-[5-chloro-8-(3-fluorophenyl)quinolin-7-yl]ethanone (76 mg, 0.25 mmol) and ammonium acetate (195 mg, 2.54 mmol) in methanol (1.4 mL) and acetonitrile (1.4 mL) was heated at 65° C. in a sealed tube for 30 minutes. After cooling, sodium cyanoborohydride (31.9 mg, 0.507 mmol) was added to the resultant mixture. The reaction was heated at 65° C. for another 4 hours, then cooled to room temperature, quenched with saturated sodium bicarbonate, and extracted with dichloromethane. The combined extracts were dried over magnesium sulfate and then evaporated to dryness. The residue was used directly in next step (52 mg, 68%). LCMS calculated for $C_{17}H_{15}ClFN_2(M+H)^+$: m/z=301.1; found: 301.0.

Step 4. N-{1-[5-chloro-8-(3-fluorophenyl)quinolin-7-yl]ethyl}-9H-purin-6-amine A mixture of 6-bromo-9H-purine (0.0688 g, 0.346 mmol), 1-[5-chloro-8-(3-fluorophenyl)quinolin-7-yl]ethanamine (0 052 g, 0.17 mmol), and N,N-diisopropylethylamine (0.0602 mL, 0.346 mmol) in ethanol (0.6 mL) was heated at reflux under nitrogen overnight. The mixture was evaporated and the resultant residue was purified on RP-HPLC (XBridge C18 column, eluting with a gradient of acetonitrile/water containing 0.05% TFA, at flow rate of 30 mL/minute) to give the desired product as bis-TFA salt. LCMS calculated for $C_{22}H_{17}ClFN_6(M+H)^+$: m/z=419.1; found: 419.0. $^1$H NMR (DMSO-$d_6$, 400 MHz) δ 9.04 (1H, br s), 8.88 (1H, dd, J=4.0 and 1.6 Hz), 8.54 (1H, dd, J=8.4 and 1.6 Hz), 8.40 (1H, m), 7.42 91H, m), m), 8.06 (1H, d, J=7.6 Hz), 7.66 (1H, dd, J=8.4 Hz and 4.0 Hz), 7.50 (1H, m), 7.42 (1H, m), 7.25 (1H, m), 7.15 (1H, m), 5.30 (1H, m), 1.50 (3H, d, J=6.8 Hz) ppm. $^{19}$F NMR (DMSO-d$_6$, 376.28 MHz) δ −75.0 ppm.

Example 16

N-{1-[5-Chloro-8-(3-fluorophenyl)cinnolin-7-yl]ethyl}-9H-purin-6-amine

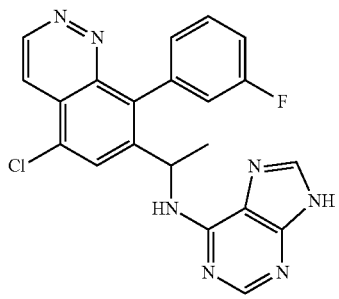

Step A: Methyl 5-chloro-2-hydroxy-4-iodobenzoate

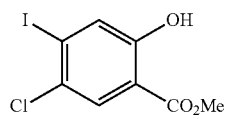

A solution of methyl 2-hydroxy-4-iodobenzoate (50 g, 0.18 mol) [Aldrich, 652636] in acetic acid (360 mL) was treated with N-chlorosuccinimide (29 g, 0.22 mol) and heated at 100° C. for 1 hour. The reaction mixture was cooled until the internal temperature was 19° C. and then the solid that precipitated was filtered, washed with cold acetic acid, and air dried. The solid was diluted with toluene and concentrated (2×200 mL) to remove residual acetic acid to give 34.8 g of the desired product. The filtrate was concentrated, and the residue was purified by flash column chromatography using ethyl acetate in hexanes (0%-20%) to give an additional 8.6 g of desired product (total yield=43 g, 77%). LCMS for C$_8$H$_7$ClIO$_3$ (M+H)$^+$: m/z=312.9; Found: 313.0.

Step B: Methyl 5-chloro-2-hydroxy-4-[(trimethylsilyl)ethynyl]benzoate

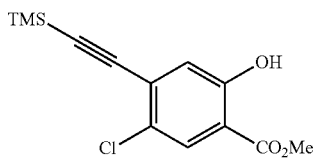 [SMILES: COC(=O)c1cc(Cl)c(C#C[Si](C)(C)C)cc1O]

A solution of copper (I) iodide (1.1 g, 5.8 mmol) in triethylamine (32 mL) was degassed with nitrogen, treated with (trimethylsilyl)acetylene (4.5 mL, 32 mmol), degassed with nitrogen, and stirred at 20° C. for 10 minutes. The reaction mixture was treated with bis(triphenylphosphine)palladium (II) chloride (0.56 g, 0.80 mmol), degassed with nitrogen, and stirred at 20° C. for 30 minutes. The reaction mixture was treated with methyl 5-chloro-2-hydroxy-4-iodobenzoate (5.0 g, 16 mmol), degassed with nitrogen, and stirred at 75° C. for 2 hours. The reaction mixture was filtered over celite, washed with ethyl acetate, and concentrated to a crude residue. Purification via flash column chromatography using ethyl acetate in hexanes (0%-20%) gave the desired product (4.31 g, 95%). LCMS for C$_{13}$H$_{16}$ClO$_3$Si (M+H)$^+$: m/z=283.1; Found: 282.9.

Step C: Methyl 5-chloro-2-hydroxy-3-nitro-4-[(trimethylsilyl)ethynyl]benzoate

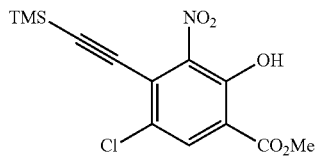 [SMILES: COC(=O)c1cc(Cl)c(C#C[Si](C)(C)C)c([N+](=O)[O-])c1O]

A solution of methyl 5-chloro-2-hydroxy-4-[(trimethylsilyl)ethynyl]benzoate (15 g, 53 mmol) in acetic acid (110 mL) at 55° C. was treated with a solution of nitric acid (7.8 mL, 190 mmol) in acetic acid (7.8 mL, 140 mmol) dropwise and stirred at 55° C. for 30 minutes. The reaction mixture contained only starting material and was treated with an additional solution of nitric acid (2.2 mL, 53 mmol) in acetic acid (2.2 mL, 39 mmol) dropwise and stirred at 55° C. for 1.5 hour. The reaction mixture was cooled to 0° C. and treated with ice followed by cold water. The reaction mixture was stirred until the ice melted, filtered, washed with cold water, and air dried to give the desired product (11.7 g, 67%) as a tan solid. This material was used without further purification. LCMS for C$_{13}$H$_{15}$ClNO$_5$Si (M+H)$^+$: m/z=328.0; Found: 327.8.

Step D: Methyl 5-chloro-3-nitro-2-{[(trifluoromethyl)sulfonyl]oxy}-4-[(trimethylsilyl)ethynyl]benzoate

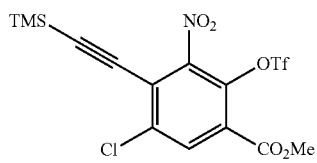

A solution of methyl 5-chloro-2-hydroxy-3-nitro-4-[(trimethylsilyl)ethynyl]benzoate (8.0 g, 24 mmol) in dichloromethane (170 mL) was treated with triethylamine (8.5 mL, 61 mmol), cooled to −10° C., treated with trifluoromethanesulfonic anhydride (8.2 mL, 49 mmol), and stirred at −10° C. for 30 minutes. The reaction mixture was quenched with water, warmed to 20° C., and diluted with dichloromethane. The organic layer was washed with water and brine, dried with sodium sulfate, filtered, and concentrated to a crude residue. The crude material was diluted with dichloromethane and adsorbed onto 50 g of silica gel. Purification by flash column chromatography using ethyl acetate in hexanes (0%-10%) gave the desired product (9.5 g, 85%). LCMS for $C_{14}H_{14}ClF_3NO_7SSi$ (M+H)$^+$: m/z=460.0; Found: 459.7.

Step E: Methyl 4-chloro-3'-fluoro-6-nitro-5-[(trimethylsilyl)ethynyl]biphenyl-2-carboxylate

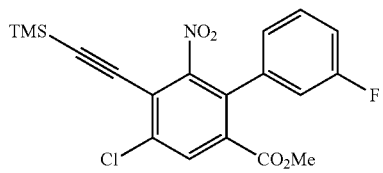

A solution of methyl 5-chloro-3-nitro-2-{[(trifluoromethyl)sulfonyl]oxy}-4-[(trimethylsilyl)ethynyl]benzoate (9.3 g, 20 mmol) and (3-fluorophenyl)boronic acid (4.3 g, 30 mmol) in toluene (200 mL) was treated with water (200 mL) saturated with sodium bicarbonate (3.4 g, 40 mmol). The reaction mixture was degassed with nitrogen for 10 minutes, treated with tetrakis(triphenylphosphine)palladium(0) (1.2 g, 1.0 mmol), degassed with nitrogen for 10 minutes, and heated at 80° C. for 6 hours. The reaction mixture was cooled to 20° C. and the organic layer was separated. The aqueous layer was extracted with ethyl acetate. The combined organic layers were dried with sodium sulfate, filtered, and concentrated to a crude residue. The crude material was diluted with dichloromethane and adsorbed onto 36 g of silica gel. Purification by flash column chromatography using ethyl acetate in hexanes (0%-40%) gave the desired product (7.1 g, 86%). LCMS for $C_{19}H_{18}ClFNO_4Si$ (M+H)$^+$: m/z=406.1; Found: 405.7.

Step F: Methyl 6-amino-4-chloro-3'-fluoro-5-[(trimethylsilyl)ethynyl]biphenyl-2-carboxylate

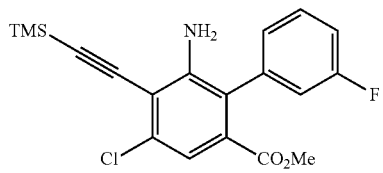 [SMILES: COC(=O)c1cc(Cl)c(C#C[Si](C)(C)C)c([N+](=O)[O-])c1-c1cccc(F)c1]

A suspension of iron (<10 micron) (1.6 g, 29 mmol) in methanol (24 mL) was treated with 6 M hydrogen chloride in water (0.4 mL, 2.4 mmol) and heated at 60° C. for 2 hours. The reaction mixture was treated with 5 M ammonium chloride in water (4.1 mL, 21 mmol) followed by methyl 4-chloro-3'-fluoro-6-nitro-5-[(trimethylsilyl)ethynyl]biphenyl-2-carboxylate (1.9 g, 4.8 mmol) and heated at 60° C. for 16 hours. The reaction mixture was filtered over celite, washed with methanol, and the filtrate was concentrated to a solid. The solid was diluted with ethyl acetate (200 mL) and saturated sodium bicarbonate (100 mL) and stirred for a few minutes. The organic layer was separated, washed with brine, dried with sodium sulfate, filtered, and concentrated to a crude residue. Purification by flash column chromatography using ethyl acetate in hexanes (0%-10%) gave the desired product (1.5 g, 86%). LCMS for $C_{19}H_{20}ClFNO_2Si$ (M+H)$^+$: m/z=376.1; Found: 376.1.

Step G: Methyl 4-chloro-6-[(1E)-3,3-diethyltriaz-1-en-1-yl]-3'-fluoro-5-[(trimethylsilyl)ethynyl]biphenyl-2-carboxylate

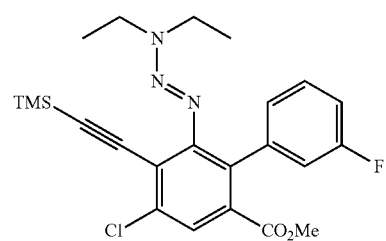 [SMILES: CCN(CC)/N=N/c1c(C#C[Si](C)(C)C)c(Cl)cc(C(=O)OC)c1-c1cccc(F)c1]

A solution of methyl 6-amino-4-chloro-3'-fluoro-5-[(trimethylsilyl)ethynyl]biphenyl-2-carboxylate (3.2 g, 8.4 mmol) in tetrahydrofuran (8.1 mL), acetonitrile (8.1 mL), and water (9.3 mL) was cooled to −5° C. and treated with 12 M of hydrogen chloride in water (5.6 mL, 68 mmol) dropwise followed by a solution of sodium nitrite (1.2 g, 17 mmol) in water (6.3 mL)/acetonitrile (2.1 mL) and stirred at −5° C. for 30 minutes. This mixture was added to a solution of diethylamine (8.7 mL, 84 mmol) and potassium carbonate (7.0 g, 51 mmol) in water (76 mL)/acetonitrile (25 mL) that was cooled at 0° C. The reaction mixture was stirred at 0° C. for 30 minutes and warmed to 20° C. The reaction mixture was diluted with saturated sodium bicarbonate (100 mL) and extracted with ethyl acetate (200 mL). The organic layer was separated, washed with brine, dried with sodium sulfate, filtered, and concentrated to a crude oil. Purification by flash column chromatography using dichloromethane in hexanes (0%-50%) gave the desired product (3.3 g, 86%). LCMS for $C_{23}H_{28}ClFN_3O_2Si$ (M+H)$^+$: m/z=460.2; Found: 459.8.

Step H: 4-Chloro-6-[(1E)-3,3-diethyltriaz-1-en-1-yl]-5-ethynyl-3'-fluorobiphenyl-2-carboxylic acid

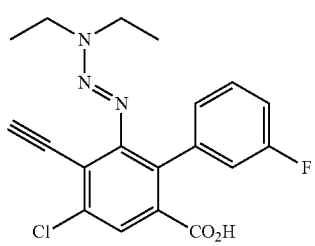 [SMILES: C#Cc1c(Cl)cc(C(=O)O)c(-c2cccc(F)c2)c1/N=N/N(CC)CC]

A solution of methyl 4-chloro-6-[(1E)-3,3-diethyltriaz-1-en-1-yl]-3'-fluoro-5-[(trimethylsilyl)ethynyl]biphenyl-2-carboxylate (3.3 g, 7.1 mmol) in methanol (11 mL) and tetrahydrofuran (11 mL) was treated with 1 M sodium hydroxide in water (29 mL, 29 mmol) dropwise and heated at 65° C. for 1 hour. The reaction mixture was cooled to 0° C. and treated with 3 M hydrogen chloride in water (12 mL, 36 mmol) dropwise. This mixture was poured into 1 M hydrogen chloride in water (100 mL) and extracted with ethyl acetate (2×100 mL). The combined organic extracts were washed with brine (50 mL), dried with sodium sulfate, filtered, and concentrated to give the desired product (quantitative). This Step I: 4-Chloro-6-[(1E)-3,3-diethyltriaz-1-en-1-yl]-5-ethynyl-3'-fluoro-N-methoxy-N-methylbiphenyl-2-carboxamide

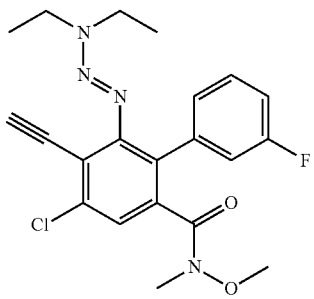 [SMILES: C#Cc1c(Cl)cc(C(=O)N(C)OC)c(-c2cccc(F)c2)c1/N=N/N(CC)CC]

A solution of 4-chloro-6-[(1E)-3,3-diethyltriaz-1-en-1-yl]-5-ethynyl-3'-fluorobiphenyl-2-carboxylic acid (2.7 g, 7.1 mmol) in N,N-dimethylformamide (14 mL) was treated with N,N-diisopropylethylamine (4.3 mL, 25 mmol) followed by O-(benzotriazol-1-yl)-N,N,N',N'-tetramethyluronium hexafluorophosphate (3.5 g, 9.3 mmol) and stirred at 20° C. for 5 minutes. The reaction mixture was treated with N,O-dimethylhydroxylamine hydrochloride (0.9 g, 9.3 mmol) and stirred at 20° C. for 1 hour. The reaction mixture was poured into 0.5 M hydrogen chloride in water (100 mL) and extracted with ethyl acetate (150 mL). The organic layer was washed with saturated sodium bicarbonate (50 mL), brine (25 mL), dried with sodium sulfate, filtered, and concentrated to a crude residue. Purification by flash column chromatography using ethyl acetate in hexanes (0%-40%) gave the desired product (2.7 g, 92% for 2 steps). LCMS for $C_{21}H_{23}ClFN_4O_2$ (M+H)$^+$: m/z=417.1; Found: 417.0.

Step J: 1-{4-Chloro-6-[(1E)-3,3-diethyltriaz-1-en-1-yl]-5-ethynyl-3'-fluorobiphenyl-2-yl}ethanone

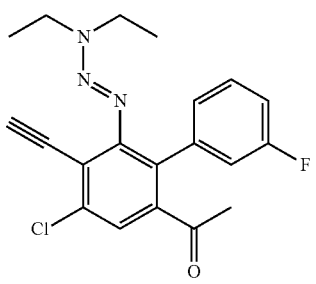 [SMILES: C#Cc1c(Cl)cc(C(C)=O)c(-c2cccc(F)c2)c1/N=N/N(CC)CC]

A solution of 4-chloro-6-[(1E)-3,3-diethyltriaz-1-en-1-yl]-5-ethynyl-3'-fluoro-N-methoxy-N-methylbiphenyl-2-carboxamide (2.7 g, 6.6 mmol) in tetrahydrofuran (26 mL) at 0° C. was treated with 3 M of methylmagnesium chloride in tetrahydrofuran (6.6 mL, 20 mmol) dropwise and stirred at 20° C. for 1 hour. The reaction mixture still contained some starting material and was, therefore, cooled to 0° C., treated with additional 3 M of methylmagnesium chloride in tetrahydrofuran (2.2 mL, 6.6 mmol) dropwise, and stirred at 20 ° C. for 2 hours. The reaction mixture was cooled to 0° C., quenched with 1 M hydrogen chloride in water (26 mL, 26 mmol), poured into 0.1 M hydrogen chloride in water (100 mL) and extracted with ethyl acetate (150 mL). The organic layer was separated, washed with saturated sodium bicarbonate and brine, dried with sodium sulfate, filtered, and concentrated to give a crude oil. Purification by flash column chromatography using ethyl acetate in hexanes (0%-20%) gave the desired product (2.3 g, 93%). LCMS for $C_{20}H_{20}ClFN_3O$ (M+H)$^+$: m/z=372.1; Found: 371.9.

Step K: 1-{4-Chloro-6-[(1E)-3,3-diethyltriaz-1-en-1-yl]-5-ethynyl-3'-fluorobiphenyl-2-yl}ethanol

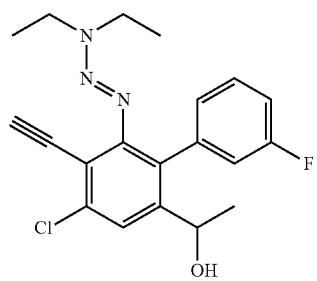 [SMILES: C#Cc1c(Cl)cc(C(C)O)c(-c2cccc(F)c2)c1/N=N/N(CC)CC]

A solution of 1-{4-chloro-6-[(1E)-3,3-diethyltriaz-1-en-1-yl]-5-ethynyl-3'-fluorobiphenyl-2-yl}ethanone (2.3 g, 6.1 mmol) in methanol (38 mL) at 0° C. was treated with sodium borohydride (0.46 g, 12 mmol) in two portions and stirred at 0° C. for 30 minutes. The reaction mixture was quenched with water at 0° C., poured into saturated sodium bicarbonate (50 mL), and extracted with ethyl acetate (2×100 mL). The combined organic extracts were washed with brine (50 mL), dried with sodium sulfate, filtered, and concentrated to give the desired product (quantitative). This material was used without further purification. LCMS for $C_{20}H_{22}ClFN_3O$ (M+H)$^+$: m/z=374.1; Found: 373.9.

Step L: 1-[5-Chloro-8-(3-fluorophenyl)cinnolin-7-yl]ethanol

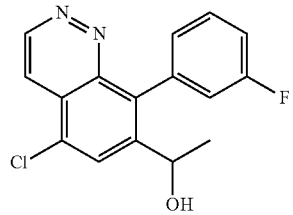 [SMILES: CC(O)c1cc(Cl)c2ccnnc2c1-c1cccc(F)c1]

A solution of 1-{4-chloro-6-[(1E)-3,3-diethyltriaz-1-en-1-yl]-5-ethynyl-3'-fluorobiphenyl-2-yl}ethanol (2.3 g, 6.1 mmol) in 1,2-dichlorobenzene (59 mL) was heated in the microwave at 200° C. for 15 minutes. The reaction mixture was concentrated to give a black residue. Purification by flash column chromatography using acetonitrile in dichloromethane (0%-30%) gave the desired product (1.4 g, 74% for 2 steps). LCMS for $C_{16}H_{13}ClFN_{20}$ (M+H)+: m/z=303.1; Found: 302.9.

Step M: 7-(1-Azidoethyl)-5-chloro-8-(3-fluorophenyl)cinnoline

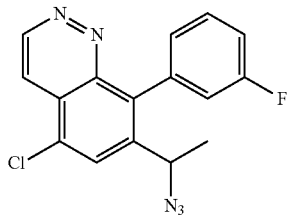 [SMILES: CC(N=[N+]=[N-])c1cc(Cl)c2ccnnc2c1-c1cccc(F)c1]

A solution of 1-[5-chloro-8-(3-fluorophenyl)cinnolin-7-yl]ethanol (1.4 g, 4.5 mmol) in dichloromethane (22 mL) at −5° C. was treated with N,N-diisopropylethylamine (1.2 mL, 7.1 mmol) followed by methanesulfonyl chloride (0.52 mL, 6.7 mmol) and stirred at −5° C. for 30 minutes. The reaction mixture was quenched with water (100 mL) and extracted with dichloromethane (100 mL). The organic layer was separated, dried with sodium sulfate, filtered, and concentrated to give the intermediate mesylate which was used without further purification. A solution of the mesylate in N,N-dimethylformamide (11 mL) was treated with sodium azide (0.87 g, 13 mmol) and heated at 60° C. for 30 minutes. The reaction mixture was diluted with ethyl acetate (200 mL), washed with solution of saturated sodium bicarbonate (50 mL)/water (50 mL) and brine, dried with sodium sulfate, filtered, and concentrated to give the crude azide. Purification by flash column chromatography using ethyl acetate in hexanes (0%-30%) gave the desired product (1.3 g, 91%). LCMS for $C_{16}H_{12}ClFN_5$ (M+H)+: m/z=328.1; Found: 327.9.

Step N: 1-[5-Chloro-8-(3-fluorophenyl)cinnolin-7-yl]ethanamine trifluoroacetate

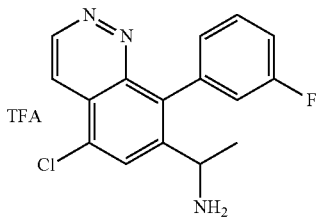 [SMILES: CC(N)c1cc(Cl)c2ccnnc2c1-c1cccc(F)c1]

A solution of 7-(1-azidoethyl)-5-chloro-8-(3-fluorophenyl)cinnoline (75 mg, 0.23 mmol) in tetrahydrofuran (1.2 mL) and water (0.25 mL) was treated with 1 M of trimethylphosphine in tetrahydrofuran and stirred at 20° C. for 30 minutes. The reaction mixture was diluted with ethyl acetate, washed with brine, dried with sodium sulfate, filtered, and concentrated to a crude residue. Purification by RP-HPLC (XBridge C18 column, eluting with a gradient of acetonitrile/water containing 0.05% TFA, at flow rate of 60 mL/minute) gave the desired product (78 mg, 82%). LCMS for $C_{16}H_{14}ClFN_3$ (M+H)+: m/z=302.1; Found: 302.1.

Step O: N-{1-[5-Chloro-8-(3-fluorophenyl)cinnolin-7-yl]ethyl}-9H-purin-6-amine

A solution of 1-[5-chloro-8-(3-fluorophenyl)cinnolin-7-yl]ethanamine trifluoroacetate (73 mg, 0.18 mmol), 6-bromo-9H-purine (70 mg, 0.35 mmol), and N,N-diisopropylethylamine (0.15 mL, 0.88 mmol) in ethanol (1 mL) was heated at 90° C. for 22 hours. The reaction mixture was concentrated to a crude residue. Purification by RP-HPLC (XBridge C18 column, eluting with a gradient of acetonitrile/water containing 0.05% TFA, at flow rate of 60 mL/minute) gave the TFA salt of the desired product that was slightly colored. This material was repurified by RP-HPLC (XBridge C18 column, eluting with a gradient of acetonitrile/water containing 0.1% ammonium hydroxide, at flow rate of 60 mL/minute) to give the desired product (18 mg, 24%) as a white solid. LCMS for $C_{21}H_{16}ClFN_7$ (M+H)+: m/z=420.1; Found: 420.1. ¹H NMR (400 MHz, DMSO-d₆): δ 12.9 (br s, 1 H), 9.47 (d, J=6.1 Hz, 1 H), 8.43 (d, J=10.2 Hz, 1 H), 8.41-8.35 (br m, 1 H), 8.26 (d, J=6.1 Hz, 1 H), 8.13 (s, 1 H), 8.05 (d, J=14.6 Hz, 1 H), 7.67-7.62 (m, 1 H), 7.59-7.53 (m, 1 H), 7.37-7.32 (m, 1 H), 7.30-7.22 (m, 1 H), 5.35 (br s, 1 H), 1.48 (d, J=6.8 Hz, 3 H).

Examples 17 and 18

Single enantiomers of N-{1-[5-Chloro-8-(3-fluorophenyl)cinnolin-7-yl]ethyl}-9H-purin-6-amine

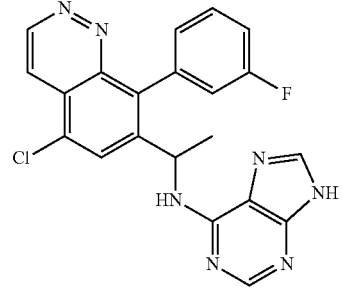 [SMILES: CC(Nc1ncnc2[nH]cnc12)c1cc(Cl)c2ccnnc2c1-c1cccc(F)c1]

Step A: Chiral separation of 7-(1-azidoethyl)-5-chloro-8-(3-fluorophenyl)cinnoline

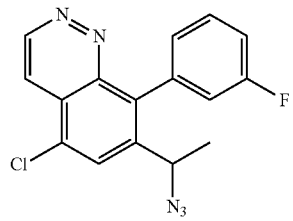 [SMILES: CC(N=[N+]=[N-])c1cc(Cl)c2ccnnc2c1-c1cccc(F)c1]

The racemic mixture of 7-(1-azidoethyl)-5-chloro-8-(3-fluorophenyl)cinnoline was separated by HPLC (Chiracel OD-H, eluting with 10% ethanol/90% hexanes, at flow rate of 20 mL/minute for 13 minutes) to give the two individual enantiomers (retention time (rt)=3.58 minutes, 6.14 minutes). The first peak (rt=3.58 minutes) that eluted off the column was designated peak 1 and advanced to the next step. The second peak (rt=6.14 minutes) that eluted off the column was designated peak 2 and advanced to step E.

Step B: Single enantiomer of 1-[5-Chloro-8-(3-fluorophenyl)cinnolin-7-yl]ethanamine (from peak 1)

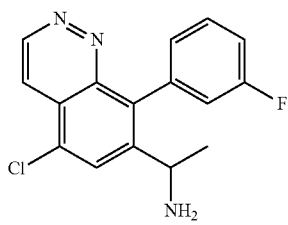 [SMILES: CC(N)c1cc(Cl)c2ccnnc2c1-c1cccc(F)c1]

A solution of peak 1 of 7-(1-azidoethyl)-5-chloro-8-(3-fluorophenyl)cinnoline (0.57 g, 1.7 mmol), from step A, in tetrahydrofuran (9.3 mL) and water (1.8 mL) was treated with 1 M of trimethylphosphine in tetrahydrofuran (2.1 mL, 2.1 mmol) and stirred at 20° C. for 30 minutes.

The reaction mixture was diluted with ethyl acetate, washed with brine, dried with sodium sulfate, filtered, and concentrated to give the desired product (quantitative). This material was used without further purification. LCMS for $C_{16}H_{14}ClFN_3$ (M+H)$^+$: m/z=302.1; Found: 301.9.

Step C: 6-bromo-9-(tetrahydro-2H-pyran-2-yl)-9H-purine

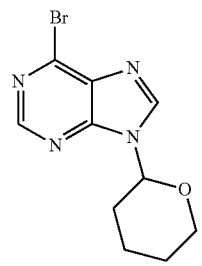 [SMILES: Brc1ncnc2c1ncn2C1CCCCO1]

A solution of 6-bromo-9H-purine (2.0 g, 10 mmol) and p-toluenesulfonic acid monohydrate (190 mg, 1.0 mmol) in chloroform (45 mL) at 0° C. was treated with dihydropyran (1.4 mL, 15 mmol) and stirred at 20° C. for 18 hours. The reaction mixture was diluted with water and extracted with ethyl acetate (3×50 mL). The combined organic extracts were washed with saturated sodium bicarbonate, water and brine, dried with sodium sulfate, filtered, and concentrated to give a crude residue. Purification by flash column chromatography using ethyl acetate in hexanes (0%-70%) gave the desired product (2.7 g, 94%). LCMS for $C_{10}H_{12}BrN_4O$ (M+H)$^+$: m/z=283.0, 285.0; Found: 283.0, 285.0.

Step D: Single enantiomer of N-{1-[5-Chloro-8-(3-fluorophenyl)cinnolin-7-yl]ethyl}-9H-purin-6-amine (from peak 1) (Example 17)

A solution of the single enantiomer of 1-[5-chloro-8-(3-fluorophenyl)cinnolin-7-yl]ethanamine (0.52 g, 1.7 mmol) from Step B, 6-bromo-9-(tetrahydro-2H-pyran-2-yl)-9H-purine (0.73 g, 2.6 mmol), and N,N-diisopropylethylamine (0.90 mL, 5.1 mmol) in ethanol (9 mL) was heated at 90° C. for 21 hours. The reaction mixture was concentrated to give the crude THP-purine intermediate which was used without further purification. A solution of this material in methanol (10 mL) was treated with 1 M hydrogen chloride in water (15 mL, 15 mmol) and stirred at 20° C. for 1 hour. The reaction mixture was concentrated and purified by RP-HPLC (XBridge C18 column, eluting with a gradient of acetonitrile/water containing 0.05% TFA, at flow rate of 60 mL/minute). The pure fractions were neutralized with ammonium hydroxide to pH~7 and concentrated to remove all of the acetonitrile and most of the water. The solid that precipitated was filtered, washed with water, and dried to give the desired product (0.44 g, 62%). % ee>99.9. LCMS for $C_{21}H_{16}ClFN_7$ (M+H)$^+$: m/z=420.1; Found: 419.9. $^1$H NMR (300 MHz, DMSO-d$_6$): δ 12.9 (br s, 1 H), 9.47 (d, J=5.9 Hz, 1 H), 8.50-8.38 (m, 2H), 8.26 (d, J=5.9 Hz, 1 H), 8.14 (br s, 1 H), 8.06 (d, J=10.8 Hz, 1 H), 7.64-7.52 (m, 2H), 7.37-7.22 (m, 2H), 5.36 (br s, 1H), 1.48 (d, J=6.7 Hz, 3H).

Step E: Single enantiomer of N-{1-[5-Chloro-8-(3-fluorophenyl)cinnolin-7-yl]ethyl}-9H-purin-6-amine (from peak 2) (Example 18)

Peak 2 from step A was processed according to steps B and D to give the other enantiomer of N-{1-[5-chloro-8-(3-fluorophenyl)cinnolin-7-yl]ethyl}-9H-purin-6-amine. % ee=98.5. LCMS for $C_{21}H_{16}ClFN_7$ (M+H)$^+$: m/z=420.1; Found: 419.8. $^1$H NMR (300 MHz, DMSO-d$_6$): δ 9.47 (d, J=6.2 Hz, 1H), 8.45-8.35 (m, 2H), 8.26 (d, J=6.2 Hz, 1H), 8.14 (s, 1H), 8.07 (d, J=11.1 Hz, 1H), 7.67-7.52 (m, 2H), 7.38-7.21 (m, 2H), 5.37 (br s, 1H), 1.48 (d, J=7.0 Hz, 3H).

Example 19

N-{1-[5-Fluoro-8-(3-fluorophenyl)cinnolin-7-yl]ethyl}-9H-purin-6-amine

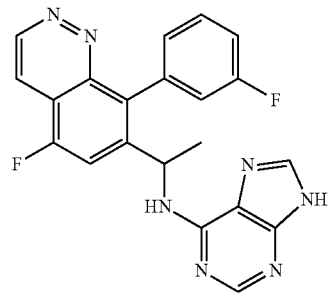 [SMILES: CC(Nc1ncnc2[nH]cnc12)c1cc(F)c2ccnnc2c1-c1cccc(F)c1]

Step A: 3-Bromo-4-fluorophenyl acetate

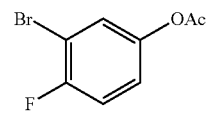

A solution of 3-bromo-4-fluorophenol (4.5 g, 23 mmol) [Ark Pharm, AK-26802] in dichloromethane (96 mL) at 0° C. was treated with triethylamine (4.9 mL, 35 mmol) followed by acetyl chloride (2.3 mL, 33 mmol) dropwise and stirred at 20° C. for 30 minutes. The reaction mixture was diluted with dichloromethane (100 mL), washed with 0.5 M hydrogen chloride in water (100 mL), saturated sodium bicarbonate (100 mL), and brine (50 mL), dried with sodium sulfate, filtered, and concentrated to give the desired product (5.5 g, quantitative) as a tan solid. This material, which did not ionize in the mass spectrometer, was used without further purification.

Step B:
1-(4-Bromo-5-fluoro-2-hydroxyphenyl)ethanone

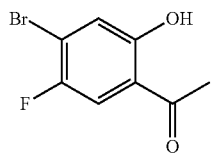

A solution of 3-bromo-4-fluorophenyl acetate (5.5 g, 23 mol) in boron trifluoride acetic acid complex (47 mL, 340 mmol) was heated at 155° C. for 14 hours. The reaction mixture was cooled to 0° C. and treated with ice. The ice bath was removed and the ice was allowed to melt. The reaction mixture was diluted with cold water and filtered. The solid was washed with cold water and air dried. This material was adsorbed onto silica gel and purified by flash column chromatography using ethyl acetate in hexanes (0%-30%) to give the desired product (4.0 g, 73%). This material did not ionize in the mass spectrometer.

Step C: 1-{5-Fluoro-2-hydroxy-4-[(trimethylsilyl)ethynyl]phenyl}ethanone

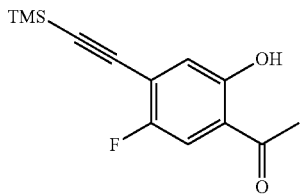 [SMILES: CC(=O)c1cc(F)c(C#C[Si](C)(C)C)cc1O]

The desired compound was prepared according to the procedure of Example 16, step B, using 1-(4-bromo-5-fluoro-2-hydroxyphenyl)ethanone as the starting material in 96% yield. LCMS for $C_{13}H_{16}FO_2Si$ (M+H)$^+$: m/z=251.1; Found: 250.9.

Step D: 1-{5-Fluoro-2-hydroxy-3-nitro-4-[(trimethylsilyl)ethynyl]phenyl}ethanone

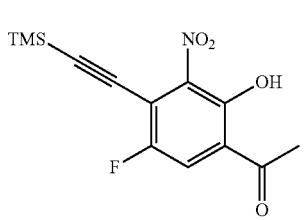 [SMILES: CC(=O)c1cc(F)c(C#C[Si](C)(C)C)c([N+](=O)[O-])c1O]

The desired compound was prepared according to the procedure of Example 16, step C, using 1-{5-fluoro-2-hydroxy-4-[(trimethylsilyl)ethynyl]phenyl}ethanone as the starting material in 80% yield. LCMS for $C_{13}H_{15}FNO_4Si$ (M+H)$^+$: m/z=296.1; Found: 295.9.

Step E: 6-Acetyl-4-fluoro-2-nitro-3-[(trimethylsilyl)ethynyl]phenyl trifluoromethanesulfonate

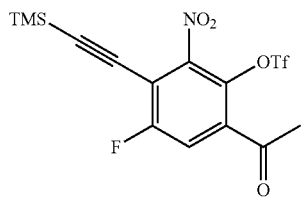 [SMILES: CC(=O)c1cc(F)c(C#C[Si](C)(C)C)c([N+](=O)[O-])c1OS(=O)(=O)C(F)(F)F]

The desired compound was prepared according to the procedure of Example 16, step D, using 1-{5-fluoro-2-hydroxy-3-nitro-4-[(trimethylsilyl)ethynyl]phenyl}ethanone as the starting material in quantitative yield. This material did not ionize in the mass spectrometer.

Step F: 1-{3',4-Difluoro-6-nitro-5-[(trimethylsilyl)ethynyl]biphenyl-2-yl}ethanone

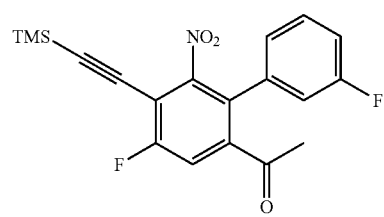 [SMILES: CC(=O)c1cc(F)c(C#C[Si](C)(C)C)c([N+](=O)[O-])c1-c1cccc(F)c1]

The desired compound was prepared according to the procedure of Example 16, step E, using 6-acetyl-4-fluoro-2-nitro-3-[(trimethylsilyl)ethynyl]phenyl trifluoromethanesulfonate as the starting material in 84% yield. LCMS for $C_{19}H_{18}F_2NO_3Si$ (M+H)$^+$: m/z=374.1; Found: 373.9.

Step G: 1-{6-Amino-3',4-difluoro-5-[(trimethylsilyl)ethynyl]biphenyl-2-yl}ethanone

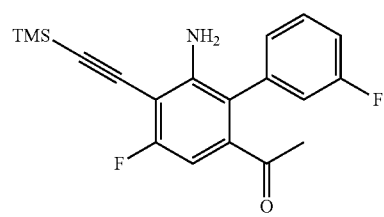 [SMILES: CC(=O)c1cc(F)c(C#C[Si](C)(C)C)c(N)c1-c1cccc(F)c1]

The desired compound was prepared according to the procedure of Example 16, step F, using ethanol (instead of methanol) and 1-{3',4-difluoro-6-nitro-5-[(trimethylsilyl)

ethynyl]biphenyl-2-yl}ethanone as the starting material in 90% yield. LCMS for $C_{19}H_{20}F_2NOSi$ (M+H)$^+$: m/z=344.1; Found: 343.9.

Step H: 1-{6-[(1E)-3,3-Diethyltriaz-1-en-1-yl]-3',4-difluoro-5-[(trimethylsilyl)ethynyl]biphenyl-2-yl}ethanone

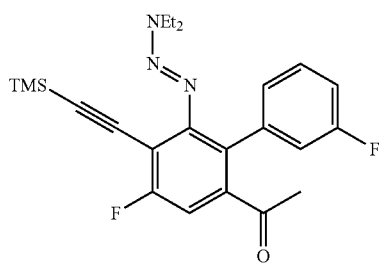

The desired compound was prepared according to the procedure of Example 16, step G, using 1-{6-amino-3',4-difluoro-5-[(trimethylsilyl)ethynyl]biphenyl-2-yl}ethanone as the starting material in 68% yield. LCMS for $C_{23}H_{28}F_2N_3OSi$ (M+H)$^+$: m/z=428.2; Found: 427.9.

Step I: 1-{6-[(1E)-3,3-Diethyltriaz-1-en-1-yl]-5-ethynyl-3',4-difluorobiphenyl-2-yl}ethanone

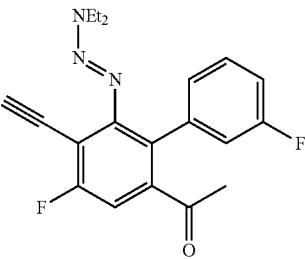

A solution of 1-{6-[(1E)-3,3-diethyltriaz-1-en-1-yl]-3',4-difluoro-5-[(trimethylsilyl)ethynyl]biphenyl-2-yl}ethanone (2.0 g, 4.6 mmol) in tetrahydrofuran (39 mL) and methanol (7.7 mL) was treated with powdered potassium carbonate (3.2 g, 23 mmol) and stirred at 0° C. for 2 hours. The reaction mixture was filtered and the filtrate was treated with a few drops of water. The filtrate was concentrated to an oil that was diluted with ethyl acetate (150 mL), washed with water (50 mL) and brine (25 mL), dried with sodium sulfate, filtered, and concentrated to give the desired product (1.6 g, 99%) that was used without further purification. LCMS for $C_{20}H_{20}F_2N_3O$ (M+H)$^+$: m/z=356.2; Found: 355.9.

Step J: 1-{6-[(1E)-3,3-Diethyltriaz-1-en-1-yl]-5-ethynyl-3',4-difluorobiphenyl-2-yl}ethanol

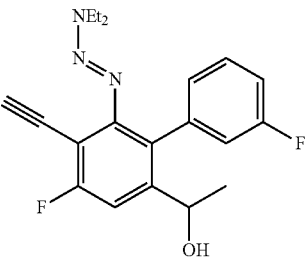

The desired compound was prepared according to the procedure of Example 16, step K, using 1-{6-[(1E)-3,3-diethyl-triaz-1-en-1-yl]-5-ethynyl-3',4-difluorobiphenyl-2-yl}ethanone as the starting material in 98% yield. LCMS for $C_{20}H_{22}F_2N_3O$ (M+H)$^+$: m/z=358.2; Found: 357.9.

Step K: 1-[5-Fluoro-8-(3-fluorophenyl)cinnolin-7-yl]ethanol

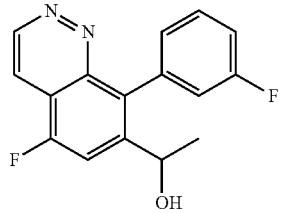 [SMILES: CC(O)c1cc(F)c2ccnnc2c1-c1cccc(F)c1]

The desired compound was prepared according to the procedure of Example 16, step L, using 1-{6-[(1E)-3,3-diethyl-triaz-1-en-1-yl]-5-ethynyl-3',4-difluorobiphenyl-2-yl}ethanol as the starting material in 69% yield. LCMS for $C_{16}H_{13}F_2N_2O$ (M+H)$^+$: m/z=287.1; Found: 286.9.

Step L: 7-(1-Azidoethyl)-5-fluoro-8-(3-fluorophenyl)cinnoline

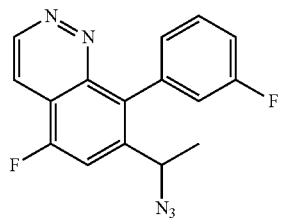 [SMILES: CC(N=[N+]=[N-])c1cc(F)c2ccnnc2c1-c1cccc(F)c1]

The desired compound was prepared according to the procedure of Example 16, step M, using 1-[5-fluoro-8-(3-fluorophenyl)cinnolin-7-yl]ethanol as the starting material in 89% yield. LCMS for $C_{16}H_{12}F_2N_5$ (M+H)$^+$: m/z=312.1; Found: 312.0.

Step M: 1-[5-Fluoro-8-(3-fluorophenyl)cinnolin-7-yl]ethanamine

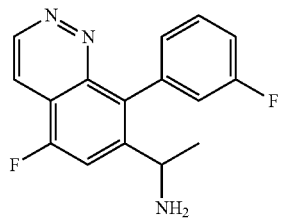 [SMILES: CC(N)c1cc(F)c2ccnnc2c1-c1cccc(F)c1]

The desired compound was prepared according to the procedure of Example 16, step N, using 7-(1-azidoethyl)-5-fluoro-8-(3-fluorophenyl)cinnoline as the starting material in quantitative yield. This material was used without further purification. LCMS for $C_{16}H_{14}F_2N_3$ (M+H)$^+$: m/z=286.1; Found: 285.9.

Step N: N-{1-[5-Fluoro-8-(3-fluorophenyl)cinnolin-7-yl]ethyl}-9H-purin-6-amine

The desired compound was prepared according to the procedure of Examples 17 and 18, step D, using 1-[5-fluoro-8-(3-fluorophenyl)cinnolin-7-yl]ethanamine as the starting material. The crude material was purified first by RP-HPLC (XBridge C18 column, eluting with a gradient of acetonitrile/ water containing 0.05% TFA, at flow rate of 60 mL/minute) and then by RP-HPLC (XBridge C18 column, eluting with a gradient of acetonitrile/water containing 0.1% ammonium hydroxide, at flow rate of 60 mL/minute) to give the desired product in 44%. LCMS for $C_{21}H_{16}F_2N_7$ (M+H)$^+$: m/z=404.1; Found: 404.0. $^1$H NMR (300 MHz, DMSO-d$_6$): δ 12.9 (br s, 1H), 9.43 (d, J=5.9 Hz, 1H), 8.34 -8.26 (m, 1H), 8.22 (d, J=5.9 Hz, 1H), 8.15-8.01 (m, 3H), 7.65 -7.52 (m, 2H), 7.375-7.20 (m, 2H), 5.39 (br s, 1H), 1.46 (d, J=7.0 Hz, 3H).

Examples 20 and 21

Single enantiomers of N-{1-[5-Fluoro-8-(3-fluorophenyl)cinnolin-7-yl]ethyl}-9H-purin-6-amine

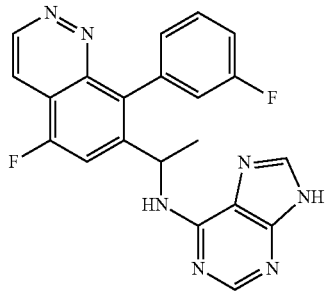 [SMILES: CC(Nc1ncnc2[nH]cnc12)c1cc(F)c2ccnnc2c1-c1cccc(F)c1]

Step A: Chiral separation of 7-(1-Azidoethyl)-5-fluoro-8-(3-fluorophenyl)cinnoline

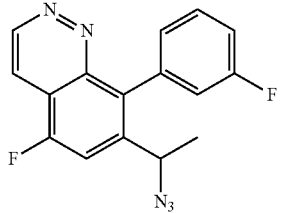 [SMILES: CC(N=[N+]=[N-])c1cc(F)c2ccnnc2c1-c1cccc(F)c1]

The racemic mixture of 7-(1-azidoethyl)-5-fluoro-8-(3-fluorophenyl)cinnoline was separated by HPLC (Chiracel OD-H, eluting with 10% ethanol/90% hexanes, at flow rate of 20 mL/minute for 14 minutes) to give the two individual enantiomers (rt=5.61 minutes, 9.23 minutes). The first peak (rt=5.61 minutes) that eluted off the column was designated peak 1 and advanced to the next step. The second peak (rt=9.23 minutes) that eluted off the column was designated peak 2 and advanced to step D.

Step B: Single enantiomers of 1-[5-Fluoro-8-(3-fluorophenyl)cinnolin-7-yl]ethanamine

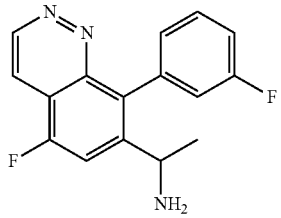 [SMILES: CC(N)c1cc(F)c2ccnnc2c1-c1cccc(F)c1]

The desired compounds were prepared according to the procedure of Examples 17 and 18, step B, using the individual enantiomers of 7-(1-azidoethyl)-5-fluoro-8-(3-fluorophenyl) cinnoline as the starting materials in quantitative yield (from peak 1) and quantitative yield (from peak 2). From peak 1: LCMS for $C_{16}H_{14}F_2N_3$ (M+H)$^+$: m/z=286.0. From peak 2: LCMS for $C_{16}H_{14}F_2N_3$ (M+H)$^+$: m/z=286.1; Found: 285.9

Step C: Single enantiomers of N-{1-[5-Fluoro-8-(3-fluorophenyl)cinnolin-7-yl]ethyl}-9H-purin-6-amine The desired compound was prepared according to the procedure of Examples 17 and 18, step D, using the individual enantiomers of 1-[5-fluoro-8-(3-fluorophenyl)cinnolin-7-yl] ethanamine as the starting materials in 47% yield (from peak 1) and 36% yield (from peak 2). Example 20 (from peak 1): LCMS for $C_{21}H_{16}F_2N_7$ (M+H)$^+$: m/z=404.1; Found: 404.3; $^1$H NMR (400 MHz, DMSO-d$_6$): δ 12.9 (s, 1H), 9.43 (d, J=6.1 Hz, 1H), 8.37-8.31 (m, 1H), 8.22 (d, J=5.9 Hz, 1H), 8.13 -8.02 (m, 3H), 7.66-7.53 (m, 2H), 7.36-7.20 (m, 2H), 5.39 (br s, 1H), 1.47 (d, J=7.0 Hz, 3H). Example 21 (from peak 2): LCMS for $C_{21}H_{16}F_2N_7$ (M+H)$^+$: m/z=404.1; Found: 403.9; $^1$H NMR (300 MHz, DMSO-d$_6$): δ 9.43 (d, J=5.9 Hz, 1H), 8.33-8.20 (m, 2H), 8.14-8.02 (m, 3H), 7.66-7.51 (m, 2H), 7.38-7.20 (m, 2H), 5.40 (br s, 1H), 1.47 (d, J=7.0 Hz, 3H).

Example 22

N(6)-{1-[5-Fluoro-8-(3-fluorophenyl)cinnolin-7-yl] ethyl}-9H-purine-2,6-diamine

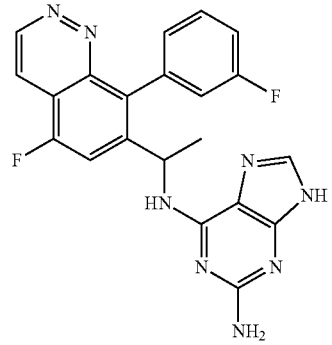 [SMILES: CC(Nc1nc(N)nc2[nH]cnc12)c1cc(F)c2ccnnc2c1-c1cccc(F)c1]

A solution of 1-[5-fluoro-8-(3-fluorophenyl)cinnolin-7-yl]ethanamine (73 mg, 0.26 mmol) [from peak 1 of Examples 20 and 21, step B] and 2-amino-6-bromopurine (82 mg, 0.38 mmol) in 1-butanol (0.51 mL, 5.6 mmol) was treated with N,N-diisopropylethylamine (67 µL, 0.38 mmol), degassed with nitrogen for 5 minutes and stirred at 120° C. for 18 hours. The reaction mixture was diluted with methanol (10 mL), stirred and filtered. The filtrate was purified first by RP-HPLC (XBridge C18 column, eluting with a gradient of acetonitrile/water containing 0.05% TFA, at flow rate of 60 mL/minute) and then by RP-HPLC (XBridge C18 column, eluting with a gradient of acetonitrile/water containing 0.1% ammonium hydroxide, at flow rate of 60 mL/minute) to give the desired product in 26%. LCMS for $C_{21}H_{17}F_2N_8$ (M+H)$^+$: m/z=419.2; Found: 418.9. $^1$H NMR (300 MHz, DMSO-d$_6$): δ 12.1 (br s, 1H), 9.44 (d, J=5.9 Hz, 1H), 8.25-8.22 (m, 1H), 8.13-8.01 (m, 1H), 7.94-7.83 (m, 1H), 7.72-7.53 (m, 3H), 7.40-7.29 (m, 1H), 7.28-7.22 (m, 1H), 5.45-5.21 (m, 3H), 1.42-1.38 (m, 3H).

Examples 23 and 24

Single enantiomers of N-{1-[5-Chloro-8-(3,5-difluorophenyl)cinnolin-7-yl]ethyl}-9H-purin-6-amine

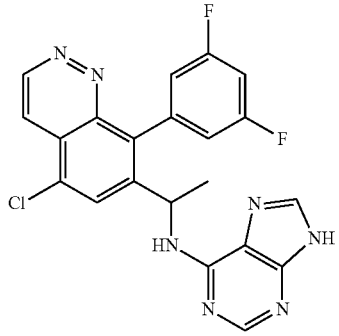 [SMILES: CC(Nc1ncnc2[nH]cnc12)c1cc(Cl)c2ccnnc2c1-c1cc(F)cc(F)c1]

Step A: Methyl 4-chloro-3',5'-difluoro-6-nitro-5-[(trimethylsilyl)ethynyl]biphenyl-2-carboxylate

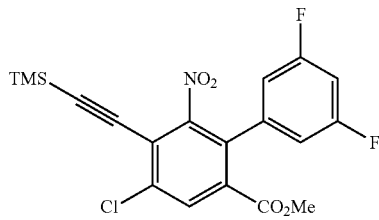 [SMILES: COC(=O)c1cc(Cl)c(C#C[Si](C)(C)C)c([N+](=O)[O-])c1-c1cc(F)cc(F)c1]

The desired compound was prepared according to the procedure of Example 16, step E, using methyl 5-chloro-3-nitro-2-{[(trifluoromethyl)sulfonyl]oxy}-4-[(trimethylsilyl)ethynyl]benzoate and (3,5-difluorophenyl)boronic acid as the starting materials in 82% yield. LCMS for $C_{19}H_{17}ClF_2NO_4Si$ (M+H)$^+$: m/z=424.1; Found: 423.9.

Step B: Methyl 6-amino-4-chloro-3',5'-difluoro-5-[(trimethylsilyl)ethynyl]biphenyl-2-carboxylate

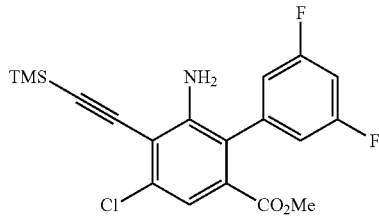

A solution of methyl 4-chloro-3',5'-difluoro-6-nitro-5-[(trimethylsilyl)ethynyl]biphenyl-2-carboxylate (4.6 g, 11 mmol) in methanol (46 mL), water (13 mL), and acetic acid (31 mL) was treated with iron (<10 micron) (3.0 g, 54 mmol) and heated at 60° C. for 2 hours. The reaction mixture was treated with additional iron (1.0 g, 18 mmol) and heated at 60° C. for 1 hour to drive the reaction to completion. The reaction mixture was diluted with ethyl acetate (50 mL) and filtered over celite. The filtrate was concentrated to a crude residue. The crude residue was diluted with ethyl acetate and filtered through a short plug of silica gel. The filtrate was concentrated to give the desired product (4.28 g, quantitative). LCMS for $C_{19}H_{19}ClF_2NO_2Si$ (M+H)$^+$: m/z=394.1; Found: 393.9.

Step C: Methyl 4-chloro-6-[(1E)-3,3-diethyltriaz-1-en-1-yl]-3',5'-difluoro-5-[(trimethylsilyl)ethynyl]biphenyl-2-carboxylate

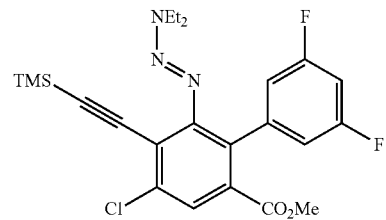

The desired compound was prepared according to the procedure of Example 16, step G, using methyl 6-amino-4-chloro-3',5'-difluoro-5-[(trimethylsilyl)ethynyl]biphenyl-2-carboxylate as the starting material in 57% yield. LCMS for $C_{23}H_{27}ClF_2N_3O_2Si$ (M+H)$^+$: m/z=478.2; Found: 478.0.

Step D: 4-Chloro-6-[(1E)-3,3-diethyltriaz-1-en-1-yl]-5-ethynyl-3',5'-difluorobiphenyl-2-carboxylic acid

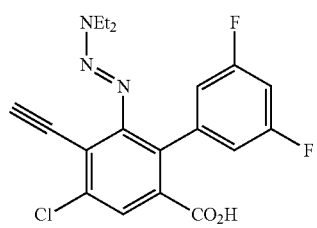

The desired compound was prepared according to the procedure of Example 16, step H, using methyl 4-chloro-6-[(1E)-3,3-diethyltriaz-1-en-1-yl]-3',5'-difluoro-5-[(trimethylsilyl)ethynyl]biphenyl-2-carboxylate as the starting material in 98% yield. LCMS for $C_{19}H_{17}ClF_2N_3O_2$ (M+H)$^+$: m/z=392.1; Found: 391.9.

Step E: 4-Chloro-6-[(1E)-3,3-diethyltriaz-1-en-1-yl]-5-ethynyl-3,'5'-difluoro-N-methoxy-N-methylbiphenyl-2-carboxamide

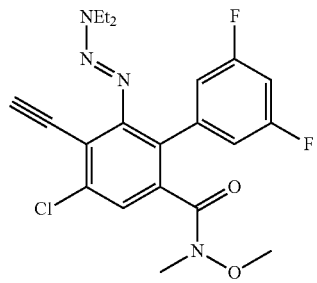

The desired compound was prepared according to the procedure of Example 16, step I, using 4-chloro-6-[(1E)-3,3-diethyltriaz-1-en-1-yl]-5-ethynyl-3',5'-difluorobiphenyl-2- carboxylic acid as the starting material in 92% yield. LCMS for $C_{21}H_{22}ClF_2N_4O_2$ (M+H)$^+$: m/z=435.1; Found: 435.0.

Step F: 1-{4-Chloro-6-[(1E)-3,3-diethyltriaz-1-en-1-yl]-5-ethynyl-3',5'-difluorobiphenyl-2-yl}ethanone

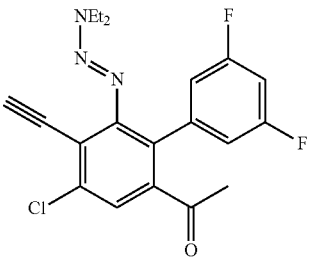

The desired compound was prepared according to the procedure of Example 16, step J, using 4-chloro-6-[(1E)-3,3-diethyltriaz-1-en-1-yl]-5-ethynyl-3',5'-difluoro-N-methoxy-N-methylbiphenyl-2-carboxamide as the starting material in 98% yield. LCMS for $C_{20}H_{19}ClF_2N_3O$ (M+H)$^+$: m/z=390.1; Found: 389.8.

Step G: 1-{4-Chloro-6-[(1E)-3,3-diethyltriaz-1-en-1-yl]-5-ethynyl-3',5'-difluorobiphenyl-2-yl}ethanol

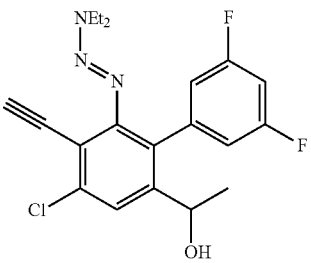

The desired compound was prepared according to the procedure of Example 16, step K, using 1-{4-chloro-6-[(1E)-3,3-diethyltriaz-1-en-1-yl]-5-ethynyl-3',5'-difluorobiphenyl-2-yl}ethanone as the starting material in 98% yield. LCMS for $C_{20}H_{21}ClF_2N_3O$ (M+H)$^+$: m/z=392.1; Found: 391.9.

Step H: 1-[5-chloro-8-(3,5-difluorophenyl)cinnolin-7-yl]ethanol

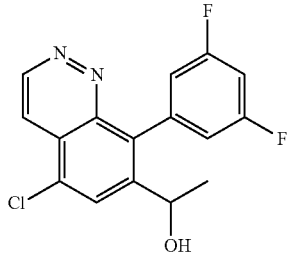 [SMILES: CC(O)c1cc(Cl)c2ccnnc2c1-c1cc(F)cc(F)c1]

The desired compound was prepared according to the procedure of Example 16, step L, using 1-{4-chloro-6-[(1E)-3,3-diethyltriaz-1-en-1-yl]-5-ethynyl-3',5'-difluorobiphenyl-2-yl}ethanol as the starting material in 70% yield. LCMS for $C_{16}H_{12}ClF_2N_2O$ (M+H)$^+$: m/z=321.1; Found: 320.9.

Step I: 7-(1-Azidoethyl)-5-chloro-8-(3,5-difluorophenyl)cinnoline

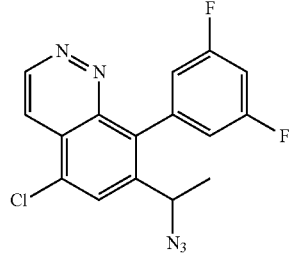 [SMILES: CC(N=[N+]=[N-])c1cc(Cl)c2ccnnc2c1-c1cc(F)cc(F)c1]

The desired compound was prepared according to the procedure of Example 16, step M, using 1-[5-chloro-8-(3,5-difluorophenyl)cinnolin-7-yl]ethanol as the starting material in 94% yield. LCMS for $C_{16}H_{11}ClF_2N_5$ (M+H)$^+$: m/z=346.1; Found: 345.9.

Step J: Chiral separation of 7-(1-azidoethyl)-5-chloro-8-(3,5-difluorophenyl)cinnoline The racemic mixture of 7-(1-azidoethyl)-5-chloro-8-(3,5-difluorophenyl)cinnoline was separated by HPLC (Chiracel OD-H, eluting with 10% ethanol/90% hexanes, at flow rate of 20 mL/minute) to give the two individual enantiomers (rt=13.6 minutes, 16.9 minutes). The first peak (rt=13.6 minutes) that eluted off the column was designated peak 1 and the second peak (rt=16.9 minutes) that eluted off the column was designated peak 2.

Step K: Single enantiomers of 1-[5-chloro-8-(3,5-difluorophenyl)cinnolin-7-yl]ethanamine

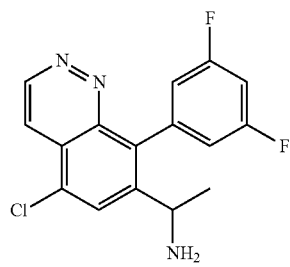 [SMILES: CC(N)c1cc(Cl)c2ccnnc2c1-c1cc(F)cc(F)c1]

The desired compounds were prepared according to the procedure of Examples 17 and 18, step B, using the individual enantiomers of 7-(1-azidoethyl)-5-chloro-8-(3,5-difluorophenyl)cinnoline as the starting materials in 99% yield (from peak 1) and 97% yield (from peak 2). From peak 1: LCMS for $C_{16}H_{13}ClF_2N_3$ (M+H)$^+$: m/z=319.9. From peak 2: LCMS for $C_{16}H_{13}ClF_2N_3$ (M+H)$^+$: m/z=320.1; Found: 319.9.

Step L: Single enantiomers of N-{1-[5-Chloro-8-(3,5-difluorophenyl)cinnolin-7-yl]ethyl)-9H-purin-6-amine The desired compounds were prepared according to the procedure of Examples 17 and 18, step D, using the individual enantiomers of 1-[5-chloro-8-(3,5-difluorophenyl)cinnolin- 7-yl]ethanamine as the starting materials in 34% yield (from peak 1) and 27% yield (from peak 2). Example 23 (from peak 1): LCMS for $C_{21}H_{15}ClF_2N_7$ (M+H)$^+$: m/z=438.1; Found: 437.9; $^1$H NMR (300 MHz, DMSO-d$_6$): δ 9.49 (d, J=6.1 Hz, 1H), 8.45-8.36 (m, 2H), 8.27 (d, J=5.6 Hz, 1H), 8.14 (s, 1H), 8.05 (s, 1H), 7.52 (d, J=9.1 Hz, 1H), 7.43-7.34 (m, 1H), 7.23 (d, J=9.1 Hz, 1H), 5.35 (br s, 1H), 1.50 (d, J=7.0 Hz, 3H). Example 24 (from peak 2): LCMS for $C_{21}H_{15}ClF_2N_7$ (M+H)$^+$: m/z=438.1; Found: 437.9; $^1$H NMR (300 MHz, DMSO-d$_6$): δ 12.9 (s, 1H), 9.49 (d, J=6.2 Hz, 1H), 8.48-8.37 (m, 2H), 8.27 (d, J=5.9 Hz, 1H), 8.13 (s, 1H), 8.04 (s, 1H), 7.52 (d, J=9.1 Hz, 1H), 7.43-7.34 (m, 1H), 7.23 (d, J=8.8 Hz, 1H), 5.36 (br s, 1H), 1.50 (d, J=6.7 Hz, 3H).

Examples 25, 26, 27, and 28

Diastereoatropisomers of N-{1-[5-Chloro-8-(2-fluorophenyl)cinnolin-7-yl]ethyl}-9H-purin-6-amine

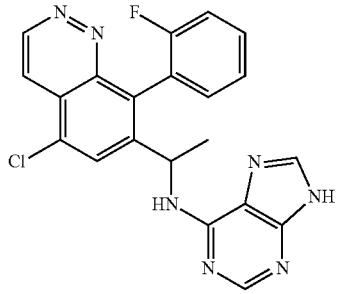 [SMILES: CC(Nc1ncnc2[nH]cnc12)c1cc(Cl)c2ccnnc2c1-c1ccccc1F]

The desired compounds were prepared according to the procedures of Examples 23 and 24 using (2-fluorophenyl) boronic acid (instead of (3,5-difluorophenyl)boronic acid in step A). In step H, atropisomers were observed. These atropisomers (labelled atropisomer 1 and atropisomer 2) each contained the R and S isomers of the stereogenic center. Atropisomer 1 and atropisomer 2 were separated and advanced forward individually in step I. In step J, atropisomer 2 could not be separated by HPLC, however, atropisomer 1 was separated by HPLC (Chiracel OJ-H, eluting with 30% ethanol/70% hexanes, at flow rate of 12 mL/min for 30 minutes) to give the two individual diastereomers (rt=15.8 minutes, 23.0 minutes). The first peak (rt=15.8 minutes) that eluted off the column was designated peak 1 and the second peak (rt=23.0 minutes) that eluted off the column was designated peak 2. Both peaks were advanced forward individually in step K and step L. In step L, the elevated temperatures of the reaction conditions produced a mixture of atropisomers for both peak 1 and peak 2 reactions. The atropisomers from both peak 1 and peak 2 were separated to give the four individual isomers (two diastereomeric pairs of atropisomers). (Example 25, peak 1, atrop 1): LCMS for $C_{21}H_{16}ClFN_7$ (M+H)$^+$: m/z=420.1; Found: 419.9; $^1$H NMR (300 MHz, DMSO-d$_6$): δ 9.50 (d, J=6.2 Hz, 1H), 8.80 (br s, 1H), 8.50 (s, 1H), 8.32-8.21 (m, 2H), 8.02 (s, 1H), 7.60-7.46 (m, 2H), 7.42-7.31 (m, 2H), 5.43 (br s, 1H), 1.67 (d, J=7.0 Hz, 3H); (Example 26, peak 1, atrop 2): LCMS for $C_{21}H_{16}ClFN_7$ (M+H)$^+$: m/z=420.1; Found: 419.9; $^1$H NMR (300 MHz, DMSO-d$_6$): δ 9.50 (d, J=5.9 Hz, 1H), 8.82 (br s, 1H), 8.38 (s, 1H), 8.33-8.25 (m, 3H), 7.89-7.82 (m, 1H), 7.62-7.53 (m, 1H), 7.46-7.34 (m, 2H), 5.41 (br s, 1H), 1.46 (d, J=7.0 Hz, 3H); (Example 27, peak 2, atrop 1): LCMS for $C_{21}H_{16}ClFN_7$ (M+H)$^+$: m/z=420.1; Found: 419.8; $^1$H NMR (300 MHz, DMSO-d$_6$): δ 9.49 (d, J=5.9 Hz, 1H), 8.68 (br s, 1H), 8.52 (s, 1H), 8.29 (d, J=5.9 Hz, 1H), 8.21 (s, 1H), 7.98 (s, 1H), 7.61-7.46 (m, 2H), 7.43-7.31 (m, 2H), 5.43 (br s, 1H), 1.66 (d, J=7.0 Hz, 3H); (Example 28, peak 2, atrop 2): LCMS for $C_{21}H_{16}ClFN_7$ (M+H)+: m/z=420.1; Found: 419.8; $^1$H NMR (300 MHz, DMSO-d$_6$): δ 9.51 (d, J=5.9 Hz, 1H), 8.96 (br s, 1H), 8.38-8.28 (m, 4H), 7.87-7.80 (m, 1H), 7.62-7.53 (m, 1H), 7.46-7.35 (m, 2H), 5.40 (br s, 1H), 1.47 (d, J=7.0 Hz, 3H).

Examples 29-30

Single enantiomers of N-{1-[8-(3,5-difluorophenyl)-5-fluorocinnolin-7-yl]ethyl}-9H-purin-6-amine trifluoroacetate

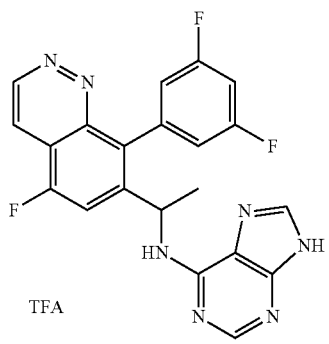 [SMILES: CC(Nc1ncnc2[nH]cnc12)c1cc(F)c2ccnnc2c1-c1cc(F)cc(F)c1]

The desired compounds were prepared according to the procedures of Examples 20 and 21 using (3,5-difluorophenyl) boronic acid (instead of (3-fluorophenyl)boronic acid)). Example 29 (peak 1): LCMS for $C_{21}H_{15}F_3N_7$ (M+H)$^+$: m/z=422.1; Found: 422.0; $^1$H NMR (300 MHz, DMSO-d$_6$): δ 9.47 (d, J=5.9 Hz, 1H), 8.91-8.81 (m, 1H), 8.34 (br s, 1H), 1H), 8.28-8.25 (m, 2H), 8.01 (d, J=10.8 Hz, 1H), 7.45-7.33 (m, 2H), 7.22 (d, J=8.8 Hz, 1H), 5.42-5.32 (m, 1H), 1.54 (d, J=7.0 Hz, 3H). Example 30 (peak 2): LCMS for $C_{21}H_{15}F_3N_7$ (M+H)$^+$: m/z=422.1; Found: 422.0; $^1$H NMR (300 MHz, DMSO-d$_6$): δ 9.47 (d, J=5.6 Hz, 1H), 8.98-8.88 (m, 1H), 8.36 (br s, 1H), 8.29-8.25 (m, 2H), 8.00 (d, J=10.5 Hz, 1H), 7.46-7.32 (m, 2H), 7.22 (d, J=8.5 Hz, 1H), 5.41-5.31 (m, 1H), 1.54 (d, J=6.4 Hz, 3H).

Example 31

N-{[5-Chloro-8-(3-fluorophenyl)cinnolin-7-yl]methyl}-9H-purin-6-amine trifluoroacetate

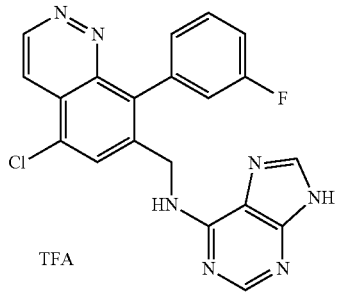 [SMILES: Fc1cccc(-c2c(CNc3ncnc4[nH]cnc34)cc(Cl)c3ccnnc23)c1]

Step A: 4-Chloro-6-[(1E)-3,3-diethyltriaz-1-en-1-yl]-5-ethynyl-3'-fluorobiphenyl-2-carbaldehyde

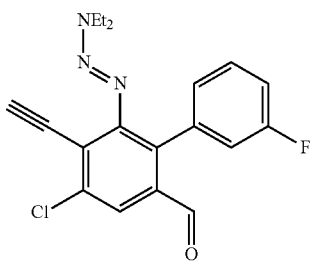

A solution of 4-chloro-6-[(1E)-3,3-diethyltriaz-1-en-1-yl]-5-ethynyl-3'-fluoro-N-methoxy-N-methylbiphenyl-2-carboxamide (0.50 g, 1.2 mmol) in tetrahydroduran (5 mL) at −78° C. was treated with 1.0 M lithium aluminum hydride in tetrahydroduran (2.5 mL, 2.5 mmol) dropwise and stirred at −78° C. for 2 hours. The reaction mixture was quenched with water (0.5 mL) at −78° C., diluted with ethyl acetate (50 mL), and warmed to 20° C. The organic layer was separated, washed with 1 M HCl (30 mL), water and brine, dried with sodium sulfate, filtered, and concentrated to a crude residue. Purification by flash column chromatography using ethyl acetate in hexanes (0%-20%) gave the desired product (0.20 g, 47%). LCMS for $C_{19}H_{18}ClFN_3O$ (M+H)$^+$: m/z=358.1; Found: 357.9.

Step B. {4-Chloro-6-[(1E)-3,3-diethyltriaz-1-en-1-yl]-5-ethynyl-3'-fluorobiphenyl-2-yl}methanol

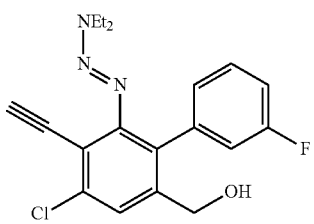

The desired compound was prepared according to the procedure of Example 16, step K, using 4-chloro-6-[(1E)-3,3-diethyltriaz-1-en-1-yl]-5-ethynyl-3'-fluorobiphenyl-2-carbaldehyde as the starting material in quantitative yield. LCMS for $C_{19}H_{20}ClFN_3O$ (M+H)$^+$: m/z=360.1; Found: 359.9.

Step C: (1E)-[6-(Azidomethyl)-4-chloro-3-ethynyl-3'-fluorobiphenyl-2-yl]-3,3-diethyltriaz-1-ene

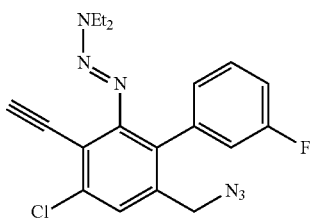

The desired compound was prepared according to the procedure of Example 16, step M, using {4-chloro-6-[(1E)-3,3-diethyltriaz-1-en-1-yl]-5-ethynyl-3'-fluorobiphenyl-2-yl}methanol as the starting material in 79% yield. LCMS for $C_{19}H_{19}ClFN_6$ (M+H)$^+$: m/z=385.1; Found: 384.9.

Step D: 7-(Azidomethyl)-5-chloro-8-(3-fluorophenyl)cinnoline

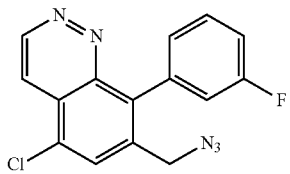 [SMILES: [N-]=[N+]=NCc1cc(Cl)c2ccnnc2c1-c1cccc(F)c1]

The desired compound was prepared according to the procedure of Example 16, step L, using (1E)-1-[6-(azidomethyl)-4-chloro-3-ethynyl-3'-fluorobiphenyl-2-yl]-3,3-diethyltriaz-1-ene as the starting material in 19% yield. LCMS for $C_{15}H_{10}ClFN_5$ (M+H)$^+$: m/z=314.1; Found: 313.8.

Step E: 1-[5-Chloro-8-(3-fluorophenyl)cinnolin-7-yl]methanamine trifluoroacetate

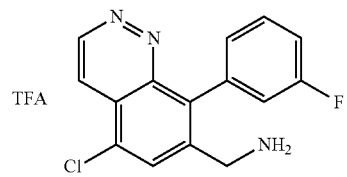 [SMILES: NCc1cc(Cl)c2ccnnc2c1-c1cccc(F)c1]

The desired compound was prepared according to the procedure of Example 16, step N, using 7-(azidomethyl)-5-chloro-8-(3-fluorophenyl)cinnoline as the starting material in 52% yield. LCMS for $C_{15}H_{12}ClFN_3$ (M+H)$^+$: m/z=288.1; Found: 287.9.

Step F: N-{[5-Chloro-8-(3-fluorophenyl)cinnolin-7-yl]methyl}-9H-purin-6-amine trifluoroacetate The desired compound was prepared according to the procedure of Examples 17 and 18, step D, using 1-[5-chloro-8-(3-fluorophenyl)cinnolin-7-yl]methanamine trifluoroacetate as the starting material in 15% yield. LCMS for $C_{20}H_{14}ClFN_7$ (M+H)$^+$: m/z=406.1; Found: 406.1; $^1$H NMR (300 MHz, CD₃OD): δ 9.45 (d, J=5.9 Hz, 1H), 8.46 (d, J=6.2 Hz, 2H), 8.36 (br s, 1H), 8.20 (s, 1H), 7.52-7.43 (m, 1H), 7.28-7.12 (m, 3H), 5.05-4.95 (m, 2H).

Examples 32-33

Single enantiomers of N-{1-[5-chloro-8-(3-fluorophenyl)cinnolin-7-yl]propyl}-9H-purin-6-amine

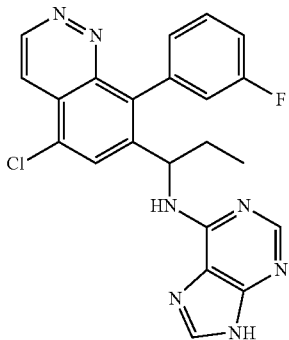 [SMILES: CCC(Nc1ncnc2[nH]cnc12)c1cc(Cl)c2ccnnc2c1-c1cccc(F)c1]

The desired compounds were prepared according to the procedures of Examples 17 and 18 using ethylmagnesium chloride (instead of methylmagnesium chloride). Example 32 (peak 1): LCMS for C₂₂H₁₈ClFN₇ (M+H)⁺: m/z=434.1; Found: 434.0; ¹H NMR (400 MHz, DMSO-d₆): δ 13.0 (br s, 1H), 9.47 (d, J=6.1 Hz, 1H), 8.48-8.33 (m, 2H), 8.26 (d, J=5.9 Hz, 1H), 8.14-8.04 (m, 2H), 7.70-7.61 (m, 1H), 7.59-7.53 (m, 1H), 7.37-7.30 (m, 1H), 7.28-7.20 (m, 1H), 5.27-5.17 (m, 1H), 2.03-1.93 (m, 1H), 1.82-1.72 (m, 1H), 0.80-0.74 (m, 3H). Example 33 (peak 2): LCMS for C₂₂H₁₈ClFN₇ (M+H)⁺: m/z=434.1; Found: 433.9; ¹H NMR (400 MHz, DMSO-d₆): δ 9.47 (d, J=5.9 Hz, 1H), 8.47 (d, J=10.2 Hz, 1H), 8.39-8.32 (m, 1H), 8.26 (d, J=6.1 Hz, 1H), 8.14-8.03 (m, 2H), 7.70-7.61 (m, 1H), 7.60-7.53 (m, 1H), 7.37-7.31 (m, 1H), 7.28-7.19 (m, 2H), 5.27-5.17 (m, 1H), 2.04-1.94 (m, 1H), 1.81-1.73 (m, 1H), 0.80-0.74 (m, 3H).

Examples 34-35

Single enantiomers of N-{1-[5-chloro-8-(5-fluoropyridin-3-yl)cinnolin-7-yl]ethyl}-9H-purin-6-amine trifluoroacetate

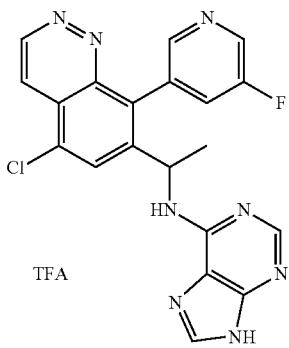 [SMILES: CC(Nc1ncnc2[nH]cnc12)c1cc(Cl)c2ccnnc2c1-c1cncc(F)c1]

The desired compounds were prepared according to the procedures of Examples 17 and 18 using (5-fluoropyridin-3-yl)boronic acid [Combi-Blocks, BB-3512] (instead of (3-fluorophenyl)boronic acid). Example 34 (peak 1): LCMS for C₂₀H₁₅ClFN₈ (M+H)⁺: m/z=421.1; Found: 421.0; ¹H NMR (300 MHz, DMSO-d₆): δ 9.53 (d, J=5.9 Hz, 1H), 8.78-8.72 (m, 1.5H), 8.55-8.48 (m, 1.5H), 8.41 (d, J=6.4 Hz, 1H), 8.37-8.32 (m, 2H), 8.14 (d, J=9.1 Hz, 0.5H), 7.99 (d, J=8.8 Hz, 0.5H), 5.38-5.28 (m, 1H), 1.60 (d, J=5.0 Hz, 3H). Example 35 (peak 2): LCMS for C₂₀H₁₅ClFN₈ (M+H)⁺: m/z=421.1; Found: 421.0; ¹H NMR (300 MHz, DMSO-d₆): δ 9.53 (d, J=6.2 Hz, 1H), 8.78-8.72 (m, 1.5H), 8.55-8.53 (m, 1.5H), 8.43-8.38 (m, 2H), 8.34 (d, J=5.9 Hz, 1H), 8.14 (d, J=9.4 Hz, 0.5H), 7.99 (d, J=9.4 Hz, 0.5H), 5.38-5.28 (m, 1H), 1.62-1.58 (m, 3H).

Examples 36-37

Single enantiomers of N-{1-[8-(3-fluorophenyl)-5-methylcinnolin-7-yl]ethyl}-9H-purin-6-amine

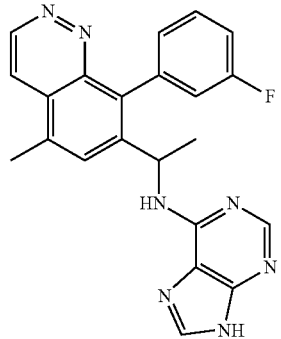 [SMILES: Cc1cc(C(C)Nc2ncnc3[nH]cnc23)c(-c2cccc(F)c2)c2nnccc12]

The desired compounds were prepared according to the procedures of Examples 20 and 21 using 3-bromo-4-methylphenol [Alfa Aesar, H28689] (instead of 3-bromo-4-fluorophenol). Example 36 (peak 1): LCMS for C₂₂H₁₉FN₇ (M+H)⁺: m/z=400.2; Found: 400.0; ¹H NMR (300 MHz, DMSO-d₆): δ 12.9 (br s, 1H), 9.32 (d, J=6.2 Hz, 1H), 8.35-8.24 (m, 1H), 8.17 (d, J=5.9 Hz, 1H), 8.11-8.02 (m, 3H), 7.65-7.49 (m, 2H), 7.34-7.25 (m, 1H), 7.23-7.16 (m, 1H), 5.41-5.29 (m, 1H), 2.63 (s, 3H), 1.46 (d, J=7.0 Hz, 3H). Example 37 (peak 2): LCMS for C₂₂H₁₉FN₇ (M+H)⁺: m/z=400.2; Found: 400.0; ¹H NMR (300 MHz, DMSO-d₆): δ 12.9 (br s, 1H), 9.32 (d, J=5.9 Hz, 1H), 8.35-8.24 (m, 1H), 8.17 (d, J=5.9 Hz, 1H), 8.11-8.01 (m, 3H), 7.65-7.50 (m, 2H), 7.34-7.25 (m, 1H), 7.23-7.16 (m, 1H), 5.41-5.28 (m, 1H), 2.63 (s, 3H), 1.46 (d, J=7.0 Hz, 3H).

Examples 38-39

Single enantiomers of N-{1-[8-(3,5-difluorophenyl)-5-methylcinnolin-7-yl]ethyl}-9H-purin-6-amine

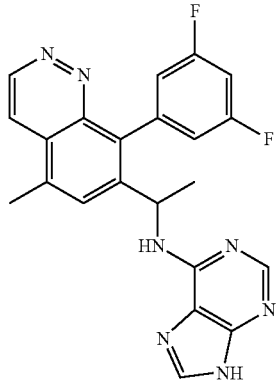 [SMILES: Cc1cc(C(C)Nc2ncnc3[nH]cnc23)c(-c2cc(F)cc(F)c2)c2nnccc12]

The desired compounds were prepared according to the procedures of Examples 20 and 21 using 3-bromo-4-methylphenol (instead of 3-bromo-4-fluorophenol) and (3,5-difluorophenyl)boronic acid (instead of (3-fluorophenyl)boronic acid)). Example 38 (peak 1): LCMS for $C_{22}H_{18}F_2N_7$ $(M+H)^+$: m/z=418.2; Found: 418.0; $^1$H NMR (300 MHz, DMSO-$d_6$): δ 12.9 (br s, 1H), 9.30 (d, J=5.9 Hz, 1H), 8.33-8.27 (m, 1H), 8.14 (d, J=6.2 Hz, 1H), 8.07-7.97 (m, 3H), 7.44 (d, J=9.4 Hz, 1H), 7.34-7.25 (m, 1H), 7.09 (d, J=8.8 Hz, 1H), 5.34-5.20 (m, 1H), 2.59 (s, 3H), 1.43 (d, J=7.0 Hz, 3H). Example 39 (peak 2): LCMS for $C_{22}H_{18}F_2N_7$ $(M+H)^+$: m/z=418.2; Found: 418.1; $^1$H NMR (300 MHz, DMSO-$d_6$): δ 12.9 (br s, 1H), 9,34 (d, J=5.9 Hz, 1H), 8.38-8.32 (m, 1H), 8.19 (d, J=5.9 Hz, 1H), 8.11-8.01 (m, 3H), 7.49 (d, J=9.4 Hz, 1H), 7.39-7.29 (m, 1H), 7.14 (d, J=8.8 Hz, 1H), 5.40-5.26 (m, 1H), 2.64 (s, 3H), 1.48 (d, J=7.0 Hz, 3H).

Example 40

3-{5-Chloro-7-[1-(9H-purin-6-ylamino)ethyl]cinnolin-8-yl}-5-fluoro-N-methylbenzamide

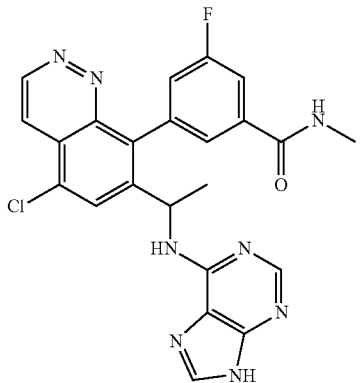 [SMILES: CNC(=O)c1cc(F)cc(-c2c(C(C)Nc3ncnc4[nH]cnc34)cc(Cl)c3ccnnc23)c1]

The desired compound was prepared according to the procedures of Example 16 using {3-fluoro-5-[(methylamino)carbonyl]phenyl}boronic acid [VWR, 101382-518] (instead of (3-fluorophenyl)boronic acid)). LCMS for $C_{23}H_{19}ClFN_8O$ $(M+H)^+$: m/z=477.1; Found: 477.1; $^1$H NMR (300 MHz, DMSO-$d_6$): δ 12.9 (br s, 1H), 9.48 (d, J=6.2 Hz, 1H), 8.63-8.55 (m, 1H), 8.50-8.38 (m, 2H), 8.28 (d, J=5.9 Hz, 1H), 8.21 (s, 0.5 H), 8.14-8.03 (m, 2H), 7.83-7.73 (m, 1.5H), 7.70 (s, 0.5H), 7.50 (d, J=8.8 Hz, 0.5H), 5.35-5.23 (m, 1H), 2.82-2.76 (m, 3H), 1.48 (d, J=7.0 Hz, 3H).

Example 41

N-{1-[5-Chloro-8-(3-fluoro-4-methoxyphenyl)cinnolin-7-yl]ethyl}-9H-purin-6-amine

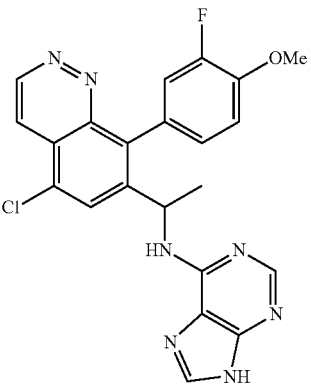 [SMILES: COc1ccc(-c2c(C(C)Nc3ncnc4[nH]cnc34)cc(Cl)c3ccnnc23)cc1F]

The desired compound was prepared according to the procedures of Example 16 using (3-fluoro-4-methoxyphenyl)boronic acid [Aldrich, 564036] (instead of (3-fluorophenyl) boronic acid)). LCMS for $C_{22}H_{18}ClFN_7O$ $(M+H)^+$: m/z=450.1; Found: 450.1; $^1$H NMR (300 MHz, DMSO-$d_6$): δ 12.9 (br s, 1H), 9.45 (d, J=5.9 Hz, 1H), 8.45-8.33 (m, 2H), 8.23 (d, J=5.9 Hz, 1H), 8.15-8.00 (m, 2H), 7.67-7.58 (m, 1H), 7.41-7.21 (m, 1.5H), 7.18-7.11 (m, 0.5H), 5.50-5.34 (m, 1H), 3.93 (s, 3H), 1.51-1.42 (m, 3H).

Example 42

N-{1-[5-Chloro-8-(2-fluoropyridin-4-yl)cinnolin-7-yl]ethyl}-9H-purin-6-amine

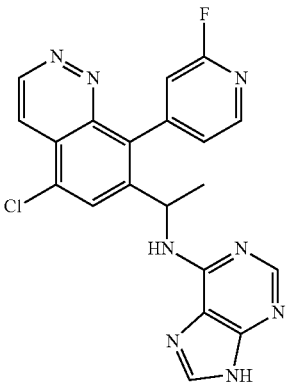 [SMILES: CC(Nc1ncnc2[nH]cnc12)c1cc(Cl)c2ccnnc2c1-c1ccnc(F)c1]

The desired compound was prepared according to the procedures of Example 16 using (2-fluoropyridin-4-yl)boronic acid [Asymchem, 111024] (instead of (3-fluorophenyl)boronic acid)). LCMS for $C_{20}H_{15}ClFN_8$ (M+H)$^+$: m/z=421.1; Found: 421.0; $^1$H NMR (300 MHz, DMSO-d$_6$): δ 9.49 (d, J=5.9 Hz, 1H), 8.51-8.38 (m, 3H), 8.29 (d, J=6.2 Hz, 1H), 8.15-8.02 (m, 2H), 7.79-7.74 (m, 0.5H), 7.59 (s, 0.5H), 7.51-7.45 (m, 0.5H), 7.37 (s, 0.5H), 5.34-5.17 (m, 1H), 1.55-1.48 (m, 3H).

Example 43

1-{5-Chloro-7-[1-(9H-purin-6-ylamino)ethyl]quinolin-8-yl}piperidin-4-ol

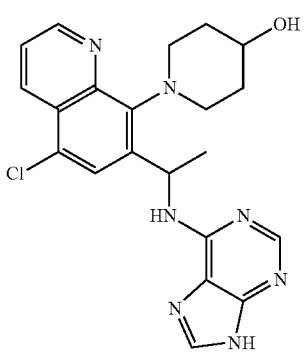 [SMILES: CC(Nc1ncnc2[nH]cnc12)c1cc(Cl)c2cccnc2c1N1CCC(O)CC1]

Step 1. 5-Chloro-8-(4-hydroxypiperidin-1-yl)-N-methoxy-N-methylquinoline-7-carboxamide

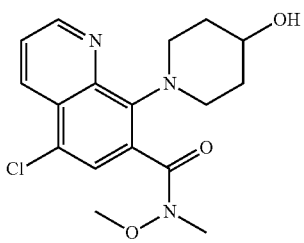 [SMILES: CON(C)C(=O)c1cc(Cl)c2cccnc2c1N1CCC(O)CC1]

A stirred mixture of 5-chloro-7-{[methoxy(methyl)amino]carbonyl}quinolin-8-yl trifluoromethanesulfonate (0.120 g, 0.301 mmol), 4-hydroxypiperidine (0.0366 g, 0.362 mmol), palladium acetate (1 mg, 0.006 mmol), (S)-(−)-2,2'-bis(diphenylphosphino)-1,1'-binaphthyl (6 mg, 0.009 mmol), and cesium carbonate (0.14 g, 0.42 mmol) in tetrahydrofuran (6 mL) was heated at 65° C. overnight. The mixture was cooled, diluted with dichloromethane and then filtered. The filtrate was washed with brine, dried over sodium sulfate and evaporated to dryness. The resulting residue was purified on silica gel, eluting with 0 to 10% methanol in dichloromethane, to give the desired product (62 mg, 59%). LCMS calculated for $C_{17}H_{21}ClN_3O_3$ (M+H)$^+$: m/z=350.1; Found: 350.1.

Step 2. 8-(4-{[tert-Butyl(dimethyl)silyl]oxy}piperidin-1-yl)-5-chloro-N-methoxy-N-methylquinoline-7-carboxamide

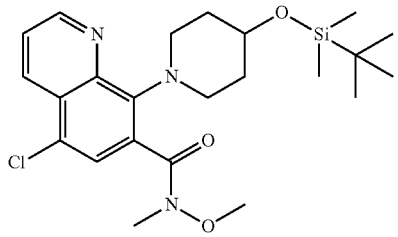 [SMILES: CON(C)C(=O)c1cc(Cl)c2cccnc2c1N1CCC(O[Si](C)(C)C(C)(C)C)CC1]

To a mixture of 5-chloro-8-(4-hydroxypiperidin-1-yl)-N-methoxy-N-methylquinoline-7-carboxamide (372 mg, 1.06 mmol) and 1H-imidazole (0.362 g, 5.32 mmol) in N,N-dimethylformamide (2 mL) was added tert-butyldimethylsilyl chloride (0.240 g, 1.60 mmol). The reaction was stirred at room temperature overnight, then quenched with sat. sodium bicarbonate and extracted with ethyl acetate. The combined organic layers were washed with water, brine, dried over sodium sulfate and evaporated to dryness. The residue was purified on silica gel, eluting with 0 to 40% ethyl acetate in hexane, to give the desired product (0.312 g, 63%). LCMS calculated for $C_{23}H_{35}ClN_3O_3Si$ (M+H)$^+$: m/z=464.2; Found: 464.2.

Step 3. 1-[8-(4-{[tert-Butyl(dimethyl)silyl]oxy}piperidin-1-yl)-5-chloroquinolin-7-yl]ethanone

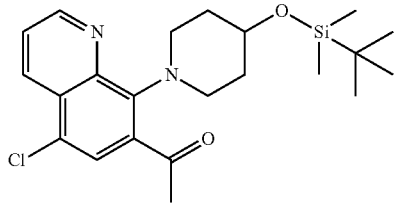 [SMILES: CC(=O)c1cc(Cl)c2cccnc2c1N1CCC(O[Si](C)(C)C(C)(C)C)CC1]

To a mixture of 8-(4-{[tert-butyl(dimethyl)silyl]oxy}piperidin-1-yl)-5-chloro-N-methoxy-N-methylquinoline-7-carboxamide (312 mg, 0.672 mmol) in tetrahydrofuran (0.9 mL) was added 1.4 M methylmagnesium bromide in tetrahydrofuran (2.9 mL, 4.0 mmol). The reaction was stirred at room temperature overnight, then quenched with sat. ammonium chloride and extracted with ethyl acetate. The combined organic layers were washed with brine, dried over magnesium sulfate and then concentrated to dryness under reduced pressure to afford the desired product (0.275 g, 98%). LCMS calculated for $C_{22}H_{32}ClN_2O_2Si$ (M+H)$^+$: m/z=419.2; Found: 419.1.

Step 4. 1-[8-(4-{[tert-Butyl(dimethyl)silyl]oxy}piperidin-1-yl)-5-chloroquinolin-7-yl]ethanamine

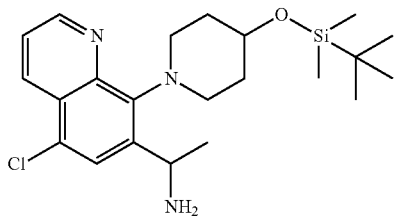 [SMILES: CC(N)c1cc(Cl)c2cccnc2c1N1CCC(O[Si](C)(C)C(C)(C)C)CC1]

A mixture of 1-[8-(4-{[tert-butyl(dimethyl)silyl]oxy}piperidin-1-yl)-5-chloroquinolin-7-yl]ethanone (275 mg, 0.656 mmol) and ammonium acetate (506 mg, 6.56 mmol) in methanol (3.7 mL) and acetonitrile (3.7 mL) was heated at 65° C. in a sealed tube for 30 minutes. After cooling to room temperature, sodium cyanoborohydride (82.5 mg, 1.31 mmol) was added to the resulting mixture. The reaction was heated at 65° C. for another 4 hours, then cooled to room temperature, quenched with sat. sodium bicarbonate and extracted with dichloromethane. The combined extracts were dried over magnesium sulfate and evaporated to dryness. The residue was used directly in the next step. LCMS calculated for $C_{22}H_{35}ClN_3OSi$ (M+H)$^+$: m/z=421.2; Found: 421.1.

Step 5. N-{1-[8-(4-{[tert-Butyl(dimethyl)silyl]oxy}piperidin-1-yl)-5-chloroquinolin-7-yl]ethyl}-9H-purin-6-amine

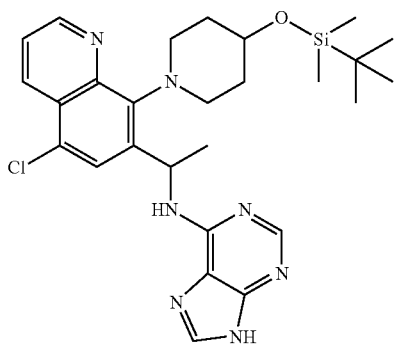 [SMILES: CC(Nc1ncnc2[nH]cnc12)c1cc(Cl)c2cccnc2c1N1CCC(O[Si](C)(C)C(C)(C)C)CC1]

A mixture of 6-bromo-9H-purine (0.262 g, 1.31 mmol), 1-[8-(4-{[tert-butyl(dimethyl)silyl]oxy}piperidin-1-yl)-5-chloroquinolin-7-yl]ethanamine (0.276 g, 0.657 mmol), and N,N-diisopropylethylamine (0.23 mL, 1.31 mmol) in ethanol (2 mL) was heated at reflux under nitrogen overnight. The mixture was evaporated and the resulting residue was diluted with water and extracted with ethyl acetate. The combined organic layers were washed with brine, dried and evaporated to dryness. The crude product was used directly in the next step (0.20 g, 57%). LCMS calculated for $C_{27}H_{37}ClN_7OSi$ (M+H)$^+$: m/z=538.2; Found: 538.2.

Step 6. 1-{5-Chloro-7-[1-(9H-purin-6-ylamino)ethyl]quinolin-8-yl}piperidin-4-ol

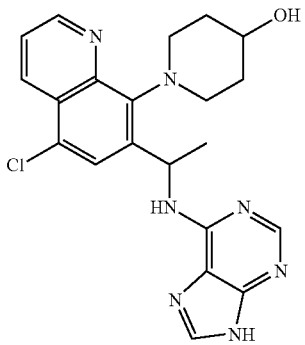 [SMILES: CC(Nc1ncnc2[nH]cnc12)c1cc(Cl)c2cccnc2c1N1CCC(O)CC1]

To a mixture of N-{1-[8-(4-{[tert-butyl(dimethyl)silyl]oxy}piperidin-1-yl)-5-chloroquinolin-7-yl]ethyl}-9H-purin-6-amine (0.200 g, 0.372 mmol) in acetonitrile (1 mL) was added 2.0 M fluorosilicic acid in water (0.929 mL, 1.86 mmol). The reaction was stirred at room temperature for 30 minutes, then neutralized with aq. sodium hydroxide and extracted with dichloromethane. The extracts were combined and evaporated to dryness. The residue was purified on a RP-HPLC (XBridge C18 column, eluting with a gradient of acetonitrile in water with 0.2% ammonium hydroxide, at a flow rate of 30 mL/min) to give the desired product as the free base. LCMS calculated for $C_{21}H_{23}ClN_7O$ (M+H)$^+$: m/z=424.2; Found: 424.1. $^1$H NMR (DMSO-d$_6$, 400 MHz) δ 12.89 (1H, s), 8.95 (1H, m), 8.44 (1H, m), 8.27 (1H, m), 8.11 (1H, s), 8.01 (1H, s), 7.99 (1H, s), 7.58 (1H, dd, J=8.4 and 4.0 Hz), 6.35 (1H, br s), 4.67 (1H, m), 4.01 (1H, m), 3.76 (1H, m), 3.61 (1H, m), 2.78 (1H, m), 1.90 (2H, m), 1.79~1.61 (3H, m), 1.52 (3H, d, J=7.2 Hz) ppm.

Example 44

N-{1-[4-(3-Fluorophenyl)-1-methylisoquinolin-3-yl]ethyl}-9H-purin-6-amine

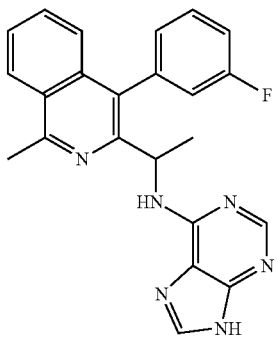 [SMILES: Cc1nc(C(C)Nc2ncnc3[nH]cnc23)c(-c2cccc(F)c2)c2ccccc12]

Step 1. Methyl 4-hydroxy-1-methylisoquinoline-3-carboxylate

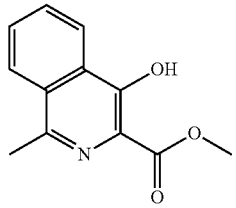 [SMILES: COC(=O)c1nc(C)c2ccccc2c1O]

A mixture of methyl 1-chloro-4-hydroxyisoquinoline-3-carboxylate (1.00 g, 4.21 mmol, from Aldrich), tetramethylstannane (3.01 g, 16.8 mmol), and bis(triphenylphosphine)palladium(II) chloride (0.295 g, 0.421 mmol) in N,N-dimethylformamide (30 mL) was stirred at 130° C. for 30 minutes. The mixture was cooled to room temperature, quenched with water and then filtered. The filtrate was extracted with ethyl acetate. The combined organic layers were washed with brine, dried over sodium sulfate and concentrated in vacuo. The residue was purified on silica gel chromatography, eluting with 0 to 10% MeOH in dichloromethane, to give the desired product (0.80 g, 88%). LCMS calculated for $C_{12}H_{12}NO_3$ (M+H)$^+$: m/z=218.1; Found: 218.1.

Step 2. Methyl 1-methyl-4-{[(trifluoromethyl)sulfonyl]oxy}isoquinoline-3-carboxylate

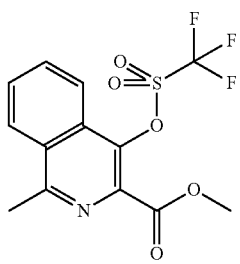 [SMILES: COC(=O)c1nc(C)c2ccccc2c1OS(=O)(=O)C(F)(F)F]

To a mixture of methyl 4-hydroxy-1-methylisoquinoline-3-carboxylate (0.800 g, 3.68 mmol) in methylene chloride (20 mL) was added N,N-diisopropylethylamine (0.96 mL, 5.5 mmol) followed by trifluoromethanesulfonic anhydride (0.74 mL, 4.4 mmol), dropwise, at −78° C. The reaction was stirred at −78° C. for 30 minutes, then allowed to warm to 0° C., diluted with dichloromethane and washed with water, brine and dried over sodium sulfate. After evaporating to dryness, the resulting residue was purified on silica gel, eluting with 0 to 80% ethyl acetate in hexane, to give the desired product (1.05 g, 82%). LCMS calculated for $C_{13}H_{11}F_3NO_5S$ (M+H)$^+$: m/z=350.0; Found: 350.0.

Step 3. Methyl 4-(3-fluorophenyl)-1-methylisoquinoline-3-carboxylate

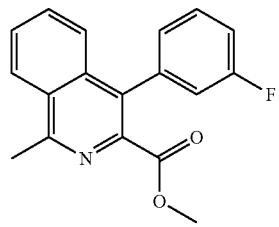 [SMILES: COC(=O)c1nc(C)c2ccccc2c1-c1cccc(F)c1]

To a mixture of methyl 1-methyl-4-{[(trifluoromethypsulfonyl]oxy}isoquinoline-3-carboxylate (0.500 g, 1.43 mmol) and (3-fluorophenyl)boronic acid (0.24 g, 1.7 mmol) in 1,4-dioxane (6 mL) was added 1 N solution of sodium carbonate in water (2.2 mL, 2.2 mmol) and tetrakis(triphenylphosphine)palladium(0) (0.083 g, 0.072 mmol). The mixture was heated at 100° C. overnight. After cooling, the mixture was diluted with ethyl acetate, washed with water, dried over MgSO$_4$, and concentrated. The residue was used directly in the next step. LCMS calculated for $C_{18}H_{15}FNO_2$ (M+H)$^+$: m/z=296.1; Found: 296.1.

Step 4. 4-(3-Fluorophenyl)-1-methylisoquinoline-3-carboxylic acid

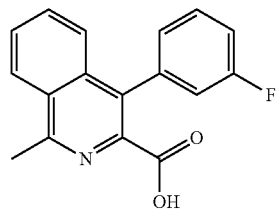 [SMILES: Cc1nc(C(=O)O)c(-c2cccc(F)c2)c2ccccc12]

A mixture of methyl 4-(3-fluorophenyl)-1-methylisoquinoline-3-carboxylate (0.423 g, 1.43 mmol) and 3.0 M lithium hydroxide in water (2.39 mL, 7.16 mmol) in tetrahydrofuran (2.4 mL) was stirred at room temperature for 3 hours. After neutralized with 1 N HCl, the resulting mixture was extracted with ethyl acetate. The combined organic layers were washed with brine, dried over magnesium sulfate and evaporated to dryness under reduced pressure. The resulting crude acid was used directly in the next step (0.40 g, 99%). LCMS calculated for $C_{17}H_{13}FNO_2$ (M+H)$^+$: m/z=282.1; Found: 282.0.

Step 5. 4-(3-Fluorophenyl)-N-methoxy-N,1-dimethylisoquinoline-3-carboxamide

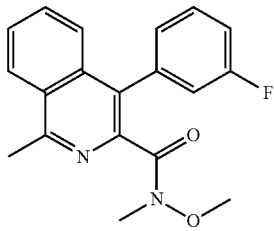 [SMILES: CON(C)C(=O)c1nc(C)c2ccccc2c1-c1cccc(F)c1]

A mixture of 4-(3-fluorophenyl)-1-methylisoquinoline-3-carboxylic acid (400 mg, 1 mmol), O-(benzotriazol-1-yl)-N,N,N',N'-tetramethyluronium hexafluorophosphate (700 mg, 1.8 mmol) and triethylamine (0.99 mL, 7.1 mmol) in N,N-dimethylformamide (2 mL) was stirred at room temperature for 10 minutes. N,O-Dimethylhydroxylamine hydrochloride (180 mg, 1.8 mmol) was added and the resulting suspension was stirred at room temperature for 2 hours. The mixture was quenched with water and then extracted with ethyl acetate. The combined organic layers were dried over $Na_2SO_4$, concentrated and the residue purified on silica gel (eluting with 0-80% ethyl acetate in hexane) to give the desired product (0.257 g, 60%). LCMS calculated for $C_{19}H_{18}FN_2O_2$ (M+H)$^+$: m/z=325.1; Found: 325.1.

Step 6. 1-[4-(3-Fluorophenyl)-1-methylisoquinolin-3-yl]ethanone

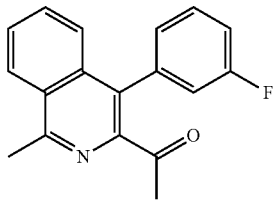 [SMILES: CC(=O)c1nc(C)c2ccccc2c1-c1cccc(F)c1]

To a mixture of 4-(3-fluorophenyl)-N-methoxy-N,1-dimethylisoquinoline-3-carboxamide (257 mg, 0.792 mmol) in tetrahydrofuran (1 mL) was added 1.4 M methylmagnesium bromide in tetrahydrofuran (3.4 mL, 4.8 mmol). The reaction was stirred at room temperature overnight, quenched with sat. ammonium chloride, and extracted with ethyl acetate. The combined organic layers were washed with brine, dried over magnesium sulfate, and concentrated to dryness to afford the desired product (0.221 g, 100%). LCMS calculated for $C_{18}H_{15}FNO$ (M+H)$^+$: m/z=280.1; Found: 280.1.

Step 7. 1-[4-(3-Fluorophenyl)-1-methylisoquinolin-3-yl]ethanamine

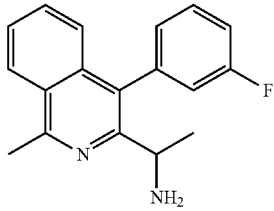 [SMILES: Cc1nc(C(C)N)c(-c2cccc(F)c2)c2ccccc12]

A mixture of 1-[4-(3-fluorophenyl)-1-methylisoquinolin-3-yl]ethanone (222 mg, 0.795 mmol) and ammonium acetate (613 mg, 7.95 mmol) in methanol (4.5 mL) and acetonitrile (4.5 mL) was heated at 65° C. in a sealed tube for 30 minutes. After cooling to room temperature, sodium cyanoborohydride (99.9 mg, 1.59 mmol) was added to the resulting mixture. The reaction was heated at 65° C. for another 4 hours, then cooled to room temperature and quenched with sat. sodium bicarbonate and extracted with dichloromethane. The combined extracts were dried over magnesium sulfate and evaporated to dryness. The crude product was used directly in the next step (215 mg, 97%). LCMS calculated for $C_{18}H_{18}FN_2$ (M+H)$^+$: m/z=281.1; Found: 281.1.

Step 8. N-{1-[4-(3-Fluorophenyl)-1-methylisoquinolin-3-yl]ethyl}-9H-purin-6-amine

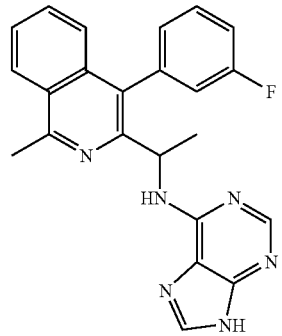 [SMILES: Cc1nc(C(C)Nc2ncnc3[nH]cnc23)c(-c2cccc(F)c2)c2ccccc12]

A mixture of 6-bromo-9H-purine (0.31 g, 1.6 mmol), 1-[4-(3-fluorophenyl)-1-methylisoquinolin-3-yl]ethanamine (0.220 g, 0.785 mmol), and N,N-diisopropylethylamine (0.27 mL, 1.57 mmol) in ethanol (3 mL) was heated at 100° C. in a sealed tube overnight. The mixture was filtered and filtrate evaporated to dryness under reduced pressure. The resulting residue was purified on a RP-HPLC (XBridge C18 column, eluting with a gradient of acetonitrile in water with 0.2% ammonium hydroxide, at a flow rate of 30 mL/min) to give the desired product as the free base. LCMS calculated for $C_{23}H_{20}FN_6$ (M+H)$^+$: m/z=399.2; Found: 399.1.

Example 45

1-{4-Chloro-2-[1-(9H-purin-6-ylamino)ethyl]-1-naphthyl}piperidin-4-ol

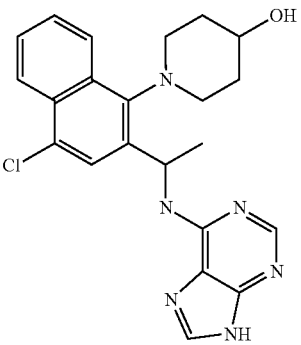 [SMILES: CC(Nc1ncnc2[nH]cnc12)c1cc(Cl)c2ccccc2c1N1CCC(O)CC1]

Step 1. 1-(4-Chloro-1-hydroxy-2-naphthyl)ethanone

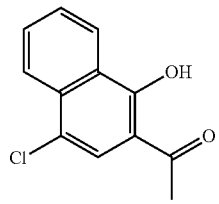

To a stirred solution of 1-(1-hydroxy-2-naphthyl)ethanone (5.00 g, 26.8 mmol, from Aldrich) in acetic acid (100 mL) was added N-chlorosuccinimide (3.94 g, 29.5 mmol) and the resulting mixture heated at 100° C. for 18 hours. After allowing to be cooled to ambient temperature, the reaction mixture was concentrated in vacuo and then diluted with ethyl acetate. The precipitated solid was collected by filtration to afford the desired product (3.98 g, 67%). LCMS calculated for $C_{12}H_{10}ClO_2$ (M+H)$^+$: m/z=221.0; Found: 221.1.

Step 2. 2-Acetyl-4-chloro-1-naphthyl trifluoromethanesulfonate

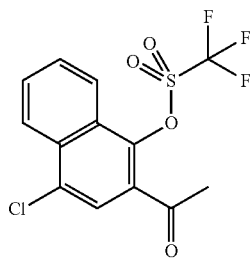 [SMILES: CC(=O)c1cc(Cl)c2ccccc2c1OS(=O)(=O)C(F)(F)F]

To a mixture of 1-(4-chloro-1-hydroxy-2-naphthyl)ethanone (1.786 g, 8.094 mmol) in methylene chloride (80 mL) was added N,N-diisopropylethylamine (3.3 mL, 18.9 mmol) followed by trifluoromethanesulfonic anhydride (2.55 mL, 15.2 mmol), dropwise, at −78° C. The reaction was stirred at −78° C. for 30 minutes., then allowed to warm to 0° C., diluted with dichloromethane and washed with water, brine and dried over sodium sulfate. After removal of the volatiles, the resulting residue was purified on silica gel, eluting with 0 to 80% ethyl acetate in hexane, to give the desired product (2.627 g, 92%). LCMS calculated for $C_{13}H_9ClF_3O_4S$ (M+H)$^+$: m/z=353.0; Found: 352.9.

Step 3. 1-[4-Chloro-1-(4-hydroxypiperidin-1-yl)-2-naphthyl]ethanone

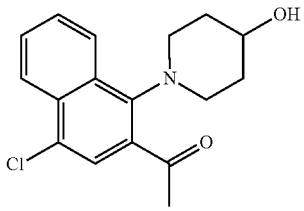 [SMILES: CC(=O)c1cc(Cl)c2ccccc2c1N1CCC(O)CC1]

A stirred mixture of 2-acetyl-4-chloro-1-naphthyl trifluoromethanesulfonate (0.106 g, 0.301 mmol), 4-hydroxypiperidine (0.0366 g, 0.362 mmol), palladium acetate (1 mg, 0.006 mmol), (S)-(−)-2,2'-bis(diphenylphosphino)-1,1'-binaphthyl (6 mg, 0.009 mmol), and cesium carbonate (0.14 g, 0.42 mmol) in tetrahydrofuran (6 mL) was heated at 65° C. overnight. The mixture was cooled, diluted with dichloromethane and filtered. The filtrate was washed with brine, dried over sodium sulfate and evaporated to dryness. The resulting residue was purified on silica gel, eluting with 0 to 60% ethyl acetate in hexane, to give the desired product (74 mg, 81%). LCMS calculated for $C_{17}H_{19}ClNO_2$ (M+H)$^+$: m/z=304.1; Found: 304.0.

Step 4. 1-[2-(1-Aminoethyl)-4-chloro-1-naphthyl]piperidin-4-ol

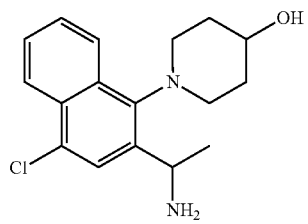 [SMILES: CC(N)c1cc(Cl)c2ccccc2c1N1CCC(O)CC1]

A mixture of 1-[4-chloro-1-(4-hydroxypiperidin-1-yl)-2-naphthyl]ethanone (74 mg, 0.24 mmol) and ammonium acetate (188 mg, 2.44 mmol) in methanol (1.4 mL) and acetonitrile (1.4 mL) was heated at 65° C. in a sealed tube for 30 minutes. After cooling to room temperature, sodium cyanoborohydride (30.6 mg, 0.487 mmol) was added to the resulting mixture. The reaction was heated at 65° C. for another 4 hours, then cooled to room temperature and quenched with sat. sodium bicarbonate and extracted with dichloromethane. The combined extracts were dried over magnesium sulfate and evaporated to dryness. The crude amine was used directly in the next step. LCMS calculated for $C_{17}H_{22}ClN_2O$ (M+H)$^+$: m/z=305.1; Found: 305.1.

Step 5. 1-{4-Chloro-2-[1-(9H-purin-6-ylamino)ethyl]-1-naphthyl}piperidin-4-ol

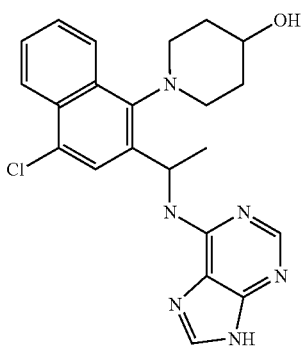 [SMILES: CC(Nc1ncnc2[nH]cnc12)c1cc(Cl)c2ccccc2c1N1CCC(O)CC1]

A mixture of 6-bromo-9H-purine (0.096 g, 0.48 mmol), 1-[2-(1-aminoethyl)-4-chloro-1-naphthyl]piperidin-4-ol (0.074 g, 0.24 mmol), and N,N-diisopropylethylamine (0.084 mL, 0.48 mmol) in ethanol (0.8 mL) was heated at reflux under nitrogen overnight. The mixture was evaporated and the resulting residue was diluted with water and extracted with ethyl acetate. The combined organic layers were washed with brine, dried and evaporated to dryness. The resulting residue was purified on a RP-HPLC (XBridge C18 column, eluting with a gradient of acetonitrile in water with 0.2% ammonium hydroxide, at a flow rate of 30 mL/min) to give the desired product as the free base. LCMS calculated for $C_{22}H_{24}ClN_6O$ $(M+H)^+$: m/z=423.2; Found: 423.2.

Example 46

N-{1-[4-Chloro-1-(3-fluorophenyl)-2-naphthyl]ethyl}-9H-purin-6-amine

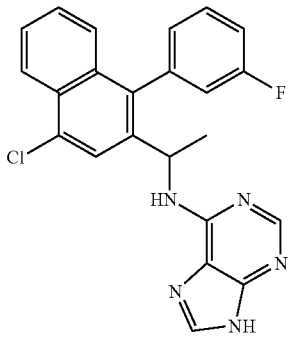 [SMILES: CC(Nc1ncnc2[nH]cnc12)c1cc(Cl)c2ccccc2c1-c1cccc(F)c1]

Step 1. 1-[4-Chloro-1-(3-fluorophenyl)-2-naphthyl]ethanone

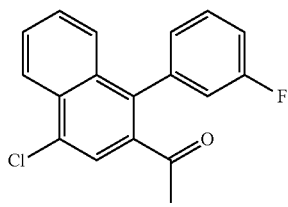

To a mixture of 2-acetyl-4-chloro-1-naphthyl trifluoromethanesulfonate (0.100 g, 0.284 mmol, from Example 45, Step 2) and (3-fluorophenyl)boronic acid (0.048 g, 0.34 mmol) in 1,4-dioxane (1 mL) was added 1 N solution of sodium carbonate in water (0.43 mL, 0.43 mmol) and tetrakis(triphenylphosphine)palladium(0) (0.016 g, 0.014 mmol). The mixture was heated at 100° C. overnight. After cooling, the mixture was diluted with ethyl acetate, washed with water, dried over MgSO₄, and concentrated. The residue was purified on silica gel, eluting with 0 to 40% ethyl acetate in hexane, to give the desired product (56 mg, 66%). LCMS calculated for $C_{18}H_{13}ClFO$ $(M+H)^+$: m/z=299.1; Found: 299.0.

Step 2. 1-[4-Chloro-1-(3-fluorophenyl)-2-naphthyl]ethanamine

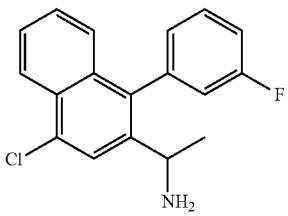 [SMILES: CC(N)c1cc(Cl)c2ccccc2c1-c1cccc(F)c1]

A mixture of 1-[4-chloro-1-(3-fluorophenyl)-2-naphthyl]ethanone (58 mg, 0.19 mmol) and ammonium acetate (150 mg, 1.94 mmol) in methanol (1.1 mL) and acetonitrile (1.1 mL) was heated at 65° C., in a sealed tube for 30 minutes. After cooling to room temperature, sodium cyanoborohydride (24.4 mg, 0.388 mmol) was added to the resulting mixture. The reaction was heated at 65° C. for another 4 hours, then cooled to room temperature and quenched with sat. sodium bicarbonate and extracted with dichloromethane. The combined extracts were dried over magnesium sulfate and evaporated to dryness. The crude material was used directly in the next step (58 mg, 100%). LCMS calculated for $C_{18}H_{13}ClF$ $(M-NH_2)^+$: m/z=283.1; Found: 283.0.

Step 3. N-{1-[4-Chloro-1-(3-fluorophenyl)-2-naphthyl]ethyl}-9H-purin-6-amine A mixture of 6-bromo-9H-purine (0.077 g, 0.39 mmol), 1-[4-chloro-1-(3-fluorophenyl)-2-naphthyl]ethanamine (0.058 g, 0.19 mmol), and N,N-diisopropylethylamine (0.067 mL, 0.39 mmol) in ethanol (0.6 mL) was heated at 100° C., in a sealed tube overnight. The volatiles were removed under reduced pressure. The residue was purified on a RP-HPLC (XBridge C18 column, eluting with a gradient of acetonitrile in water with 0.2% ammonium hydroxide, at a flow rate of 30 mL/min) to give the desired product. LCMS calculated for $C_{23}H_{18}ClFN_5$ (M+H)⁺: m/z=418.1; Found: 418.1.

Example 47

N-{1-[5-Chloro-8-(4,4-difluoropiperidin-1-yl)quinolin-7-yl]ethyl}-9H-purin-6-amine

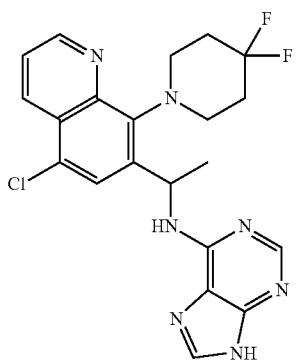 [SMILES: CC(Nc1ncnc2[nH]cnc12)c1cc(Cl)c2cccnc2c1N1CCC(F)(F)CC1]

Step 1. 1-(5-Chloro-8-hydroxyquinolin-7-yl)ethanone

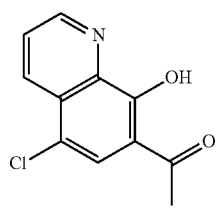

A mixture of 5-chloro-8-quinolinol (6.67 g, 37.1 mmol, from Aldrich), aluminum trichloride (20.00 g, 150.0 mmol), and acetyl chloride (12.1 mL, 170 mmol) was stirred at 0° C. for 4 hours, then heated at 130° C. for 12 hours, cooled, and decomposed with water (39 mL) (caution!) and conc. HCl (13 mL). The solid product was filtered, and dried under reduced pressure. The solid obtained was then dissolved in 50 mL of water. To the solution was added 100 mL of dichloromethane. The mixture was cooled with an ice bath and its pH was adjusted to 4 with 20% NaOH. The mixture was filtered under reduced pressure. The solid collected was washed with water and air dried to give the desired product (~2 g). The layers of the filtrate were separated and the aqueous layer was extracted with dichloromethane. The combined organic layers were washed with water, brine, dried over magnesium sulfate and concentrated to give additional desired product (total 5.6 g, 68%). LCMS calculated for $C_{11}H_9ClNO_2$ (M+H)⁺: m/z=222.0; Found: 222.0.

Step 2. 7-Acetyl-5-chloroquinolin-8-yl trifluoromethanesulfonate

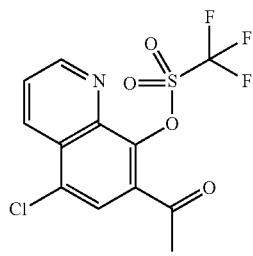 [SMILES: CC(=O)c1cc(Cl)c2cccnc2c1OS(=O)(=O)C(F)(F)F]

To a mixture of 1-(5-chloro-8-hydroxyquinolin-7-yl)ethanone (3.80 g, 17.1 mmol) in methylene chloride (80 mL) was added triethylamine (3.58 mL, 25.7 mmol), followed by trifluoromethanesulfonic anhydride (3.46 mL, 20.6 mmol), at −78° C. The reaction was allowed to warm to room temperature after addition, then quenched with water and extracted with dihcloromethane. The combined organic layers were dried over sodium sulfate and evaporated to dryness under reduced pressure. The residue was purified on silica gel, eluting with 0 to 70% ethyl acetate in hexane, to give the desired product (3.21 g, 53%). LCMS calculated for $C_{12}H_8ClF_3NO_4S$ (M+H)⁺: m/z=354.0; Found: 353.9.

Step 3. 1-[5-Chloro-8-(4,4-difluoropiperidin-1-yl)quinolin-7-yl]ethanone

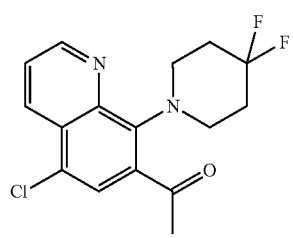 [SMILES: CC(=O)c1cc(Cl)c2cccnc2c1N1CCC(F)(F)CC1]

A stirred mixture of 7-acetyl-5-chloroquinolin-8-yl trifluoromethanesulfonate (0.106 g, 0.301 mmol), 4,4-difluoropiperidine hydrochloride (0.0570 g, 0.362 mmol), palladium acetate (1 mg, 0.006 mmol), (S)-(−)-2,2'-bis(diphenylphosphino)-1,1'-binaphthyl (6 mg, 0.009 mmol), and cesium carbonate (0.274 g, 0.843 mmol) in tetrahydrofuran (3 mL) was heated at 65° C. overnight. The mixture was cooled, diluted with dichloromethane and filtered. The filtrate was washed with brine, dried over sodium sulfate and evaporated to dryness. The resulting residue was purified on silica gel, eluting with 0 to 50% ethyl acetate in hexane, to give the Step 4. 1-[5-Chloro-8-(4,4-difluoropiperidin-1-yl)quinolin-7-yl]ethanamine

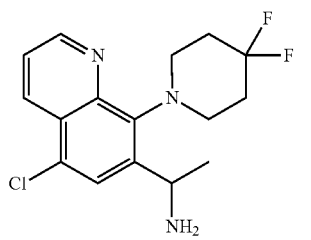 [SMILES: CC(N)c1cc(Cl)c2cccnc2c1N1CCC(F)(F)CC1]

A mixture of 1-[5-chloro-8-(4,4-difluoropiperidin-1-yl)quinolin-7-yl]ethanone (20 mg, 0.06 mmol) and ammonium acetate (47.5 mg, 0.616 mmol) in methanol (0.35 mL) and acetonitrile (0.35 mL) was heated at 65° C. in a sealed tube for 30 minutes. After cooling to room temperature, sodium cyanoborohydride (7.7 mg, 0.12 mmol) was added to the resulting mixture. The reaction was heated at 65° C. for another 4 hours, then cooled to room temperature and quenched with sat. sodium bicarbonate and extracted with dichloromethane. The combined extracts were dried over magnesium sulfate and evaporated to dryness. The crude amine was used directly in the next step. LCMS calculated for $C_{16}H_{19}ClF_2N_3$ (M+H)$^+$: m/z=326.1; Found: 326.0.

Step 5. N-{1-[5-Chloro-8-(4,4-difluoropiperidin-1-yl)quinolin-7-yl]ethyl}-9H-purin-6-amine

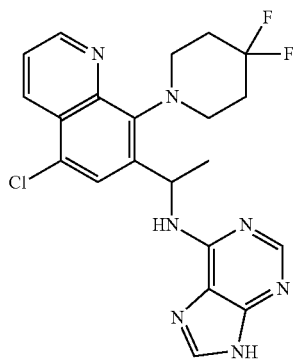 [SMILES: CC(Nc1ncnc2[nH]cnc12)c1cc(Cl)c2cccnc2c1N1CCC(F)(F)CC1]

A mixture of 6-bromo-9H-purine (0.0244 g, 0.123 mmol), 1-[5-chloro-8-(4,4-difluoropiperidin-1-yl)quinolin-7-yl]ethanamine (0.020 g, 0.061 mmol), and N,N-diisopropylethylamine (0.021 mL, 0.12 mmol) in ethanol (0.2 mL) was heated at reflux under nitrogen overnight. The mixture was evaporated and the resulting residue was purified on a RP-HPLC (XBridge C18 column, eluting with a gradient of acetonitrile in water with 0.2% ammonium hydroxide, at a flow rate of 30 mL/min) to give the desired product. LCMS calculated for $C_{21}H_{21}ClF_2N_7$ (M+H)$^+$: m/z=444.1; Found: 444.0.

Example 48

(3S)-1-{5-Chloro-7-[1-(9H-purin-6-ylamino)ethyl]quinolin-8-yl}piperidin-3-ol

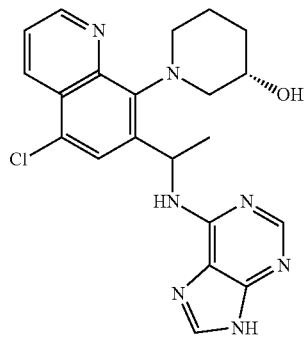 [SMILES: CC(Nc1ncnc2[nH]cnc12)c1cc(Cl)c2cccnc2c1N1CCC[C@H](O)C1]

Step 1. 1-{5-Chloro-8-[(3S)-3-hydroxypiperidin-1-yl]quinolin-7-yl}ethanone

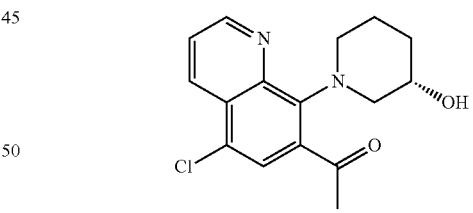

A stirred mixture of 7-acetyl-5-chloroquinolin-8-yl trifluoromethanesulfonate (0.106 g, 0.301 mmol, from Example 47, Step 2), (3S)-piperidin-3-ol hydrochloride (0.0498 g, 0.362 mmol), palladium acetate (1 mg, 0.006 mmol), (S)-(–)-2,2'-bis(diphenylphosphino)-1,1'-binaphthyl (6 mg, 0.009 mmol), and cesium carbonate (0.274 g, 0.843 mmol) in tetrahydrofuran (3 mL) was heated at 65° C. overnight. The mixture was cooled, diluted with dichloromethane and filtered. The filtrate was washed with brine, dried over sodium sulfate and evaporated to dryness. The resulting residue was purified on silica gel, eluting with 0 to 100% ethyl acetate in hexane, to give the desired product. LCMS calculated for $C_{16}H_{18}ClN_2O_2$ (M+H)$^+$: m/z=305.1; Found: 305.0.

Step 2. (3S)-1-[7-(1-Aminoethyl)-5-chloroquinolin-8-yl]piperidin-3-ol

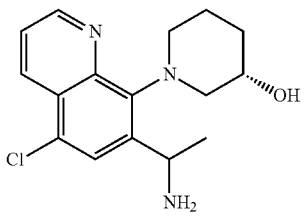 [SMILES: CC(N)c1cc(Cl)c2cccnc2c1N1CCC[C@H](O)C1]

A mixture of 1-{5-chloro-8-[(3S)-3-hydroxypiperidin-1-yl]quinolin-7-yl}ethanone (18 mg, 0.059 mmol) and ammonium acetate (45.5 mg, 0.591 mmol) in methanol (0.33 mL) and acetonitrile (0.34 mL) was heated at 65° C. in a sealed tube for 30 minutes. After cooling to room temperature, sodium cyanoborohydride (7.42 mg, 0.118 mmol). The reaction was heated at 65° C. for another 4 hours, then cooled to room temperature and quenched with sat. sodium bicarbonate, extracted with dichloromethane. The combined extracts were dried over magnesium sulfate and evaporated to dryness. The crude amine was used directly in the next step. LCMS calculated for $C_{16}H_{21}ClN_3O$ (M+H)$^+$: m/z=306.1; Found: 306.1.

Step 3. (3S)-1-{5-Chloro-7-[1-(9H-purin-6-ylamino)ethyl]quinolin-8-yl}piperidin-3-ol

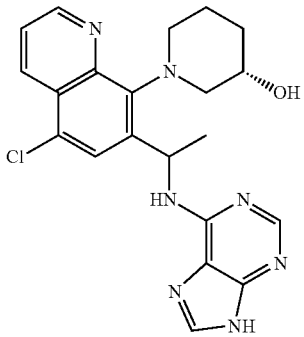 [SMILES: CC(Nc1ncnc2[nH]cnc12)c1cc(Cl)c2cccnc2c1N1CCC[C@H](O)C1]

A mixture of 6-bromo-9H-purine (0.0234 g, 0.118 mmol), (3S)-1-[7-(1-aminoethyl)-5-chloroquinolin-8-yl]piperidin-3-ol (0.018 g, 0.059 mmol), and N,N-diisopropylethylamine (0.0205 mL, 0.118 mmol) in ethanol (0.2 mL) was heated at reflux under nitrogen overnight. The mixture was evaporated and the resulting residue was purified on a RP-HPLC (XBridge C18 column, eluting with a gradient of acetonitrile in water with 0.2% ammonium hydroxide, at a flow rate of 30 mL/min) to give the products. First peak retention time 1.482 minutes, LCMS calculated for $C_{21}H_{23}ClN_7O$ (M+H)$^+$: m/z=424.2; Found: 424.0. Second peak retention time 1.583 minutes, LCMS calculated for $C_{21}H_{23}ClN_7O$ (M+H)$^+$: m/z=424.2; Found: 424.0.

Example 49

1-{5-Chloro-7-[1-(9H-purin-6-ylamino)ethyl]quinolin-8-yl}-4-phenylpiperidin-4-ol

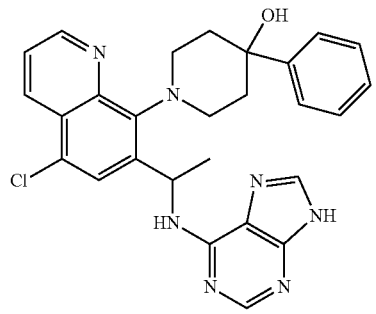 [SMILES: CC(Nc1ncnc2[nH]cnc12)c1cc(Cl)c2cccnc2c1N1CCC(O)(c2ccccc2)CC1]

Step 1. 1-[5-Chloro-8-(4-hydroxy-4-phenylpiperidin-1-yl)quinolin-7-yl]ethanone

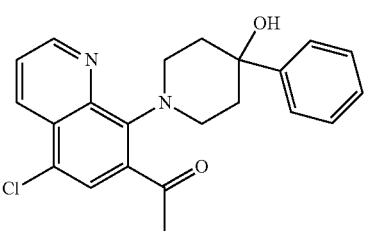 [SMILES: CC(=O)c1cc(Cl)c2cccnc2c1N1CCC(O)(c2ccccc2)CC1]

A stirred mixture of 7-acetyl-5-chloroquinolin-8-yl trifluoromethanesulfonate (0.106 g, 0.301 mmol, from Example 47, Step 2), 4-phenylpiperidin-4-ol (0.0641 g, 0.362 mmol), palladium acetate (1 mg, 0.006 mmol), (S)-(−)-2,2'-bis(diphenylphosphino)-1,1'-binaphthyl (6 mg, 0.009 mmol), and cesium carbonate (0.274 g, 0.843 mmol) in tetrahydrofuran (3 mL) was heated at 65° C. overnight. The mixture was cooled, diluted with dichloromethane and filtered. The filtrate was washed with brine, dried over sodium sulfate and evaporated to dryness. The residue was purified on silica gel, eluting with 0 to 50% ethyl acetate in hexane, to give the desired product. LCMS calculated for $C_{22}H_{22}ClN_2O_2(M+E)^+$: m/z=381.1; Found: 380.9.

Step 2. 1-[7-(1-Aminoethyl)-5-chloroquinolin-8-yl]-4-phenylpiperidin-4-ol

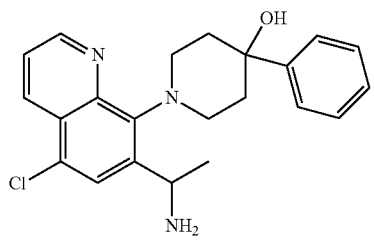 [SMILES: CC(N)c1cc(Cl)c2cccnc2c1N1CCC(O)(c2ccccc2)CC1]

A mixture of 1-[5-chloro-8-(4-hydroxy-4-phenylpiperidin-1-yl) quinolin-7-yl]ethanone (37 mg, 0.097 mmol) and ammonium acetate (74.9 mg, 0.971 mmol) in methanol (0.55 mL) and acetonitrile (0.55 mL) was heated at 65° C. in a sealed tube for 30 minutes. After cooling to room temperature, sodium cyanoborohydride (12.2 mg, 0.194 mmol). The reaction was heated at 65° C. for another 4 hours, then cooled to room temperature and quenched with sat. sodium bicarbonate, extracted with dichloromethane. The combined extracts were dried over magnesium sulfate and evaporated to dryness (35 mg, 94%). LCMS calculated for $C_{22}H_{25}ClN_3O$ $(M+H)^+$: m/z=382.2; Found: 382.1.

Step 3. 1-{5-Chloro-7-[1-(9H-purin-6-ylamino) ethyl]quinolin-8-yl}-4-phenylpiperidin-4-ol

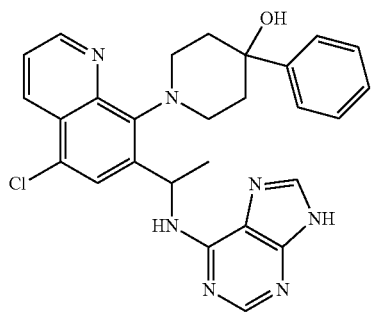 [SMILES: CC(Nc1ncnc2[nH]cnc12)c1cc(Cl)c2cccnc2c1N1CCC(O)(c2ccccc2)CC1]

A mixture of 6-bromo-9H-purine (0.036 g, 0.18 mmol), 1-[7-(1-aminoethyl)-5-chloroquinolin-8-yl]-4-phenylpiperidin-4-ol (0.035 g, 0.092 mmol), and N,N-diisopropylethylamine (0.032 mL, 0.18 mmol) in ethanol (0.32 mL) was heated at reflux under nitrogen overnight. The mixture was evaporated and the resulting residue was purified on a RP-HPLC (XBridge C18 column, eluting with a gradient of acetonitrile in water with 0.2% ammonium hydroxide, at a flow rate of 30 mL/min) to give the product as the free base. LCMS calculated for $C_{27}H_{27}ClN_7O$ $(M+H)^+$: m/z=500.2; Found: 500.1.

Example 50

N-{1-[8-(3-Fluorophenyl)-5-methylquinolin-7-yl] ethyl}-9H-purin-6-amine

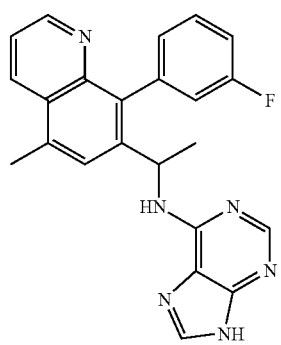 [SMILES: Cc1cc(C(C)Nc2ncnc3[nH]cnc23)c(-c2cccc(F)c2)c2ncccc12]

Step 1. 1-(8-Hydroxy-5-methylquinolin-7-yl)ethanone

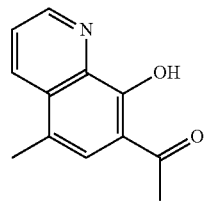

A mixture of 5-methylquinolin-8-ol (5.91 g, 37.1 mmol, from ChemBridge), aluminum trichloride (20.00 g, 150.0 mmol), and acetyl chloride (12.1 mL, 170 mmol) was stirred at 0° C. for 4 hours, then heated at 130° C. for 12 hours, cooled, and decomposed with water (39 mL) (caution! with external ice-cooling if necessary) and conc. HCl (13 mL). The precipitate was filtered, and dried under reduced pressure. The solid obtained was then dissolved in 50 mL of water. To the solution was added 100 mL of dichloromethane. The mixture was cooled with an ice bath and the pH adjusted to 4 with slow addition of 20% NaOH. The layers were separated and the aqueous layer was extracted with dichloromethane. The combined organic layers were washed with water, brine and dried over sodium sulfate. The suspension was filtered through a plug of cotton and concentrated to dryness. The residue was used directly in the next step (5.8 g, 78%). LCMS calculated for $C_{12}H_{12}NO_2$ (M+H)⁺: m/z=202.1; Found: 202.0.

Step 2. 7-Acetyl-5-methylquinolin-8-yl trifluoromethanesulfonate

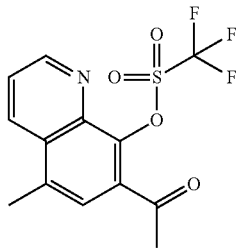 [SMILES: CC(=O)c1cc(C)c2cccnc2c1OS(=O)(=O)C(F)(F)F]

To a mixture of 1-(8-hydroxy-5-methylquinolin-7-yl)ethanone (4.9 g, 24 mmol) in methylene chloride (100 mL) was added triethylamine (10 mL, 73 mmol) followed by trifluoromethanesulfonic anhydride (6.1 mL, 36 mmol) at −78° C. The reaction was allowed to warm to room temperature gradually and stirred at room temperature for 30 minutes. After quenching with water, the mixture was extracted with dichloromethane. The combined organic layers were washed with brine, dried over sodium sulfate and concentrated to dryness. The residue was purified on silica gel, eluting with 0 to 80% ethyl acetate in hexane, to give the desired product (5.7 g, 70%). LCMS calculated for $C_{13}H_{11}F_3NO_4S$ (M+H)⁺: m/z=334.0; Found: 333.9

Step 3. 1-[8-(3-Fluorophenyl)-5-methylquinolin-7-yl]ethanone

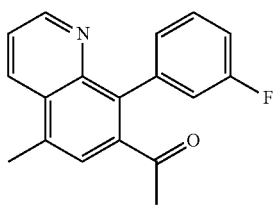 [SMILES: CC(=O)c1cc(C)c2cccnc2c1-c1cccc(F)c1]

To a mixture of 7-acetyl-5-methylquinolin-8-yl trifluoromethanesulfonate (0.833 g, 2.50 mmol) in tetrahydrofuran (20 mL), with stirring, was added 0.5 M (3-fluorophenyl)(iodo)zinc in THF (10.0 mL, 5.0 mmol), followed by tetrahydrofurantetrakis(triphenylphosphine)palladium(0) (289 mg, 0.250 mmol). The reaction mixture was heated at 60° C. overnight, cooled to room temperature and quenched with sat. sodium bicarbonate. The mixture was filtered through a Celite pad. The filtrate was extracted with ethyl acetate. The combined organic layers were washed with brine, dried and concentrated under reduced pressure. The residue was purified on silica gel, eluting with 0 to 80% ethyl acetate in hexane, to give the desired product (0.379 g, 54%). LCMS calculated for C18H14FNO (M+H)⁺: m/z=280.1; Found: 280.0.

Step 4. 1-[8-(3-Fluorophenyl)-5-methylquinolin-7-yl]ethanamine

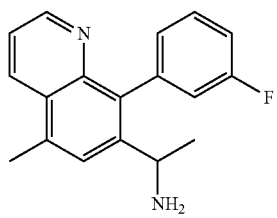 [SMILES: Cc1cc(C(C)N)c(-c2cccc(F)c2)c2ncccc12]

A mixture of 1-[8-(3-fluorophenyl)-5-methylquinolin-7-yl]ethanone (50 mg, 0.2 mmol) and ammonium acetate (138 mg, 1.79 mmol) in methanol (1.0 mL) and acetonitrile (1.0 mL) was heated at 65° C. in a sealed tube for 30 minutes. After cooling to room temperature, sodium cyanoborohydride (22.5 mg, 0.358 mmol). The reaction was heated at 65° C. for another 4 hours, then cooled to room temperature and quenched with sat. sodium bicarbonate, extracted with dichloromethane. The combined extracts were dried over magnesium sulfate and evaporated to dryness. The residue was used directly in the next step. LCMS calculated for $C_{18}H_{18}FN_2$ (M+H)⁺: m/z=281.1; Found: 281.1.

Step 5. N-{1-[8-(3-Fluorophenyl)-5-methylquinolin-7-yl]ethyl}-9H-purin-6-amine

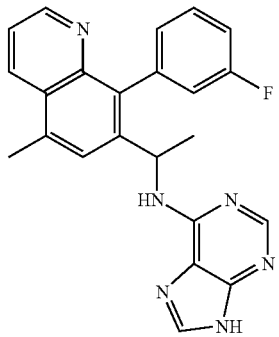 [SMILES: Cc1cc(C(C)Nc2ncnc3[nH]cnc23)c(-c2cccc(F)c2)c2ncccc12]

A mixture of 6-bromo-9H-purine (0.0712 g, 0.358 mmol), 1-[8-(3-fluorophenyl)-5-methylquinolin-7-yl]ethanamine (0.050 g, 0.18 mmol), and N,N-diisopropylethylamine (0.0623 mL, 0.358 mmol) in ethanol (0.6 mL) was heated at reflux under nitrogen overnight. The mixture was evaporated and the resulting residue was purified on a RP-HPLC (XBridge C18 column, eluting with a gradient of acetonitrile in water with 0.2% ammonium hydroxide, at a flow rate of 30 mL/min) to give the product. LCMS calculated for C$_{23}$H$_{20}$FN$_6$ (M+H)$^+$: m/z=399.2; Found: 399.0.

Example 51

N-{1-[5-Ethyl-8-(3-fluorophenyl)quinolin-7-yl]ethyl}-9H-purin-6-amine bis(trifluoroacetate)

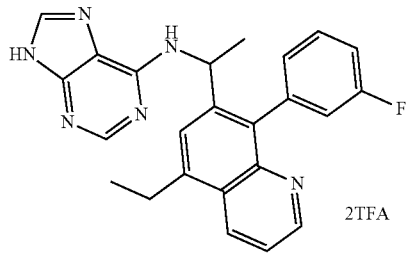

Step 1. Methyl 8-(3-fluorophenyl)-5-vinylquinoline-7-carboxylate

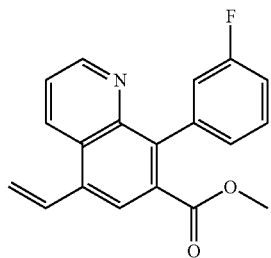 [SMILES: C=Cc1cc(C(=O)OC)c(-c2cccc(F)c2)c2ncccc12]

A mixture methyl 5-bromo-8-(3-fluorophenyl)quinoline-7-carboxylate (0.33 g, 0.92 mmol, from Example 10, Step 4), (2-ethenyl)tri-n-butyltin (0.581 g, 1.83 mmol) in N,N-dimethylformamide (3 mL) was degassed for 5 minutes. To the resulting mixture was then added bis(triphenylphosphine)palladium(II) chloride (32.1 mg, 0.0458 mmol). The reaction was heated at 130° C. for 1 hour, cooled and filtered. The filtrate was extracted with ethyl acetate. The combined organic layers were washed with water, brine, dried over sodium sulfate, then concentrated under reduced pressure. The residue was purified on silica gel, eluting with 0 to 50% ethyl acetate in hexane, to give the desired product (69 mg, 24%). LCMS calculated for C$_{19}$H$_{15}$FNO$_2$ (M+H)$^+$: m/z=308.1; Found: 308.0.

Step 2. 8-(3-Fluorophenyl)-5-vinylquinoline-7-carboxylic acid

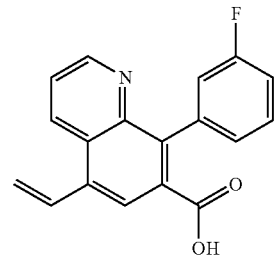 [SMILES: C=Cc1cc(C(=O)O)c(-c2cccc(F)c2)c2ncccc12]

A mixture of methyl 8-(3-fluorophenyl)-5-vinylquinoline-7-carboxylate (0.069 g, 0.22 mmol) and 1.0 M sodium hydroxide in water (2 mL, 2 mmol) in methanol (2 mL) was stirred at room temperature overnight. After acidified with 1 N HCl, the mixture was extracted with dichloromethane. The combined organic layers were dried over magnesium sulfate and concentrated to dryness. The crude acid was used directly in the next step (66 mg, 100%). LCMS calculated for C$_{18}$H$_{13}$FNO$_2$ (M+H)$^+$: m/z=294.1; Found: 294.0.

Step 3. 8-(3-Fluorophenyl)-N-methoxy-N-methyl-5-vinylquinoline-7-carboxamide

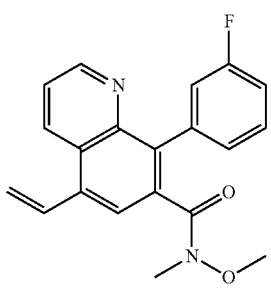 [SMILES: C=Cc1cc(C(=O)N(C)OC)c(-c2cccc(F)c2)c2ncccc12]

To a mixture of 8-(3-fluorophenyl)-5-vinylquinoline-7-carboxylic acid (66 mg, 0.22 mmol), N,O-dimethylhydroxylamine hydrochloride (32.9 mg, 0.338 mmol) in N,N-dimethylformamide (0.4 mL) was added benzotriazol-1-yloxytris(dimethylamino) phosphonium hexafluorophosphate (0.149 g, 0.338 mmol). After stirring at room temperature for 30 minutes, N,N-diisopropylethylamine (0.118 mL, 0.675 mmol) was added to the resulting mixture. The reaction was stirred at room temperature overnight, quenched with water and extracted with ethyl acetate. The combined organic layers were washed with brine, dried over sodium sulfate and concentrated to dryness under reduced pressure. The resdiue was purified on silica gel, eluting 0 to 50% ethyl acetate in hexane, to give the desired product (32 mg, 42%). LCMS calculated for $C_{20}H_{18}FN_2O_2$ (M+H)+: m/z=337.1; Found: 337.1.

give the desired product (6.1 mg, 20%). LCMS calculated for $C_{19}H_{17}FNO$ (M+H)+: m/z=294.1; Found: 294.1.

Step 4. 1-[8-(3-Fluorophenyl)-5-vinylquinolin-7-yl]ethanone

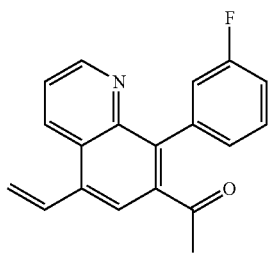 [SMILES: C=Cc1cc(C(C)=O)c(-c2cccc(F)c2)c2ncccc12]

To a mixture of 8-(3-fluorophenyl)-N-methoxy-N-methyl-5-vinylquinoline-7-carboxamide (32 mg, 0.095 mmol) in tetrahydrofuran (0.2 mL) was added 1.4 M methylmagnesium bromide in tetrahydrofuran (0.20 mL, 0.29 mmol) at 0° C. The reaction was stirred at room temperature for 1 hour, quenched with sat. ammonium chloride. The resulting mixture was extracted with ethyl acetate. The combined organic layers were washed with brine, dried over magnesium sulfate and concentrated to dryness. The crude product was used directly in the next step (26 mg, 94%). LCMS calculated for $C_{19}H_{15}FNO$ (M+H)+: m/z=292.1; Found: 292.1.

Step 6. 1-[5-Ethyl-8-(3-fluorophenyl)quinolin-7-yl]ethanamine

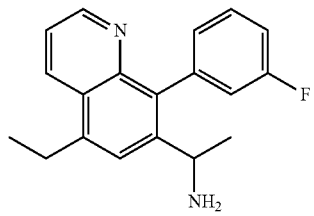

A mixture of 1-[5-ethyl-8-(3-fluorophenyl)quinolin-7-yl]ethanone (6.1 mg, 0.021 mmol) and ammonium acetate (0.017 g, 0.22 mmol) in methanol (0.3 mL) and acetonitrile (0.3 mL) was heated at 65° C. in a sealed tube for 1 hour. After cooling to room temperature, 1.0 M sodium cyanoborohydride in tetrahydrofuran (0.052 mL, 0.052 mmol) was added to the mixture. The reaction was heated at 65° C. overnight. The mixture was cooled to room temperature, quenched with sat. NaHCO3 solution and extracted with dichloromethane. The combined organic layers were dried over MgSO4 and concentrated to give the desired product. LCMS calculated for $C_{19}H_{20}FN_2$ (M+H)+: m/z=295.2; Found: 295.1.

Step 5. 1-[5-Ethyl-8-(3-fluorophenyl)quinolin-7-yl]ethanone

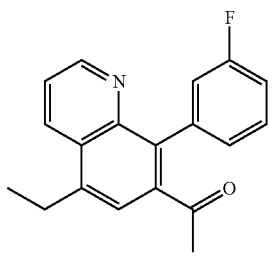 [SMILES: CCc1cc(C(C)=O)c(-c2cccc(F)c2)c2ncccc12]

A mixture of 1-[8-(3-fluorophenyl)-5-vinylquinolin-7-yl]ethanone (0.03 g, 0.1 mmol) and 5% palladium on carbon (3 mg) in methanol (1 mL) was treated with hydrogen under balloon pressure, at room temperature, for 3 hours. The mixture was filtered. The filtrate was concentrated and purified on silica gel (eluting with 0 to 10% Ethyl acetate in hexane) to

Step 7. N-{1-[5-Ethyl-8-(3-fluorophenyl)quinolin-7-yl]ethyl}-9H-purin-6-amine bis(trifluoroacetate)

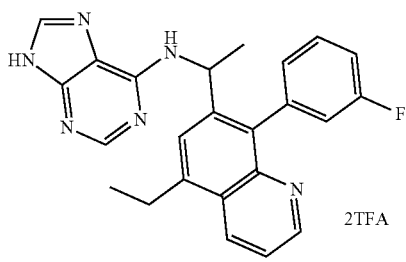 [SMILES: CCc1cc(C(C)Nc2ncnc3[nH]cnc23)c(-c2cccc(F)c2)c2ncccc12]

A mixture of 1-[5-ethyl-8-(3-fluorophenyl)quinolin-7-yl]ethanamine (7.3 mg, 0.025 mmol), 6-bromo-9H-purine (9.9 mg, 0.050 mmol) and N,N-diisopropylethylamine (0.013 mL, 0.074 mmol) in ethanol (0.2 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{24}$H$_{22}$FN$_6$ (M+H)$^+$: m/z=413.2; Found: 413.1.

Example 52

8-(3-fluorophenyl)-7-[1-(9H-purin-6-ylamino)ethyl]quinoline-5-carbonitrile

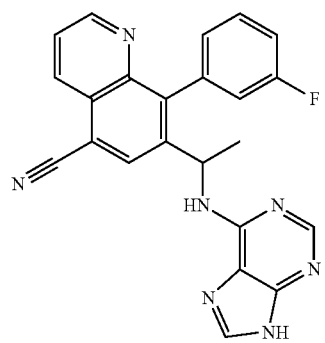 [SMILES: CC(Nc1ncnc2[nH]cnc12)c1cc(C#N)c2cccnc2c1-c1cccc(F)c1]

Step 1.
[5-Bromo-8-(3-fluorophenyl)quinolin-7-yl]methanol

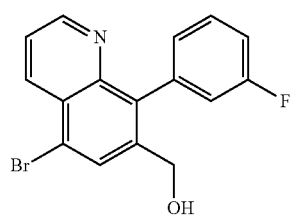 [SMILES: OCc1cc(Br)c2cccnc2c1-c1cccc(F)c1]

To a mixture of methyl 5-bromo-8-(3-fluorophenyl)quinoline-7-carboxylate (0.360 g, 1.00 mmol, from Example 10, Step 4) in tetrahydrofuran (1 mL) was added 1.0 M lithium tetrahydroaluminate in tetrahydrofuran (1.00 mL, 1.00 mmol) at 0° C. The reaction was stirred at room temperature for 30 minutes then quenched by successive addition of 0.038 mL of water, 0.038 mL of 15% NaOH, 0.11 mL of water. After stirred for 30 minutes, the mixture was filtered. The filtrate was dried over magnesium sulfate and evaporated to dryness. The residue was purified on silica gel, eluting with 0 to 80% ethyl acetate in hexane, to give the desired product (150 mg, 45%). LCMS calculated for C$_{16}$H$_{12}$BrFNO (M+H)$^+$: m/z=332.0; Found: 332.0.

Step 2.
5-Bromo-8-(3-fluorophenyl)quinoline-7-carbaldehyde

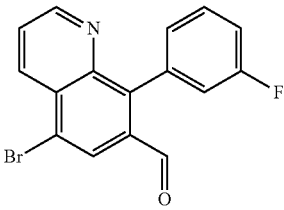 [SMILES: O=Cc1cc(Br)c2cccnc2c1-c1cccc(F)c1]

Dimethyl sulfoxide (0.038 mL, 0.54 mmol) was added to oxalyl chloride (0.0286 mL, 0.339 mmol) in methylene chloride (1.26 mL) at −78° C. After 10 minutes, [5-bromo-8-(3-fluorophenyl)quinolin-7-yl]methanol (0.075 g, 0.22 mmol) in methylene chloride (2.53 mL) was added and the resulting mixture was stirred at −78° C. for 30 minutes. Triethylamine (0.157 mL, 1.13 mmol) was then added and the mixture was stirred for 5 hours to room temperature. After quenching with water, the mixture was extracted with methylene chloride. The organic layers were combined, washed with brine, dried over magnesium sulfate and evaporated to dryness. The resulting mixture was purified on silica gel, eluting with 0 to 50% ethyl acetate in hexane, to give the desired product (49 mg, 66%). LCMS calculated for C$_{16}$H$_{10}$BrFNO (M+H)$^+$: m/z=330.0; Found: 330.0.

Step 3. 8-(3-Fluorophenyl)-7-formylquinoline-5-carbonitrile

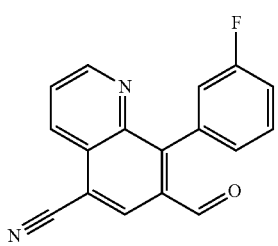 [SMILES: N#Cc1cc(C=O)c(-c2cccc(F)c2)c2ncccc12]

A mixture of 5-bromo-8-(3-fluorophenyl)quinoline-7-carbaldehyde (0.049 g, 0.15 mmol), zinc cyanide (0.035 g, 0.30 mmol) and tetrakis(triphenylphosphine)palladium(0) (0.034 g, 0.030 mmol) in dry N,N-dimethylformamide (0.50 mL) was stirred at 130° C. overnight. The mixture was filtered, diluted with water, extracted with ethyl acetate. The combined extracts were dried over MgSO$_4$, concentrated and purified on silica gel (eluting with 0 to 60% ethyl acetate in hexane) to give the desired product (20 mg, 50%). LCMS calculated for $C_{17}H_{10}FN_2O$ (M+H)$^+$: m/z=277.1; Found: 277.0.

Step 4. 8-(3-Fluorophenyl)-7-(1-hydroxyethyl)quinoline-5-carbonitrile

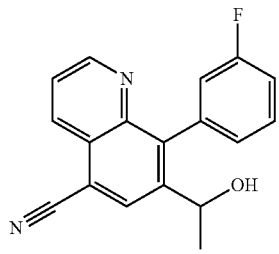 [SMILES: CC(O)c1cc(C#N)c2cccnc2c1-c1cccc(F)c1]

To a mixture of 8-(3-fluorophenyl)-7-formylquinoline-5-carbonitrile (20 mg, 0.07 mmol) in tetrahydrofuran (1 mL) was added 1.4 M methylmagnesium bromide in tetrahydrofuran (0.12 mL, 0.17 mmol) at −78° C. The reaction was stirred at −78° C. for 30 minutes, quenched with water at −78° C. The mixture was neutralized with 1 N HCl, and then extracted with ethyl acetate. The combined orgagnic layers were washed with brine, dried over magnesium sulfate and evaporated to dryness. The residue was used directly in the next step (20 mg, 90%). LCMS calculated for $C_{18}H_{14}FN_2O$ (M+H)$^+$: m/z=293.1; Found: 293.0.

Step 5. 1-[5-Cyano-8-(3-fluorophenyl)quinolin-7-yl]ethyl methanesulfonate

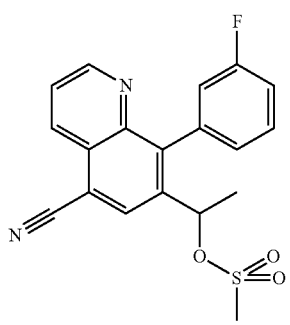 [SMILES: CC(OS(C)(=O)=O)c1cc(C#N)c2cccnc2c1-c1cccc(F)c1]

To a mixture of 8-(3-fluorophenyl)-7-(1-hydroxyethyl) quinoline-5-carbonitrile (20 mg, 0.07 mmol) in methylene chloride (1 mL) was added triethylamine (0.28 mL, 2.0 mmol) followed by methanesulfonyl chloride (0.12 mL, 1.5 mmol). The reaction was stirred at room temperature for 30 minutes, quenched with water and then extracted with dichloromethane. The combined organic layers were washed with brine and dried over magnesium sulfate and concentrated to dryness under reduced pressure. The residue was used directly in the next step (28 mg, 100%). LCMS calculated for $C_{19}H_{16}FN_2O_3S$ (M+H)$^+$: m/z=371.1; Found: 371.1.

Step 6. 7-(1-Azidoethyl)-8-(3-fluorophenyl)quinoline-5-carbonitrile

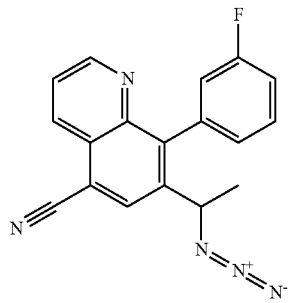 [SMILES: CC(N=[N+]=[N-])c1cc(C#N)c2cccnc2c1-c1cccc(F)c1]

A mixture of 1-[5-cyano-8-(3-fluorophenyl)quinolin-7-yl] ethyl methanesulfonate (28 mg, 0.076 mmol) and sodium azide (24 mg, 0.38 mmol) in N,N-dimethylformamide (0.5 mL) was stirred at room temperature overnight. The mixture was then quenched with water, extracted with ethyl acetate. The combined organic layers were washed with water and brine, and then dried over magnesium sulfate and evaporated to dryness. The residue was used directly in the next step (20 mg, 83%). LCMS calculated for $C_{18}H_{13}FN_5$ (M+H)$^+$: m/z = 318.1; Found: 318.1.

Step 7. 7-(1-Aminoethyl)-8-(3-fluorophenyl)quinoline-5-carbonitrile

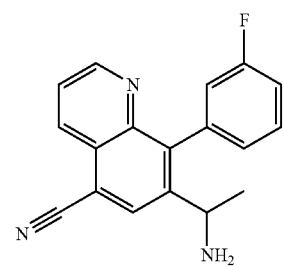 [SMILES: CC(N)c1cc(C#N)c2cccnc2c1-c1cccc(F)c1]

To a stirred solution of 7-(1-azidoethyl)-8-(3-fluorophenyl)quinoline-5-carbonitrile (0.020 g, 0.063 mmol) in tetrahydrofuran (0.2 mL) and water (0.0455 mL, 2.52 mmol) was added 1.0 M trimethylphosphine in tetrahydrofuran (0.076 mL, 0.076 mmol) at room temperature and the mixture was stirred at room temperature for 1 hour. To the mixture was added ethyl acetate and the mixture was extracted with 1 N HCl two times. The combined extracts were neutralized with solid sodium bicarbonate, and extracted with dichloromethane. The combined organic layers were washed with brine, dried over magnesium sulfate, and concentrated under reduced pressure. The LCMS of the crude, showed two peaks with the same desired mass, and was used directly in the next step (18 mg, 98%). LCMS calculated for C₁₈H₁₅FN₃ (M+H)⁺: m/z =292.1; Found: 292.1.

Step 8. 8-(3-Fluorophenyl)-7-[1-(9H-purin-6-ylamino)ethyl]quinoline-5-carbonitrile

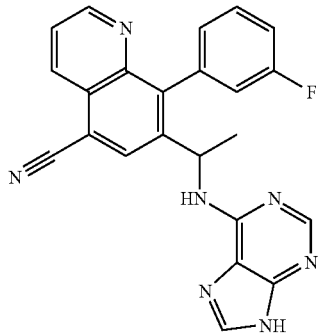 [SMILES: CC(Nc1ncnc2[nH]cnc12)c1cc(C#N)c2cccnc2c1-c1cccc(F)c1]

A mixture of 6-bromo-9H-purine (0.0246 g, 0.124 mmol), 7-(1-aminoethyl)-8-(3-fluorophenyl)quinoline-5-carbonitrile (0.018 g, 0.062 mmol), and N,N-diisopropylethylamine (0.0216 mL, 0.124 mmol) in ethanol (0.2 mL) was heated at reflux under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for C₂₃H₁₇FN₇ (M+H)⁺: m/z =410.2; Found: 410.1.

Example 53

(3R)-1-{5-fluoro-7-[1-(9H-purin-6-ylamino)ethyl]quinolin-8-yl}pyrrolidin-3-ol

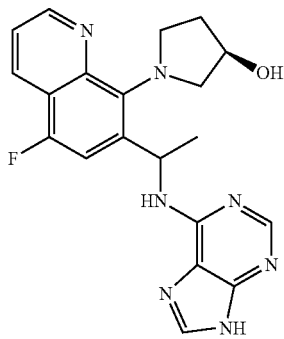

Step 1.
1-(5-Fluoro-8-hydroxyquinolin-7-yl)ethanone

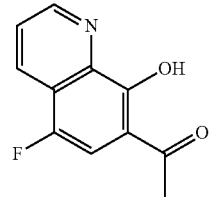

A mixture of 5-fluoroquinolin-8-ol (15.0 g, 91.9 mmol, from TCI), aluminum trichloride (50.00 g, 375.0 mmol), and acetyl chloride (30.2 mL, 425 mmol) was stirred at 0° C. for 4 hours, then heated at 130° C. for 12 hours, cooled, and decomposed with water (98 mL) (with external ice-cooling when necessary) and conc. hydrogen chloride in water (33 mL). The precipitate was filtered, and dried under reduced pressure. The solid obtained was then dissolved in 100 mL of water. The mixture was cooled with an ice bath and its pH was adjusted to 4 with slow addition of 20% NaOH. The suspension was filtered, washed with water and air dried to give the desired product (18.9 g, 100%). LCMS calculated for C₁₁H₉FNO₂ (M+H)⁺: m/z =206.1; Found: 206.0.

Step 2. 7-Acetyl-5-fluoroquinolin-8-yl trifluoromethanesulfonate

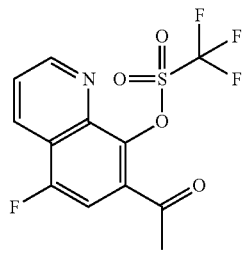 [SMILES: CC(=O)c1cc(F)c2cccnc2c1OS(=O)(=O)C(F)(F)F]

To a mixture of 1-(5-fluoro-8-hydroxyquinolin-7-yl)ethanone (2.3 g, 11 mmol) in methylene chloride (50 mL) was added triethylamine (4.7 mL, 34 mmol) followed by trifluoromethanesulfonic anhydride (2.8 mL, 17 mmol) at −78° C. The reaction was allowed to warm to room temperature gradually and stirred at room temperature for 30 minutes. After quenching with water, the mixture was extracted with dichloromethane. The combined organic layers were washed with brine, dried over sodium sulfate and concentrated to dryness. The residue was purified on silica gel, eluting with 0 to 60% ethyl acetate in hexane, to give the desired product. LCMS calculated for $C_{12}H_8F_4NO_4S$ (M+H)$^+$: m/z=338.0; Found: 338.0.

Step 3. 1-{5-Fluoro-8-[(3R)-3-hydroxypyrrolidin-1-yl]quinolin-7-yl}ethanone

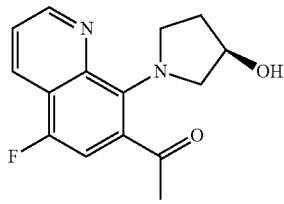 [SMILES: CC(=O)c1cc(F)c2cccnc2c1N1CC[C@@H](O)C1]

A stirred mixture of 7-acetyl-5-fluoroquinolin-8-yl trifluoromethanesulfonate (0.101 g, 0.301 mmol), (3R)-pyrrolidin-3-ol (0.0315 g, 0.362 mmol), palladium acetate (1 mg, 0.006 mmol), (S)-(−)-2,2′-bis(diphenylphosphino)-1,1′-binaphthyl (6 mg, 0.009 mmol), and cesium carbonate (0.147 g, 0.451 mmol) in tetrahydrofuran (3 mL) was heated at 65° C. overnight. The mixture was cooled, diluted with dichloromethane and filtered. The filtrate was washed with brine, dried over sodium sulfate and evaporated to dryness. The resulting residue was purified on silica gel, eluting with 0 to 10% MeOH in dichloromethane, to give the desired product (10 mg, 10%). LCMS calculated for $C_{15H16}FN_2O_2$ (M+H)$^±$: m/z=275.1; Found: 275.1.

Step 4. (3R)-1-[7-(1-Aminoethyl)-5-fluoroquinolin-8-yl]pyrrolidin-3-ol

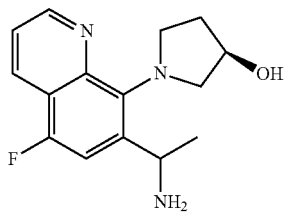 [SMILES: CC(N)c1cc(F)c2cccnc2c1N1CC[C@@H](O)C1]

A mixture of 1-{5-fluoro-8-[(3R)-3-hydroxypyrrolidin-1-yl]quinolin-7-yl}ethanone (10 mg, 0.04 mmol) and ammonium acetate (28.1 mg, 0.364 mmol) in methanol (0.20 mL) and acetonitrile (0.21 mL) was heated at 65° C. in a sealed tube for 30 minutes. After cooling to room temperature, sodium cyanoborohydride (4.6 mg, 0.073 mmol) was added. The reaction was heated at 65° C. for another 4 hours, then cooled to room temperature and quenched with sat. sodium bicarbonate, extracted with dichloromethane. The combined extracts were dried over magnesium sulfate and evaporated to dryness. The residue was used directly in the next step. LCMS calculated for $C_{15}H_{19}FN_3O$ (M+H)$^+$: m/z=276.1; Found: 276.1.

Step 5. (3R)-1-{5-Fluoro-7-[1-(9H-purin-6-ylamino)ethyl]quinolin-8-yl}pyrrolidin-3-ol

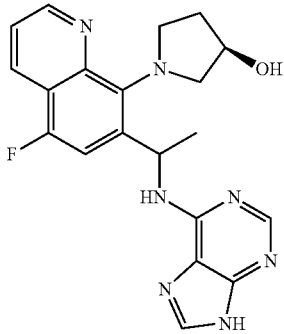 [SMILES: CC(Nc1ncnc2[nH]cnc12)c1cc(F)c2cccnc2c1N1CC[C@@H](O)C1]

A mixture of 6-bromo-9H-purine (14.5 mg, 0.0727 mmol), (3R)-1-[7-(1-aminoethyl)-5-fluoroquinolin-8-yl]pyrrolidin-3-ol (10 mg, 0.04 mmol), and N,N-diisopropylethylamine (0.013 mL, 0.073 mmol) in isopropyl alcohol (0.1 mL) was heated at reflux under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. First peak retention time 1.32 minutes, LCMS calculated for $C_{20}H_{21}FN_7O$ (M+H)$^+$: m/z=394.2; Found: 394.2. Second peak retention time 1.40 minutes, LCMS calculated for $C_{20}H_{21}FN_7O$ (M+H)$^+$: m/z=394.2; Found: 394.2.

Example 54

4-(3-fluorophenyl)-3-[1-(9H-purin-6-ylamino)ethyl]isoquinoline-1-carbonitrile

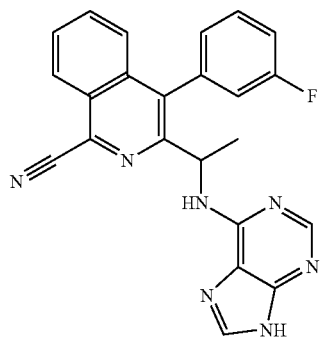 [SMILES: CC(Nc1ncnc2[nH]cnc12)c1nc(C#N)c2ccccc2c1-c1cccc(F)c1]

Step 1. 3-Acetyl-4-hydroxyisoquinolin-1(2H)-one

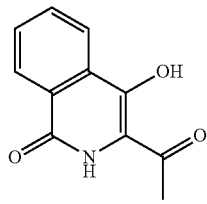

To a refluxed mixture of 4.63 M sodium methoxide in methanol (55.0 mL, 254 mmol) and methanol (500 mL) was added solid N-acethonylphthalimide (25.00 g, 123.0 mmol, from TCI) in one portion. After addition, the reaction was heated at reflux for 2 hours, then cooled at 0° C. and neutralized with 1 N HCl. The resulting suspension was stirred at 0° C. for 30 minutes and then filtered under reduced pressure, washed with a small amount of water and air dried. The resulting solid was further dried under vacuum, over $P_2O_5$, to give the desired product (21.2 g, 85%). LCMS calculated for $C_{11}H_{10}NO_3$ (M+H)$^+$: m/z=204.1; Found: 204.0.

Step 2. 1-(1-Chloro-4-hydroxyisoquinolin-3-yl)ethanone

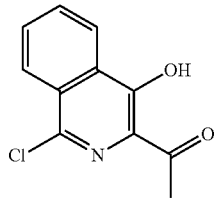

A mixture of 3-acetyl-4-hydroxyisoquinolin-1(2H)-one (10.0 g, 49.2 mmol) and phosphoryl chloride (45.87 mL) was heated at 70° C. for 24 hours. After cooling to room temperature, the mixture was poured onto crushed ice and stirred for 30 minutes. The precipitated solid was collected by filtration in vacuum and air dried (9.82 g, 90%). LCMS calculated for $C_{11}H_9ClNO_2$ (M+H)$^+$: m/z=222.0; Found: 222.1.

Step 3. 3-Acetyl-1-chloroisoquinolin-4-yl trifluoromethanesulfonate

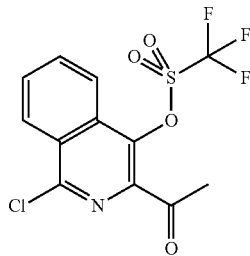 [SMILES: CC(=O)c1nc(Cl)c2ccccc2c1OS(=O)(=O)C(F)(F)F]

To a mixture of 1-(1-chloro-4-hydroxyisoquinolin-3-yl) ethanone (9.00 g, 40.6 mmol) in methylene chloride (200 mL) was added N,N-diisopropylethylamine (10.61 mL, 60.91 mmol) followed by trifluoromethanesulfonic anhydride (8.198 mL, 48.73 mmol), dropwise, at −78° C. The reaction was stirred at −78° C. for 30 minutes, then allowed to warm to 0° C., diluted with dichloromethane and washed with water, brine and dried over sodium sulfate. After evaporated to dry, the resulting residue was purified on silica gel, eluting with 0 to 50% ethyl acetate in hexane, to give the desired product (10.38 g, 72%). LCMS calculated for $C_{12}H_8ClF_3NO_4S$ (M+H)$^+$: m/z=354.0; Found: 354.0.

Step 4. 1-[1-Chloro-4-(3-fluorophenyl)isoquinolin-3-yl]ethanone

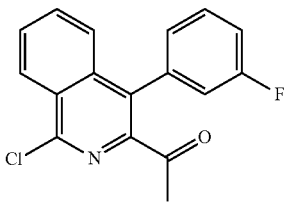

To a mixture of 3-acetyl-1-chloroisoquinolin-4-yl trifluoromethanesulfonate (10.38 g, 29.35 mmol) in tetrahydrofuran (300 mL), with stirring, was added tetrakis(triphenylphosphine)palladium(0) (1.70 g, 1.47 mmol). The reaction mixture was heated at 60° C. overnight, cooled to room temperature and quenched with sat. sodium bicarbonate. The mixture was filtered through a Celite pad. The filtrate was extracted with ethyl acetate. The combined organic layers were washed with brine, dried and concentrated under reduced pressure. The residue was purified on silica gel, eluting with 0 to 40% ethyl acetate in hexane, to give the desired products (4.62 g, 53%). LCMS calculated for $C_{17}H_{12}ClFNO$ (M+H)$^+$: m/z=300.1; Found: 300.1.

Step 5. 3-Acetyl-4-(3-fluorophenyl)isoquinoline-1-carbonitrile

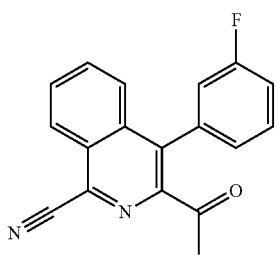 [SMILES: CC(=O)c1nc(C#N)c2ccccc2c1-c1cccc(F)c1]

A mixture of 1-[1-chloro-4-(3-fluorophenyl)isoquinolin-3-yl]ethanone (100 mg, 0.334 mmol), zinc cyanide (78 mg, 0.66 mmol) and tetrakis(triphenylphosphine)palladium(0) (77 mg, 0.067 mmol) in dry N,N-dimethylformamide (1.1 mL) was stirred at 130° C. overnight. The mixture was filtered, diluted with water, extracted with dichloromethane. The combined extracts were dried over MgSO$_4$, concentrated and purified on silica gel (0-60% ethyl acetate in hexane) to give the desired product (6 mg, 6%). LCMS calculated for C$_{18}$H$_{12}$FN$_2$O (M+H)$^+$: m/z=291.1; Found: 291.1.

Step 6. 3-(1-Aminoethyl)-4-(3-fluorophenyl)isoquinoline-1-carbonitrile

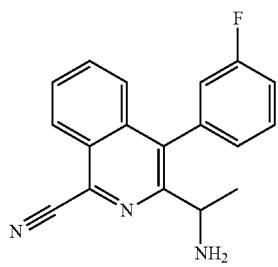 [SMILES: CC(N)c1nc(C#N)c2ccccc2c1-c1cccc(F)c1]

A mixture of 3-acetyl-4-(3-fluorophenyl)isoquinoline-1-carbonitrile (4 mg, 0.01 mmol) and ammonium acetate (10.6 mg, 0.138 mmol) in methanol (0.078 mL) and acetonitrile (0.078 mL) was heated at 65° C. in a sealed tube for 30 minutes. After cooling to room temperature, sodium cyanoborohydride (1.7 mg, 0.028 mmol) was added. The reaction was heated at 65° C. for another 4 hours, then cooled to room temperature and quenched with sat. sodium bicarbonate, extracted with dichloromethane. The combined extracts were dried over magnesium sulfate and evaporated to dryness. The residue was used directly in the next step. LCMS calculated for C$_{18}$H$_{15}$FN$_3$ (M+H)$^+$: m/z=292.1; Found: 292.1.

Step 7. 4-(3-Fluorophenyl)-3-[1-(9H-purin-6-ylamino)ethyl]isoquinoline-1-carbonitrile

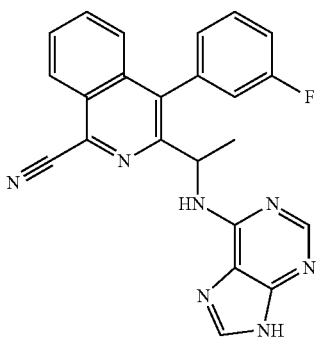 [SMILES: CC(Nc1ncnc2[nH]cnc12)c1nc(C#N)c2ccccc2c1-c1cccc(F)c1]

A mixture of 6-bromo-9H-purine (5.48 mg, 0.0275 mmol), 3-(1-aminoethyl)-4-(3-fluorophenyl)isoquinoline-1-carbonitrile (4 mg, 0.01 mmol), and N,N-diisopropylethylamine (0.00480 mL, 0.0276 mmol) in ethanol (0.05 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for C$_{23}$H$_{17}$FN$_7$ (M+H)$^+$: m/z=410.2; Found: 410.1.

Example 55

N-{1-[8-(4-Cyclobutylpiperazin-1yl)-5-fluoroquinolin-7-yl]ethyl}-9H-purin-6-amine

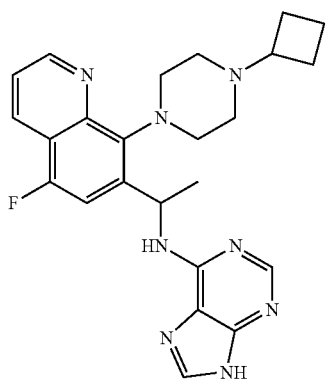 [SMILES: CC(Nc1ncnc2[nH]cnc12)c1cc(F)c2cccnc2c1N1CCN(C2CCC2)CC1]

Step 1. 1-[8-(4-Cyclobutylpiperazin-1-yl)-5-fluoraquinolin-7-yl]ethanone

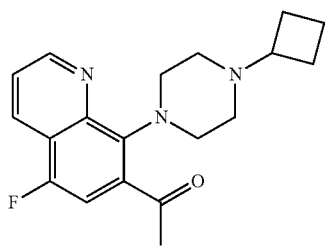 [SMILES: CC(=O)c1cc(F)c2cccnc2c1N1CCN(C2CCC2)CC1]

A stirred mixture of 7-acetyl-5-fluoroquinolin-8-yl trifluoromethanesulfonate (0.101 g, 0.301 mmol), 1-cyclobutylpiperazine dihydrochloride (0.0771 g, 0.362 mmol, from Example 13, Step 2), and N,N-diisopropylethylamine (0.236 mL, 1.35 mmol) in tetrahydrofuran (2.4 mL) was heated at 85° C. overnight. The mixture was cooled, diluted with dichloromethane, washed with brine, dried over sodium sulfate and evaporated to dryness. The resulting residue was purified on silica gel, eluting with 0 to 10% methanol in dichloromethane, to give the desired product (75 mg, 76%). LCMS calculated for $C_{19}H_{23}FN_3O$ (M+H)$^+$: m/z=328.2; Found: 328.1.

Step 2. 1-[8-(4-Cyclobutylpiperazin-1-yl)-5-fluoroquinolin-7-yl]ethanamine

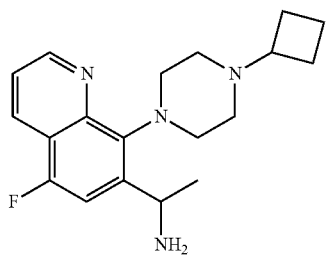 [SMILES: CC(N)c1cc(F)c2cccnc2c1N1CCN(C2CCC2)CC1]

A mixture of 1-[8-(4-cyclobutylpiperazin-1-yl)-5-fluoroquinolin-7-yl]ethanone (16 mg, 0.049 mmol) and ammonium acetate (37.7 mg, 0.489 mmol) in methanol (0.27 mL) and acetonitrile (0.28 mL) was heated at 65° C. in a sealed tube for 30 minutes. After cooling to room temperature, sodium cyanoborohydride (6 mg, 0.01 mmol) was added. The reaction was heated at 65° C. for another 4 hours, then cooled to room temperature and quenched with sat. sodium bicarbonate, extracted with dichloromethane. The combined extracts were dried over magnesium sulfate and evaporated to dryness. The residue was used directly in the next step. LCMS calculated for $C_{19}H_{26}FN_4$ (M+H)$^+$: m/z=329.2; Found: 329.2.

Step 3. N-{1-[-(4-Cyclobutylpiperazin-1-yl)-5-fluoroquinolin-7-yl]ethyl}-9H-purin-6-amine

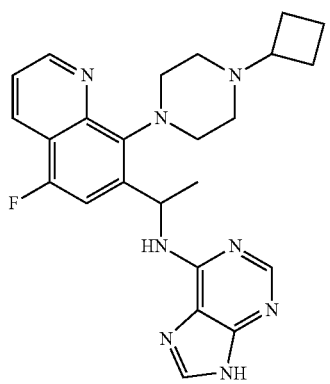 [SMILES: CC(Nc1ncnc2[nH]cnc12)c1cc(F)c2cccnc2c1N1CCN(C2CCC2)CC1]

A mixture of 6-bromo-9H-purine (91.6 mg, 0.460 mmol), 1-[8-(4-cyclobutylpiperazin-1-yl)-5-fluoroquinolin-7-yl] ethanamine (76 mg, 0.23 mmol), and N,N-diisopropylethylamine (0.080 mL, 0.46 mmol) in isopropyl alcohol (0.9 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for $C_{24}H_{28}FN_8$ (M+H)$^+$: m/z=447.2; Found: 447.1.

Example 56

N-{1-[5-Chloro-8-(3-fluorophenyl)isoquinolin-7-yl] ethyl}-9H-purin-6-amine

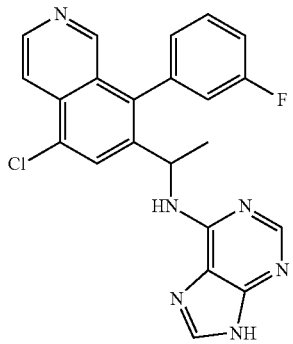 [SMILES: CC(Nc1ncnc2[nH]cnc12)c1cc(Cl)c2ccncc2c1-c1cccc(F)c1]

Step 1. 1-(3-Bromo-5-chloro-2-hydroxy-4-methylphenyl)ethanone

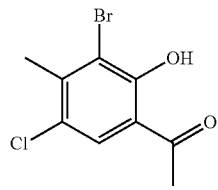

To a stirred solution of 1-(5-chloro-2-hydroxy-4-methylphenyl)ethanone (10.0 g, 54.2 mmol) in acetic acid (100 mL) was added N-bromosuccinimide (11.6 g, 65.0 mmol) and the resulting mixture was stirred at room temperature for 18 hours. The reaction mixture was concentrated in vacuo, then neutralized with sat. sodium bicarbonate, insoluble succinimide filtered off and extracted with ethyl acetate. The combined organic layers were washed with brine, dried over sodium sulfate and then concentrated to dryness under reduced pressure. The crude product was recrystalized from a mixture of ethyl acetate and hexane (11.42 g, 80%). ¹H NMR (CDCl₃, 300 MHz) δ 12.96 (1H, s), 7.72 (1H, s), 2.64 (3H, s), 2.59 (3H, s) ppm.

Step 2. 3-Acetyl-5-chloro-2-hydroxy-6-methylbenzonitrile

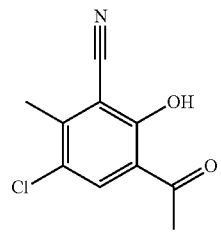

A mixture of 1-(3-bromo-5-chloro-2-hydroxy-4-methylphenyl)ethanone (4.85 g, 18.4 mmol) and copper cyanide (2.47 g, 27.6 mmol) in N-methylpyrrolidinone (15 mL) was heated at 200° C. for 1 hour. After cooling to room temperature, the mixture was diluted with ethyl acetate and 1 N HCl. The layers were separated and the aqeous layer was extracted with ethyl acetate. The combined organic layers were washed with water, then brine and dried over magnesium sulfate. After concentration to dryness under reduced pressure, the residue was used directly in the next step (3.7 g, 96%). LCMS calculated for $C_{10}H_9ClNO_2$ (M+H)⁺: m/z=210.0; Found: 210.1.

Step 3. 6-Acetyl-4-chloro-2-cyano-3-methylphenyl trifluoromethanesulfonate

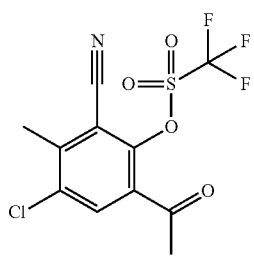 [SMILES: CC(=O)c1cc(Cl)c(C)c(C#N)c1OS(=O)(=O)C(F)(F)F]

To a mixture of 3-acetyl-5-chloro-2-hydroxy-6-methylbenzonitrile (3.70 g, 17.6 mmol) in methylene chloride (70 mL) was added triethylamine (7.4 mL, 53 mmol) followed by trifluoromethanesulfonic anhydride (4.4 mL, 26 mmol) at −78° C. The reaction was allowed to warm to room temperature gradually and stirred at room temperature for 30 minutes. After quenching with water, the mixture was extracted with dichloromethane. The combined organic layers were washed with brine, dried over sodium sulfate and concentrated to dryness. The residue was purified on silica gel, eluting with 0 to 40% ethyl acetate in hexane, to give the desired product (2.537 g, 42%). LCMS calculated for $C_{11}H_8ClF_3NO_4S$ (M+H)⁺: m/z=342.0; Found: 342.1.

Step 4. 6-Acetyl-4-chloro-3'-fluoro-3-methylbiphenyl-2-carbonitrile

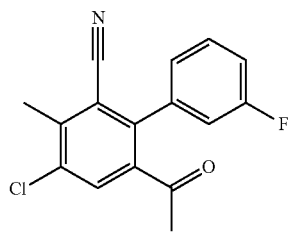 [SMILES: CC(=O)c1cc(Cl)c(C)c(C#N)c1-c1cccc(F)c1]

A biphasic solution of 6-acetyl-4-chloro-2-cyano-3-methylphenyl trifluoromethanesulfonate (2.537 g, 7.425 mmol) and (3-fluorophenyl)boronic acid (1.56 g, 11.1 mmol) in toluene (70 mL) and 0.8 M sodium hydrogenecarbonate in water (70 mL, 50 mmol) was bubbled with N₂ to degas. Tetrakis(triphenylphosphine)palladium(0) (0.429 g, 0.371 mmol) was added. The mixture was degassed with N₂ for an additional 5 minutes and then heated at 80° C. for 2 hours. After cooling to room temperature, the mixture was diluted with ethyl acetate. The layers were separated and the aq. layer was extracted with ethyl acetate. The combined extracts were washed with brine, dried over Na₂SO₄, filtered, and concentrated to a dark solid. The material was dissolved in CHCl₃ and was purified on silica gel column, eluting with 0 to 40% ethyl acetate in hexane, to give the desired product (2.105 g, 99%). LCMS calculated for $C_{16}H_{12}ClFNO$ (M+H)⁺: m/z=288.1; Found: 288.1.

Step 5. 6-Acetyl-3-(bromomethyl)-4-chloro-3'-fluorobiphenyl-2-carbonitrile

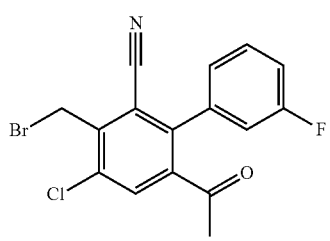 [SMILES: CC(=O)c1cc(Cl)c(CBr)c(C#N)c1-c1cccc(F)c1]

A mixture of 6-acetyl-4-chloro-3'-fluoro-3-methylbiphenyl-2-carbonitrile (1.00 g, 3.48 mmol), N-bromosuccinimide (0.650 g, 3.65 mmol), and benzoyl peroxide (0.0421 g, 0.174 mmol) in carbon tetrachloride (10 mL) was heated at reflux overnight. After cooling to room temperature, the mixture was diluted with dichloromethane and washed with water. The organic layers were dried over magnesium sulfate and evaporated to dryness. The residue was purified on silica gel, eluting with 0 to 20% ethyl acetate in hexane, to give the desired product (0.57 g, 45%). LCMS calculated for C$_{16}$H$_{11}$BrClFNO (M+H)$^+$: m/z=366.0; Found: 366.0.

Step 6. 6-Acetyl-4-chloro-3-(cyanomethyl)-3'-fluorobiphenyl-2-carbonitrile

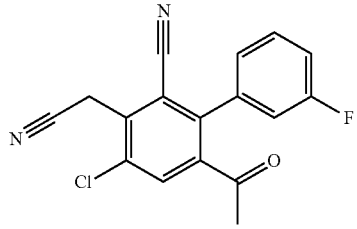 [SMILES: CC(=O)c1cc(Cl)c(CC#N)c(C#N)c1-c1cccc(F)c1]

To a mixture of sodium cyanide (562 mg, 11.5 mmol) in water (3 mL) was carefully added mixture of sulfuric acid (2.9 mL, 5.5 mmol) at 0° C. (the reaction generates hydrogen cyanide and must be run in a fume hood with good ventilation), followed by a solution of 6-acetyl-3-(bromomethyl)-4-chloro-3'-fluorobiphenyl-2-carbonitrile (414 mg, 1.13 mmol) in acetonitrile (10 mL). The reaction was heated at 60° C. for 1 hour with pH adjusting to 9 by the addition of solid sodium cyanide. The reaction was cooled and extracted with ethyl acetate. The combined organic layers were washed with brine, dried over sodium sulfate and then concentrated to dryness under reduced pressure. The residue was purified on silica gel, eluting with 0 to 40% ethyl acetate in hexane (146 mg, 41%). LCMS calculated for C$_{17}$H$_{11}$ClFN2O (M+H)$^+$: m/z=313.1; Found: 313.1.

Step 7. 4-Chloro-3'-fluoro-6-(1-hydroxyethyl)-3-(2-oxoethyl)biphenyl-2-carbaldehyde

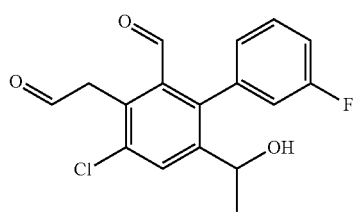 [SMILES: CC(O)c1cc(Cl)c(CC=O)c(C=O)c1-c1cccc(F)c1]

To a mixture of 6-acetyl-4-chloro-3-(cyanomethyl)-3'-fluorobiphenyl-2-carbonitrile (0.167 g, 0.534 mmol) in methylene chloride (2 mL) was added 1.0 M diisobutylaluminum hydride in hexane (2.9 mL, 2.9 mmol) at −78° C. The reaction was warmed to room temperature over 2 hours with stirring. Hydrogen chloride (5.0 M) in water (10 mL, 50 mmol) was added slowly and stirring was continued for 1 hour. Aqueous NaOH was used to render the solution alkaline, and the resulting mixture was extracted with dichloromethane. The combined organic layers were dried over sodium sulfate and evaporated to dryness. The residue was used in the next step. LCMS calculated for C$_{17}$H$_{12}$ClFO$_2$ (M-18)$^+$: m/z=302.1; Found: 302.1

Step 8. 1-[5-Chloro-8-(3-fluorophenyl)isoquinolin-7-yl]ethanol

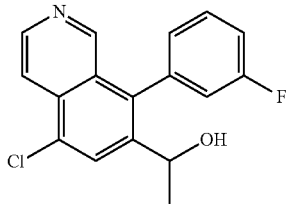 [SMILES: CC(O)c1cc(Cl)c2ccncc2c1-c1cccc(F)c1]

A solution of ammonium chloride (28.5 mg, 0.533 mmol) and sodium acetate (43.7 mg, 0.533 mmol) in water (0.4 mL) was added to a solution of 4-chloro-3'-fluoro-6-(1-hydroxyethyl)-3-(2-oxoethyl)biphenyl-2-carbaldehyde (0.171 g, 0.533 mmol) in tetrahydrofuran (0.4 mL, 5 mmol). The reaction mixture was stirred at room temperature overnight and then extracted with dichloromethane. The combined organic layers were dried over magnesium sulfate, concentrated to dryness under reduced pressure. The crude product was used in the next step (0.16 g, 99%). LCMS calculated for C$_{17}$H$_{14}$ClFNO (M+H)$^+$: m/z=302.1; Found: 302.1

Step 9. 7-(1-Azidoethyl)-5-chloro-8-(3-fluorophenyl)isoquinoline

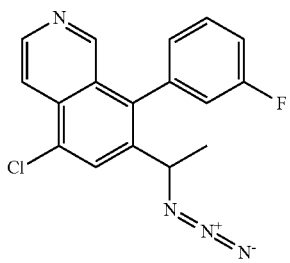 [SMILES: CC(N=[N+]=[N-])c1cc(Cl)c2ccncc2c1-c1cccc(F)c1]

To a mixture of 1-[5-chloro-8-(3-fluorophenyl)isoquinolin-7-yl]ethanol (0.100 g, 0.331 mmol) in methylene chloride (0.6 mL) was added triethylamine (0.092 mL, 0.66 mmol) followed by methanesulfonyl chloride (0.038 mL, 0.50 mmol) at 0° C. The reaction was stirred at room temperature for 30 minutes, then diluted with dichloromethane and washed with water. The organic layers were dried over magnesium sulfate and concentrated to dryness under reduced pressure. The resulting sulfonate was used in the next step. LCMS (M+H)$^+$380.1. To the this crude 1-[5-chloro-8-(3-fluorophenyl)isoquinolin-7-yl]ethyl methanesulfonate in N,N-dimethylformamide (0.6 mL) was added sodium azide (0.11 g, 1.6 mmol). The reaction was stirred at room temperature for 1 hour, then quenched with water and extracted with ethyl acetate. The combined organic layers were washed with brine, dried over sodium sulfate and evaporated to dryness to provide crude desired azide (0.105 mg, 97%). LCMS calculated for $C_{17}H_{13}ClFN_4$ (M+H)$^+$: m/z=327.1; Found: 327.1.

Step 10. 1-[5-Chloro-8-(3-fluorophenyl)isoquinolin-7-yl]ethanamine

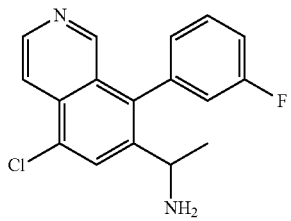 [SMILES: CC(N)c1cc(Cl)c2ccncc2c1-c1cccc(F)c1]

To a stirred mixture of 7-(1-azidoethyl)-5-chloro-8-(3-fluorophenyl)isoquinoline (0.105 g, 0.321 mmol) in tetrahydrofuran (2 mL) and water (0.4 mL) was added 1.0 M trimethylphosphine in THF (0.39 mL, 0.39 mmol). The mixture was stirred at room temperature for 1 hour. After nitrogen was passed through the reaction solution, the reaction mixture was extracted with dichloromethane. The extracts were washed with brine, dried over magnesium sulfate and evaporated to dryness. The crude residue was used directly in the next step (75 mg, 78%). LCMS calculated for $C_{17}H_{15}ClFN2$ (M+H)$^+$: m/z=301.1; Found: 301.1.

Step 11. N-{1-[5-Chloro-8-(3-fluorophenyl)isoquinolin-7-yl]ethyl}-9H-purin-6-amine

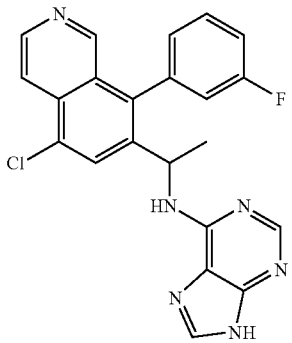 [SMILES: CC(Nc1ncnc2[nH]cnc12)c1cc(Cl)c2ccncc2c1-c1cccc(F)c1]

A mixture of 6-bromo-9H-purine (74 mg, 0.37 mmol), 1-[5-chloro-8-(3-fluorophenyl)isoquinolin-7-yl]ethanamine (0.075 g, 0.25 mmol), and N,N-diisopropylethylamine (0.087 mL, 0.50 mmol) in isopropyl alcohol (2 mL) was heated at 90° C., under nitrogen, overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for $C_{22}H_{17}ClFN_6$ (M+H)$^+$: m/z=419.1; Found: 419.1. $^1$H NMR (DMSO-d$_6$, 400 MHz) δ 8.58 (2H, m), 8.30 (2H, m), 8.06 (1H, s), 8.00 (1H, d, J=5.2 Hz), 7.92 (1H, d, J=6.0 Hz), 7.58 (2H, m), 7.37~7.20 (2H, m), 5.19 (1H, m), 3.29 (1H, br s), 1.39 (3H, m) ppm. $^{19}$F NMR (DMSO-d$_6$, 376 MHz) δ −113.5 ppm.

Example 57

N-(1-{5-Chloro-8-[(3S)-3-fluoropyrrolidin-1-yl]quinolin-7-yl}ethyl)-9H-purin-6-amine bis(trifluoroacetate)

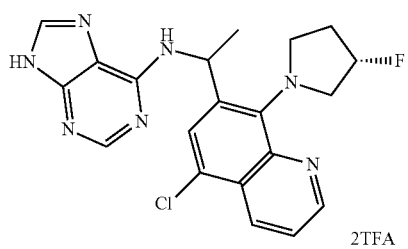 [SMILES: CC(Nc1ncnc2[nH]cnc12)c1cc(Cl)c2cccnc2c1N1CC[C@H](F)C1]

Step 1. 1-{5-Chloro-8-[(3S)-3-fluoropyrrolidin-1-yl]quinolin-7-yl}ethanone

A stirred mixture of 7-acetyl-5-chloroquinolin-8-yl trifluoromethanesulfonate (0.12 g, 0.34 mmol, from Example 47, Step 2), (3S)-3-fluoropyrrolidine hydrochloride (0.051 g, 0.41 mmol), palladium acetate (1.5 mg, 0.0068 mmol), (S)-(−)-2,2'-bis(diphenylphosphino)-1,1'-binaphthyl (6.3 mg, 0.010 mmol) and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The resulting residue was purified on silica gel (eluting with 0 to 30% ethyl acetate in hexane) to give the desired product (0.10 g). LCMS calculated for $C_{15}H_{15}ClFN_2O$ (M+H)$^+$: m/z=293.1; Found: 293.0.

Step 2. 1-{5-Chloro-8-[(3S)-3-fluoropyrrolidin-1-yl]quinolin-7-yl}ethanamine

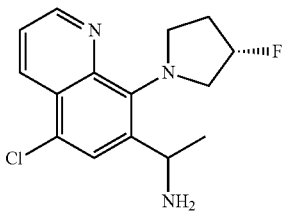 [SMILES: CC(N)c1cc(Cl)c2cccnc2c1N1CC[C@H](F)C1]

A mixture of 1-{5-chloro-8-[(3S)-3-fluoropyrrolidin-1-yl]quinolin-7-yl}ethanone (0.10 g, 0.34 mmol) and ammonium acetate (0.263 g, 3.42 mmol) in methanol (1.5 mL) and acetonitrile (1.5 mL) was heated at 65° C. in a sealed tube for 1 hour. After cooling to room temperature, sodium cyanoborohydride (0.064 g, 1.0 mmol). The reaction was heated at 65° C. overnight, cooled to room temperature and quenched with sat. NaHCO₃ solution and extracted with Ethyl acetate. The combined organic layers were dried over MgSO4, concentrated and purified on a preparative LCMS (pH=10) to give the desired product. LCMS calculated for $C_{15}H_{18}ClFN_3$ (M+H)⁺: m/z=294.1; Found: 294.0.

Step 3. N-(1-{5-Chloro-8-[(3S)-3-fluoropyrrolidin-1-yl]quinolin-7-yl}ethyl)-(9H-purin-6-amine bis(trifluoroacetate)

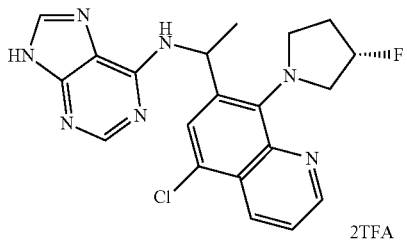 [SMILES: CC(Nc1ncnc2[nH]cnc12)c1cc(Cl)c2cccnc2c1N1CC[C@H](F)C1]

2TFA

A mixture of 1-{5-chloro-8-[(3S)-3-fluoropyrrolidin-1-yl]quinolin-7-yl}ethanamine (5.2 mg, 0.018 mmol), 6-bromo-9H-purine (5.6 mg, 0.028 mmol) and N,N-diisopropylethylamine (0.0093 mL, 0.053 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a mixture of diastereoisomers. LCMS calculated for $C_{20}H_{20}ClFN_7$ (M+H)⁺: m/z=412.1; Found: 412.0.

Example 58

2-(4-{5-Chloro-7-[1-(9H-purin-6-ylamino)ethyl]quinolin-8-yl}piperazin-1-yl)ethanol tris(trifluoroacetate)

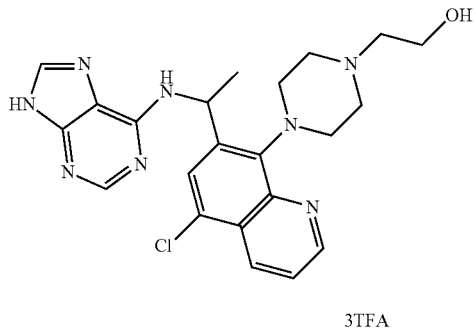 [SMILES: CC(Nc1ncnc2[nH]cnc12)c1cc(Cl)c2cccnc2c1N1CCN(CCO)CC1]

3TFA

Step 1. 1-{5-Chloro-8-[4-(2-hydroxyethyl)piperazin-1-yl]quinolin-7-yl}ethanone

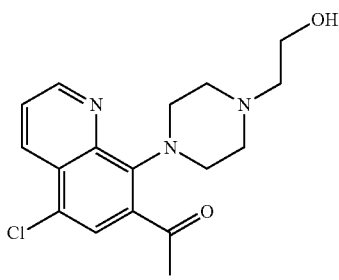 [SMILES: CC(=O)c1cc(Cl)c2cccnc2c1N1CCN(CCO)CC1]

A stirred mixture of 7-acetyl-5-chloroquinolin-8-yl trifluoromethanesulfonate (0.12 g, 0.34 mmol, from Example 47, Step 2), 1-piperazineethanol (0.053 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with water, dried over MgSO₄, evaporated to dryness. The resulting residue was purified on silica gel (eluting with 0 to 10% MeOH in dichloromethane) to give the desired product (16 mg, 14%). LCMS calculated for $C_{17}H_{21}ClN_3O_2$ (M+H)⁺: m/z=334.1; Found: 334.0.

Step 2. 2-{4-[7-(1-Aminoethyl)-5-chloroquinolin-8-yl]piperazin-1-yl}ethanol

A mixture of 1-{5-chloro-8-[4-(2-hydroxyethyl)piperazin-1-yl]quinolin-7-yl}ethanone (0.016 g, 0.048 mmol) and ammonium acetate (0.0369 g, 0.479 mmol) in methanol (1.0 mL) and acetonitrile (1.0 mL) was heated at 65° C. in a sealed tube for 1 hour. After cooling to room temperature, sodium cyanoborohydride (9.0 mg, 0.14 mmol). The reaction was heated at 65° C. overnight, then cooled to room temperature and quenched with sat. NaHCO₃ solution, and extracted with dichloromethane. The combined organic layers were dried over MgSO₄ and concentrated to give the desired product. LCMS calculated for $C_{17}H_{24}ClN_4O$ (M+H)⁺: m/z=335.2; Found: 335.1.

Step 3. 2-(4-{5-Chloro-7-[1-(9H-purin-6-ylamino)ethyl]quinolin-8-yl}piperazin-1-yl)ethanol tris(trifluoroacetate)

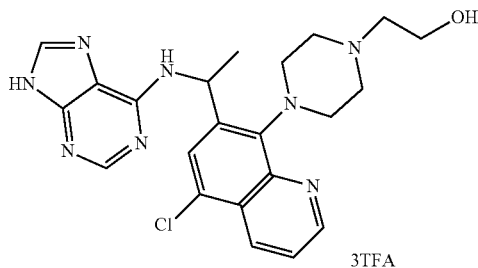 [SMILES: CC(Nc1ncnc2[nH]cnc12)c1cc(Cl)c2cccnc2c1N1CCN(CCO)CC1]

3TFA

A mixture of 2-{4-[7-(1-aminoethyl)-5-chloroquinolin-8-yl]piperazin-1-yl}ethanol (0.016 g, 0.048 mmol), 6-bromo-9H-purine (0.019 g, 0.096 mmol) and N,N-diisopropylethylamine (0.025 mL, 0.14 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{22}H_{26}ClN_8O$ (M+H)⁺: m/z=453.2; Found: 453.0.

Example 59

1-{5-Chloro-7-[1-(9H-purin-6-ylamino)ethyl]quinolin-8-yl}piperidine-4-carbonitrile bis(trifluoroacetate)

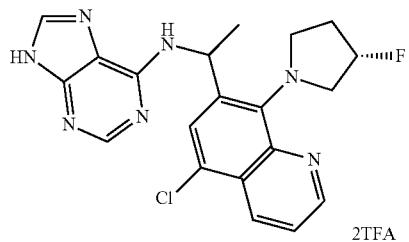 [SMILES: CC(Nc1ncnc2[nH]cnc12)c1cc(Cl)c2cccnc2c1N1CC[C@H](F)C1]

2TFA

Step 1. 1-(7-Acetyl-5-chloroquinolin-8-yl)piperidine-4-carbonitrile

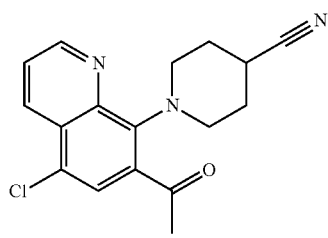 [SMILES: CC(=O)c1cc(Cl)c2cccnc2c1N1CCC(C#N)CC1]

A stirred mixture of 7-acetyl-5-chloroquinolin-8-yl trifluoromethanesulfonate (0.12 g, 0.34 mmol, from Example 47, Step 2), piperidine-4-carbonitrile (0.045 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO₄ and evaporated to dryness. The resulting residue was purified on silica gel (eluting with 0 to 5% MeOH in dichloromethane) to give the desired product (7 mg, 6%). LCMS calculated for $C_{17}H_{17}ClN_3O$ (M+H)⁺: m/z=314.1; Found: 314.0.

Step 2. 1-[7-(1-Aminoethyl)-5-chloraquinolin-8-yl]piperidine-4-carbonitrile

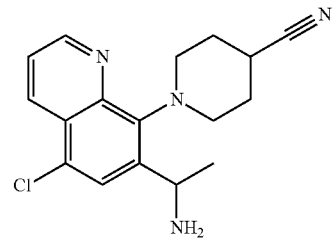 [SMILES: CC(N)c1cc(Cl)c2cccnc2c1N1CCC(C#N)CC1]

A mixture of 1-(7-acetyl-5-chloroquinolin-8-yl)piperidine-4-carbonitrile (7.0 mg, 0.022 mmol) and ammonium acetate (0.0172 g, 0.223 mmol) in methanol (1.0 mL) and acetonitrile (1.0 mL) was heated at 65° C. in a sealed tube for 1 hour. After cooling to room temperature, sodium cyanoborohydride (4.2 mg, 0.067 mmol) was added. The reaction was heated at 65° C. overnight. The mixture was cooled to room temperature, quenched with sat. NaHCO₃ solution and extracted with dichloromethane. The combined extracts were dried over MgSO₄ and concentrated to give the desired product. LCMS calculated for $C_{17}H_{20}ClN_4$ (M+H)⁺: m/z=315.1; Found: 315.0.

Step 3. 1-{5-Chloro-7-[1-(9H-purin-6-ylamino)ethyl]quinolin-8-yl}piperidine-4-carbonitrile bis(trifluoroacetate)

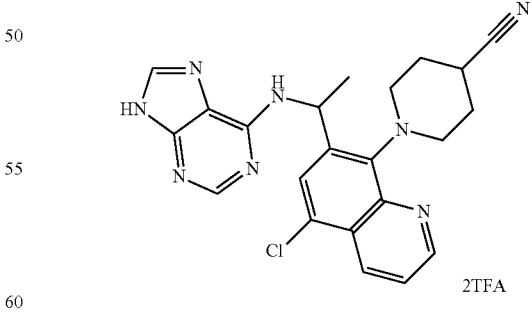

2TFA

A mixture of 1-[7-(1-aminoethyl)-5-chloroquinolin-8-yl]piperidine-4-carbonitrile (5.4 mg, 0.017 mmol), 6-bromo-9H-purine (6.8 mg, 0.034 mmol) and N,N-diisopropylethylamine (0.0090 mL, 0.051 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{22}H_{22}ClN_8$ $(M+H)^+$: m/z=433.2; Found: 433.0.

Example 60

1-{5-Chloro-7-[1-(9H-purin-6-ylamino)ethyl]quinolin-8-yl}pyrrolidine-3-carbonitrile bis(trifluoroacetate)

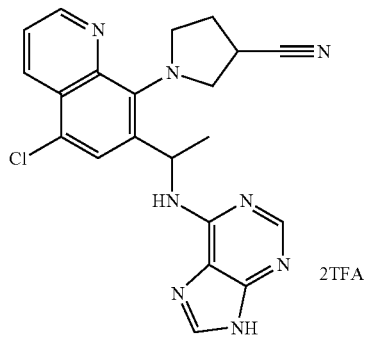 [SMILES: CC(Nc1ncnc2[nH]cnc12)c1cc(Cl)c2cccnc2c1N1CCC(C#N)C1]

2TFA

Step 1. 1-(7-Acetyl-5-chloroquinolin-8-yl)pyrrolidine-3-carbonitrile

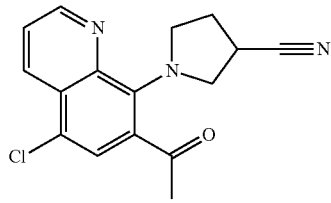 [SMILES: CC(=O)c1cc(Cl)c2cccnc2c1N1CCC(C#N)C1]

A stirred mixture of 7-acetyl-5-chloroquinolin-8-yl trifluoromethanesulfonate (0.12 g, 0.34 mmol, from Example 47, Step 2), pyrrolidine-3-carbonitrile hydrochloride (0.054 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The resulting residue was purified on silica gel (eluting with 0 to 5% MeOH in dichloromethane) to give the desired product (16 mg, 16%). LCMS calculated for $C_{16}H_{15}ClN_3O$ $(M+H)^+$: m/z=300.1; Found: 300.0.

Step 2. 1-[7-(1-Aminoethyl)-5-chloroquinolin-8-yl]pyrrolidine-3-carbonitrile

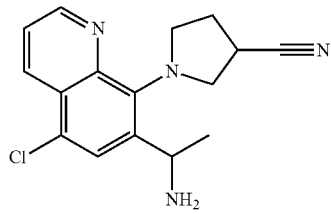 [SMILES: CC(N)c1cc(Cl)c2cccnc2c1N1CCC(C#N)C1]

A mixture of 1-(7-acetyl-5-chloroquinolin-8-yl)pyrrolidine-3-carbonitrile (0.016 g, 0.053 mmol) and ammonium acetate (0.0411 g, 0.534 mmol) in methanol (1.0 mL) and acetonitrile (1.0 mL) was heated at 65° C. in a sealed tube for 1 hour. After cooling to room temperature, sodium cyanoborohydride (0.010 g, 0.16 mmol) was added. The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for $C_{16}H_{18}ClN_4$ $(M+H)^+$: m/z=301.1; Found: 301.1.

Step 3. 1-{5-Chloro-7-[1-(9H-purin-6-ylamino)ethyl]quinolin-8-yl}pyrrolidine-3-carbonitrile bis(trifluoroacetate)

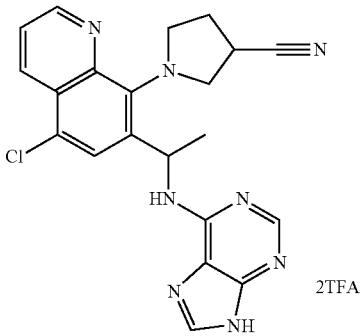 [SMILES: CC(Nc1ncnc2[nH]cnc12)c1cc(Cl)c2cccnc2c1N1CCC(C#N)C1]

2TFA

A mixture of 1-[7-(1-aminoethyl)-5-chloroquinolin-8-yl]pyrrolidine-3-carbonitrile (0.017 g, 0.056 mmol), 6-bromo-9H-purine (0.022 g, 0.11 mmol) and N,N-diisopropylethylamine (0.030 mL, 0.17 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a mixture of diastereoisomers. LCMS calculated for C$_{21}$H$_{20}$ClN$_8$ (M+H)$^+$: m/z=419.1; Found: 419.0.

Example 61

N-{1-[5-Chloro-8-(3-fluoropiperidin-1-yl)quinolin-7-yl]ethyl}-9H-purin-6-amine bis(trifluoroacetate)

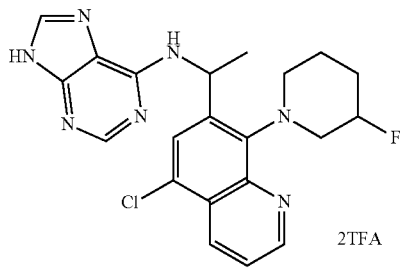 [SMILES: CC(Nc1ncnc2[nH]cnc12)c1cc(Cl)c2cccnc2c1N1CCCC(F)C1]

Step 1. 1-[5-Chloro-8-(3-fluoropiperidin-1-yl)quino-lin-7-yl]ethanone

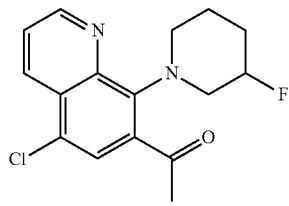 [SMILES: CC(=O)c1cc(Cl)c2cccnc2c1N1CCCC(F)C1]

A stirred mixture of 7-acetyl-5-chloroquinolin-8-yl trifluoromethanesulfonate (0.12 g, 0.34 mmol, from Example 47, Step 2), 3-fluoropiperidine hydrochloride (0.057 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The residue was purified on silica gel (eluting with 0 to 5% methanol in dichloromethane) to give the desired product (28.7 mg, 28%). LCMS calculated for C$_{16}$H$_{17}$ClFN$_2$O (M+H)$^+$: m/z=307.1; Found 307.0.

Step 2. 1-[5-Chloro-8-(3-fluoropiperidin-1-yl)quino-lin-7-yl]ethanamine

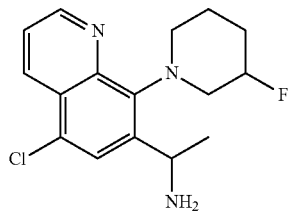 [SMILES: CC(N)c1cc(Cl)c2cccnc2c1N1CCCC(F)C1]

A mixture of 1-[5-chloro-8-(3-fluoropiperidin-1-yl)quino-lin-7-yl]ethanone (0.0287 g, 0.0936 mmol) and ammonium acetate (0.0721 g, 0.936 mmol) in methanol (1.0 mL) and acetonitrile (1.0 mL) was heated at 65° C. in a sealed tube for 1 hour. After cooling to room temperature, to the resulting mixture was added 1.0 M sodium cyanoborohydride in tetrahydrofuran (0.234 mL, 0.234 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{16}$H$_{20}$ClFN$_3$ (M+H)$^+$: m/z=308.1; Found: 308.1.

Step 3. N-{1-[5-Chloro-8-(3-fluoropiperidin-1-yl) quinolin-7-yl]ethyl}-9H-purin-6-amine bis(trifluoro-acetate)

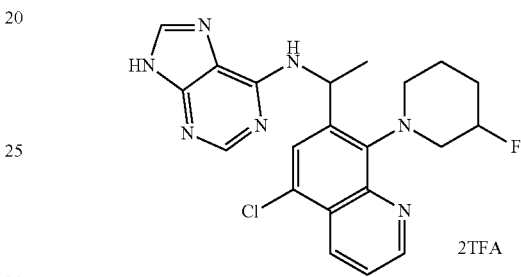

A mixture of 1-[5-chloro-8-(3-fluoropiperidin-1-yl)quino-lin-7-yl]ethanamine (0.026 g, 0.084 mmol), 6-bromo-9H-purine (0.034 g, 0.17 mmol) and N,N-diisopropylethylamine (0.044 mL, 0.25 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{21}$H$_{22}$ClFN$_7$(M+H)$^+$: m/z=426.2; Found: 426.0.

Example 62

N-{1-[5-Chloro-8-(4-fluoropiperidin-1-yl)quinolin-7-yl]ethyl}-9H-purin-6-amine bis(trifluoroacetate)

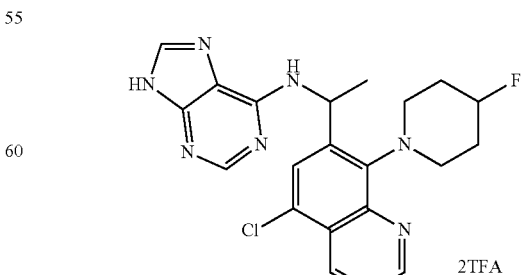

Step 1. 1-[5-Chloro-8-(4-fluoropiperidin-1-yl)quinolin-7-yl]ethanone

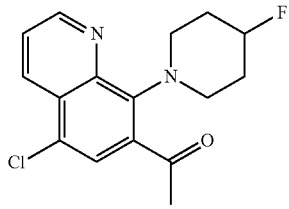 [SMILES: CC(=O)c1cc(Cl)c2cccnc2c1N1CCC(F)CC1]

A stirred mixture of 7-acetyl-5-chloroquinolin-8-yl trifluoromethanesulfonate (0.12 g, 0.34 mmol, from Example 47, Step 2), 4-fluoropiperidine hydrochloride (0.057 g, 0.41 mmol), palladium acetate (1.5 mg, 0.0068 mmol), (S)-(−)-2,2′-bis(diphenylphosphino)-1,1′-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The residue was purified on silica gel (eluting with 0 to 5% methanol in dichloromethane) to give the desired product (36.4 mg, 35%). LCMS calculated for C$_{16}$H$_{17}$ClFN$_2$O (M+H)$^+$: m/z=307.1; Found: 307.0.

Step 2. 1-[5-Chloro-8-(4-fluoropiperidin-1-yl)quinolin-7-yl]ethanamine

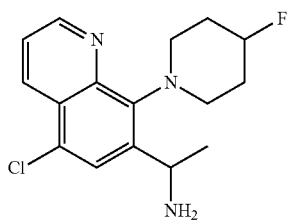 [SMILES: CC(N)c1cc(Cl)c2cccnc2c1N1CCC(F)CC1]

A mixture of 1-[5-chloro-8-(4-fluoropiperidin-1-yl)quinolin-7-yl]ethanone (0.0364 g, 0.119 mmol) and ammonium acetate (0.0915 g, 1.19 mmol) in methanol (1.0 mL) and acetonitrile (1.0 mL) was heated at 65° C. in a sealed tube for 1 hour. After cooling to room temperature, to the resulting mixture was added 1.0 M sodium cyanoborohydride in tetrahydrofuran (0.297 mL, 0.297 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{16}$H$_{20}$ClFN$_3$ (M+H)$^+$: m/z=308.1; Found: 308.1.

Step 3. N-{1-[5-Chloro-8-(4-fluoropiperidin-1-yl)quinolin-7-yl]ethyl}-9H-purin-6-amine bis(trifluoroacetate)

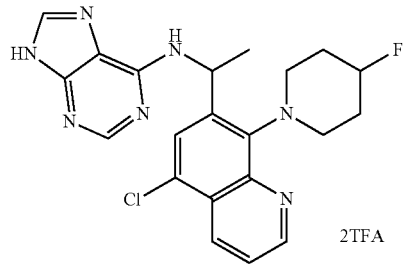 [SMILES: CC(Nc1ncnc2[nH]cnc12)c1cc(Cl)c2cccnc2c1N1CCC(F)CC1]

A mixture of 1-[5-chloro-8-(4-fluoropiperidin-1-yl)quinolin-7-yl]ethanamine (0.040 g, 0.13 mmol), 6-bromo-9H-purine (0.052 g, 0.26 mmol) and N,N-diisopropylethylamine (0.068 mL, 0.39 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{21}$H$_{22}$ClFN$_7$ (M+H)$^+$: m/z=426.2; Found: 426.0.

Example 63

(1-{5-Chloro-7-[1-(9H-purin-6-ylamino)ethyl]quinolin-8-yl]piperidin-3-yl)methanol tris(trifluoroacetate)

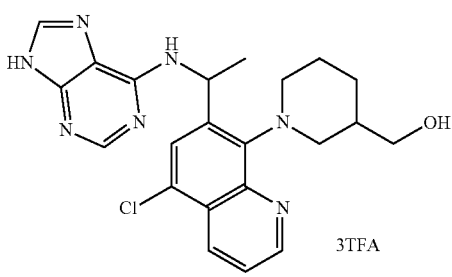 [SMILES: CC(Nc1ncnc2[nH]cnc12)c1cc(Cl)c2cccnc2c1N1CCCC(CO)C1]

Step 1. 1-{5-Chloro-8-[3-(hydroxymethyl)piperidin-1-yl]quinolin-7-yl}ethanone

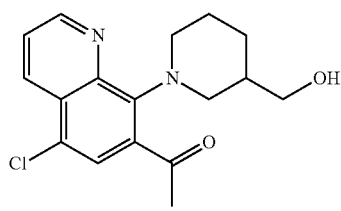 [SMILES: CC(=O)c1cc(Cl)c2cccnc2c1N1CCCC(CO)C1]

A stirred mixture of 7-acetyl-5-chloroquinolin-8-yl trifluoromethanesulfonate (0.12 g, 0.34 mmol, from Example 47, Step 2), piperidin-3-ylmethanol (0.047 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The residue was purified on silica gel (eluting with 0 to 5% methanol in dichloromethane) to give the desired product (23.5 mg, 22%). LCMS calculated for C$_{17}$H$_{20}$ClN$_2$O$_2$ (M+H)$^+$: m/z=319.1; Found Step 2. {1-[7-(1-Aminoethyl)-5-chloroquinolin-8-yl]piperidin-3-yl}methanol

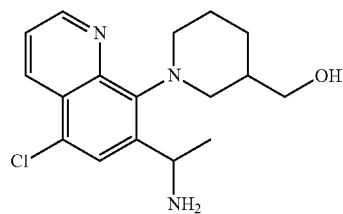 [SMILES: CC(N)c1cc(Cl)c2cccnc2c1N1CCCC(CO)C1]

A mixture of 1-{5-chloro-8-[3-(hydroxymethyl)piperidin-1-yl]quinolin-7-yl}ethanone (0.0235 g, 0.0737 mmol) and ammonium acetate (0.0568 g, 0.737 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.184 mL, 0.184 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{17}$H$_{23}$ClN$_3$O (M+H)$^+$: m/z=320.2; Found: 320.2.

Step 3. (1-{5-Chloro-7-[1-(9H-purin-6-ylamino)ethyl]quinolin-8-yl}piperidin-3-yl)methanol tris(trifluoroacetate)

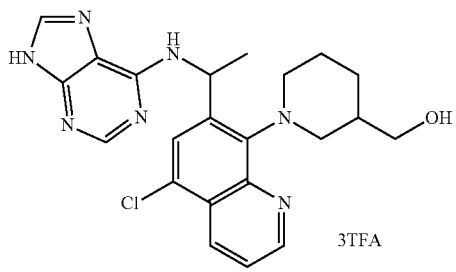 [SMILES: CC(Nc1ncnc2[nH]cnc12)c1cc(Cl)c2cccnc2c1N1CCCC(CO)C1]

A mixture of 1-[7-(1-aminoethyl)-5-chloroquinolin-8-yl]piperidin-3-yl}methanol (0.025 g, 0.078 mmol), 6-bromo-9H-purine (0.031 g, 0.16 mmol) and N,N-diisopropylethylamine (0.041 mL, 0.23 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.536 minutes, LCMS calculated for C$_{22}$H$_{25}$ClN$_7$O (M+H)$^±$: m/z=438.2; Found: 438.0. Second peak retention time 1.677 minutes, LCMS calculated for C$_{22}$H$_{25}$ClN$_7$O (M+H)$^+$: m/z=438.2; Found: 438.0.

Example 64

(1-{5-Chloro-7-[1-(9H-purin-6-ylamino)ethyl]quinolin-8-yl}piperidin-4-yl)methanol tris(trifluoroacetate)

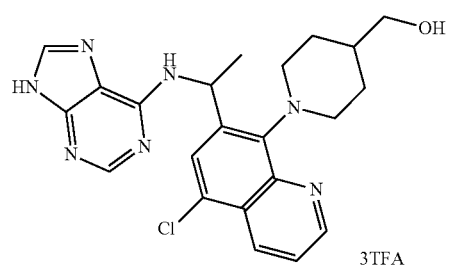 [SMILES: CC(Nc1ncnc2[nH]cnc12)c1cc(Cl)c2cccnc2c1N1CCC(CO)CC1]

Step 1. 1-{5-Chloro-8-[4-(hydroxymethyl)piperidin-1-yl]quinolin-7-yl}ethanone

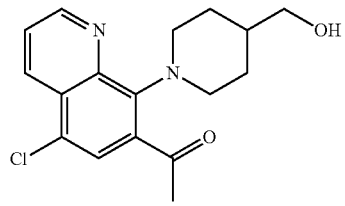 [SMILES: CC(=O)c1cc(Cl)c2cccnc2c1N1CCC(CO)CC1]

A stirred mixture of 7-acetyl-5-chloroquinolin-8-yl trifluoromethanesulfonate (0.12 g, 0.34 mmol, from Example 47, Step 2), 4-piperidinemethanol (0.047 g, 0.41 mmol), palladium acetate (1.5 mg, 0068 mmol), (S)-(−)-2,2'-bs(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$, evaporated to dryness. The residue was purified on silica gel (eluting with 0 to 5% MeOH in dichloromethane) to give the desired product (30 mg, 28%). LCMS calculated for C$_{17}$H$_{20}$ClN$_2$O$_2$ (M+H)$^+$: m/z=319.1; Found: 319.1.

Step 2. {1-[7-(1-Aminoethyl)-5-chloroquinolin-8-yl]piperidin-4-yl}methanol

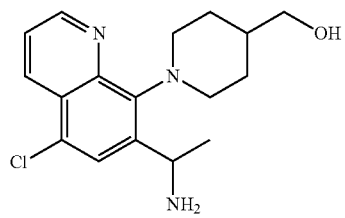 [SMILES: CC(N)c1cc(Cl)c2cccnc2c1N1CCC(CO)CC1]

A mixture of 1-{5-chloro-8-[4-(hydroxymethyl)piperidin-1-yl]quinolin-7-yl) ethanone (0.030 g, 0.094 mmol) and ammonium acetate (0.0725 g, 0.941 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.235 mL, 0.235 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for $C_{17}H_{23}ClN_3O$ (M+H)$^+$: m/z=320.2; Found: 320.1.

Step 3. (1-{5-Chloro-7-[1-(9H-purin-6-ylamino) ethyl]quinolin-8-yl}piperidin-4-yl)methanol tris(trifluoroacetate)

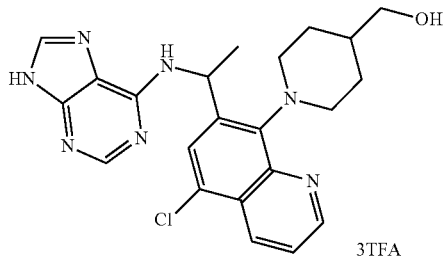 [SMILES: CC(Nc1ncnc2[nH]cnc12)c1cc(Cl)c2cccnc2c1N1CCC(CO)CC1]

A mixture of {1-[7-(1-aminoethyl)-5-chloroquinolin-8-yl] piperidin-4-yl}methanol (0.026 g, 0.081 mmol), 6-bromo-9H-purine (0.032 g, 0.16 mmol) and N,N-diisopropylethylamine (0.042 mL, 0.24 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{22}H_{25}ClN_7O$ (M+H)$^+$: m/z=438.2; Found: 438.0.

Example 65

N-{1-[5-Chloro-8-(4-cyclohexylpiperazin-1-yl) quinolin-7-yl]ethyl}-9H-purin-6-amine tris(trifluoroacetate)

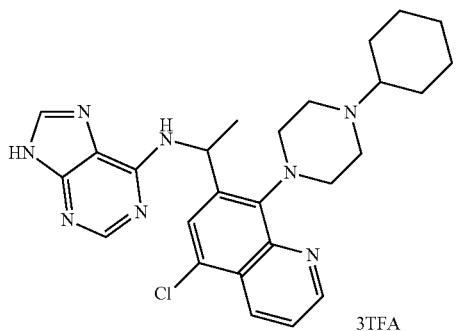 [SMILES: CC(Nc1ncnc2[nH]cnc12)c1cc(Cl)c2cccnc2c1N1CCN(C2CCCCC2)CC1]

Step 1. 1-[5-Chloro-8-(4-cyclohexylpiperazin-1-yl) quinolin-7-yl]ethanone

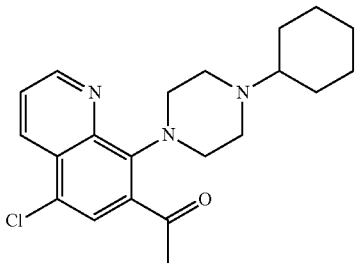 [SMILES: CC(=O)c1cc(Cl)c2cccnc2c1N1CCN(C2CCCCC2)CC1]

A stirred mixture of 7-acetyl-5-chloroquinolin-8-yl trifluoromethanesulfonate (0.12 g, 0.34 mmol, from Example 47, Step 2), 1-cyclohexylpiperazine (0.068 g, 0.41 mmol), palladium acetate (1.5 mg, 0.0068 mmol), (S)-(−)-2,2'-bis (diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The residue was purified on silica gel (eluting with 0 to 5% methanol in dichloromethane) to give the desired product (94 mg, 74%). LCMS calculated for $C_{21}H_{27}ClN_3O$ (M+H)$^+$: m/z=372.2; Found: 372.1.

Step 2. 1-[5-Chloro-8-(4-cyclohexylpiperazin-1-yl) quinolin-7-yl]ethanamine

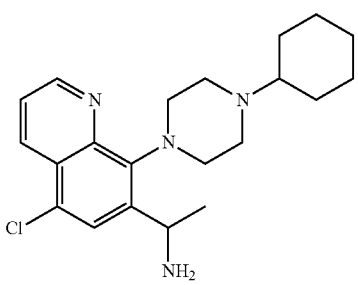 [SMILES: CC(N)c1cc(Cl)c2cccnc2c1N1CCN(C2CCCCC2)CC1]

A mixture of 1-[5-chloro-8-(4-cyclohexylpiperazin-1-yl) quinolin-7-yl]ethanone (0.094 g, 0.25 mmol) and ammonium acetate (0.195 g, 2.53 mmol) in methanol (1 mL) and acetonitrile (1 mL) was heated at 65° C. in a sealed tube for 1 hour. After cooling to room temperature, to the resulting mixture was added 1.0 M sodium cyanoborohydride in tetrahydrofuran (0.632 mL, 0.632 mmol). The reaction was heated at 65° C. overnight. The mixture was cooled to room temperature, quenched with sat. NaHCO$_3$ solution and extracted with dichloromethane. The combined organic layers were dried over MgSO₄ and concentrated to give the desired product. LCMS calculated for $C_{21}H_{30}ClN_4$ (M+H)⁺: m/z=373.2; Found: 373.3.

Step 3. N-{1-15-Chloro-8-(4-cyclohexylpiperazin-1-yl)quinolin-7-yl]ethyl}-9H-purin-6-amine tris(trifluoroacetate)

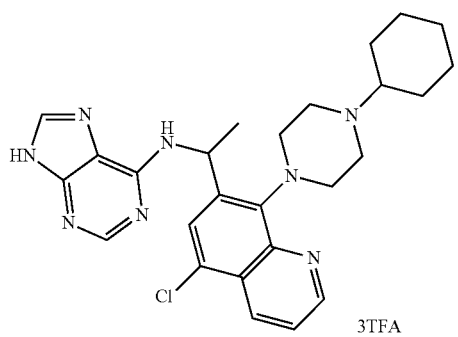 [SMILES: CC(Nc1ncnc2[nH]cnc12)c1cc(Cl)c2cccnc2c1N1CCN(C2CCCCC2)CC1]

A mixture of 1-[5-chloro-8-(4-cyclohexylpiperazin-1-yl)quinolin-7-yl]ethanamine (0.097 g, 0.26 mmol), 6-bromo-9H-purine (0.10 g, 0.52 mmol) and N,N-diisopropylethylamine (0.14 mL, 0.78 mmol) in ethanol (1 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{26}H_{32}ClN_8$ (M+H)⁺: m/z=491.2; Found: 491.0.

Example 66

N-{1-[5-Chloro-8-(4-cyclopropylpiperazin-1-yl)quinolin-7-yl]ethyl}-9H-purin-6-amine tris(trifluoroacetate)

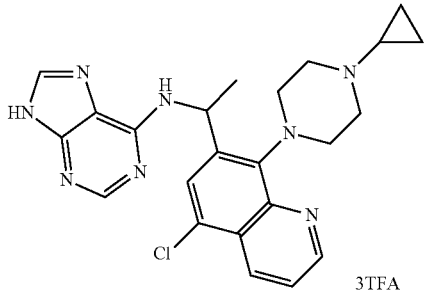 [SMILES: CC(Nc1ncnc2[nH]cnc12)c1cc(Cl)c2cccnc2c1N1CCN(C2CC2)CC1]

Step 1. 1-Cyclobutylpiperazine dihydrochloride

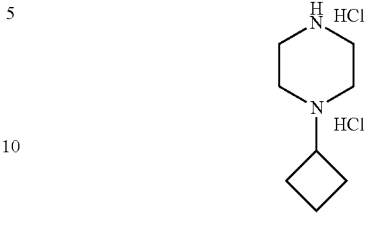

To a mixture of tert-butyl piperazine-1-carboxylate (0.72 g, 0.0039 mol) and cyclobutanone (0.87 mL, 0.012 mol) in acetonitrile (10 mL) and tetrahydrofuran (10 mL) was added sodium triacetoxyborohydride (2.4 g, 0.012 mol). The resulting mixture was stirred at room temperature for 4 hours. The reaction was quenched with aq. NaHCO₃ solution and extracted with dichloromethane. The combined organic layers were dried over MgSO₄ and concentrated to give tert-butyl 4-cyclobutylpiperazine-1-carboxylate, which was treated with 4.57 M hydrogen chloride in 1,4-dioxane (10 mL, 0.04 mol) at room temperature for 2 hours and then evaporated to dryness to give the desired product. LCMS calculated for $C_8H_{17}N_2$ (M+H)⁺: m/z=141.1; Found: 141.2

Step 2. 1-[5-Chloro-8-(4-cyclopropylpiperazin-1-yl)quinolin-7-yl]ethanone

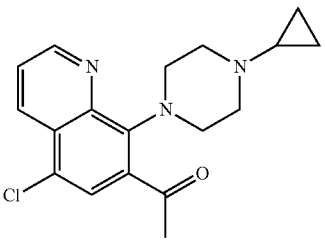 [SMILES: CC(=O)c1cc(Cl)c2cccnc2c1N1CCN(C2CC2)CC1]

A stirred mixture of 7-acetyl-5-chloroquinolin-8-yl trifluoromethanesulfonate (0.12 g, 0.34 mmol, from Example 47, Step 2), 1-cyclopropylpiperazine dihydrochloride (0.081 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.44 g, 1.4 mmol) in tetrahydrofuran (3 mL) was heated at 65° C. overnight. The mixture was cooled, diluted with dichloromethane and filtered. The filtrate was washed with brine, dried over MgSO₄ and evaporated to dryness. The residue was purified on silica gel (eluting with 0 to 10% MeOH in dichloromethane) to give the desired product (61.1 mg, 55%). LCMS calculated for $C_{18}H_{21}ClN_3O$ (M+H)⁺: m/z=330.1; Found: 330.1.

Step 3. 1-[5-Chloro-8-(4-cyclopropylpiperazin-1-yl)quinolin-7-yl]ethanamine

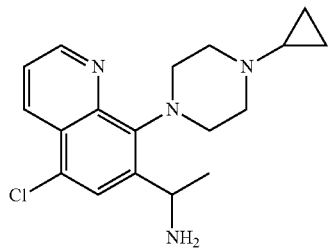 [SMILES: CC(N)c1cc(Cl)c2cccnc2c1N1CCN(C2CC2)CC1]

A mixture of 1-[5-chloro-8-(4-cyclopropylpiperazin-1-yl)quinolin-7-yl]ethanone (0.0611 g, 0.185 mmol) and ammonium acetate (0.143 g, 1.85 mmol) in methanol (0.8 mL) and acetonitrile (0.8 mL) was heated at 65° C. in a sealed tube for 1 hour. After cooling to room temperature, to the resulting mixture was added 1.0 M sodium cyanoborohydride in tetrahydrofuran (0.46 mL, 0.46 mmol). The reaction was heated at 65° C. overnight. The mixture was cooled to room temperature, quenched with sat. NaHCO₃ solution and extracted with dichloromethane. The combined organic layers were dried over MgSO₄ and concentrated to give the desired product. LCMS calculated for $C_{18}H_{24}ClN_4$ (M+H)⁺: m/z=331.2; Found: 331.1.

Step 4. N-{1-[5-Chloro-8-(4-cyclopropylpiperazin-1-yl)quinolin-7-yl]ethyl}-9H-purin-6-amine tris(trifluoroacetate)

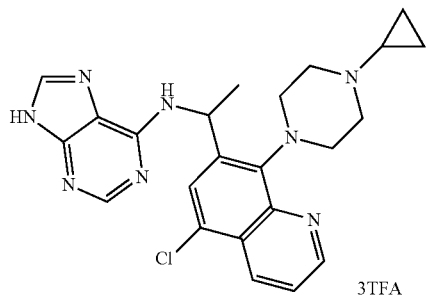 [SMILES: CC(Nc1ncnc2[nH]cnc12)c1cc(Cl)c2cccnc2c1N1CCN(C2CC2)CC1]

A mixture of 1-[5-chloro-8-(4-cyclopropylpiperazin-1-yl)quinolin-7-yl]ethanamine (0.062 g, 0.19 mmol), 6-bromo-9H-purine (0.074 g, 0.37 mmol) and N,N-diisopropylethylamine (0.098 mL, 0.56 mmol) in ethanol (0.6 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{23}H_{26}ClN_8$ (M+H)⁺: m/z=449.2; Found: 449.0.

Example 67

N-{1-[5-Chloro-8-(3-methoxypiperidin-1-yl)quinolin-7-yl]ethyl}-9H-purin-6-amine tris(trifluoroacetate)

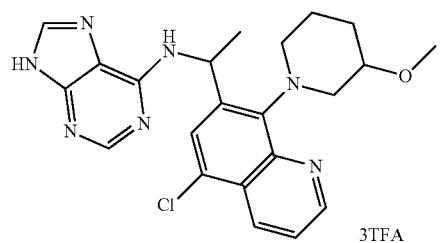 [SMILES: COC1CCCN(c2c(C(C)Nc3ncnc4[nH]cnc34)cc(Cl)c3cccnc23)C1]

Step 1. 1-[5-Chloro-8-(3-methoxypiperidin-1-yl)quinolin-7-yl]ethanone

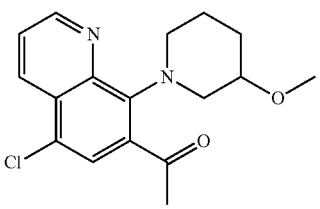 [SMILES: COC1CCCN(c2c(C(C)=O)cc(Cl)c3cccnc23)C1]

A stirred mixture of 7-acetyl-5-chloroquinolin-8-yl trifluoromethanesulfonate (0.12 g, 0.34 mmol, from Example 47, Step 2), 3-methoxypiperidine (0.047 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO₄ and evaporated under reduced pressure. The residue was purified on silica gel (eluting with 0 to 10% methanol in dichloromethane) to give the desired product (37.3 mg, 34%). LCMS calculated for $C_{17}H_{20}ClN_2O_2$ (M+H)⁺: m/z=319.1; Found: 319.1.

Step 2. 1-[5-Chloro-8-(3-methoxypiperidin-1-yl)quinolin-7-yl]ethanamine

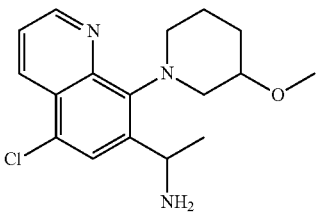 [SMILES: COC1CCCN(c2c(C(C)N)cc(Cl)c3cccnc23)C1]

A mixture of 1-[5-chloro-8-(3-methoxypiperidin-1-yl)quinolin-7-yl]ethanone (0.0373 g, 0.117 mmol) and ammonium acetate (0.0902 g, 1.17 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.29 mL, 0.29 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{17}$H$_{23}$ClN$_3$O (M+H)$^+$: m/z=320.2; Found: 320.1.

Step 3. N-{1-[5-Chloro-8-(3-methoxypiperidin-1-yl)quinolin-7-yl]ethyl}-9H-purin-6-amine tris(trifluoroacetate)

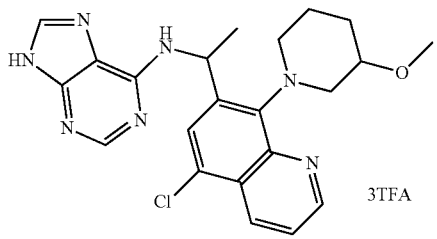 [SMILES: COC1CCCN(c2c(C(C)Nc3ncnc4[nH]cnc34)cc(Cl)c3cccnc23)C1]

A mixture of 1-[5-chloro-8-(3-methoxypiperidin-1-yl)quinolin-7-yl]ethanamine (0.033 g, 0.10 mmol) (10033-24), 6-bromo-9H-purine (0.041 g, 0.21 mmol) and N,N-diisopropylethylamine (0.054 mL, 0.31 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.668 minutes, LCMS calculated for C$_{22}$H$_{25}$ClN$_7$O (M+H)$^+$: m/z=438.2; Found: 438.0. Second peak retention time 1.708 minutes, LCMS calculated for C$_{22}$H$_{25}$ClN$_7$O (M+H)$^+$: m/z=438.2; Found: 438.0.

Example 68

N-{1-[5-Chloro-8-(3-methoxypyrrolidin-1-yl)quinolin-7-yl]ethyl}-9H-purin-6-amine tris(trifluoroacetate)

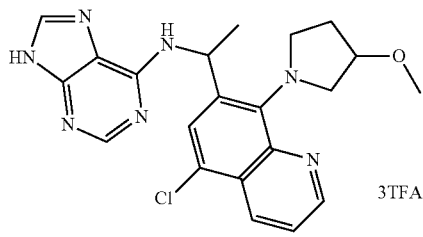 [SMILES: COC1CCN(c2c(C(C)Nc3ncnc4[nH]cnc34)cc(Cl)c3cccnc23)C1]

Step 1. 1-[5-Chloro-8-(3-methoxypyrrolidin-1-yl)quinolin-7-yl]ethanone

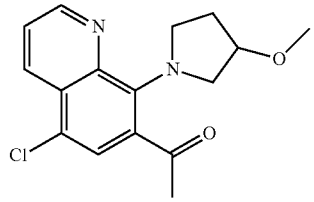 [SMILES: COC1CCN(c2c(C(C)=O)cc(Cl)c3cccnc23)C1]

A stirred mixture of 7-acetyl-5-chloroquinolin-8-yl trifluoromethanesulfonate (0.12 g, 0.34 mmol, from Example 47, Step 2), 3-methoxypyrrolidine hydrochloride (0.056 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.33 g, 1.0 mmol) in tetrahydrofuran (3 mL) was heated at 65° C. overnight. The mixture was cooled, diluted with dichloromethane and filtered. The filtrate was washed with brine, dried over MgSO$_4$ and evaporated under reduced pressure. The residue was purified on silica gel (eluting with 0 to 10% methanol in dichloromethane) to give the desired product (44.5 mg, 43%). LCMS calculated for C$_{16}$H$_{18}$ClN$_2$O$_2$ (M+H)$^+$: m/z=305.1; Found: 305.1.

Step 2. 1-[5-Chloro-8-(3-methoxypyrrolidin-1-yl)quinolin-7-yl]ethanamine

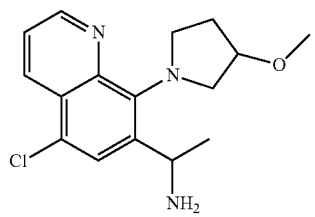 [SMILES: COC1CCN(c2c(C(C)N)cc(Cl)c3cccnc23)C1]

A mixture of 1-[5-chloro-8-(3-methoxypyrrolidin-1-yl)quinolin-7-yl]ethanone (0.0445 g, 0.146 mmol) and ammonium acetate (0.112 g, 1.46 mmol) in methanol (0.8 mL) and acetonitrile (0.8 mL) was heated at 65° C. in a sealed tube for 1 hour. After cooling to room temperature, to the resulting mixture was added 1.0 M sodium cyanoborohydride in tetrahydrofuran (0.36 mL, 0.36 mmol). The reaction was heated at 65° C. overnight. The mixture was cooled to room temperature, quenched with sat. NaHCO$_3$ solution and extracted with dichloromethane. The organic layers were combined, dried over MgSO₄ and concentrated to give the desired product. LCMS calculated for $C_{16}H_{21}ClN_3O$ (M+H)⁺: m/z=306.1; Found: 306.1.

Step 3. N-{1-[5-Chloro-8-(3-methoxypyrrolidin-1-yl)quinolin-7-yl]ethyl}-9H-purin-6-amine tris(trifluoroacetate)

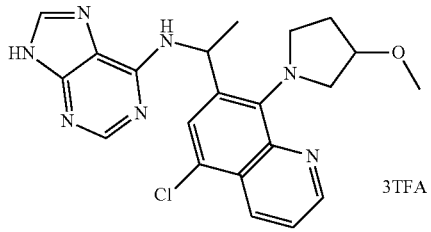 [SMILES: COC1CCN(c2c(C(C)Nc3ncnc4[nH]cnc34)cc(Cl)c3cccnc23)C1]

A mixture of 1-[5-chloro-8-(3-methoxypyrrolidin-1-yl)quinolin-7-yl]ethanamine (0.0345 g, 0.113 mmol), 6-bromo-9H-purine (0.0449 g, 0.226 mmol) and N,N-diisopropylethylamine (0.0590 mL, 0.338 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.521 minutes, LCMS calculated for $C_{21}H_{23}ClN_7O$ (M+H)⁺: m/z=424.2; Found: 424.0. Second peak retention time 1.546 minutes, LCMS calculated for $C_{21}H_{23}ClN_7O$ (M+H)⁺: m/z=424.2; Found: 424.0.

Example 69

N-{1-[5-Chloro-8-(4-cyclobutylpiperazin-1-yl)quinolin-7-yl]ethyl}-9H-purin-6-amine tris(trifluoroacetate)

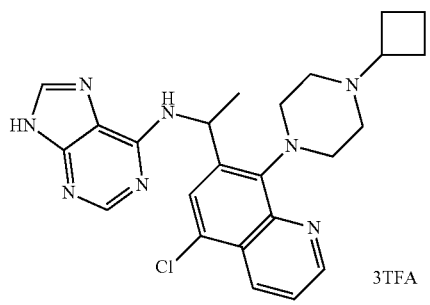 [SMILES: CC(Nc1ncnc2[nH]cnc12)c1cc(Cl)c2cccnc2c1N1CCN(C2CCC2)CC1]

Step 1. 1-[5-Chloro-8-(4-cyclobutylpiperazin-1-yl)quinolin-7-yl]ethanone

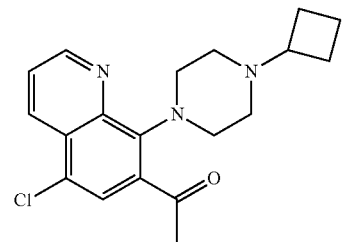 [SMILES: CC(=O)c1cc(Cl)c2cccnc2c1N1CCN(C2CCC2)CC1]

A stirred mixture of 7-acetyl-5-chloroquinolin-8-yl trifluoromethanesulfonate (0.12 g, 0.34 mmol, from Example 47, Step 2), 1-cyclobutylpiperazine dihydrochloride (0.087 g, 0.41 mmol), palladium acetate (1.5 mg, 0.0068 mmol), (S)-(−)-2,2'-bis(diphenylphosphino)-1,1'-binaphthyl (6.3 mg, 0.010 mmol), and cesium carbonate (0.44 g, 1.4 mmol) in tetrahydrofuran (3 mL) was heated at 65° C. overnight. The mixture was cooled, diluted with dichloromethane and filtered. The filtrate was washed with brine, dried over MgSO₄ and and evaporated to dryness. The residue was purified on silica gel (eluting with 0 to 10% methanol in dichloromethane) to give the desired product (69.2 mg, 59%). LCMS calculated for $C_{19}H_{23}ClN_3O$ (M+H)⁺: m/z 344.2; Found: 344.1

Step 2. 1-[5-Chloro-8-(4-cyclobutylpiperazin-1-yl)quinolin-7-yl]ethanamine

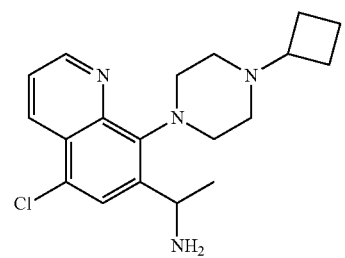 [SMILES: CC(N)c1cc(Cl)c2cccnc2c1N1CCN(C2CCC2)CC1]

A mixture of 1-[5-chloro-8-(4-cyclobutylpiperazin-1-yl)quinolin-7-yl]ethanone (0.0692 g, 0.201 mmol) and ammonium acetate (0.155 g, 2.01 mmol) in methanol (0.8 mL) and acetonitrile (0.8 mL) was heated at 65° C. in a sealed tube for 1 hour. After cooling to room temperature, to the resulting mixture was added 1.0 M sodium cyanoborohydride in tetrahydrofuran (0.50 mL, 0.50 mmol). The reaction was heated at 65° C. overnight. The mixture was cooled to room temperature, quenched with sat. NaHCO₃ solution and extracted with dichloromethane. The combined organic layers were dried over MgSO₄ and concentrated to give the desired product. LCMS calculated for $C_{19}H_{26}ClN_4$ (M+H)⁺: m/z=345.2; Found: 345.1.

Step 3. N-{1-[5-Chloro-8-(4-cyclobutylpiperazin-1-yl)quinolin-7-yl]ethyl}-9H-purin-6-amine tris(trifluoroacetate)

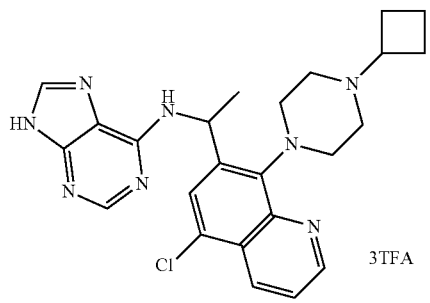 [SMILES: CC(Nc1ncnc2[nH]cnc12)c1cc(Cl)c2cccnc2c1N1CCN(C2CCC2)CC1]

A mixture of 1-[5-chloro-8-(4-cyclobutylpiperazin-1-yl)quinolin-7-yl]ethanamine (0.063 g, 0.18 mmol), 6-bromo-9H-purine (0.074 g, 0.37 mmol) and N,N-diisopropylethylamine (0.095 mL, 0.55 mmol) in ethanol (0.6 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{24}H_{28}ClN_8$ (M+H)⁺: m/z=463.2; Found: 463.2. ¹H NMR (DMSO-d₆, 300 MHz) δ 9.88 (1H, br s), 8.97 (1H, dd, J=3.9 and 1.5 Hz), 8.51 (1H, dd, J=8.4 and 1.5 Hz), 8.42 (1H, s), 8.32 (1H, s), 7.98 (1H, s), 7.67 (1H, dd, J=8.4 and 4.2 Hz), 6.44 (1H, m), 4.38 (1H, m), 4.15 (1H, m), 3.82 (1H, m), 3.56~3.45 (3H, m), 3.20~3.04 (3H, m), 2.25 (4H, m), 1.81~1.69 (3H, m), 1.57 (3H, d, J=6.9 Hz) ppm.

Example 70

N-{1-[8-(1,4'-Bipiperidin-1'-yl)-5-chloroquinolin-7-yl]ethyl}-9H-purin-6-amine tris(trifluoroacetate)

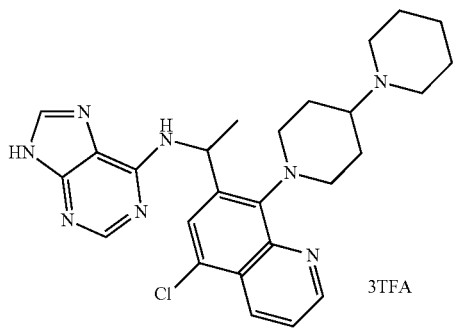

Step 1. 1-[8-(1,4'-Bipiperidin-1'-yl)-5-chloroquinolin-7-yl]ethanone

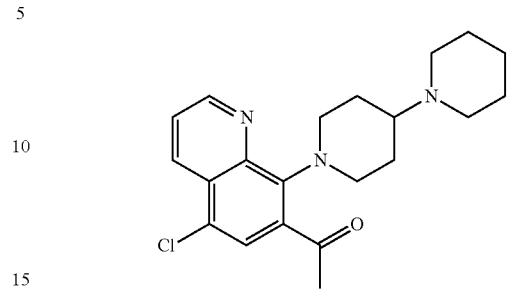

A stirred mixture of 7-acetyl-5-chloroquinolin-8-yl trifluoromethanesulfonate (0.14 g, 0.40 mmol, from Example 47, Step 2), 1,4'-bipiperidine (0.0799 g, 0.475 mmol), palladium acetate (1.8 mg, 0.0080 mmol), (S)-(−)-2,2'-bis(diphenylphosphino)-1,1'-binaphthyl (7.4 mg, 0.012 mmol), and cesium carbonate (0.361 g, 1.11 mmol) in tetrahydrofuran (3 mL) was heated at 65° C. overnight. The mixture was cooled, diluted with dichloromethane and filtered. The filtrate was washed with brine, dried over MgSO₄ and evaporated. The resulting residue was purified on silica gel (eluting with 0 to 10% methanol in dichloromethane) to give the desired product (16.5 mg, 11%). LCMS calculated for $C_{21}H_{27}ClN_3O$ (M+H)⁺: m/z=372.2; Found: 372.1.

Step 2. 1-[8-(1,4'-Bipiperidin-1'-yl)-5-chloroquinolin-7-yl]ethanamine

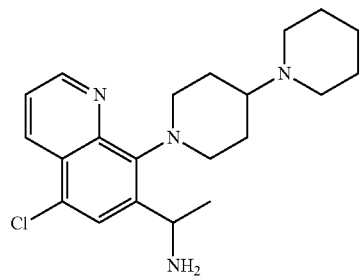

A mixture of 1-[8-(1,4'-bipiperidin-1'-yl)-5-chloroquinolin-7-yl]ethanone (0.0165 g, 0.0444 mmol) and ammonium acetate (0.0342 g, 0.444 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.11 mL, 0.11 mmol). The reaction was heated at 65° C. overnight. The mixture was cooled to room temperature, quenched with sat. NaHCO₃ solution and extracted with dichloromethane. The combined organic phases were dried over MgSO₄ and concentrated to give the desired product. LCMS calculated for $C_{21}H_{30}ClN_4$ (M+H)⁺: m/z=373.2; Found: 373.2.

Step 3. N-{1-[8-(1,4'-Bipiperidin-1'-yl)-5-chloro-quinolin-7-yl]ethyl}-9H-purin-6-tris(trifluoroacetate)

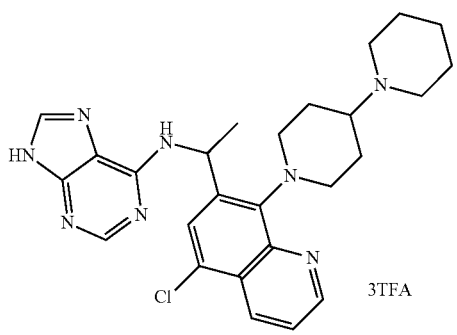 [SMILES: CC(Nc1ncnc2[nH]cnc12)c1cc(Cl)c2cccnc2c1N1CCC(N2CCCCC2)CC1]

A mixture of 1-[8-(1,4'-bipiperidin-1'-yl)-5-chloroquinolin-7-yl]ethanamine (0.015 g, 0.040 mmol), 6-bromo-9H-purine (0.016 g, 0.080 mmol) and N,N-diisopropylethylamine (0.021 mL, 0.12 mmol) in ethanol (0.3 mL) was heated at 110° C. overnight. The resulting mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{26}H_{32}ClN_8$ (M+H)⁺: m/z=491.2; Found: 491.2.

Example 71

N-{1-[5-Chloro-8-(4-methoxypiperidin-1-yl)quinolin-7-yl]ethyl}-9H-purin-6-amine bis(trifluoroacetate)

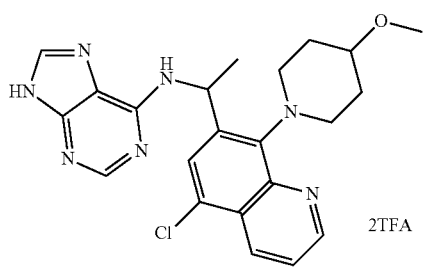 [SMILES: COC1CCN(c2c(C(C)Nc3ncnc4[nH]cnc34)cc(Cl)c3cccnc23)CC1]

Step 1. 1-[5-Chloro-8-(4-methoxypiperidin-1-yl)quinolin-7-yl]ethanone

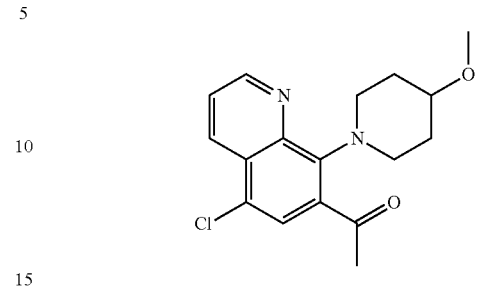

A stirred mixture of 7-acetyl-5-chloroquinolin-8-yl trifluoromethanesulfonate (0.12 g, 0.34 mmol, from Example 47, Step 2), 4-methoxypiperidine hydrochloride (0.062 g, 0.41 mmol), palladium acetate (1.5 mg, 0.0067 mmol), (S)-(+2,2'-bis(diphenylphosphino)-1,1'-binaphthyl (6.3 mg, 0.010 mmol), and cesium carbonate (0.42 g, 1.3 mmol) in tetrahydrofuran (4 mL) was heated at 65° C. overnight. The mixture was cooled, diluted with dichloromethane and filtered. The filtrate was washed with brine, dried over MgSO₄ and evaporated to dryness. The residue was purified on silica gel (eluting with 0 to 5% methanol in dichloromethane) to give the desired product (20.6 mg, 19%). LCMS calculated for $C_{17}H_{20}ClN_2O_2$ (M+H)⁺: m/z=319.1; Found: 319.1.

Step 2. 1-[5-Chloro-8-(4-methoxypiperidin-1-yl)quinolin-7-yl]ethanamine

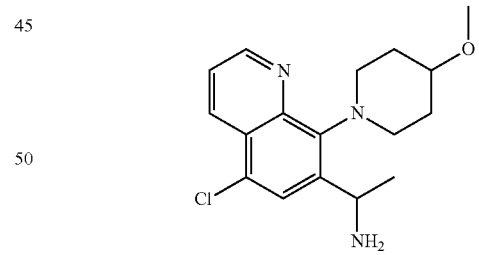

A mixture of 1-[5-chloro-8-(4-methoxypiperidin-1-yl)quinolin-7-yl]ethanone (0.0206 g, 0.0646 mmol) and ammonium acetate (0.0498 g, 0.646 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.16 mL, 0.16 mmol). The reaction was heated at 65° C. overnight. The resulting mixture was cooled to room temperature, quenched with sat. NaHCO₃ solution and extracted with dichloromethane. The combined extracts were dried over MgSO$_4$ and concentrated to give the desired product. LCMS calculated for C$_{17}$H$_{23}$ClN$_3$O (M+H)$^+$: m/z=320.2; Found: 320.1.

Step 3. N-{1-[5-Chloro-8-(4-methoxypiperidin-1-yl)quinolin-7-yl]ethyl}-9H-purin-6-amine bis(trifluoroacetate)

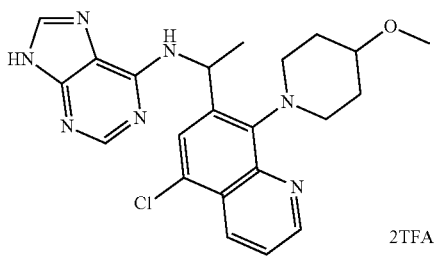 [SMILES: COC1CCN(c2c(C(C)Nc3ncnc4[nH]cnc34)cc(Cl)c3cccnc23)CC1 ; "2TFA"]

A mixture of 1-[5-chloro-8-(4-methoxypiperidin-1-yl)quinolin-7-yl]ethanamine (0.023 g, 0.072 mmol), 6-bromo-9H-purine (0.029 g, 0.14 mmol) and N,N-diisopropylethylamine (0.038 mL, 0.22 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{22}$H$_{25}$ClN$_7$O (M+H)$^+$: m/z=438.2; Found: 438.2.

Example 72

N-{1-[5-Chloro-8-(4-phenylpiperidin-1-yl)quinolin-7-yl]ethyl}-9H-purin-6-amine bis(trifluoroacetate)

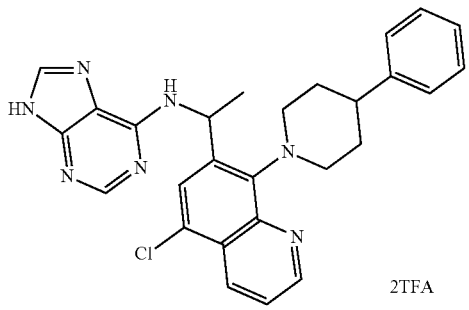 [SMILES: CC(Nc1ncnc2[nH]cnc12)c1cc(Cl)c2cccnc2c1N1CCC(c2ccccc2)CC1 ; "2TFA"]

Step 1. 1-[5-Chloro-8-(4-phenylpiperidin-1-yl)quinolin-7-yl]ethanone

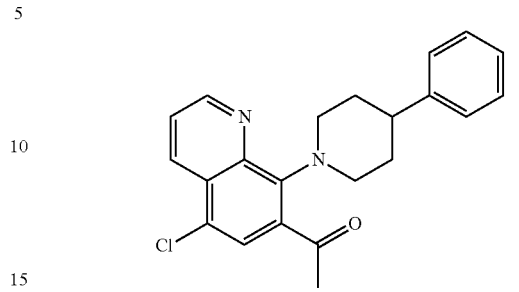

A stirred mixture of 7-acetyl-5-chloroquinolin-8-yl trifluoromethanesulfonate (0.12 g, 0.34 mmol, from Example 47, Step 2), 4-phenylpiperidine (0.066 g, 0.41 mmol), palladium acetate (1.5 mg, 0.0067 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated to dryness. The residue was purified on silica gel (eluting with 0 to 2% methanol in dichloromethane) to give the desired product (25.6 mg, 21%). LCMS calculated for C$_{22}$H$_{22}$ClN$_2$O (M+H)$^+$: m/z=365.1; Found: 365.1.

Step 2. 1-[5-Chloro-8-(4-phenylpiperidin-1-yl)quinolin-7-yl]ethanamine

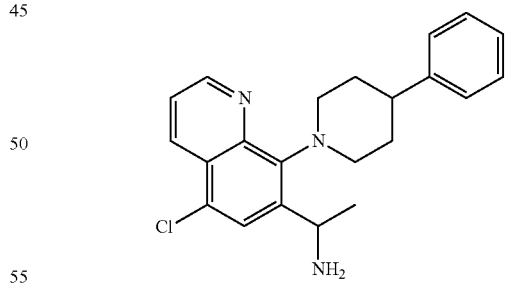

A mixture of 1-[5-chloro-8-(4-phenylpiperidin-1-yl)quinolin-7-yl]ethanone (0.0293 g, 0.0803 mmol) and ammonium acetate (0.0619 g, 0.803 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.20 mL, 0.20 mmol). The reaction was heated at 65° C. overnight. The mixture was cooled to room temperature, quenched with sat. NaHCO$_3$ solution and extracted with dichloromethane. The organic layers were combined, dried over MgSO₄ and concentrated to give the desired product. LCMS calculated for $C_{22}H_{25}ClN_3$ (M+H)⁺: m/z=366.2; Found: 366.2.

Step 3. N-{1-[5-Chloro-8-(4-phenylpiperidin-1-yl)quinolin-7-yl]ethyl}-9H-purin-6-amine bis(trifluoroacetate)

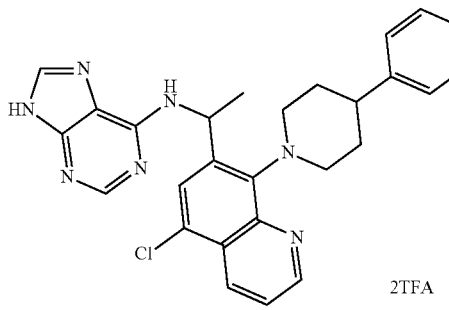

A mixture of 1-[5-chloro-8-(4-phenylpiperidin-1-yl)quinolin-7-yl]ethanamine (0.026 g, 0.071 mmol), 6-bromo-9H-purine (0.028 g, 0.14 mmol) and N,N-diisopropylethylamine (0.037 mL, 0.21 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{27}H_{27}ClN_7$ (M+H)⁺: m/z=484.2; Found: 484.2. ¹H NMR (DMSO-d₆, 300 MHz) δ 9.02 (1H, dd, J=3.9 and 1.5 Hz), 8.50 (1H, dd, J=8.4 and 1.5 Hz), 8.36 (2H, m), 7.93 (1H, s), 7.65 (1H, dd, J=9.0 and 4.2 Hz), 7.31 (4H, m), 7.19 (1H, m), 6.43 (1H, br s), 4.16 (1H, m), 3.97 (1H, m), 3.35 (1H, m), 2.94 (1H, m), 2.78 (1H, m), 2.42 (1H, m), 1.86 (4H, m), 1.63 (3H, d, J=7.2 Hz) ppm.

Example 73

2-(1-{5-Chloro-7-[1-(9H-purin-6-ylamino)ethyl]quinolin-8-yl}piperidin-4-yl)ethanol bis(trifluoroacetate)

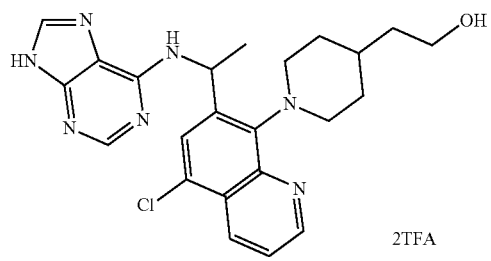 [SMILES: CC(Nc1ncnc2[nH]cnc12)c1cc(Cl)c2cccnc2c1N1CCC(CCO)CC1 ; "2TFA"]

Step 1. 1-{5-Chloro-8-[4-(2-hydroxyethyl)piperidin-1-yl]quinolin-7-yl}ethanone A stirred mixture of 7-acetyl-5-chloroquinolin-8-yl trifluoromethanesulfonate (0.12 g, 0.34 mmol, from Example 47, Step 2), 4-ethanolpiperidine (0.052 g, 0.41 mmol), palladium acetate (1.5 mg, 0.0067 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO₄ and then evaporated to dryness. The residue was purified on silica gel (eluting with 0 to 5% methanol in dichloromethane) to give the desired product (94.8 mg, 84%). LCMS calculated for $C_{18}H_{22}ClN_2O_2$ (M+H)⁺: m/z=333.1; Found: 333.1.

Step 2. 2-{1-[7-(1-Aminoethyl)-5-chloroquinolin-8-yl]piperidin-4-yl}ethanol

A mixture of 1-{5-chloro-8-[4-(2-hydroxyethyl)piperidin-1-yl]quinolin-7-yl}ethanone (0.0948 g, 0.285 mmol) and ammonium acetate (0.220 g, 2.85 mmol) in methanol (1 mL) and acetonitrile (1 mL) was heated at 65° C. in a sealed tube for 1 hour. After cooling to room temperature, to the resulting mixture was added 1.0 M sodium cyanoborohydride in tetrahydrofuran (0.71 mL, 0.71 mmol). The reaction was heated at 65° C. overnight. The resulting mixture was cooled to room temperature, quenched with sat. NaHCO₃ solution and extracted with dichloromethane. The combined organic layers were dried over MgSO$_4$ and concentrated to give the desired product. LCMS calculated for C$_{18}$H$_{25}$ClN$_3$O (M+H)$^+$: m/z=334.2; Found: 334.2.

Step 3. 2-(1-{5-Chloro-7-[1-(9H-purin-6-ylamino) ethyl]quinolin-8-yl}piperidin-4-yl)ethanol bis(trifluoroacetate)

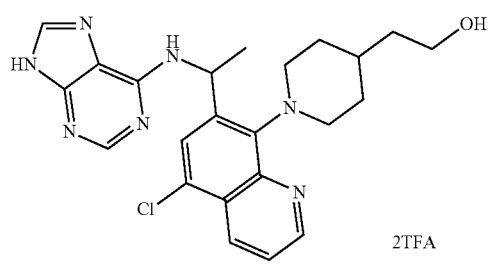

A mixture of 2-{1-[7-(1-aminoethyl)-5-chloroquinolin-8-yl]piperidin-4-yl}ethanol (0.109 g, 0.326 mmol), 6-bromo-9H-purine (0.130 g, 0.654 mmol) and N,N-diisopropylethylamine (0.171 mL, 0.979 mmol) in ethanol (2 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{23}$H$_{27}$ClN$_7$O (M+H)$^+$: m/z=452.2; Found: 452.2.

Example 74

N-(1-{5-Chloro-8-[4-(pyridin-4-ylmethyl)piperazin-1-yl]quinolin-7-yl}ethyl)-9H-purin-6-amine tris(trifluoroacetate)

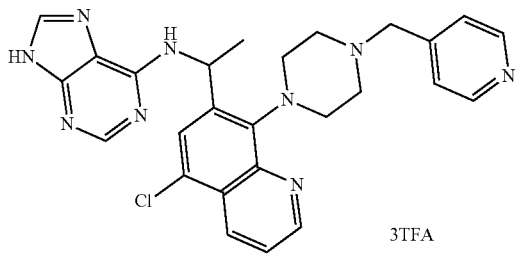 [SMILES: CC(Nc1ncnc2[nH]cnc12)c1cc(Cl)c2cccnc2c1N1CCN(Cc2ccncc2)CC1 ; "3TFA"]

Step 1. 1-{5-Chloro-8-[4-(pyridin-4-ylmethyl)piperazin-1-yl]quinolin-7-yl}ethanone

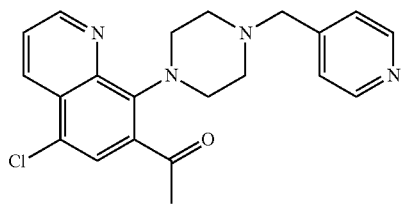 [SMILES: CC(=O)c1cc(Cl)c2cccnc2c1N1CCN(Cc2ccncc2)CC1]

A stirred mixture of 7-acetyl-5-chloroquinolin-8-yl trifluoromethanesulfonate (0.12 g, 0.34 mmol, from Example 47, Step 2), 1-(pyridin-4-ylmethyl)piperazine (0.072 g, 0.41 mmol), palladium acetate (1.5 mg, 0.0067 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated. The resulting residue was purified on silica gel (eluting with 0 to 10% methanol in dichloromethane) to give the desired product (20.2 mg, 16%). LCMS calculated for C$_{21}$H$_{22}$ClN$_4$O (M+H)$^+$: m/z=381.1; Found: 381.1.

Step 2. 1-{5-Chloro-8-[4-(pyridin-4-ylmethyl)piperazin-1-yl]quinolin-7-yl}ethanamine

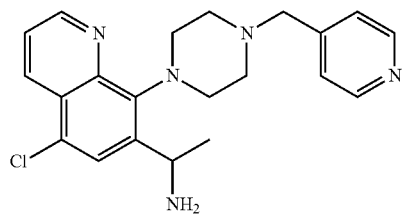 [SMILES: CC(N)c1cc(Cl)c2cccnc2c1N1CCN(Cc2ccncc2)CC1]

A mixture of 1-{5-chloro-8-[4-(pyridin-4-ylmethyl)piperazin-1-yl]quinolin-7-yl}ethanone (0.0202 g, 0.0530 mmol) and ammonium acetate (0.0409 g, 0.530 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.13 mL, 0.13 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{21}$H$_{25}$ClN$_6$ (M+H)$^+$: m/z=382.2; Found: 382.2.

Step 3. N-(1-{5-Chloro-8-[4-(pyridin-4-ylmethyl) piperazin-1-yl]quinolin-7-yl}ethyl)-6-amine tris(trifluoroacetate)

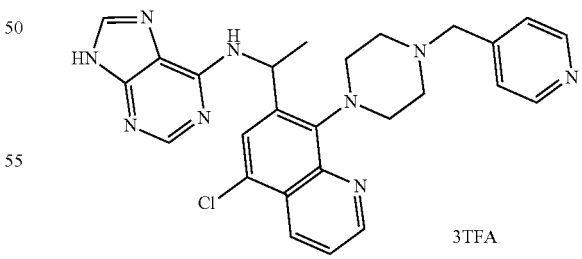

A mixture of 1-{5-chloro-8-[4-(pyridin-4-ylmethyl)piperazin-1-yl]quinolin-7-yl}ethanamine (0.021 g, 0.055 mmol), 6-bromo-9H-purine (0.022 g, 0.11 mmol) and N,N-diisopropylethylamine (0.029 mL, 0.16 mmol) in ethanol (0.5 mL) was heated at 110° C. overnight. The mixture was purified on a preparative LCMS (XBridge C18 column, eluting with a gradient of acetonitrile in water with 0.05% trifluoroacetic

Example 75

N-{1-[5-Chloro-8-(4-phenoxypiperidin-1yl)quinolin-7-yl]ethyl}-9H-purin-6-amine bis(trifluoroacetate)

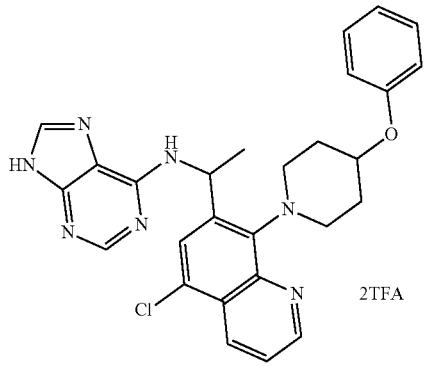 [SMILES: CC(Nc1ncnc2[nH]cnc12)c1cc(Cl)c2cccnc2c1N1CCC(Oc2ccccc2)CC1]

acid, at a flow rate of 30 mL/min) to give the desired product as a TFA salt. LCMS calculated for $C_{26}H_{27}ClN_9$ (M+H)$^+$: m/z=500.2; Found: 500.3.

Step 1. 1-[5-Chloro-8-(4-phenoxypiperidin-1-yl)quinolin-7-yl]ethanone

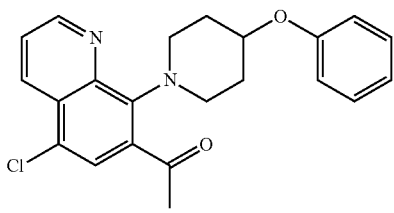 [SMILES: CC(=O)c1cc(Cl)c2cccnc2c1N1CCC(Oc2ccccc2)CC1]

A stirred mixture of 7-acetyl-5-chloroquinolin-8-yl trifluoromethanesulfonate (0.12 g, 0.34 mmol, from Example 47, Step 2), 4-phenoxypiperidine hydrochloride (0.087 g, 0.41 mmol), palladium acetate (1.5 mg, 0.0067 mmol), (S)-(−)-2,2'-bis(diphenylphosphino)-1,1'-binaphthyl (6.3 g, 0.010 mmol), and cesium carbonate (0.42 g, 1.3 mmol) in tetrahydrofuran (4 mL) was heated at 65° C. overnight. The mixture was cooled, diluted with dichloromethane and filtered. The filtrate was washed with brine, dried over MgSO$_4$, evaporated and purified on silica gel (eluting with 100% dichloromethane) to give the desired product (23.6 mg, 18%). LCMS calculated for $C_{22}H_{22}ClN_2O_2$ (M+H)$^+$: m/z=380.1; Found: 381.1.

Step 2. 1-[5-Chloro-8-(4-phenoxypiperidin-1-yl)quinolin-7-yl]ethanamine

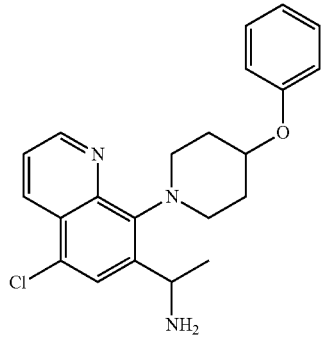 [SMILES: CC(N)c1cc(Cl)c2cccnc2c1N1CCC(Oc2ccccc2)CC1]

A mixture of 1-[5-chloro-8-(4-phenoxypiperidin-1-yl)quinolin-7-yl]ethanone (0.0236 g, 0.0620 mmol) and ammonium acetate (0.0478 g, 0.620 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.15 mL, 0.15 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for $C_{22}H_{25}ClN_3O$ (M+H)$^+$: m/z=382.2; Found: 382.2.

Step 3. N-{1-[5-Chloro-8-(4-phenoxypiperidin-1-yl)quinolin-7-yl]ethyl}-9H-purin-6-amine bis(trifluoroacetate)

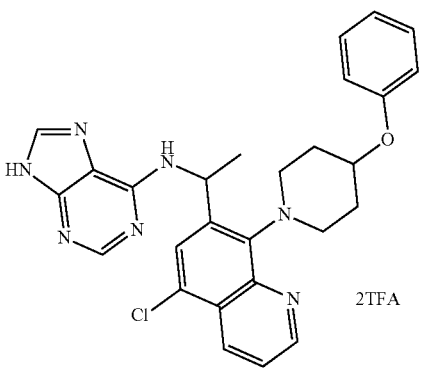 [SMILES: CC(Nc1ncnc2[nH]cnc12)c1cc(Cl)c2cccnc2c1N1CCC(Oc2ccccc2)CC1]

A mixture of 1-[5-chloro-8-(4-phenoxypiperidin-1-yl)quinolin-7-yl]ethanamine (0.023 g, 0.060 mmol), 6-bromo-9H-purine (0.024 g, 0.12 mmol) and N,N-diisopropylethylamine (0.031 mL, 0.18 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{27}H_{27}ClN_7O$ (M+H)$^+$: m/z=500.2; Found: 500.2.

Example 76

N-{1-[5-Chloro-8-(3-phenylpyrrolidin-1-yl)quinolin-7-yl]ethyl}-9H-purin-6-amine tris(trifluoroacetate)

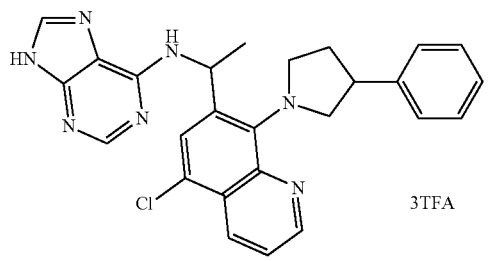 [SMILES: CC(Nc1ncnc2[nH]cnc12)c1cc(Cl)c2cccnc2c1N1CCC(c2ccccc2)C1]

3TFA

Step 1. 1-[5-Chloro-8-(3-phenylpyrrolidin-1-yl)quinolin-7-yl]ethanone

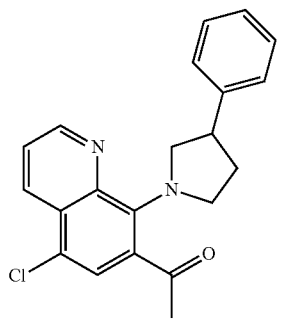 [SMILES: CC(=O)c1cc(Cl)c2cccnc2c1N1CCC(c2ccccc2)C1]

A stirred mixture of 7-acetyl-5-chloroquinolin-8-yl trifluoromethanesulfonate (0.12 g, 0.34 mmol, from Example 47, Step 2), 3-phenylpyrrolidine (0.060 g, 0.41 mmol), palladium acetate (1.5 mg, 0.0067 mmol), (S)-(−)-2,2'-bis(diphenylphosphino)-1,1'-binaphthyl (6.3 mg, 0.010 mmol), and cesium carbonate (0.31 g, 0.95 mmol) in tetrahydrofuran (3 mL) was heated at 65° C. overnight. The mixture was cooled, diluted with dichloromethane and filtered. The filtrate was washed with brine, dried over MgSO$_4$ and evaporated. The residue was purified on silica gel (eluting with dichloromethane) to give the desired product (22.6 mg, 19%). LCMS calculated for $C_{21}H_{20}ClN_2O$ (M+H)$^+$: m/z=351.1; Found: 351.1.

Step 2. 1-[5-Chloro-8-(3-phenylpyrrolidin-1-yl)quinolin-7-yl]ethanamine

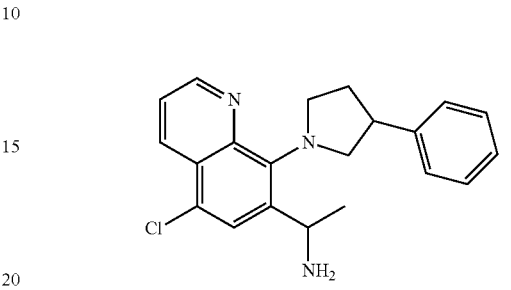

A mixture of 1-[5-chloro-8-(3-phenylpyrrolidin-1-yl)quinolin-7-yl]ethanone (0.0226 g, 0.0644 mmol) and ammonium acetate (0.0496 g, 0.644 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.16 mL, 0.16 mmol). The reaction was heated at 65° C. overnight. The mixture was cooled to room temperature, quenched with sat. NaHCO$_3$ solution and extracted with dichloromethane. The combined organic phases were dried over MgSO$_4$ and concentrated to give the desired product. LCMS calculated for $C_{21}H_{23}ClN_3$ (M+H)$^+$: m/z=352.2; Found: 352.1.

Step 3. N-{1-[5-Chloro-8-(3-phenylpyrrolidin-1-yl)quinolin-7-yl]ethyl}-9H-purin-6-amine tris (trifluoroacetate)

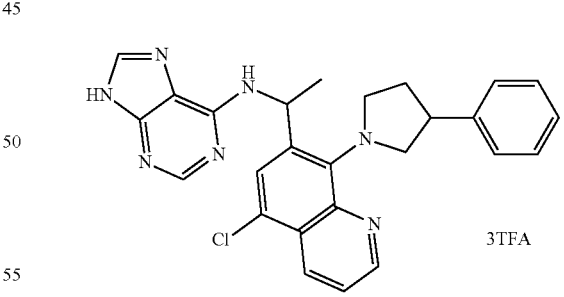

3TFA

A mixture of 1-[5-chloro-8-(3-phenylpyrrolidin-1-yl)quinolin-7-yl]ethanamine (0.024 g, 0.068 mmol), 6-bromo-9H-purine (0.027 g, 0.14 mmol) and N,N-diisopropylethylamine (0.036 mL, 0.20 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 2.273 minutes, LCMS calculated for $C_{26}H_{25}ClN_7$ (M+H)$^+$: m/z=470.2; Found:

470.2. Second peak retention time 2.345 minutes, LCMS calculated for $C_{26}H_{25}ClN_7$ (M+H)$^+$: m/z=470.2; Found: 470.2.

Example 77

N-((3S)-1-{5-Chloro-7-[1-(9H-purin-6-ylamino)ethyl]quinolin-8-yl}pyrrolidin-3-yl)propanamide tris(trifluoroacetate)

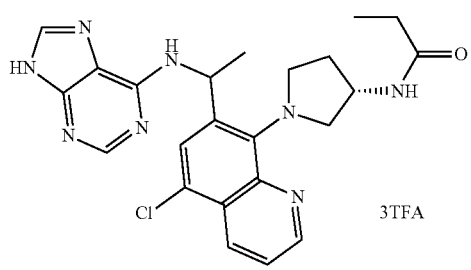 [SMILES: CCC(=O)N[C@H]1CCN(c2c(C(C)Nc3ncnc4[nH]cnc34)cc(Cl)c3cccnc23)C1]

Step 1. N-[(3S)-Pyrrolidin-3-yl]propanamide hydrochloride

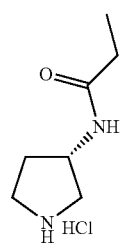

tert-Butyl (3S)-3-aminopyrrolidine-1-carboxylate (0.09 mL, 0.5 mmol) was combined with propanoyl chloride (0.055 mL, 0.64 mmol) and triethylamine (0.22 mL, 1.6 mmol) in methylene chloride (2 mL) at room temperature and stirred for 2 hours. The reaction was diluted with dichloromethane, washed with water, and dried over MgSO$_4$, then concentrated. The resulting residue was purified on silica gel (eluting with 0 to 10% MeOH in dichloromethane) to give tert-butyl (3S)-3-(propionylamino)pyrrolidine-1-carboxylate, LCMS [M+Na] 265.2. The later was treated with 4.57 M hydrogen chloride in 1,4-dioxane (1 mL, 4 mmol) at room temperature for 1 hour. The mixture was concentrated to give crude product (0.057 g) which was used directly in the next step. LCMS calculated for $C_7H_{15}N_2O$ (M+H)$^+$: m/z=143.1; Found: 143.2.

Step 2. N-[(3S)-1-(7-Acetyl-5-chloroquinolin-8-yl)pyrrolidin-3-yl]propanamide

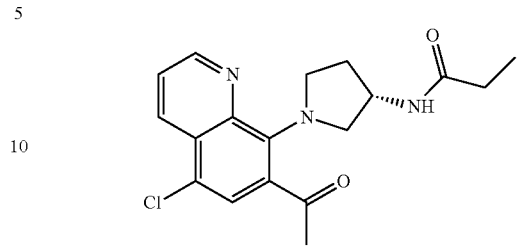

A stirred mixture of 7-acetyl-5-chloroquinolin-8-yl trifluoromethanesulfonate (0.19 g, 0.27 mmol, from Example 47, Step 2), N-[(3S)-pyrrolidin-3-yl]propanamide hydrochloride (0.040 g, 0.22 mmol), palladium acetate (1.0 mg, 0.0045 mmol), (S)-(−)-2,2'-bis(diphenylphosphino)-1,1'-binaphthyl (4.2 mg, 0.0067 mmol), and cesium carbonate (0.28 g, 0.85 mmol) in tetrahydrofuran (4 mL) was heated at 65° C. overnight. The mixture was cooled, diluted with dichloromethane and filtered. The filtrate was washed with brine, dried over MgSO$_4$ and evaporated. The residue was purified on silica gel (eluting with 0 to 5% MeOH in dichloromethane) to give the desired product (11 mg, 14%). LCMS calculated for $C_{18}H_{21}ClN_3O_2$ (M+H)$^+$: m/z=345.1; Found: 346.3.

Step 3. N-{(3S)-1-[7-(1-Aminoethyl)-5-chloroquinolin-8-yl]pyrrolidin-3-yl}propanamide

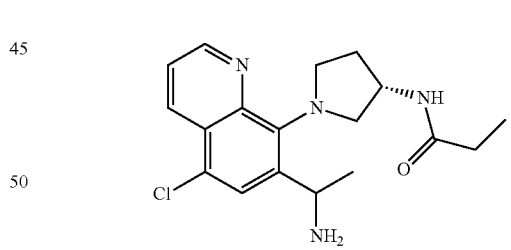

A mixture of N-[(3S)-1-(7-acetyl-5-chloroquinolin-8-yl)pyrrolidin-3-yl]propanamide (0.011 g, 0.032 mmol) and ammonium acetate (0.0245 g, 0.318 mmol) in methanol (0.15 mL) and acetonitrile (0.15 mL) was heated at 65° C. in a sealed tube for 1 hour. After cooling to room temperature, to the resulting mixture was added 1.0 M sodium cyanoborohydride in tetrahydrofuran (0.080 mL, 0.080 mmol). The reaction was heated at 65° C. overnight, then cooled to room temperature, quenched with sat. NaHCO$_3$ solution and extracted with dichloromethane. The combined organic phase were dried over MgSO$_4$ and concentrated to give the desired product. LCMS calculated for $C_{18}H_{24}ClN_4O$ (M+H)⁺: m/z=347.2; Found: 347.1.

Step 4. N-((3S)-1-{5-Chloro-7-[1-(9H-purin-6-ylamino)ethyl]quinolin-8-yl}pyrrolidin-3-yl)propanamide tris(trifluoroacetate)

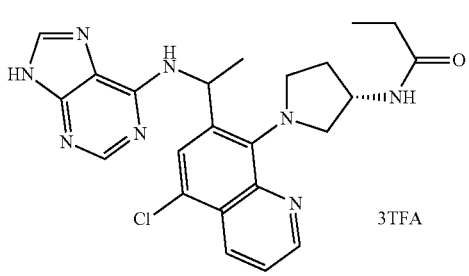 [SMILES: CCC(=O)N[C@H]1CCN(c2c(C(C)Nc3ncnc4[nH]cnc34)cc(Cl)c3cccnc23)C1]

A mixture of N-{(3S)-1-[7-(1-aminoethyl)-5-chloroquinolin-8-yl]pyrrolidin-3-yl}propanamide (0.010 g, 0.029 mmol), 6-bromo-9H-purine (0.011 g, 0.058 mmol) and N,N-diisopropylethylamine (0.015 mL, 0.086 mmol) in ethanol (0.3 mL) was heated at 110° C. overnight. The mixture was purified on a preparative LCMS (XBridge C 18 column, eluting with a gradient of acetonitrile in water with 0.05% trifluoroacetic acid, at a flow rate of 30 mL/min) to give the desired product as a TFA salt. First peak retention time 1.715 minutes, LCMS calculated for $C_{23}H_{26}ClN_8O$ (M+H)⁺: m/z=465.2; Found: 465.1. Second peak retention time 1.750 minutes, LCMS calculated for $C_{23}H_{26}ClN_8O$ (M+H)⁺: m/z=465.2; Found: 465.1.

Example 78

N-((3S)-1-{5-Chloro-7-[1-(9H-purin-6-ylamino)ethyl]quinolin-8-yl}pyrrolidin-3-yl)-2-methylpropanamide tris(trifluoroacetate)

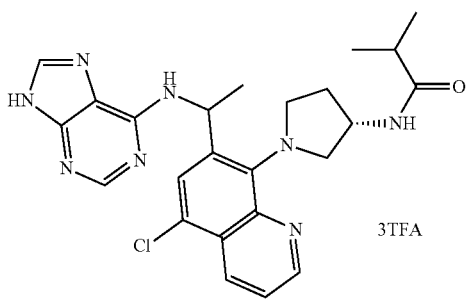 [SMILES: CC(C)C(=O)N[C@H]1CCN(c2c(C(C)Nc3ncnc4[nH]cnc34)cc(Cl)c3cccnc23)C1]

Step 1. 2-Methyl-N-[(3S)-pyrrolidin-3-yl]propanamide hydrochloride

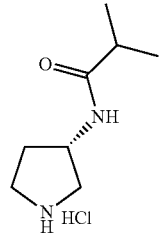

tert-Butyl (3S)-3-aminopyrrolidine-1-carboxylate (0.09 mL, 0.5 mmol) was combined with isobutyryl chloride (0.067 mL, 0.64 mmol) and triethylamine (0.22 mL, 1.6 mmol) in methylene chloride (2 mL) at room temperature and stirred for 2 hours. The reaction was diluted with dichloromethane, washed with water, dried over MgSO₄ and concentrated. The residue was purified on silica gel (eluting with 0 to 10% methanol in dichloromethane) to give tert-butyl (3S)-3-(isobutyrylamino)pyrrolidine-1-carboxylate, LCMS [M+Na] 279.2. The latter was treated with 4.57 M hydrogen chloride in 1,4-dioxane (1 mL, 4 mmol) at room temperature for 1 hour. The mixture was concentrated to give the crude product (35 mg, 30%), which was used directly in the next step. LCMS calculated for $C_8H_{17}N_2O$ (M+H)⁺: m/z=157.1; Found: 157.2.

Step 2. N-[(3S)-1-(7-Acetyl-5-chloroquinolin-8-yl)pyrrolidin-3-yl]-2-methylpropanamide

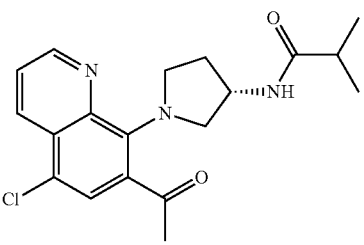 [SMILES: CC(=O)c1cc(Cl)c2cccnc2c1N1CC[C@H](NC(=O)C(C)C)C1]

A stirred mixture of 7-acetyl-5-chloroquinolin-8-yl trifluoromethanesulfonate (0.17 g, 0.24 mmol, from Example 47, Step 2), 2-methyl-N-[(3S)-pyrrolidin-3-yl]propanamide hydrochloride (0.035 g, 0.18 mmol), palladium acetate (0.82 mg, 0.0036 mmol), (S)-(−)-2,2'-bis(diphenylphosphino)-1,1'-binaphthyl (3.4 mg, 0.0054 mmol), and cesium carbonate (0.22 g, 0.69 mmol) in tetrahydrofuran (4 mL) was heated at 65° C. overnight. The mixture was cooled, diluted with dichloromethane and filtered. The filtrate was washed with brine, dried over MgSO₄ and evaporated under reduced pressure. The residue was purified on silica gel (eluting with 0 to 5% MeOH in dichloromethane) to give the desired product (31 mg, 47%). LCMS calculated for $C_{19}H_{23}ClN_3O_2$ (M+H)$^+$: m/z=360.1; Found: 360.1.

Step 3. N-{(3S)-1-[7-(1-Aminoethyl)-5-chloroquinolin-8-yl)pyrrolidin-3-yl}-2-methylpropanamide

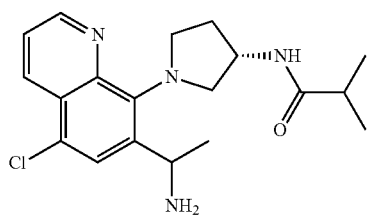 [SMILES: CC(C)C(=O)N[C@H]1CCN(c2c(C(C)N)cc(Cl)c3cccnc23)C1]

A mixture of N-[(3S)-1-(7-acetyl-5-chloroquinolin-8-yl)pyrrolidin-3-yl]-2-methylpropanamide (0.031 g, 0.086 mmol) and ammonium acetate (0.066 g, 0.86 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.21 mL, 0.21 mmol). The reaction was heated at 65° C. overnight and then cooled to room temperature. The mixture was quenched with sat. NaHCO$_3$ solution, extracted with dichloromethane, dried over MgSO$_4$ and concentrated to give the desired product. LCMS calculated for $C_{19}H_{26}ClN_4O$ (M+H)$^+$: m/z=361.2; Found: 361.2.

Step 4. N-((3S)-1-{5-Chloro-7-[7-(9H-purin-6-ylamino)ethyl]quinolin-8-yl}pyrrolidin-3-yl)-2-methylpropanamide tris(trifluoroacetate)

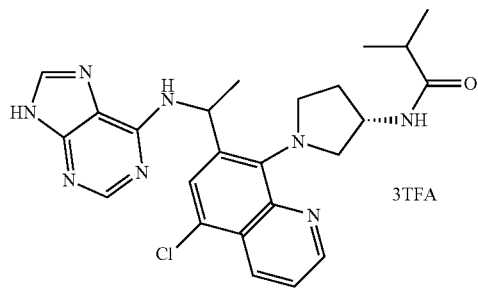

A mixture of N-{(3S)-1-[7-(1-aminoethyl)-5-chloroquinolin-8-yl]pyrrolidin-3-yl}-2-methylpropanamide (0.023 g, 0.064 mmol), 6-bromo-9H-purine (0.025 g, 0.13 mmol) and N,N-diisopropylethylamine (0.033 mL, 0.19 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.912 minutes, LCMS calculated for $C_{24}H_{28}ClN_8O$ (M+H)$^+$: m/z=479.2; Found: 479.1. Second peak retention time 1.943 minutes, LCMS calculated for $C_{24}H_{28}ClN_8O$ (M+H)$^+$: m/z=479.2; Found: 479.1.

Example 79

Methyl((3S)-1-{5-Chloro-7-[1-(9H-purin-6-ylamino)ethyl]quinolin-8-yl}pyrrolidin-3-yl)carbamate tris(trifluoroacetate)

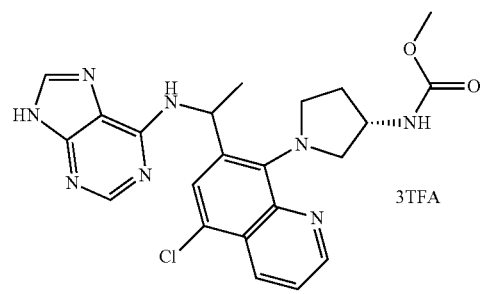 [SMILES: COC(=O)N[C@H]1CCN(c2c(C(C)Nc3ncnc4[nH]cnc34)cc(Cl)c3cccnc23)C1]

Step 1. Methyl(3S)-pyrrolidin-3-ylcarbamate hydrochloride

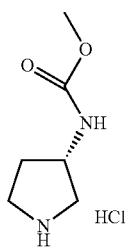

tert-Butyl(3S)-3-aminopyrrolidine-1-carboxylate (0.09 mL, 0.5 mmol) was combined with methyl chloroformate (0.049 mL, 0.64 mmol) and triethylamine (0.22 mL, 1.6 mmol) in methylene chloride (2 mL) at room temperature and stirred for 2 hours. The reaction was diluted with dichloromethane, washed with water, dried over MgSO$_4$ and concentrated. The residue was purified on silica gel (eluting with 0 to 10% methanol in dichloromethane) to give tert-butyl (3S)-3-[(methoxycarbonyl)amino]pyrrolidine-1-carboxylate, LCMS [M+Na] 267.1. The latter was treated with 4.57 M hydrogen chloride in 1,4-dioxane (1 mL, 4 mmol) at room temperature for 1 hour. The mixture was concentrated to give the crude product (35 mg, 40%), which was used directly in the next step. LCMS calculated for $C_6H_{13}N_2O_2$ (M+H)$^+$: m/z=145.1; Found: 145.1.

Step 2. Methyl[(3S)-1-(7-acetyl-5-chloroquinolin-8-yl)pyrrolidin-3-yl]carbamate

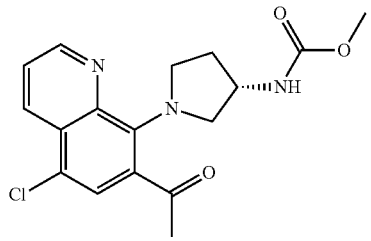 [SMILES: COC(=O)N[C@H]1CCN(c2c(C(C)=O)cc(Cl)c3cccnc23)C1]

A stirred mixture of 7-acetyl-5-chloroquinolin-8-yl trifluoromethanesulfonate (0.16 g, 0.23 mmol, from Example 47, Step 2), methyl (3S)-pyrrolidin-3-ylcarbamate hydrochloride (0.035 g, 0.19 mmol), palladium acetate (0.87 mg, 0.0039 mmol), (S)-(−)-2,2'-bis(diphenylphosphino)-1,1'-binaphthyl (3.6 mg, 0.0058 mmol), and cesium carbonate (0.24 g, 0.74 mmol) in tetrahydrofuran (4 mL) was heated at 65° C. overnight. The mixture was cooled, diluted with dichloromethane and filtered. The filtrate was washed with brine, dried over MgSO$_4$ and evaporated. The residue was purified on silica gel (eluting with 0 to 5% MeOH in dichloromethane) to give the desired product (47 mg, 70%). LCMS calculated for $C_{17}H_{19}ClN_3O_3$ (M+H)$^+$: m/z=348.1; Found: 348.4.

Step 3. Methyl{(3S)-1-[7-(1-aminoethyl)-5-chloroquinolin-8-yl]pyrrolidin-3-yl}carbamate

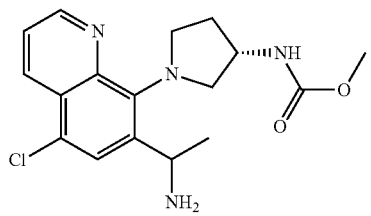 [SMILES: COC(=O)N[C@H]1CCN(c2c(C(C)N)cc(Cl)c3cccnc23)C1]

A mixture of methyl[(3S)-1-(7-acetyl-5-chloroquinolin-8-yl)pyrrolidin-3-yl]carbamate (0.047 g, 0.14 mmol) and ammonium acetate (0.104 g, 1.35 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.34 mL, 0.34 mmol). The reaction was heated at 65° C. overnight. The mixture was then cooled to room temperature, quenched with sat. NaHCO$_3$ solution, extracted with dichloromethane, dried over MgSO$_4$ and concentrated to give the desired product. LCMS calculated for $C_{17}H_{22}ClN_4O_2$ (M+H)$^+$: m/z=349.1; Found: 349.1.

Step 4. Methyl((3S)-1-{5-Chloro-7-[1-(9H-purin-6-ylamino)ethyl]quinolin-8-yl}pyrrolidin-3-yl)carbamate tris(trifluoroacetate)

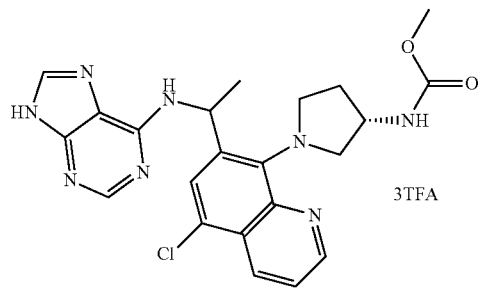 [SMILES: COC(=O)N[C@H]1CCN(c2c(C(C)Nc3ncnc4[nH]cnc34)cc(Cl)c3cccnc23)C1]

A mixture of methyl{(3S)-1-[7-(1-aminoethyl)-5-chloroquinolin-8-yl]pyrrolidin-3-yl}carbamate (0.042 g, 0.12 mmol), 6-bromo-9H-purine (0.048 g, 0.24 mmol) and N,N-diisopropylethylamine (0.063 mL, 0.36 mmol) in ethanol (0.6 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.923 minutes, LCMS calculated for $C_{22}H_{24}ClN_8O_2$ (M+H)$^+$: m/z=467.2; Found: 467.1. Second peak retention time 1.935 minutes, LCMS calculated for $C_{22}H_{24}ClN_8O_2$ (M+H)$^+$: m/z=467.2; Found: 467.1.

Example 80

N-((3S)-1-{5-Chloro-7-[1-(9H-purin-6-ylamino)ethyl]quinolin-8-yl}pyrrolidin-3-yl)methanesulfonamide tris(trifluoroacetate)

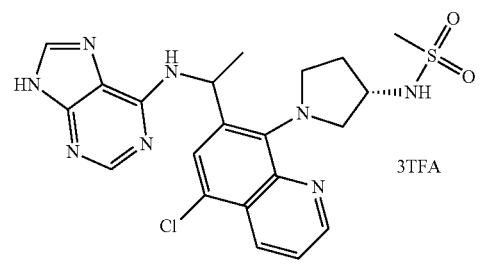 [SMILES: CC(Nc1ncnc2[nH]cnc12)c1cc(Cl)c2cccnc2c1N1CC[C@H](NS(C)(=O)=O)C1]

Step 1. N-[(3S)-Pyrrolidin-3-yl]methanesulfonamide hydrochloride

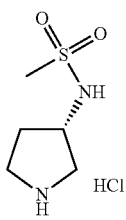

tert-Butyl(3S)-3-aminopyrrolidine-1-carboxylate (0.09 mL, 0.5 mmol) was combined with methanesulfonyl chloride (0.050 mL, 0.64 mmol) and triethylamine (0.22 mL, 1.6 mmol) in methylene chloride (2 mL) at room temperature and stirred for 2 hours. The reaction was diluted with dichloromethane, washed with water, dried over MgSO$_4$, and concentrated. The residue was purified on silica gel (eluting with 0-10% methanol in dichloromethane) to give tert-butyl(3S)-3-[(methylsulfonyl)amino]pyrrolidine-1-carboxylate, LCMS [M+Na]$^+$: m/z=287.1. The latter was treated with 4.57 M hydrogen chloride in 1,4-dioxane (1 mL, 4 mmol) at room temperature for 1 hour. The mixture was concentrated to give the desired product, which was used directly in the next step. LCMS calculated for $C_5H_{13}N_2O_2S$ (M+H)$^+$: m/z=165.1; Found: 165.1.

Step 2. N-[(3S)-1-(7-Acetyl-5-chloroquinolin-8-yl)pyrrolidin-3-yl]methanesulfonamide

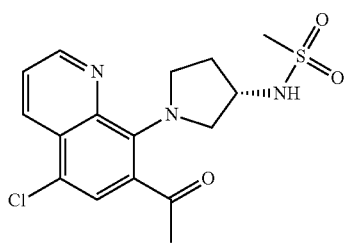 [SMILES: CC(=O)c1cc(Cl)c2cccnc2c1N1CC[C@H](NS(C)(=O)=O)C1]

A stirred mixture of 7-acetyl-5-chloroquinolin-8-yl trifluoromethanesulfonate (0.17 g, 0.25 mmol, from Example 47, Step 2), N-[(3S)-pyrrolidin-3-yl]methanesulfonamide hydrochloride (0.062 g, 0.31 mmol), palladium acetate (1.1 mg, 0.0049 mmol), (S)-(−)-2,2'-bis(diphenylphosphino)-1,1'-binaphthyl (4.6 mg, 0.0074 mmol), and cesium carbonate (0.31 g, 0.94 mmol) in tetrahydrofuran (4 mL, 50 mmol) was heated at 65° C. overnight. The mixture was cooled, diluted with dichloromethane and filtered. The filtrate were washed with brine, dried over MgSO$_4$, evaporated and purified on silica gel (eluting with 0 to 5% methanol in dichloromethane) to give the desired product (37 mg, 41%). LCMS calculated for $C_{16}H_{19}ClN_3O_3S$ (M+H)$^+$: m/z=368.1; Found: 368.1.

Step 3. N-{(3S)-1-[7-(1-Aminoethyl)-5-chloroquinolin-8-yl]pyrrolidin-3-yl}methanesulfonamide

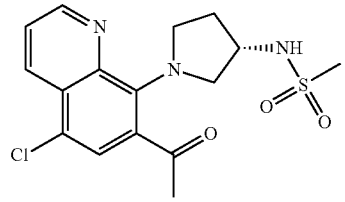 [SMILES: CC(=O)c1cc(Cl)c2cccnc2c1N1CC[C@H](NS(C)(=O)=O)C1]

A mixture of N-[(3S)-1-(7-acetyl-5-chloroquinolin-8-yl)pyrrolidin-3-yl]methanesulfonamide (0.037 g, 0.10 mmol) and ammonium acetate (0.0775 g, 1.00 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.25 mL, 0.25 mmol). The reaction was heated at 65° C. overnight. The mixture was cooled to room temperature, quenched with sat. NaHCO$_3$ solution, extracted with dichloromethane, dried over MgSO$_4$, concentrated and purified on a preparative LCMS (pH 10) to give the desired product. LCMS calculated for $C_{16}H_{22}ClN_4O_2S$ (M+H)$^+$: m/z=369.1; Found: 369.1.

Step 4. N-((3S)-1-{5-Chloro-7-[1-(9H-purin-6-ylamino)ethyl]quinolin-8-yl}pyrrolidin-3-yl)methanesulfonamide tris(trifluoroacetate)

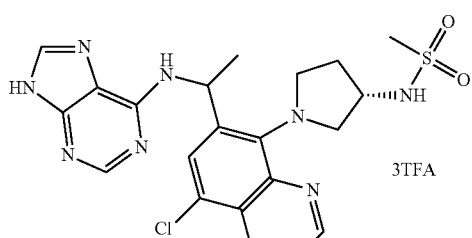

A mixture of N-{(3S)-1-[7-(1-aminoethyl)-5-chloroquinolin-8-yl]pyrrolidin-3-yl}methanesulfonamide (0.0033 g, 0.0089 mmol), 6-bromo-9H-purine (0.0036 g, 0.018 mmol) and N,N-diisopropylethylamine (0.0047 mL, 0.027 mmol) in ethanol (0.1 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. First peak retention time 1.822 minutes, LCMS calculated for $C_{22}H_{24}ClN_8O_2S$ (M+H)$^+$: m/z=487.1; Found: 487.0. Second peak retention time 1.790 minutes, LCMS calculated for $C_{22}H_{24}ClN_8O_2S$ (M+H)⁺: m/z=487.1; Found: 487.0.

Example 81

N-(1-{5-Chloro-7-[1-(9H-purin-6-ylamino)ethyl]quinolin-8-yl}piperidin-4-yl)methanesulfonamide bis(trifluoroacetate)

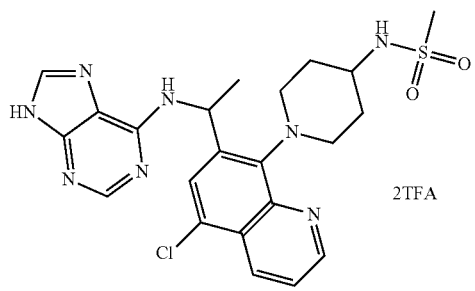 [SMILES: CC(Nc1ncnc2[nH]cnc12)c1cc(Cl)c2cccnc2c1N1CCC(NS(C)(=O)=O)CC1]

Step 1. N-Piperidin-4-ylmethanesulfonamide hydrochloride

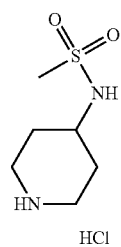

tert-Butyl 4-aminopiperidine-1-carboxylate (0.10 g, 0.50 mol) was combined with methanesulfonyl chloride (0.043 mL, 0.56 mol) and triethylamine (0.21 mL, 1.5 mmol) in methylene chloride (2 mL) at room temperature and stirred for 2 hours. The reaction was diluted with dichloromethane, washed with water, dried over MgSO₄, concentrated and purified on silica gel (eluting with 0 to 5% methanol in dichloromethane) to give tert-butyl 4-[(methylsulfonyl)amino]piperidine-1-carboxylate, LCMS [M+Na]⁺: m/z=301.0. The later was treated with 4.57 M hydrogen chloride in 1,4-dioxane (1 mL, 4 mmol) at room temperature for 1 hour. The mixture was concentrated to give the desired HCl salt, which was used directly in the next step. LCMS calculated for $C_6H_{15}N_2O_2S$ (M+H)⁺: m/z=179.1; Found: 179.1.

Step 2. N-[1-(7-Acetyl-5-chloroquinolin-8-yl)piperidin-4-yl]methanesulfonamide

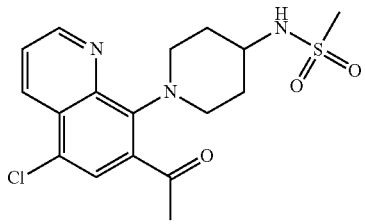 [SMILES: CC(=O)c1cc(Cl)c2cccnc2c1N1CCC(NS(C)(=O)=O)CC1]

A stirred mixture of 7-acetyl-5-chloroquinolin-8-yl trifluoromethanesulfonate (0.16 g, 0.22 mmol, from Example 47, Step 2), N-piperidin-4-ylmethanesulfonamide hydrochloride (0.040 g, 0.19 mmol), palladium acetate (0.84 mg, 0.0037 mmol), (S)-(−)-2,2'-bis(diphenylphosphino)-1,1'-binaphthyl (3.5 mg, 0.0056 mmol), and cesium carbonate (0.23 g, 0.71 mmol) in tetrahydrofuran (4 mL) was heated at 65° C. overnight. The mixtures was cooled, diluted with dichloromethane and filtered. The filtrate was washed with brine, dried over MgSO₄, evaporated and purified on silica gel (eluting with 0 to 5% methanol in dicholomethane) to give the desired product (27 mg, 38%). LCMS calculated for $C_{17}H_{21}ClN_3O_3S$ (M+H)⁺: m/z=382.1; Found: 382.0.

Step 3. N-{1-[7-(1-Aminoethyl)-5-chloroquinolin-8-yl]piperidin-4-yl}methanesulfonamide

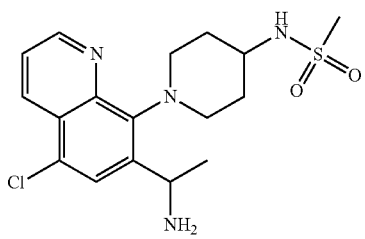 [SMILES: CC(N)c1cc(Cl)c2cccnc2c1N1CCC(NS(C)(=O)=O)CC1]

A mixture of N-[1-(7-acetyl-5-chloroquinolin-8-yl)piperidin-4-yl]methanesulfonamide (0.027 g, 0.071 mmol) and ammonium acetate (0.0545 g, 0.707 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.17 mL, 0.17 mmol). The reaction was heated at 65° C. overnight. The mixture was cooled to room temperature, quenched with sat. NaHCO₃ solution, extracted with dichloromethane, dried over MgSO₄ and concentrated to give the desired product. LCMS calculated for C$_{17}$H$_{24}$ClN$_4$O$_2$S (M+H)$^+$: m/z=383.1; Found: 383.1.

Step 4. N-(1-{5-Chloro-7-[1-(9H-purin-6-ylamino)ethyl]quinolin-8-yl}piperidin-4-yl)methanesulfonamide bis(trifluoroacetate)

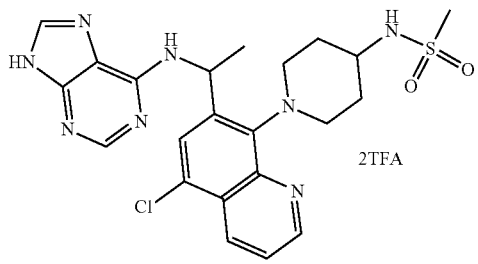 [SMILES: CC(Nc1ncnc2[nH]cnc12)c1cc(Cl)c2cccnc2c1N1CCC(NS(C)(=O)=O)CC1]

A mixture of N-{1-[7-(1-aminoethyl)-5-chloroquinolin-8-yl]piperidin-4-yl}methanesulfonamide (0.025 g, 0.065 mmol), 6-bromo-9H-purine (0.026 g, 0.13 mmol) and N,N-diisopropylethylamine (0.034 mL, 0.20 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{22}$H$_{26}$ClN$_8$O$_2$S (M+H)$^+$: m/z=501.2; Found: 501.2.

Example 82

N-(1-{5-Chloro-7-[1-(9H-purin-6-ylamino)ethyl]quinolin-8-yl}piperidin-4-yl)acetamide bis(trifluoroacetate)

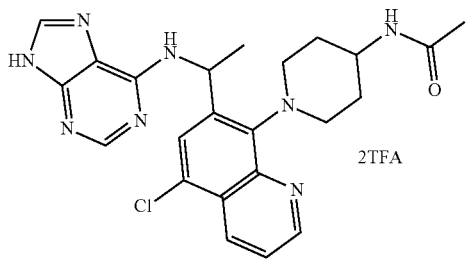 [SMILES: CC(=O)NC1CCN(c2c(C(C)Nc3ncnc4[nH]cnc34)cc(Cl)c3cccnc23)CC1]

Step 1. N-Piperidin-4-ylacetamide hydrochloride

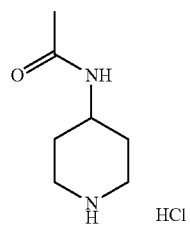

tert-Butyl 4-aminopiperidine-1-carboxylate (0.10 g, 0.50 mmol) was combined with acetic anhydride (0.052 mL, 0.55 mmol) and triethylamine (0.21 mL, 1.5 mmol) in methylene chloride (2 mL) at room temperature and stirred for 2 hours. The reaction was diluted with dichloromethane, washed with water, dried over MgSO$_4$ and concentrated. The resulted residue was purified on silica gel (eluting with 0 to 5% MeOH in dichloromethane) to give tert-butyl 4-(acetylamino)piperidine-1-carboxylate, LCMS [M+Na]$^+$: m/z=265.1. The later was treated with 4.57 M hydrogen chloride in 1,4-dioxane (1 mL, 4 mmol) at room temperature for 1 hour. The mixture was concentrated to give crude HCl salt product (0.057 g), which was used directly in the next step. LCMS calculated for C$_7$H$_{15}$N$_2$O (M+H)$^+$: m/z=143.1; Found: 143.1.

Step 2. N-[1-(7-Acetyl-5-chloroquinolin-8-yl)piperidin-4-yl]acetamide

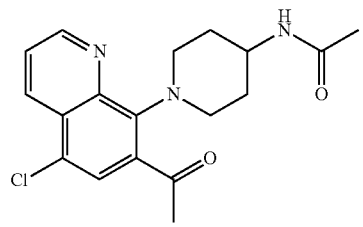 [SMILES: CC(=O)NC1CCN(c2c(C(C)=O)cc(Cl)c3cccnc23)CC1]

A stirred mixture of 7-acetyl-5-chloroquinolin-8-yl trifluoromethanesulfonate (0.17 g, 0.25 mmol, from Example 47, Step 2), N-piperidin-4-ylacetamide hydrochloride (0.040 g, 0.22 mmol), palladium acetate (1.0 mg, 0.0045 mmol), (S)-(–)-2,2'-bis(diphenylphosphino)-1,1'-binaphthyl (4.2 mg, 0.0067 mmol), and cesium carbonate (0.28 g, 0.85 mmol) in tetrahydrofuran (4 mL) was heated at 65° C. overnight. The mixture was cooled, diluted with dichloromethane and filtered. The filtrate was washed with brine, dried over MgSO$_4$, evaporated and purified on silica gel (eluting with 0 to 5% MeOH in dichloromethane) to give the desired product (42 mg, 54%). LCMS calculated for C$_{18}$H$_{21}$ClN$_3$O$_2$ (M+H)$^+$: m/z=346.1; Found: 346.1.

Step 3. N-{1-[7-(1-Aminoethyl)-5-chloroquinolin-8-yl]piperidin-4-yl}acetamide

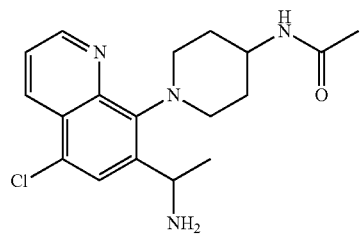 [SMILES: CC(=O)NC1CCN(c2c(C(C)N)cc(Cl)c3cccnc23)CC1]

A mixture of N-[1-(7-acetyl-5-chloroquinolin-8-yl)piperidin-4-yl]acetamide (0.042 g, 0.12 mmol) and ammonium acetate (0.0936 g, 1.21 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.30 mL, 0.30 mmol). The reaction was heated at 65° C. overnight. The mixture was cooled to room temperature, quenched with sat. NaHCO$_3$ solution and extracted with dichloromethane. The combined organic layers were dried over MgSO$_4$ and concentrated to give the desired product. LCMS calculated for C$_{18}$H$_{24}$ClN$_4$O (M+H)$^+$: m/z=347.2; Found: 347.1.

Step 4. N-(1-{5-Chloro-7-[1-(9H-purin-6-ylamino)ethyl]quinolin-8-yl}piperidin-4-yl)acetamide bis(trifluoroacetate)

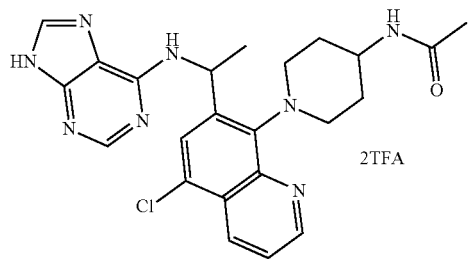 [SMILES: CC(=O)NC1CCN(c2c(C(C)Nc3ncnc4[nH]cnc34)cc(Cl)c3cccnc23)CC1]

A mixture of N-{1-[7-(1-aminoethyl)-5-chloroquinolin-8-yl]piperidin-4-yl}acetamide (0.040 g, 0.12 mmol), 6-bromo-9H-purine (0.046 g, 0.23 mmol) and N,N-diisopropylethylamine (0.060 mL, 0.34 mmol) in ethanol (0.6 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{23}$H$_{26}$ClN$_8$O (M+H)$^+$: m/z=465.2; Found: 465.1. $^1$H NMR (DMSO-d$_6$, 300 MHz) δ 9.39 (1H, br s), 9.00 (1H, dd, J=4.2 and 1.5 Hz), 8.51~8.43 (3H, m), 7.87 (1H, s), 7.63 (1H, dd, J=8.7 and 4.2 Hz), 6.45 (1H, m), 4.05 (1H, m), 3.86 (1H, m), 3.76 (1H, m), 3.27 (1H, m), 2.84 (1H, m), 1.89~1.84 (3H, m), 1.80 (3H, s), 1.68~1.62 (2H, m), 1.59 (3H, d, J=6.9 Hz) ppm.

Example 83

Methyl(1-{5-Chloro-7-[1-(9H-purin-6-ylamino)ethyl]quinolin-8-yl}piperidin-4-yl)carbamate bis(trifluoroacetate)

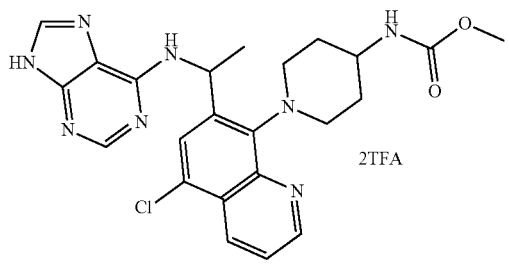 [SMILES: COC(=O)NC1CCN(c2c(C(C)Nc3ncnc4[nH]cnc34)cc(Cl)c3cccnc23)CC1]

Step 1. Methyl piperidin-4-ylcarbamate hydrochloride

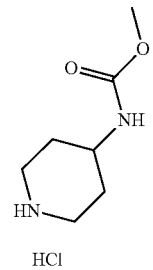

tert-Butyl 4-aminopiperidine-1-carboxylate (0.1 g, 0.5 mmol) was combined with methyl chloroformate (0.046 mL, 0.59 mmol) and triethylamine (0.22 mL, 1.6 mmol) in methylene chloride (2 mL) at room temperature and stirred for 2 hours. The reaction was diluted with dichloromethane, washed with water, dried over MgSO$_4$, and then concentrated. The resulting residue was purified on silica gel (eluting with 0 to 5% methanol in dichloromethane) to give tert-butyl 4-[(methoxycarbonyl)amino]piperidine-1-carboxylate, LCMS [M+Na] 281.1. The later was treated with 4.57 M hydrogen chloride in 1,4-dioxane (1 mL, 4 mmol) at room temperature for 1 hour. The mixture was concentrated to give crude product which was used directly in the next step. LCMS calculated for C$_7$H$_{15}$N$_2$O$_2$ (M+H)$^+$: m/z=159.1; Found: 159.1.

Step 2. Methyl[1-(7-acetyl-5-chloroquinolin-8-yl)piperidin-4-yl]carbamate

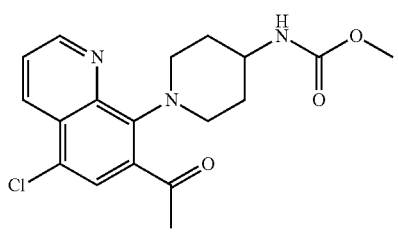 [SMILES: COC(=O)NC1CCN(c2c(C(C)=O)cc(Cl)c3cccnc23)CC1]

A stirred mixture of 7-acetyl-5-chloroquinolin-8-yl trifluoromethanesulfonate (0.12 g, 0.17 mmol, from Example 47, Step 2), methyl piperidin-4-ylcarbamate hydrochloride (0.028 g, 0.14 mmol), palladium acetate (0.64 mg, 0.0029 mmol), (S)-(−)-2,2'-bis(diphenylphosphino)-1,1'-binaphthyl (2.7 mg, 0.0043 mmol), and cesium carbonate (0.18 g, 0.55 mmol) in tetrahydrofuran (3 mL) was heated at 65° C. overnight. The mixture was cooled, diluted with dichloromethane and filtered. The filtrate was washed with brine, dried over MgSO$_4$, evaporated and then purified on silica gel (eluting with 0 to 5% methanol in dichloromethane) to give the desired product (21 mg, 40%). LCMS calculated for C$_{18}$H$_{21}$ClN$_3$O$_3$ (M+H)$^+$: m/z=362.1; Found: 362.1.

acid, at a flow rate of 30 mL/min) to give the desired product as a TFA salt. LCMS calculated for C$_{23}$H$_{26}$ClN$_8$O$_2$ (M+H)$^+$: m/z=481.2; Found: 481.2.

Step 3. Methyl}1-[7-(1-aminoethyl)-5-chloroquinolin-8-yl]piperidin-4-yl}carbamate

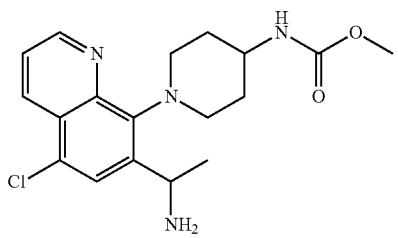 [SMILES: COC(=O)NC1CCN(c2c(C(C)N)cc(Cl)c3cccnc23)CC1]

A mixture of methyl[1-(7-acetyl-5-chloroquinolin-8-yl)piperidin-4-yl]carbamate (0.021 g, 0.058 mmol) and ammonium acetate (0.0447 g, 0.580 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.14 mL, 0.14 mmol). The reaction was heated at 65° C. overnight. The mixture was cooled to room temperature, quenched with sat. NaHCO$_3$ solution, extracted with dichloromethane, dried over MgSO$_4$ and concentrated to give the crude product. LCMS calculated for C$_{18}$H$_{24}$ClN$_4$O$_2$ (M+H)$^+$: m/z=363.2; Found: 363.1.

Step 4. Methyl(1-{5-Chloro-7-[1-(9H-purin-6-ylamino)ethyl]quinolin-8-yl}piperidin-4-yl)carbamate bis(trifluoroacetate)

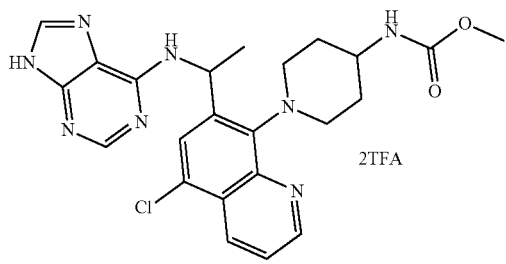 [SMILES: COC(=O)NC1CCN(c2c(C(C)Nc3ncnc4[nH]cnc34)cc(Cl)c3cccnc23)CC1]

A mixture of methyl{1-[7-(1-aminoethyl)-5-chloroquinolin-8-yl]piperidin-4-yl}carbamate (0.020 g, 0.055 mmol), 6-bromo-9H-purine (0.022 g, 0.11 mmol) and N,N-diisopropylethylamine (0.029 mL, 0.16 mmol) in ethanol (0.5 mL) was heated at 110° C. overnight. The mixture was purified on a preparative LCMS (XBridge C18 column, eluting with a gradient of acetonitrile in water with 0.05% trifluoroacetic Example 84

N-(1-{5-Chloro-8-[4-(cyclopropylcarbonyl)piperazin-1-yl]quinolin-7-yl}ethyl)-9H-purin-6-amine bis(trifluoroacetate)

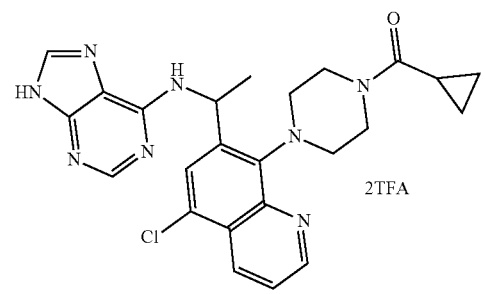 [SMILES: CC(Nc1ncnc2[nH]cnc12)c1cc(Cl)c2cccnc2c1N1CCN(C(=O)C2CC2)CC1]

Step 1.
1-(5-Chloro-8-piperazin-1-ylquinolin-7-yl)ethanone

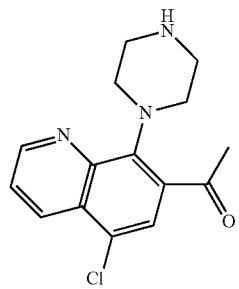 [SMILES: CC(=O)c1cc(Cl)c2cccnc2c1N1CCNCC1]

A stirred mixture of 7-acetyl-5-chloroquinolin-8-yl trifluoromethanesulfonate (1.1 g, 3.1 mmol, from Example 47, Step 2), piperazine (0.40 g, 4.7 mmol) and cesium carbonate (2.8 g, 8.7 mmol) in tetrahydrofuran (20 mL) was heated at 65° C. overnight. The mixture was cooled, diluted with water, and extracted with dichloromethane. The organic phases were combined, dried over MgSO$_4$ and concentrated. The resulting residue was purified on silica gel (eluting with 15% methanol in dichloromethane) to give the desired product (0.57 g, 63%). LCMS calculated for $C_{15}H_{17}ClN_3O$ (M+H)$^+$: m/z=290.1; Found: 290.1.

extracted with dichloromethane, dried over MgSO$_4$ and concentrated to give the desired product. LCMS calculated for $C_{19}H_{24}ClN_4O$ (M+H)$^+$: m/z=359.2; Found: 359.1.

Step 2. 1-{5-Chloro-8-[4-(cyclopropylcarbonyl)piperazin-1-yl]quinolin-7-yl}ethanone

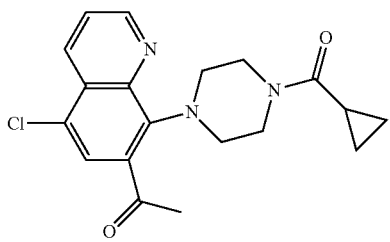 [SMILES: CC(=O)c1cc(Cl)c2cccnc2c1N1CCN(C(=O)C2CC2)CC1]

1-(5-chloro-8-piperazin-1-ylquinolin-7-yl)ethanone (0.063 g, 0.22 mmol) was combined with cyclopropanecarbonyl chloride (0.029 mL, 0.32 mmol) and triethylamine (0.090 mL, 0.64 mmol) in methylene chloride (1.0 mL) at room temperature and stirred for 2 hours. The reaction was diluted with dichloromethane, washed with water, dried over MgSO$_4$ and concentrated. The resulting residue was purified on silica gel (eluting with 0 to 5% methanol in dichloromthane) to give the desired product (21 mg, 27%). LCMS calculated for $C_{19}H_{21}ClN_3O_2$ (M+H)$^+$: m/z=358.1; Found: 358.0.

Step 3. 1-{5-Chloro-8-[4-(cyclopropylcarbonyl)piperazin-1-yl]quinolin-7-yl}ethanamine

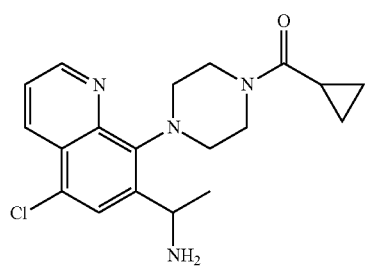 [SMILES: CC(N)c1cc(Cl)c2cccnc2c1N1CCN(C(=O)C2CC2)CC1]

A mixture of 1-{5-chloro-8-[4-(cyclopropylcarbonyl)piperazin-1-yl]quinolin-7-yl}ethanone (0.021 g, 0.059 mmol) and ammonium acetate (0.0452 g, 0.587 mmol) in methanol (0.2 mL) and acetonitrile (0.2 mL) was heated at 65° C. in a sealed tube for 1 hour. After cooling to room temperature, to the resulting mixture was added 1.0 M sodium cyanoborohydride in tetrahydrofuran (0.14 mL, 0.14 mmol). The reaction was heated at 65° C. overnight. The mixture was cooled to room temperature, quenched with sat. NaHCO$_3$ solution,

Step 4. N-(1-{5-Chloro-8-[4-(cyclopropylcarbonyl)piperazin-1-yl]quinolin-7-yl}ethyl)-9H-purin-6-amine bis(trifluoroacetate)

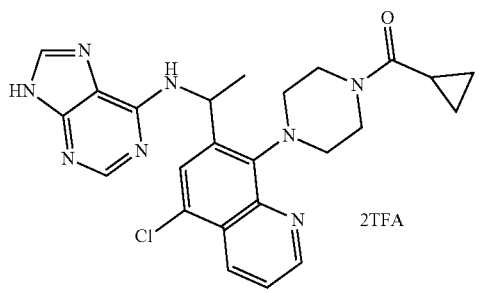 [SMILES: CC(Nc1ncnc2[nH]cnc12)c1cc(Cl)c2cccnc2c1N1CCN(C(=O)C2CC2)CC1]

A mixture of 1-{5-chloro-8-[4-(cyclopropylcarbonyl)piperazin-1-yl]quinolin-7-yl}ethanamine (0.018 g, 0.050 mmol), 6-bromo-9H-purine (0.020 g, 0.10 mmol) and N,N-diisopropylethylamine (0.026 mL, 0.15 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{24}H_{26}ClN_8O$ (M+H)$^+$: m/z=477.2; Found: 477.2.

Example 85

Methyl 4-{5-Chloro-7-[1-(9H-purin-6-ylamino)ethyl]quinolin-8-yl}piperazine-1-carboxylatebis(trifluoroacetate)

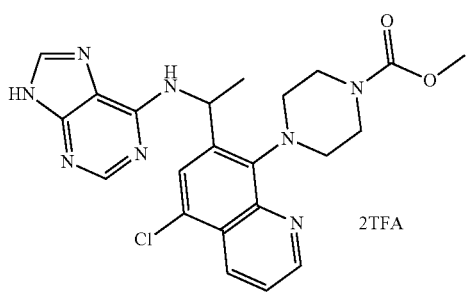 [SMILES: COC(=O)N1CCN(c2c(C(C)Nc3ncnc4[nH]cnc34)cc(Cl)c3cccnc23)CC1]

Step 1. Methyl 4-(7-acetyl-5-chloroquinalin-8-yl)piperazine-1-carboxylate

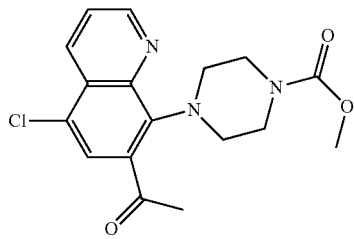 [SMILES: COC(=O)N1CCN(c2c(C(C)=O)cc(Cl)c3cccnc23)CC1]

1-(5-chloro-8-piperazin-1-ylquinolin-7-yl)ethanone (0.063 g, 0.22 mmol, from Example 47, Step 1) was combined with methyl chloroformate (0.025 mL, 0.32 mmol) and triethylamine (0.090 mL, 0.64 mmol) in methylene chloride (1.0 mL) at room temperature and stirred for 2 hrs. The reaction was diluted with dichloromethane, washed with water, then dried over MgSO$_4$ and concentrated. The resulting residue was purified on silica gel (eluting with 0 to 5% methanol in dichloromethane) to give the desired product (18 mg, 24%). LCMS calculated for C$_{17}$H$_{19}$ClN$_3$O$_3$ (M+H)$^+$: m/z=348.1; Found: 348.0.

Step 2. Methyl 4-[7-(1-aminoethyl)-5-chloroquinolin-8-yl]piperazine-1-carboxylate

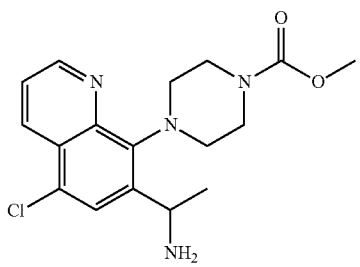 [SMILES: COC(=O)N1CCN(c2c(C(C)N)cc(Cl)c3cccnc23)CC1]

A mixture of methyl 4-(7-acetyl-5-chloroquinolin-8-yl)piperazine-1-carboxylate (0.018 g, 0.052 mmol) and ammonium acetate (0.0399 g, 0.518 mmol) in methanol (0.2 mL) and acetonitrile (0.2 mL) was heated at 65° C. in a sealed tube for 1 hour. After cooling to room temperature, to the resulting mixture was added 1.0 M sodium cyanoborohydride in tetrahydrofuran (0.13 mL, 0.13 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{17}$H$_{22}$ClN$_4$O$_2$ (M+H)$^+$: m/z=349.1; Found: 349.1.

Step 3. Methyl 4-{5-Chloro-7-[1-(9H-purin-6-ylamino)ethyl]quinolin-8-yl}piperazine-1-carboxylate bis(trifluoroacetate)

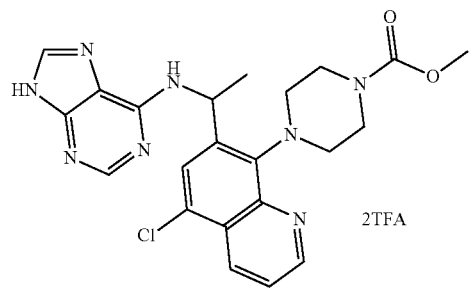 [SMILES: COC(=O)N1CCN(c2c(C(C)Nc3ncnc4[nH]cnc34)cc(Cl)c3cccnc23)CC1]

A mixture of methyl 4-[7-(1-aminoethyl)-5-chloroquinolin-8-yl]piperazine-1-carboxylate (0.019 g, 0.055 mmol), 6-bromo-9H-purine (0.022 g, 0.11 mmol) and N,N-diisopropylethylamine (0.029 mL, 0.16 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{22}$H$_{24}$ClN$_8$O$_2$ (M+H)$^+$: m/z=467.2; Found: 467.1.

Example 86

N-(1-{5-Chloro-8-[4-(cyclobutylcarbonyl)piperazin-1-yl]quinolin-7-yl}ethyl)-9H-purin-6-amine bis(trifluoroacetate)

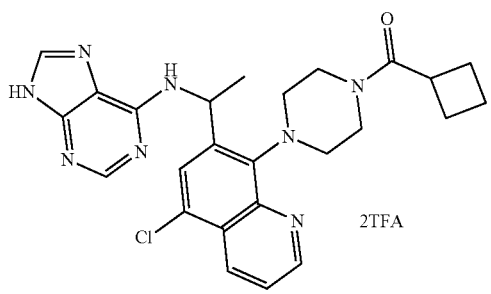 [SMILES: CC(Nc1ncnc2[nH]cnc12)c1cc(Cl)c2cccnc2c1N1CCN(C(=O)C2CCC2)CC1]

Step 1. 1-{5-Chloro-8-[4-(cyclobutylcarbonyl)piperazin-1-yl]quinolin-7-yl}ethanone

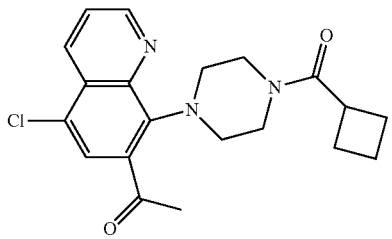 [SMILES: CC(=O)c1cc(Cl)c2cccnc2c1N1CCN(C(=O)C2CCC2)CC1]

1-(5-chloro-8-piperazin-1-ylquinolin-7-yl)ethanone (0.063 g, 0.22 mmol, from Example 47, Step 1) was combined with cyclobutanecarboxylic acid chloride (0.037 mL, 0.32 mmol) and triethylamine (0.090 mL, 0.64 mmol) in methylene chloride (1.0 mL) at room temperature and stirred for 2 hours. The reaction was diluted with dichloromethane, washed with water, dried over MgSO$_4$ and then concentrated. The resulted residue was purified on silica gel (eluting with 0 to 5% methanol in dichloromethane) to give the desired product (18 mg, 22%). LCMS calculated for C$_{20}$H$_{23}$ClN$_3$O$_2$ (M+H)$^+$: m/z=372.1; Found: 372.1.

Step 2. 1-{5-Chloro-8-[4-(cyclobutylcarbonyl)piperazin-1-yl]quinolin-7-yl}ethanamine

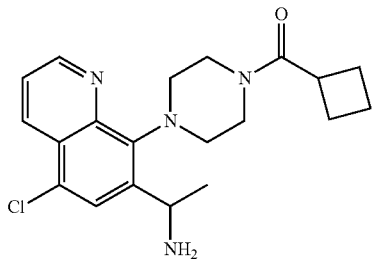 [SMILES: CC(N)c1cc(Cl)c2cccnc2c1N1CCN(C(=O)C2CCC2)CC1]

A mixture of 1-{5-chloro-8-[4-(cyclobutylcarbonyl)piperazin-1-yl]quinolin-7-yl}ethanone (0.018 g, 0.048 mmol) and ammonium acetate (0.0373 g, 0.484 mmol) in methanol (0.2 mL) and acetonitrile (0.2 mL) was heated at 65° C. in a sealed tube for 1 hour. After cooling to room temperature, to the resulting mixture was added 1.0 M sodium cyanoborohydride in tetrahydrofuran (0.12 mL, 0.12 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{20}$H$_{26}$ClN$_4$O (M+H)$^+$: m/z=373.2; Found: 373.2.

Step 3. N-(1-{5-Chloro-8-[4-(cyclobutylcarbonyl)piperazin-1-yl]quinolin-7-yl}ethyl)-9H-purin-6-amine bis(trifluoroacetate)

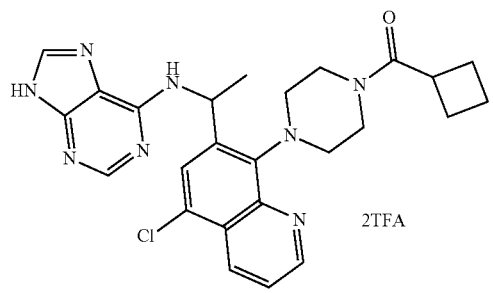 [SMILES: CC(Nc1ncnc2[nH]cnc12)c1cc(Cl)c2cccnc2c1N1CCN(C(=O)C2CCC2)CC1]

A mixture of 1-{5-chloro-8-[4-(cyclobutylcarbonyl)piperazin-1-yl]quinolin-7-yl}ethanamine (0.010 g, 0.027 mmol), 6-bromo-9H-purine (0.011 g, 0.054 mmol) and N,N-diisopropylethylamine (0.014 mL, 0.080 mmol) in ethanol (0.2 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{25}$H$_{28}$ClN$_8$O (M+H)$^+$: m/z=491.2; Found: 491.2.

Example 87

N-(1-{5-Chloro-8-[4-(methoxyacetyl)piperazin-1-yl]quinolin-7-yl}ethyl)-9H-purin-6-amine bis(trifluoroacetate)

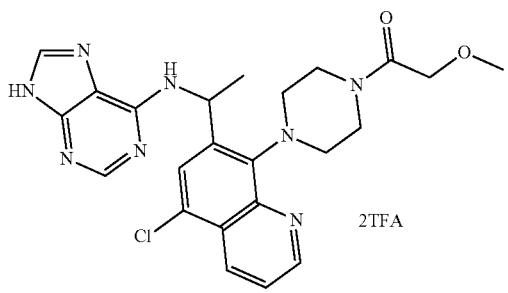 [SMILES: COCC(=O)N1CCN(c2c(C(C)Nc3ncnc4[nH]cnc34)cc(Cl)c3cccnc23)CC1]

Step 1. 1-{5-Chloro-8-[4-(methoxyacetyl)piperazin-1-yl]quinolin-7-yl}ethanone

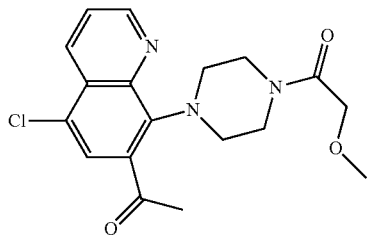 [SMILES: COCC(=O)N1CCN(c2c(C(C)=O)cc(Cl)c3cccnc23)CC1]

1-(5-chloro-8-piperazin-1-ylquinolin-7-yl)ethanone (0.030 g, 0.10 mmol, from Example 47, Step 1) was combined with methoxyacetyl chloride (0.014 mL, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$ and then concentrated. The resulted residue was purified on silica gel (eluting with 0 to 5% methanol in dichloromethane) to give the desired product (23 mg, 61%). LCMS calculated for C$_{18}$H$_{21}$ClN$_3$O$_3$ (M+H)$^+$: m/z=362.1; Found: 362.0.

Step 2. 1-{5-Chloro-8-[4-(methoxyacetyl)piperazin-1-yl]quinolin-7-yl}ethanamine

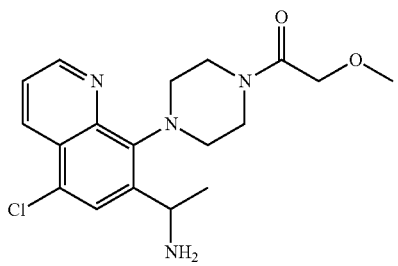 [SMILES: COCC(=O)N1CCN(c2c(C(C)N)cc(Cl)c3cccnc23)CC1]

A mixture of 1-{5-chloro-8-[4-(methoxyacetyl)piperazin-1-yl]quinolin-7-yl}ethanone (0.023 g, 0.064 mmol) and ammonium acetate (0.0490 g, 0.636 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.16 mL, 0.16 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{18}$H$_{24}$ClN$_4$O$_2$ (M+H)$^+$: m/z=363.2; Found: 363.1.

Step 3. N-(1-{5-Chloro-8-[4-(methoxyacetyl)piperazin-1-yl]quinolin-7-yl}ethyl)-9H-purin-6-amine bis(trifluoroacetate)

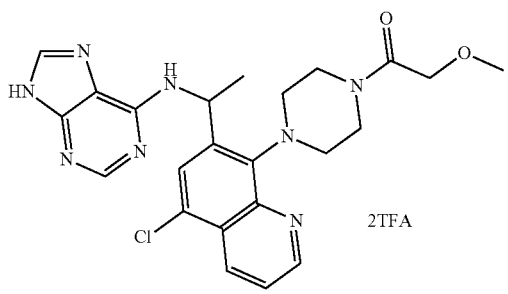 [SMILES: COCC(=O)N1CCN(c2c(C(C)Nc3ncnc4[nH]cnc34)cc(Cl)c3cccnc23)CC1]

A mixture of 1-{5-chloro-8-[4-(methoxyacetyl)piperazin-1-yl]quinolin-7-yl}ethanamine (0.011 g, 0.030 mmol), 6-bromo-9H-purine (0.012 g, 0.061 mmol) and N,N-diisopropylethylamine (0.016 mL, 0.091 mmol) in ethanol (0.3 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{23}$H$_{26}$ClN$_8$O$_2$ (M+H)$^+$: m/z=481.2; Found: 481.2.

Example 88

4-{5-Chloro-7-[1-(9H-purin-6-ylamino)ethyl]quinolin-8-yl}-N,N-dimethylpiperazine-1-carboxamide bis(trifluoroacetate)

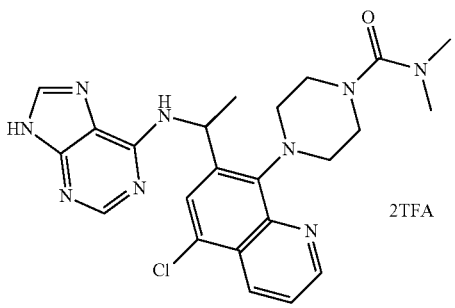 [SMILES: CC(Nc1ncnc2[nH]cnc12)c1cc(Cl)c2cccnc2c1N1CCN(C(=O)N(C)C)CC1]

Step 1. 4-(7-Acetyl-5-chloroquinolin-8-yl)-N,N-dimethylpiperazine-1-carboxamide

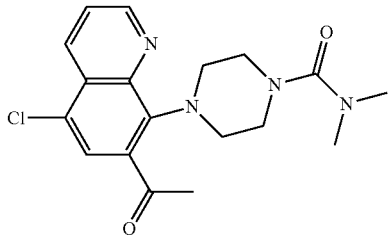 [SMILES: CC(=O)c1cc(Cl)c2cccnc2c1N1CCN(C(=O)N(C)C)CC1]

1-(5-Chloro-8-piperazin-1-ylquinolin-7-yl)ethanone (0.030 g, 0.10 mmol, from Example 47, Step 1) was combined with N,N-dimethylcarbamoyl chloride (0.014 mL, 0.16 mmol) and triethylamine (0.043 mL, 0.31 mmol) in methylene chloride (1.0 mL, 16 mmol) at room temperature and stirred for 2 hours. The reaction was diluted with dichloromethane, washed with water, dried over MgSO$_4$, concentrated and purified on silica gel (eluting with 0 to 5% MeOH in dichloromethane) to give the desired product (27 mg, 72%). LCMS calculated for $C_{18}H_{22}ClN_4O_2$ (M+H)$^+$: m/z=361.1; Found: 361.0.

Step 2. 4-[7-(1-Aminoethyl)-5-chloroquinolin-8-yl]-N,N-dimethylpiperazine-1-carboxamide

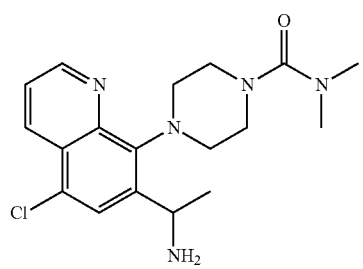 [SMILES: CC(N)c1cc(Cl)c2cccnc2c1N1CCN(C(=O)N(C)C)CC1]

A mixture of 4-(7-acetyl-5-chloroquinolin-8-yl)-N,N-dimethylpiperazine-1-carboxamide (0.027 g, 0.075 mmol) and ammonium acetate (0.0576 g, 0.747 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.19 mL, 0.19 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{15}H_{25}ClN_5O$ (M+H)$^+$: m/z=362.2; Found: 362.2.

Step 3. 4-{5-Chloro-7-[1-(9H-purin-6-ylamino)ethyl]quinolin-8-yl}-N,N-dimethylpiperazine-1-carboxamide bis(trifluoroacetate)

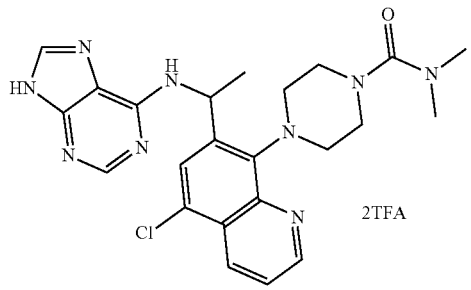 [SMILES: CC(Nc1ncnc2[nH]cnc12)c1cc(Cl)c2cccnc2c1N1CCN(C(=O)N(C)C)CC1]

A mixture of 4-[7-(1-aminoethyl)-5-chloroquinolin-8-yl]-N,N-dimethyl-piperazine-1-carboxamide (0.028 g, 0.077 mmol), 6-bromo-9H-purine (0.031 g, 0.15 mmol) and N,N-diisopropylethylamine (0.040 mL, 0.23 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{23}H_{27}ClN_9O$ (M+H)$^+$: m/z=480.2; Found: 480.2.

Example 89

N-(1-[8-(4-Benzoylpiperazin-1-yl)-5-chloroquinolin-7-yl]ethyl}-9H-purin-6-amine bis(trifluoroacetate)

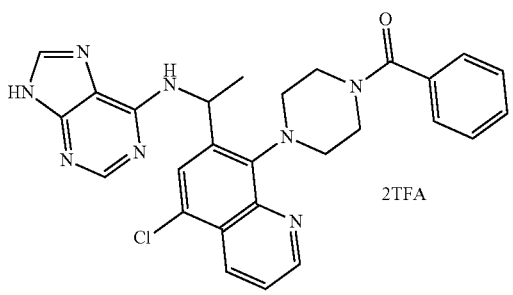 [SMILES: CC(Nc1ncnc2[nH]cnc12)c1cc(Cl)c2cccnc2c1N1CCN(C(=O)c2ccccc2)CC1]

Step 1. 1-[8-(4-Benzoylpiperazin-1-yl)-5-chloro-quinolin-7-yl]ethanone

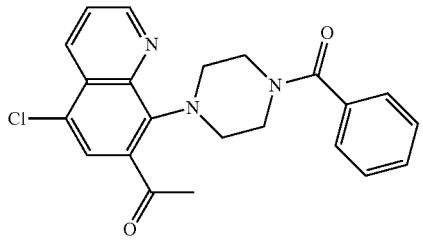 [SMILES: CC(=O)c1cc(Cl)c2cccnc2c1N1CCN(C(=O)c2ccccc2)CC1]

1-(5-Chloro-8-piperazin-1-ylquinolin-7-yl)ethanone (0.030 g, 0.10 mmol, from Example 47, Step 1) was combined with benzoyl chloride (0.018 mL, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$ and concentrated. The resulting residue was purified on silica gel (eluting with 0 to 5% MeOH in dichloromthane) to give the desired product (51 mg). LCMS calculated for $C_{22}H_{21}ClN_3O_2$ (M+H)$^+$: m/z=394.1; Found: 394.0.

Step 2. 1-[8-(4-Benzoylpiperazin-1-yl-5-chloro-quinolin-7-yl]ethanamine

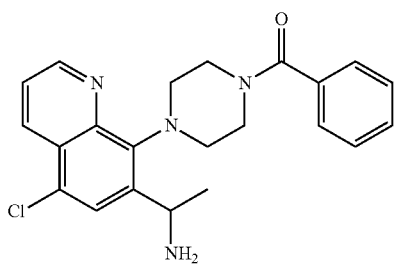 [SMILES: CC(N)c1cc(Cl)c2cccnc2c1N1CCN(C(=O)c2ccccc2)CC1]

A mixture of 1-[8-(4-benzoylpiperazin-1-yl)-5-chloro-quinolin-7-yl]ethanone (0.051 g, 0.13 mmol) and ammonium acetate (0.0998 g, 1.29 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.32 mL, 0.32 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{22}H_{24}ClN_4O$ (M+H)$^+$: m/z=395.2; Found: 395.1.

Step 3. N-{1-[8-(4-Benzoylpiperazin-1-yl)-5-chloro-quinolin-7-yl]ethyl}-9H-purin-6-amine bis(trifluoroacetate)

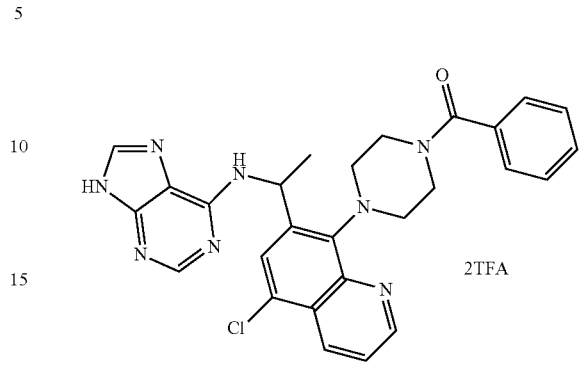

A mixture of 1-[8-(4-benzoylpiperazin-1-yl)-5-chloro-quinolin-7-yl]ethanamine (0.043 g, 0.11 mmol), 6-bromo-9H-purine (0.044 g, 0.22 mmol) and N,N-diisopropylethylamine (0.057 mL, 0.33 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{27}H_{26}ClN_8O$ (M+H)$^+$: m/z=513.2; Found: 513.2. $^1$H NMR (DMSO-d$_6$, 300 MHz) δ 9.45 (1H, br s), 9.02 (1H, d, J=3.9 and 1.8 Hz), 8.50~8.43 (3H, m), 7.90 (1H, s), 7.64 (1H, dd, J=8.4 and 4.2 Hz), 7.46 (5H, m), 6.51 (1H, m), 4.62 (1H, m), 4.05~2.80 (8H, m), 1.61 (3H, d, J=6.3 Hz) ppm.

Example 90

2-(4-{5-Chloro-7-[1-(9H-purin-6-ylamino)ethyl]quinolin-8-yl}piperazin-1-yl)-N,N-dimethylacetamide tris(trifluoroacetate)

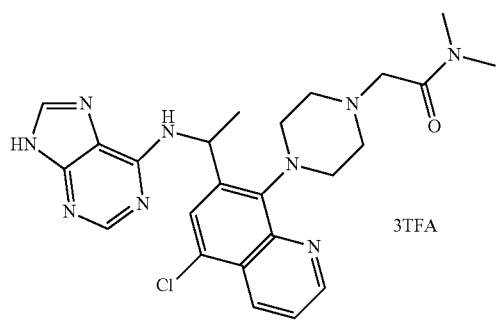 [SMILES: CC(Nc1ncnc2[nH]cnc12)c1cc(Cl)c2cccnc2c1N1CCN(CC(=O)N(C)C)CC1]

Step 1. 2-[4-(7-Acetyl-5-chloroquinolin-8-yl)piperazin-1-yl]-N,N-dimethylacetamide

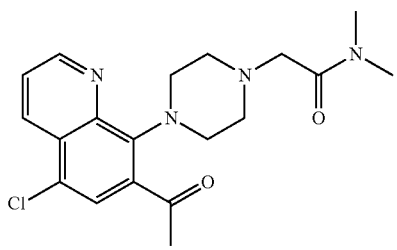 [SMILES: CC(=O)c1cc(Cl)c2cccnc2c1N1CCN(CC(=O)N(C)C)CC1]

To a mix of 1-(5-chloro-8-piperazin-1-ylquinolin-7-yl)ethanone (0.030 g, 0.10 mmol, from Example 47, Step 1) and potassium carbonate (0.043 g, 0.31 mmol) in N,N-dimethylformamide (1 mL) was added 2-chloro-N,N-dimethylacetamide (0.012 mL, 0.11 mmol). The reaction mixture was stirred at room temperature for 4 hrs, and then diluted with dichloromethane, washed with water, dried over MgSO$_4$, concentrated and purified on silica gel (eluting with 0 to 5% methanol in dichloromethane) to give the desired product (19 mg, 49%). LCMS calculated for $C_{19}H_{24}ClN_4O_2$ (M+H)$^+$: m/z=375.2; Found: 375.1.

Step 2. 2-{4-[7-(1-Aminoethyl)-5-chloroquinolin-8-yl]piperazin-1-yl}-N,N-dimethylacetamide

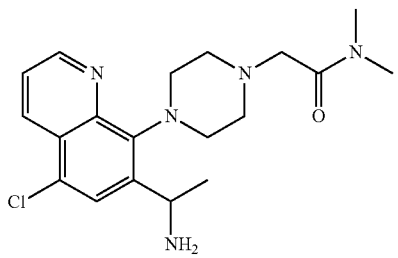 [SMILES: CC(N)c1cc(Cl)c2cccnc2c1N1CCN(CC(=O)N(C)C)CC1]

A mixture of 2-[4-(7-acetyl-5-chloroquinolin-8-yl)piperazin-1-yl]-N,N-dimethylacetamide (0.019 g, 0.051 mmol) and ammonium acetate (0.0391 g, 0.507 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.12 mL). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{19}H_{27}ClN_5O$ (M+H)$^+$: m/z=376.2; Found: 376.2.

Step 3. 2-(4-{5-Chloro-7-[7-(9H-purin-6-ylamino)ethyl]quinolin-8-yl}piperazin-1-yl)-N,N-dimethylacetamide tris(trifluoroacetate)

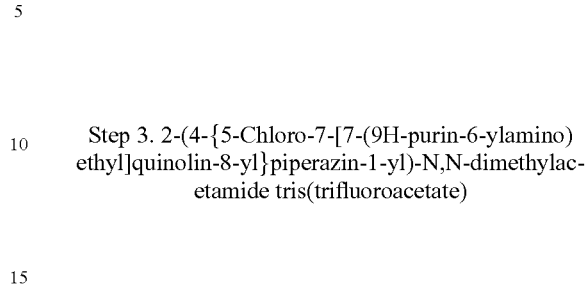

A mixture of 2-{4-[7-(1-aminoethyl)-5-chloroquinolin-8-yl]piperazin-1-yl}-N,N-dimethylacetamide (0.019 g, 0.050 mmol), 6-bromo-9H-purine (0.020 g, 0.10 mmol) and N,N-diisopropylethylamine (0.026 mL, 0.15 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{24}H_{29}ClN_9O$ (M+H)$^+$: m/z=494.2; Found: 494.2.

Example 91

N-(1-{5-Chloro-8-[4-(4-fluorobenzoyl)piperazin-1-yl]quinolin-7-yl}ethyl)-9H-purin-6-amine bis(trifluoroacetate)

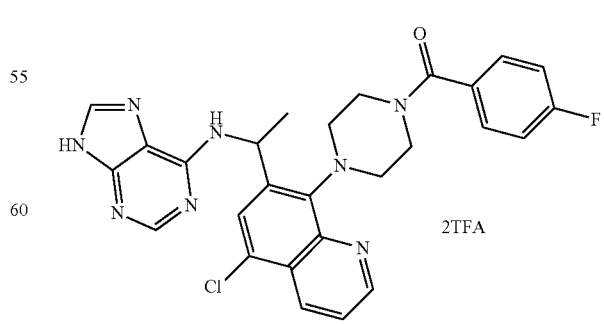

Step 1. 1-{5-Chloro-8-[4-(4-fluorobenzoyl)piperazin-1-yl]quinolin-7-yl}ethanone

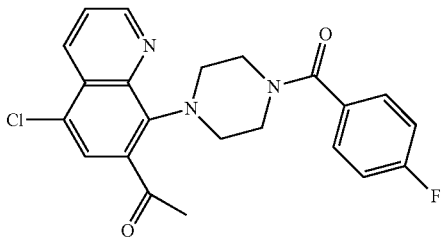 [SMILES: CC(=O)c1cc(Cl)c2cccnc2c1N1CCN(C(=O)c2ccc(F)cc2)CC1]

1-(5-Chloro-8-piperazin-1-ylquinolin-7-yl)ethanone (0.030 g, 0.10 mmol, from Example 47, Step 1) was combined with 4-fluorobenzoyl chloride, (0.018 mL, 0.16 mmol) and triethylamine (0.043 mL, 0.31 mmol) in methylene chloride (1.0 mL) at room temperature and stirred for 2 hours. The reaction was diluted with dichloromethane, washed with water, dried over $MgSO_4$, concentrated and purified on silica gel (eluting with 0 to 5% methanol in dichloromethane) to give the desired product (35 mg, 82%). LCMS calculated for $C_{22}H_{20}ClFN_3O_2$ $(M+H)^+$: m/z=412.1; Found: 412.1.

Step 2. 1-{5-Chloro-8-[4-(4-fluorobenzoyl)piperazin-1-yl]quinolin-7-yl}ethanamine

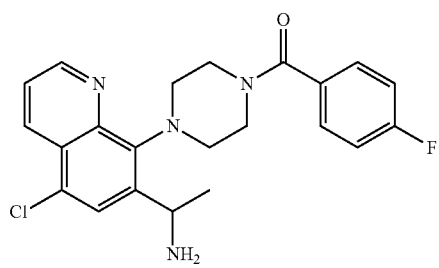 [SMILES: CC(N)c1cc(Cl)c2cccnc2c1N1CCN(C(=O)c2ccc(F)cc2)CC1]

A mixture of 1-{5-chloro-8-[4-(4-fluorobenzoyl)piperazin-1-yl]quinolin-7-yl}ethanone (0.035 g, 0.085 mmol) and ammonium acetate (0.0655 g, 0.850 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.21 mL, 0.21 mmol). The reaction was heated at 65° C. overnight. The mixture was cooled to room temperature, quenched with sat. $NaHCO_3$ solution, extracted with dichloromethane, dried over $MgSO_4$ and concentrated to give the desired product. LCMS calculated for $C_{22}H_{23}ClFN_4O$ $(M+H)^+$: m/z=413.2; Found: 413.2.

Step 3. N-(1-{5-Chloro-8-[4-(4-fluorobenzoyl)piperazin-1-yl]quinolin-7-yl}ethyl)-9H-purin-6-amine bis(trifluoroacetate)

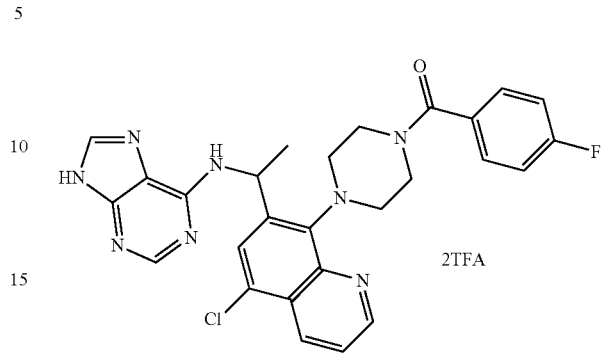

A mixture of 1-{5-chloro-8-[4-(4-fluorobenzoyl)piperazin-1-yl]quinolin-7-yl}ethanamine (0.034 g, 0.082 mmol), 6-bromo-9H-purine (0.033 g, 0.16 mmol) and N,N-diisopropylethylamine (0.043 mL, 0.25 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product. LCMS calculated for $C_{27}H_{25}ClFN_8O$ $(M+H)^+$: m/z=531.2; Found: 531.2. $^1H$ NMR (DMSO-$d_6$, 300 MHz) δ 9.49 (1H, br s), 9.01 (1H, dd, J=3.9 and 1.5 Hz), 8.51~8.47 (3H, m), 7.90 (1H, s), 7.64 (1H, dd, J=8.7 and 4.2 Hz), 7.54 (2H, m), 7.30 (2H, m), 6.52 (1H, m), 4.60 (1H, m), 4.04 (1H, m), 3.86 (1H, m), 3.69~3.17 (5H, m), 2.88 (1H, m), 1.61 (3H, d, J=6.6 Hz) ppm.

Example 92

N-(1-{5-Chloro-8-[4-(3-fluorobenzoyl)piperazin-1-yl]quinolin-7-yl}ethyl)-9H-purin-6-amine bis(trifluoroacetate)

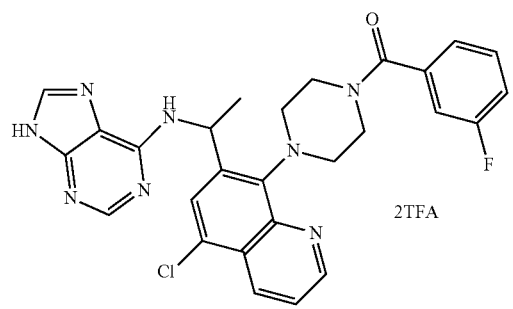 [SMILES: CC(Nc1ncnc2[nH]cnc12)c1cc(Cl)c2cccnc2c1N1CCN(C(=O)c2cccc(F)c2)CC1]

Step 1. 1-{5-Chloro-8-[4-(3-fluorobenzoyl)piperazin-1-yl]quinolin-7-yl}ethanone

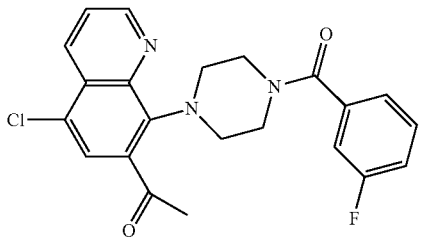 [SMILES: CC(=O)c1cc(Cl)c2cccnc2c1N1CCN(C(=O)c2cccc(F)c2)CC1]

1-(5-Chloro-8-piperazin-1-ylquinolin-7-yl)ethanone (0.030 g, 0.10 mmol, from Example 47, Step 1) was combined with 3-fluorobenzoyl chloride (0.019 mL, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$, concentrated and purified on silica gel (eluting with 0 to 5% methanol in dichloromethane) to give the desired product (45.3 mg). LCMS calculated for $C_{22}H_{20}ClFN_3O_2$ (M+H)$^+$: m/z=412.1; Found: 412.1.

Step 2. 1-{5-Chloro-8-[4-(3-fluorobenzoyl)piperazin-1-yl]quinolin-7-yl}ethanamine

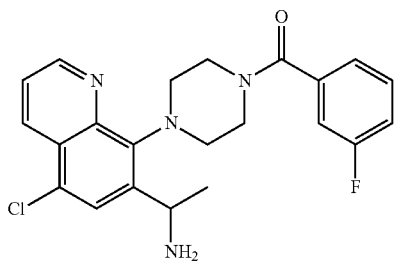 [SMILES: CC(N)c1cc(Cl)c2cccnc2c1N1CCN(C(=O)c2cccc(F)c2)CC1]

A mixture of 1-{5-chloro-8-[4-(3-fluorobenzoyl)piperazin-1-yl]quinolin-7-yl}ethanone (0.045 g, 0.11 mmol) and ammonium acetate (0.0842 g, 1.09 mmol) in methanol (0.4 mL) and acetonitrile (0.4 mL) was heated at 65° C. in a sealed tube for 1 hour. After cooling to room temperature, to the resulting mixture was added 1.0 M sodium cyanoborohydride in tetrahydrofuran (0.27 mL, 0.27 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{22}H_{23}ClFN_4O$ (M+H)$^+$: m/z=413.2; Found: 413.1.

Step 3. N-(1-{5-Chloro-8-[4-(3-fluorobenzoyl)piperazin-1-yl]quinolin-7-yl}ethyl)-9H-purin-6-amine bis(trifluoroacetate)

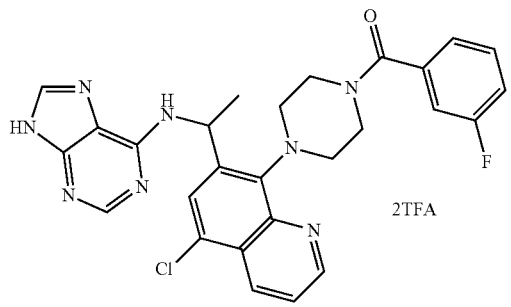 [SMILES: CC(Nc1ncnc2[nH]cnc12)c1cc(Cl)c2cccnc2c1N1CCN(C(=O)c2cccc(F)c2)CC1]

A mixture of 1-{5-chloro-8-[4-(3-fluorobenzoyl)piperazin-1-yl]quinolin-7-yl}ethanamine (0.034 g, 0.082 mmol), 6-bromo-9H-purine (0.033 g, 0.16 mmol) and N,N-diisopropylethylamine (0.043 mL, 0.25 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{27}H_{25}ClFN_8O$ (M+H)$^+$: m/z=531.2; Found: 531.2. NMR (DMSO-d$_6$, 300 MHz) δ 9.54 (1H, br s), 9.02 (1H, dd, J=3.9 and 1.5 Hz), 8.53 (1H, s), 8.49 (2H, m), 7.89 (1H, s), 7.64 (1H, dd, J=9.0 and 4.5 Hz), 7.57 (1H, m), 7.32 (3H, m), 6.52 (1H, m), 4.61 (1H, m), 4.04 (1H, m), 3.86 (1H, m), 3.66~2.80 (6H, m), 1.61 (3H, d, J=6.0 Hz) ppm.

Example 93

N-(1-{5-Chloro-8-[4-(2-fluorobenzoyl)piperazin-1-yl]quinolin-7-yl}ethyl)-9H-purin-6-amine bis(trifluoroacetate)

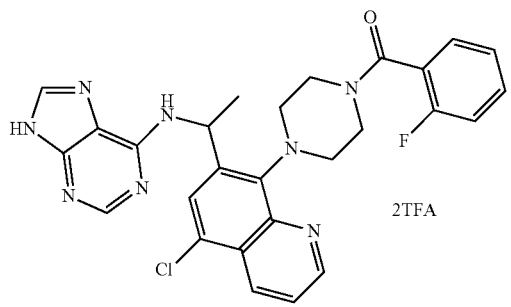 [SMILES: CC(Nc1ncnc2[nH]cnc12)c1cc(Cl)c2cccnc2c1N1CCN(C(=O)c2ccccc2F)CC1]

Step 1. 1-{5-Chloro-8-[4-(2-fluorobenzoyl)piper-azin-1-yl]quinolin-7-yl}ethanone

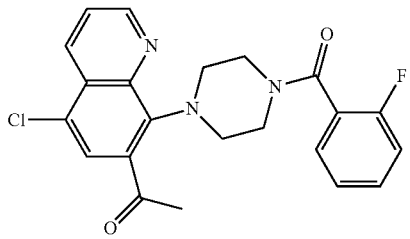 [SMILES: CC(=O)c1cc(Cl)c2cccnc2c1N1CCN(C(=O)c2ccccc2F)CC1]

1-(5-Chloro-8-piperazin-1-ylquinolin-7-yl)ethanone (0.030 g, 0.10 mmol, from Example 47, Step 1) was combined with 2-fluorobenzoyl chloride (0.018 mL, 0.16 mmol) and triethylamine (0.043 mL, 0.31 mmol) in methylene chloride (1.0 mL) at room temperature and stirred for 2 hrs. The reaction was diluted with dichloromethane, washed with water, dried over $MgSO_4$, concentrated and purified on silica gel (eluting with 0 to 5% methanol in dichloromethane) to give the desired product (50 mg). LCMS calculated for $C_{22}H_{20}ClFN_3O_2$ $(M+H)^+$: m/z=412.1; Found: 412.1.

Step 2. 1-{5-Chloro-8-[4-(2-fluorobenzoyl)piper-azin-1-yl]quinolin-7-yl}ethanamine

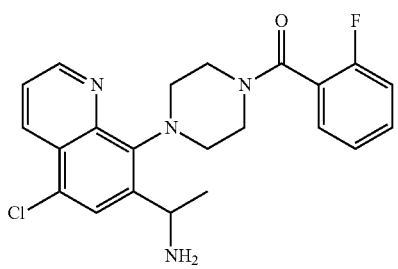 [SMILES: CC(N)c1cc(Cl)c2cccnc2c1N1CCN(C(=O)c2ccccc2F)CC1]

A mixture of 1-{5-chloro-8-[4-(2-fluorobenzoyl)piper-azin-1-yl]quinolin-7-yl}ethanone (0.050 g, 0.12 mmol) and ammonium acetate (0.0936 g, 1.21 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.30 mL, 0.30 mmol). The reaction was heated at 65° C. overnight. The mixture was cooled to room temperature, quenched with sat. $NaHCO_3$ solution, extracted with dichloromethane, dried over $MgSO_4$ and concentrated to give the desired product. LCMS calculated for $C_{22}H_{23}ClFN_4O$ $(M+H)^+$: m/z=413.2; Found: 413.2.

Step 3. N-(1-{5-Chloro-8-[4-(2-fluorobenzoyl)piper-azin-1-yl]quinolin-7-yl}ethyl)-9H-purin-6-amine bis(trifluoroacetate)

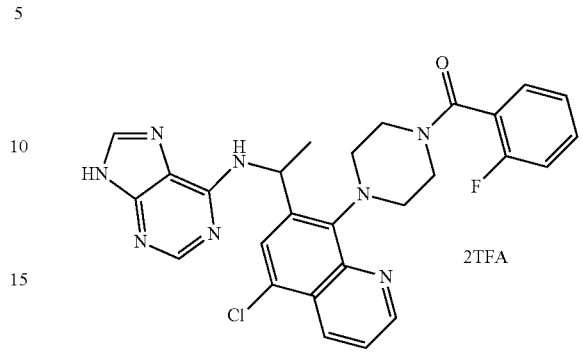

A mixture of 1-{5-chloro-8-[4-(2-fluorobenzoyl)piper-azin-1-yl]quinolin-7-yl}ethanamine (0.036 g, 0.087 mmol), 6-bromo-9H-purine (0.035 g, 0.17 mmol) and N,N-diisopropylethylamine (0.046 mL, 0.26 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{27}H_{25}ClFN_8O$ $(M+H)^+$: m/z 531.2; Found: 531.2. $^1H$ NMR (DMSO-$d_6$, 300 MHz) δ 9.47 (1H, br s), 9.01 (1H, m), 8.52~8.42 (3H, m), 7.89 (1H, d, J=5.7 Hz), 7.64 (1H, dd, J=8.7 and 4.2 Hz), 7.49 (2H, m), 7.32 (2H, m), 6.50 (1H, m), 4.64 (1H, m), 4.07 (1H, m), 3.88 (1H, m), 3.49~2.77 (6H, m), 1.61 (3H, m) ppm.

Example 94

N-[1-(8-{4-[(1-Acetylpiperidin-4-yl)carbonyl]piper-azin-1-yl}-5-chloroquinolin-7-yl)ethyl]-9H-purin-6-amine bis(trifluoroacetate)

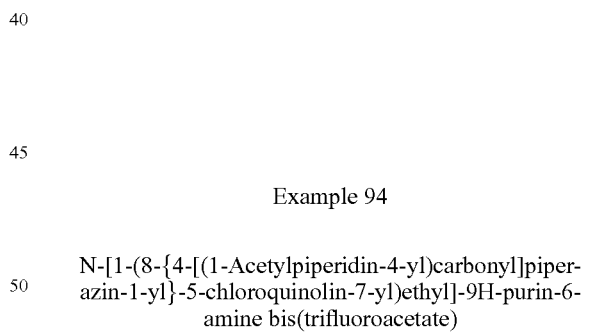

Step 1. 1-(8-{4-[(1-Acetylpiperidin-4-yl)carbonyl]piperazin-1-yl}-5-chloroquinolin-7-yl)ethanone

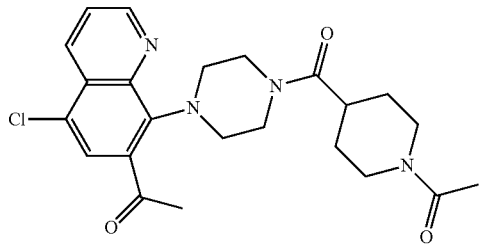 [SMILES: CC(=O)c1cc(Cl)c2cccnc2c1N1CCN(C(=O)C2CCN(C(C)=O)CC2)CC1]

1-(5-Chloro-8-piperazin-1-ylquinolin-7-yl)ethanone (0.030 g, 0.10 mmol, from Example 47, Step 1) was combined with 1-acetylpiperidine-4-carbonyl chloride (0.029 g, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$, concentrated and purified on silica gel (eluting with 0 to 5% methanol in dichloromethane) to give the desired product (30 mg, 65%). LCMS calculated for $C_{23}H_{28}ClN_4O_3$ (M+H)$^+$: m/z=443.2; Found: 443.2.

Step 2. 1-(8-{4-[(1-Acetylpiperidin-4-yl)carbonyl]piperazin-1-yl}-5-chloroquinolin-7-yl)ethanamine

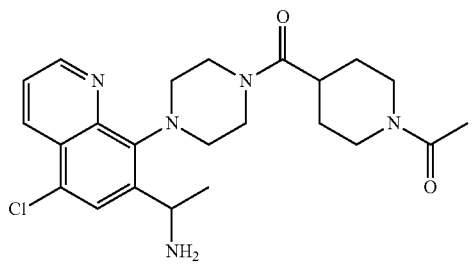 [SMILES: CC(=O)N1CCC(C(=O)N2CCN(c3c(C(C)N)cc(Cl)c4cccnc34)CC2)CC1]

A mixture of 1-(8-{4-[(1-acetylpiperidin-4-yl)carbonyl]piperazin-1-yl}-5-chloroquinolin-7-yl)ethanone (0.030 g, 0.068 mmol) and ammonium acetate (0.0522 g, 0.677 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.17 mL, 0.17 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{23}H_{31}ClN_5O_2$ (M+H)$^+$: m/z=444.2; Found: 444.2.

Step 3. N-[1-(8-{4-[(1-Acetylpiperidin-4-yl)carbonyl)piperazin-1-yl}-5-chloroquinolin-7-yl)ethyl]-9H-purin-6-amine bis(trifluoroacetate)

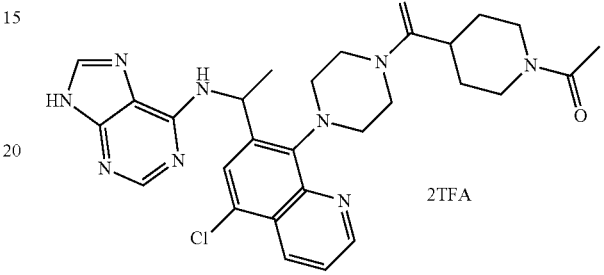

A mixture of 1-(8-{4-[(1-acetylpiperidin-4-yl)carbonyl]piperazin-1-yl}-5-chloroquinolin-7-yl)ethanamine (0.027 g, 0.061 mmol), 6-bromo-9H-purine (0.024 g, 0.12 mmol) and N,N-diisopropylethylamine (0.032 mL, 0.18 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{28}H_{33}ClN_9O_2$ (M+H)$^+$: m/z=562.2; Found: 562.3. $^1$H NMR (DMSO-d$_6$, 300 MHz) δ 9.53 (1H, br s), 8.98 (1H, dd, J=4.2 and 1.2 Hz), 8.55~8.48 (3H, m), 7.90 (1H, s), 7.64 (1H, dd, J=8.7 and 4.5 Hz), 6.50 (1H, m), 4.49 (1H, m), 4.38 (1H, m), 4.08 (2H, m), 3.82 (3H, m), 3.37 (1H, m), 3.27 (1H, m), 3.09 (1H, m), 2.96~2.84 (4H, m), 2.60 (1H, m), 1.99 (3H, s), 1.68 (3H, m), 1.62 (3H, d, J=7.2 Hz) ppm.

Example 95

N-(1-{5-Chloro-8-[4-(pyridin-2-ylcarbonyl)piperazin-1-yl]quinolin-7-yl}ethyl)-9H-purin-6-amine tris(trifluoroacetate)

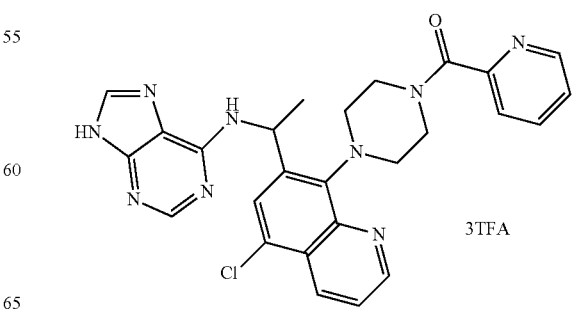

Step 1. 1-{5-Chloro-8-[4-(pyridin-2-ylcarbonyl)piperazin-1-yl]quinolin-7-yl}ethanone

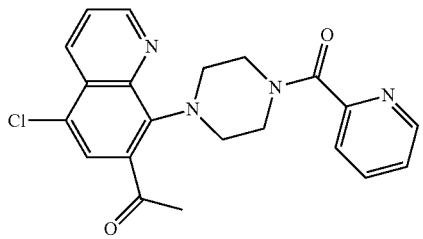 [SMILES: CC(=O)c1cc(Cl)c2cccnc2c1N1CCN(C(=O)c2ccccn2)CC1]

1-(5-Chloro-8-piperazin-1-ylquinolin-7-yl)ethanone (0.030 g, 0.10 mmol, from Example 47, Step 1) was combined with pyridine-2-carbonyl chloride hydrochloride (0.028 g, 0.16 mmol) and triethylamine (0.058 mL, 0.41 mmol) in methylene chloride (1.0 mL) at room temperature and stirred overnight. The reaction was diluted with dichloromethane, washed with water, dried over MgSO$_4$, concentrated and purified on silica gel (eluting with 0 to 5% methanol in dichloromethane) to give the desired product (15 mg, 37%). LCMS calculated for $C_{21}H_{20}ClN_4O_2$ (M+H)$^+$: m/z=395.1; Found: 395.1.

Step 2. 1-{5-Chloro-8-[4-(pyridin-2-ylcarbonyl)piperazin-1-yl]quinolin-7-yl}ethanamine

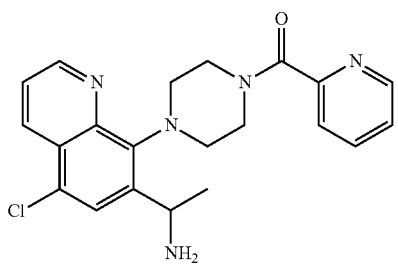 [SMILES: CC(N)c1cc(Cl)c2cccnc2c1N1CCN(C(=O)c2ccccn2)CC1]

A mixture of 1-{5-chloro-8-[4-(pyridin-2-ylcarbonyl)piperazin-1-yl]quinolin-7-yl}ethanone (0.015 g, 0.038 mmol) and ammonium acetate (0.0293 g, 0.380 mmol) in methanol (0.2 mL) and acetonitrile (0.2 mL) was heated at 65° C. in a sealed tube for 1 hour. After cooling to room temperature, to the resulting mixture was added 1.0 M sodium cyanoborohydride in tetrahydrofuran (0.095 mL, 0.095 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{21}H_{23}ClN_5O$ (M+H)$^+$: m/z=396.2; Found: 396.2.

Step 3. N-(1-{5-Chloro-8-[4-(pyridin-2-ylcarbonyl)piperazin-1-yl]quinolin-7-yl}ethyl)-9H-purin-6-amine tris(trifluoroacetate)

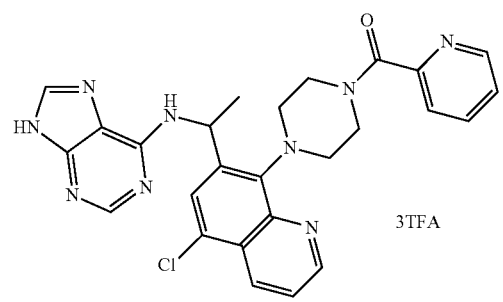 [SMILES: CC(Nc1ncnc2[nH]cnc12)c1cc(Cl)c2cccnc2c1N1CCN(C(=O)c2ccccn2)CC1]

A mixture of 1-{5-chloro-8-[4-(pyridin-2-ylcarbonyl)piperazin-1-yl]quinolin-7-yl}ethanamine (0.015 g, 0.038 mmol), 6-bromo-9H-purine (0.015 g, 0.076 mmol) and N,N-diisopropylethylamine (0.020 mL, 0.11 mmol) in ethanol (0.3 mL, 5 mmol) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{26}H_{25}ClN_9O$ (M+H)$^+$: m/z=514.2; Found: 514.2.

Example 96

N-(1-{5-Chloro-8-[4-(pyridin-3-ylcarbonyl)piperazin-1-yl]quinolin-7-yl}ethyl)-9H-purin-6-amine tris(trifluoroacetate)

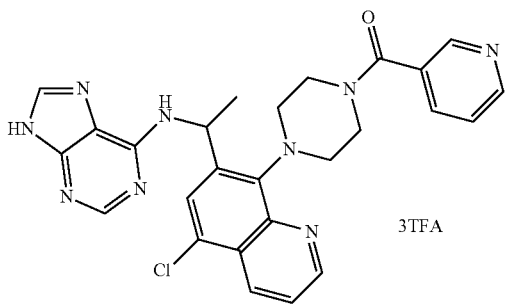 [SMILES: CC(Nc1ncnc2[nH]cnc12)c1cc(Cl)c2cccnc2c1N1CCN(C(=O)c2cccnc2)CC1]

Step 1. 1-{5-Chloro-8-[4-(pyridin-3-ylcarbonyl)piperazin-1-yl]quinolin-7-yl}ethanone

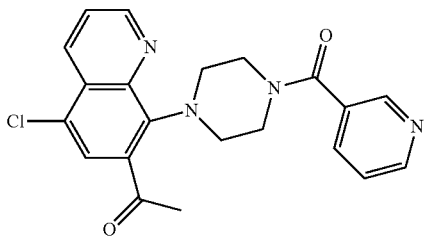 [SMILES: CC(=O)c1cc(Cl)c2cccnc2c1N1CCN(C(=O)c2cccnc2)CC1]

1-(5-Chloro-8-piperazin-1-ylquinolin-7-yl)ethanone (0.030 g, 0.10 mmol, from Example 47, Step 1) was combined with nicotinoyl chloride hydrochloride (0.028 g, 0.16 mmol) and triethylamine (0.058 mL, 0.41 mmol) in methylene chloride (1.0 mL) at room temperature and stirred for 2 hours. The reaction was diluted with dichloromethane, washed with water, dried over MgSO$_4$, concentrated and purified on silica gel (eluting with 0 to 5% methanol in dichloromethane) to give the desired product (39 mg, 95%). LCMS calculated for $C_{21}H_{20}ClN_4O_2$ (M+H)$^+$: m/z=395.1; Found: 395.1.

Step 2. 1-{5-Chloro-8-[4-(pyridin-3-ylcarbonyl)piperazin-1-yl]quinolin-7-yl}ethanamine

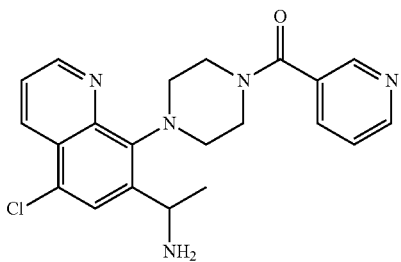 [SMILES: CC(N)c1cc(Cl)c2cccnc2c1N1CCN(C(=O)c2cccnc2)CC1]

A mixture of 1-{5-chloro-8-[4-(pyridin-3-ylcarbonyl)piperazin-1-yl]quinolin-7-yl}ethanone (0.039 g, 0.099 mmol) and ammonium acetate (0.0761 g, 0.988 mmol) in methanol (0.4 mL) and acetonitrile (0.4 mL) was heated at 65° C. in a sealed tube for 1 hour. After cooling to room temperature, to the resulting mixture was added 1.0 M sodium cyanoborohydride in tetrahydrofuran (0.25 mL, 0.25 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{21}H_{23}ClN_5O$ (M+H)$^+$: m/z=396.2; Found: 396.2.

Step 3. N-(1-{5-Chloro-8-[4-(pyridin-3-ylcarbonyl)piperazin-1-yl]quinolin-7-yl}ethyl)-9H-purin-6-amine tris(trifluoroacetate)

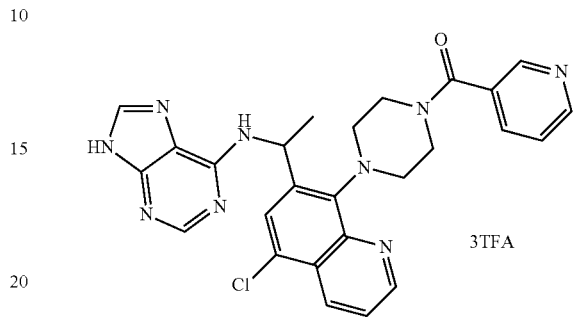

A mixture of 1-{5-chloro-8-[4-(pyridin-3-ylcarbonyl)piperazin-1-yl]quinolin-7-yl}ethanamine (0.045 g, 0.11 mmol), 6-bromo-9H-purine (0.045 g, 0.23 mmol) and N,N-diisopropylethylamine (0.059 mL, 0.34 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{26}H_{25}ClN_9O$ (M+H)$^+$: m/z=514.2; Found: 514.2. $^1$H NMR (DMSO-d$_5$, 300 MHz) δ 9.55 (1H, m), 9.01 (1H, m), 8.78 (1H, s), 8.73 (1H, m), 8.53~8.44 (3H, m), 8.07 (1H, m), 7.90 (1H, s), 7.64 (2H, m), 6.54 (1H, m), 4.63 (1H, m), 4.07 (1H, m), 3.88 (1H, m), 3.58 (2H, m), 3.39 (1H, m), 3.22 (1H, m), 2.96 (1H, m), 2.80 (1H, m), 1.61 (3H, m) ppm.

Example 97

N-(1-{5-Chloro-8-[4-(pyrazin-2-ylcarbonyl)piperazin-1-yl]quinolin-7-yl}ethyl)-9H-purin-6-amine bis(trifluoroacetate)

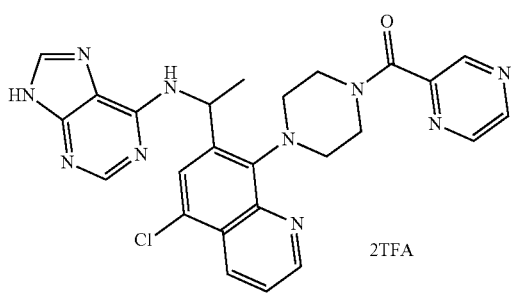 [SMILES: CC(Nc1ncnc2[nH]cnc12)c1cc(Cl)c2cccnc2c1N1CCN(C(=O)c2cnccn2)CC1]

Step 1. 1-{5-Chloro-8-[4-(pyrazin-2-ylcarbonyl)piperazin-1-yl]quinolin-7-yl}ethanone

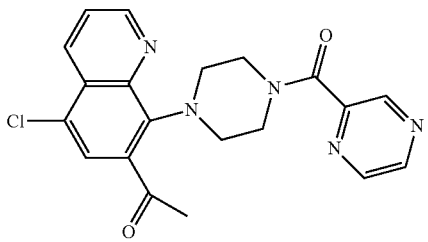 [SMILES: CC(=O)c1cc(Cl)c2cccnc2c1N1CCN(C(=O)c2cnccn2)CC1]

1-(5-Chloro-8-piperazin-1-ylquinolin-7-yl)ethanone (0.030 g, 0.10 mmol, from Example 47, Step 1) was combined with pyrazine-2-carbonyl chloride (0.022 g, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$, concentrated and purified on silica gel (eluting with 0 to 5% methanol in dichloromethane) to give the desired product (28 mg, 68%). LCMS calculated for $C_{20}H_{19}ClN_5O_2$ (M+H)$^+$: m/z=396.1; Found: 396.1.

Step 2. 1-{5-Chloro-8-[4-(pyrazin-2-ylcarbonyl)piperazin-1-yl]quinolin-7-yl}ethanamine

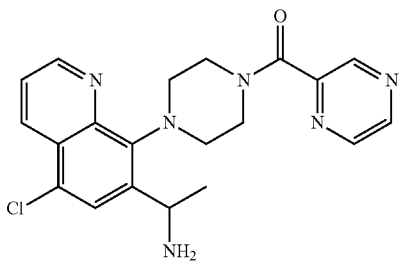

A mixture of 1-{5-chloro-8-[4-(pyrazin-2-ylcarbonyl)piperazin-1-yl]quinolin-7-yl}ethanone (0.028 g, 0.071 mmol) and ammonium acetate (0.0545 g, 0.707 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.17 mL, 0.17 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{20}H_{22}ClN_6O$ (M+H)$^+$: m/z=397.2; Found: 397.1.

Step 3. N-(1-{5-Chloro-8-[4-(pyrazin-2-ylcarbonyl)piperazin-1-yl]quinolin-7yl}ethyl)-9H-purin-6-amine bis(trifluoroacetate)

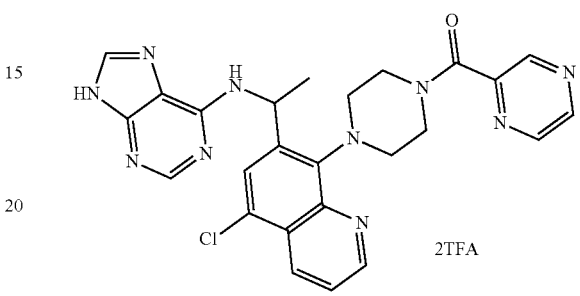

A mixture of 1-{5-chloro-8-[4-(pyrazin-2-ylcarbonyl)piperazin-1-yl]quinolin-7-yl}ethanamine (0.030 g, 0.076 mmol), 6-bromo-9H-purine (0.030 g, 0.15 mmol) and N,N-diisopropylethylamine (0.039 mL, 0.23 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for $C_{25}H_{24}ClN_{10}O$ (M+H)$^+$: m/z=515.2; Found: 515.2.

Example 98

N-{1-[5-Chloro-8-(4-isonicotinoylpiperazin-1-yl)quinolin-7-yl]ethyl}-9H-purin-6-amine tris(trifluoroacetate)

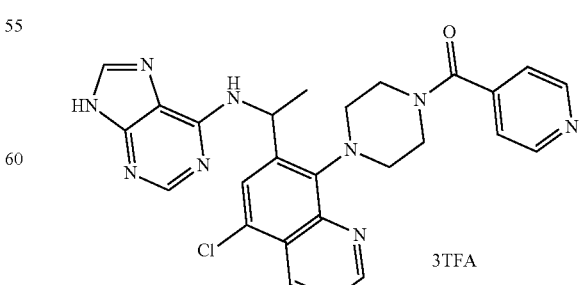

Step 1. 1-[5-Chloro-8-(4-isonicotinoylpiperazin-1-yl)quinolin-7-yl]ethanone

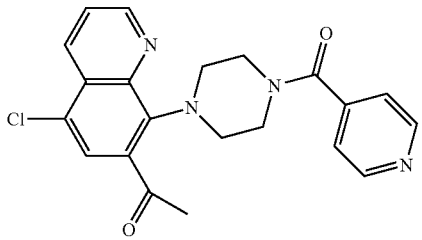 [SMILES: CC(=O)c1cc(Cl)c2cccnc2c1N1CCN(C(=O)c2ccncc2)CC1]

1-(5-Chloro-8-piperazin-1-ylquinolin-7-yl)ethanone (0.030 g, 0.10 mmol, from Example 47, Step 1) was combined with isonicotinoyl chloride hydrochloride (0.028 g, 0.16 mmol) and triethylamine (0.058 mL, 0.41 mmol) in methylene chloride (1.0 mL) at room temperature and stirred for 2 hrs. The reaction was diluted with dichloromethane, washed with water, dried over MgSO$_4$, concentrated and purified on silica gel (eluting with 0 to 5% methanol in dichloromethane) to give the desired product (30 mg, 73%). LCMS calculated for C$_{21}$H$_{20}$ClN$_4$O$_2$ (M+H)$^+$: m/z=395.1; Found: 395.1.

Step 2. 1-[5-Chloro-8-(4-isonicotinoylpiperazin-1-yl)quinolin-7-yl]ethanamine

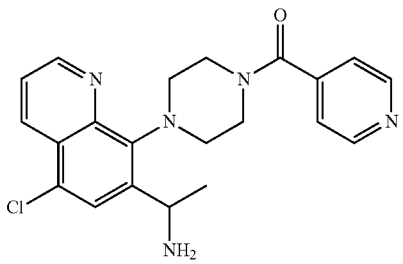 [SMILES: CC(N)c1cc(Cl)c2cccnc2c1N1CCN(C(=O)c2ccncc2)CC1]

A mixture of 1-[5-chloro-8-(4-isonicotinoylpiperazin-1-yl)quinolin-7-yl]ethanone (0.030 g, 0.076 mmol) and ammonium acetate (0.0586 g, 0.760 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.19 mL, 0.19 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{21}$H$_{23}$ClN$_5$O (M+H)$^+$: m/z=396.2; Found: 396.2.

Step 3. N-{1-[5-Chloro-8-(4-isonicotinoylpiperazin-1-yl)quinolin-7-yl]ethyl}-9H-purin-6-amine tris(trifluoroacetate)

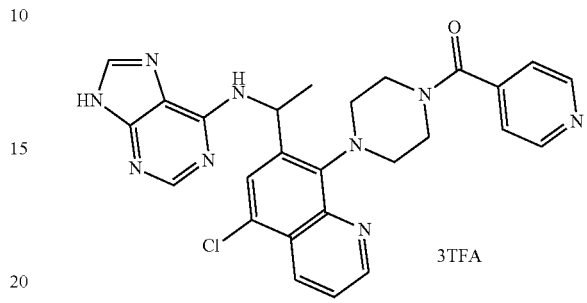

A mixture of 1-[5-chloro-8-(4-isonicotinoylpiperazin-1-yl)quinolin-7-yl]ethanamine (0.028 g, 0.071 mmol), 6-bromo-9H-purine (0.028 g, 0.14 mmol) and N,N-diisopropylethylamine (0.037 mL, 0.21 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{26}$H$_{25}$ClN$_9$O (M+H)$^+$: m/z=514.2; Found: 514.2.

Example 99

N-[1-(5-Chloro-8-{4-[(5-methylisoxazol-3-yl)carbonyl]piperazin-1-yl}quinolin-7-yl)ethyl]-9H-purin-6-amine bis(trifluoroacetate)

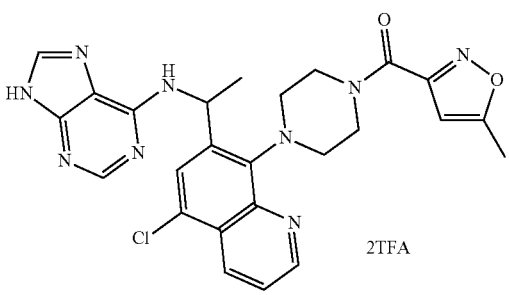 [SMILES: Cc1cc(C(=O)N2CCN(c3c(C(C)Nc4ncnc5[nH]cnc45)cc(Cl)c4cccnc34)CC2)no1]

Step 1. 1-(5-Chloro-8-{4-[(5-methylisoxazol-3-yl)carbonyl]piperazin-1-yl}quinolin-7-yl)ethanone

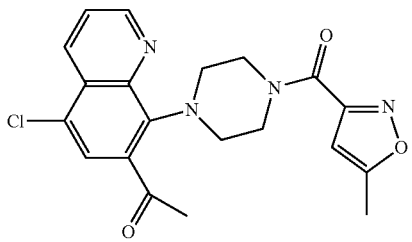 [SMILES: CC(=O)c1cc(Cl)c2cccnc2c1N1CCN(C(=O)c2cc(C)on2)CC1]

1-(5-Chloro-8-piperazin-1-ylquinolin-7-yl)ethanone (0.030 g, 0.10 mmol from Example 47, Step 1) was combined with 5-methylisoxazole-3-carbonyl chloride (0.023 g, 0.16 mmol) and triethylamine (0.043 mL, 0.31 mmol) in methylene chloride (1.0 mL) at room temperature and stirred for 2 hours. The reaction was diluted with dichloromethane, washed with water, dried over MgSO$_4$, concentrated and purified on silica gel (0 to 5% methanol in dichloromethane) to give the desired product (32 mg, 77%). LCMS calculated for C$_{20}$H$_{20}$ClN$_4$O$_3$ (M+H)$^+$: m/z=399.1; Found: 399.1.

Step 2. 1-(5-Chloro-8-{4-[(5-methylisoxazol-3-yl)carbonyl]piperazin-1-yl}quinolin-7-yl)ethanamine

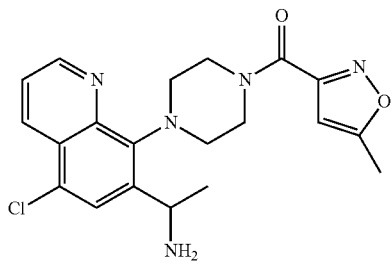 [SMILES: Cc1cc(C(=O)N2CCN(c3c(C(C)N)cc(Cl)c4cccnc34)CC2)no1]

A mixture of 1-(5-chloro-8-{4-[(5-methylisoxazol-3-yl)carbonyl]piperazin-1-yl}quinolin-7-yl)ethanone (0.032 g, 0.080 mmol) and ammonium acetate (0.0618 g, 0.802 mmol) in methanol (0.3 mL) and acetonitrile (0.3 mL) was heated at 65° C. in a sealed tube for 1 hour. After cooling to room temperature, to the resulting mixture was added 1.0 M sodium cyanoborohydride in tetrahydrofuran (0.20 mL, 0.20 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{20}$H$_{23}$ClN$_5$O$_2$ (M+H)$^+$: m/z=400.2; Found: 400.2.

Step 3. N-[1-(5-Chloro-8-{4-[(5-methylisoxazol-3-yl)carbonyl]piperazin-1-yl}quinolin-7-yl)ethyl]-9H-purin-6-amine bis(trifluoroacetate)

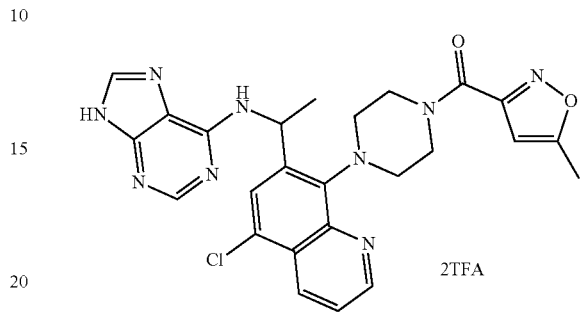

A mixture of 1-(5-chloro-8-{4-[(5-methylisoxazol-3-yl)carbonyl]piperazin-1-yl}quinolin-7-yl)ethanamine (0.033 g, 0.082 mmol), 6-bromo-9H-purine (0.033 g, 0.16 mmol) and N,N-diisopropylethylamine (0.043 mL, 0.25 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{25}$H$_{25}$ClN$_9$O$_2$ (M+H)$^+$: m/z=518.2; Found: 518.2. $^1$H NMR (DMSO-d$_6$, 300 MHz) δ 9.41 (1H, br s), 9.00 (1H, d, J=4.2 Hz), 8.51~8.44 (3H, m), 7.91 (1H, s), 7.64 (1H, dd, J=9.0 and 4.5 Hz), 6.52 (2H, m), 4.60 (1H, m), 4.07 (2H, m), 3.88 (1H, m), 3.49~3.28 (3H, m), 3.16 (1H, m), 2.90 (1H, m), 2.46 (3H, s), 1.61 (3H, m) ppm.

Example 100

N-[1-(5-Chloro-8-{4-[(3,5-dimethylisoxazol-4-yl)carbonyl]piperazin-1-yl}quinolin-7-yl)ethyl]-9H-purin-6-amine bis(trifluoroacetate)

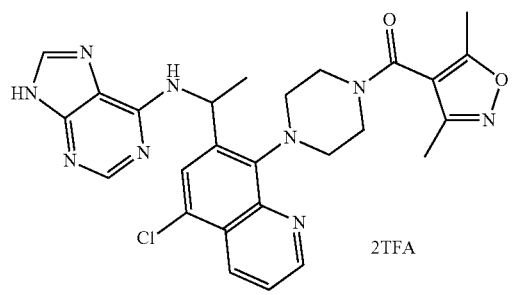 [SMILES: Cc1noc(C)c1C(=O)N1CCN(c2c(C(C)Nc3ncnc4[nH]cnc34)cc(Cl)c3cccnc23)CC1]

Step 1. 1-(5-Chloro-8-{4-[(3,5-dimethylisoxazol-4-yl)carbonyl]piperazin-1-yl}quinolin-7-yl)ethanone

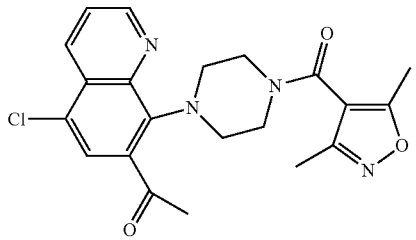 [SMILES: CC(=O)c1cc(Cl)c2cccnc2c1N1CCN(C(=O)c2c(C)noc2C)CC1]

1-(5-Chloro-8-piperazin-1-ylquinolin-7-yl)ethanone (0.030 g, 0.10 mmol, from Example 47, Step 1) was combined with 3,5-dimethylisoxazole-4-carbonyl chloride (0.022 mL, 0.16 mmol) and triethylamine (0.058 mL, 0.41 mmol) in methylene chloride (1.0 mL) at room temperature and stirred for 2 hr. The reaction was diluted with dichloromethane, washed with water, dried over MgSO$_4$, concentrated and purified on silica gel (eluting with 0 to 5% methanol in dichloromethane) to give the desired product (44 mg, 100%). LCMS calculated for C$_{21}$H$_{22}$ClN$_4$O$_3$ (M+H)$^+$: m/z=413.1; Found: 413.1.

Step 2. 1-(5-Chloro-8-{4-[(3,5-dimethylisoxazol-4-yl)carbonyl]piperazin-1-yl}quinolin-7-yl)ethanamine

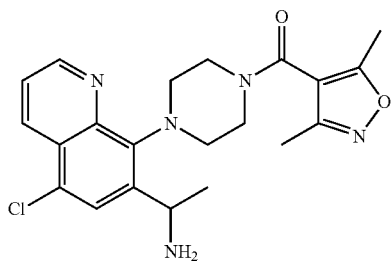 [SMILES: Cc1noc(C)c1C(=O)N1CCN(c2c(C(C)N)cc(Cl)c3cccnc23)CC1]

A mixture of 1-(5-chloro-8-{4-[(3,5-dimethylisoxazol-4-yl)carbonyl]piperazin-1-yl}quinolin-7-yl)ethanone (0.044 g, 0.11 mmol) and ammonium acetate (0.0821 g, 1.06 mmol) in methanol (0.4 mL) and acetonitrile (0.4 mL) was heated at 65° C. in a sealed tube for 1 hour. After cooling to room temperature, to the resulting mixture was added 1.0 M sodium cyanoborohydride in tetrahydrofuran (0.26 mL, 0.26 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for C$_{21}$H$_{23}$ClN$_5$O$_2$ (M+H)$^+$: m/z=414.2; Found:414.2.

Step 3. N-[1-(5-Chloro-8-{4-[(3,5-dimethylisoxazol-4-yl)carbonyl]piperazin-1-yl}quinolin-7-yl)ethyl]-9H-purin-6-amine bis(trifluoroacetate)

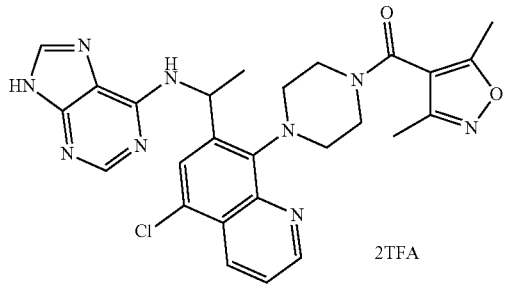 [SMILES: Cc1noc(C)c1C(=O)N1CCN(c2c(C(C)Nc3ncnc4[nH]cnc34)cc(Cl)c3cccnc23)CC1]

A mixture of 1-(5-chloro-8-{4-[(3,5-dimethylisoxazol-4-yl)carbonyl]piperazin-1-yl}quinolin-7-yl)ethanamine (0.046 g, 0.11 mmol), 6-bromo-9H-purine (0.044 g, 0.22 mmol) and N,N-diisopropylethylamine (0.058 mL, 0.33 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{26}$H$_{27}$ClN$_9$O$_2$ (M+H)$^+$: m/z=532.2; Found: 532.3. $^1$H NMR (DMSO-d$_6$, 300 MHz) δ 9.54 (1H, br d, J=5.1 Hz), 8.98 (1H, dd, J=4.2 and 1.5 Hz), 8.54~8.47 (3H, m), 7.90 (1H, s), 7.63 (1H, dd, J=8.4 and 4.2 Hz), 6.52 (1H, m), 4.54 (1H, m), 4.03~2.87 (8H, m), 2.44 (3H, s), 2.26 (3H, s), 1.62 (3H, d, J=7.2 Hz) ppm.

Example 101

N-[1-(5-Chloro-8-{4-[(1-methyl-1H-pyrazol-3-yl)carbonyl]piperazin-1-yl}quinolin-7-yl)ethyl]-9H-purin-6-amine bis(trifluoroacetate)

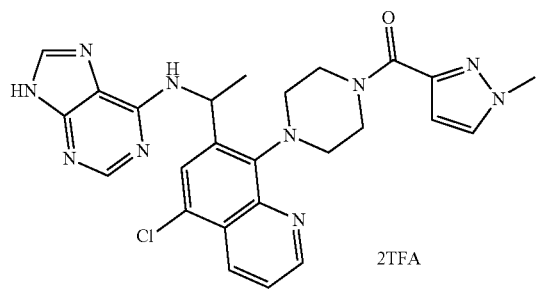 [SMILES: CC(Nc1ncnc2[nH]cnc12)c1cc(Cl)c2cccnc2c1N1CCN(C(=O)c2ccn(C)n2)CC1]

Step 1. 1-(5-Chloro-8-{4-[(1-methyl-1H-pyrazol-3-yl)carbonyl]piperazin-1-yl}quinolin-7-yl)ethanone

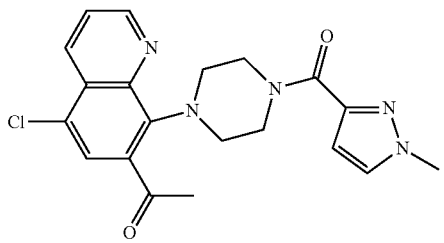 [SMILES: CC(=O)c1cc(Cl)c2cccnc2c1N1CCN(C(=O)c2ccn(C)n2)CC1]

1-(5-Chloro-8-piperazin-1-ylquinolin-7-yl)ethanone (0.030 g, 0.10 mmol, from Example 47, Step 1) was combined with 1-methyl-1H-pyrazole-3-carbonyl chloride (0.022 g, 0.16 mmol) and triethylamine (0.058 mL, 0.41 mmol) in methylene chloride (1.0 mL) at room temperature and the resulting mixture was stirred for 2 hrs. The reaction was diluted with dichloromethane, washed with water, dried over MgSO$_4$, concentrated and purified on silica gel (eluting with 0 to 5% methanol in dichloromethane) to give the desired porduct (32 mg, 78%). LCMS calculated for C$_{20}$H$_{21}$ClN$_5$O$_2$ (M+H)$^+$: m/z=398.1; Found: 398.1.

Step 2. 1-(5-Chloro-8-{4-[(1-methyl-1H-pyrazol-3-yl)carbonyl]piperazin-1-yl}quinolin-7-yl)ethanamine

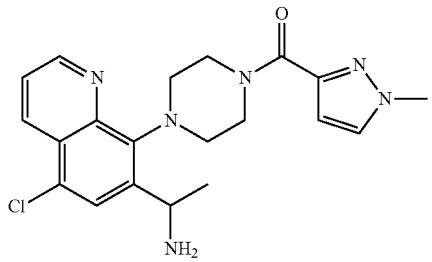 [SMILES: CC(N)c1cc(Cl)c2cccnc2c1N1CCN(C(=O)c2ccn(C)n2)CC1]

A mixture of 1-(5-chloro-8-{4-[(1-methyl-1H-pyrazol-3-yl)carbonyl]piperazin-1-yl}quinolin-7-yl)ethanone (0.032 g, 0.080 mmol) and ammonium acetate (0.0620 g, 0.804 mmol) in methanol (0.3 mL,) and acetonitrile (0.3 mL) was heated at 65° C. in a sealed tube for 1 hour. After cooling to room temperature, to the resulting mixture was added 1.0 M sodium cyanoborohydride in tetrahydrofuran (0.20 mL, 0.20 mmol). The reaction was heated at 65° C. overnight. The mixture was cooled to room temperature, quenched with sat. NaHCO$_3$ solution, extracted with dichloromethane, dried over MgSO$_4$ and concentrated to give the crude product. LCMS calculated for C$_{20}$H$_{24}$ClN$_6$O (M+H)$^+$: m/z=399.2; Found: 399.2.

Step 3. N-[1-(5-Chloro-8-{4-[(1-methyl-1H-pyrazol-3-yl)carbonyl]piperazin-1-yl}quinolin-7-yl)ethyl]-9H-purin-6-amine bis(trifluoroacetate)

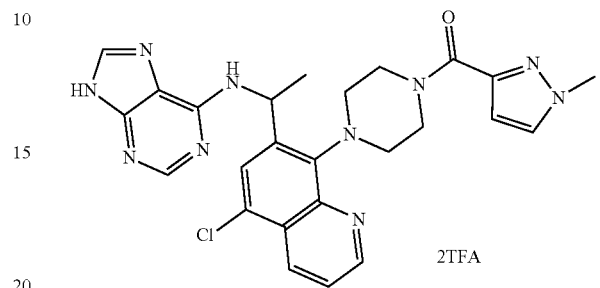

A mixture of 1-(5-chloro-8-{4-[(1-methyl-1H-pyrazol-3-yl)carbonyl]piperazin-1-yl}quinolin-7-yl)ethanamine (0.035 g, 0.088 mmol), 6-bromo-9H-purine (0.035 g, 0.18 mmol) and N,N-diisopropylethylamine (0.046 mL, 0.26 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min) to give the desired product as a TFA salt. LCMS calculated for C$_{25}$H$_{26}$ClN$_{10}$O (M+H)$^+$: m/z=517.2; Found: 517.2.

Example 102

Single Enantiomers of N-{1-[5-fluoro-8-(3-fluorophenyl)quinolin-7-yl]ethyl}-9H-purin-6-amine

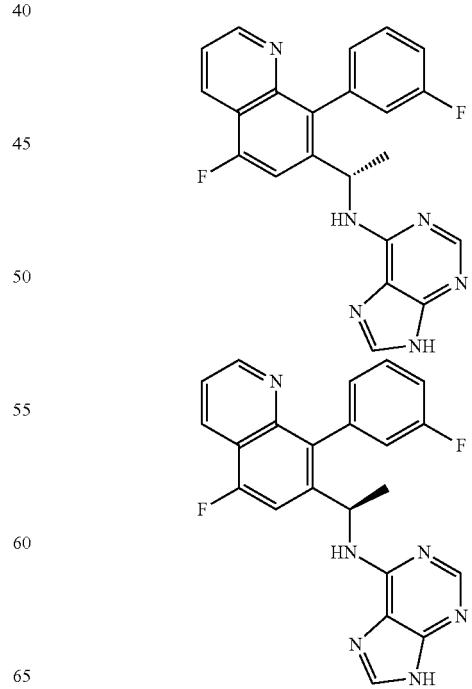

Step 1. 1-[5-Fluoro-8-(3-fluorophenyl)quinolin-7-yl]ethanone

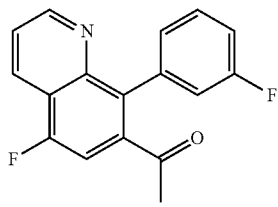

A mixture of 7-acetyl-5-fluoroquinolin-8-yl trifluoromethanesulfonate (3.4 g, 10. mmol, from Example 53, Step 2) in tetrahydrofuran (10 mL) was degassed for 10 minutes, to which was added tetrakis(triphenylphosphine)palladium(0) (1.2 g, 1.0 mmol) and 0.5 M (3-fluorophenyl)(iodo)zinc in tetrahydrofuran (50 mL). The reaction mixture was heated at 65° C. overnight, and then cooled to room temperature. The reaction was quenched with sat. NaHCO$_3$ solution. The mixture was filtered through a Celite pad. The filtrate was extracted with dichloromethane. The combined organic layers were wash with brine, dried over MgSO$_4$, concentrated and purified on silica gel (eluting with 0 to 30% ethyl acetate in hexane) to give the desired product (0.32 g, 11%). LCMS calculated for $C_{17}H_{12}F_2NO$ (M+H)$^+$: m/z=284.1; Found: 284.1.

Step 2. 1-[5-Fluoro-8-(3-fluorophenyl)quinolin-7-yl]ethanamine

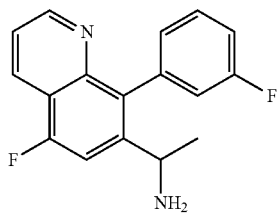

A mixture of 1-[5-fluoro-8-(3-fluorophenyl)quinolin-7-yl]ethanone (0.32 g, 1.1 mmol) and ammonium acetate (0.871 g, 11.3 mmol) in methanol (3.0 mL) and acetonitrile (3.0 mL) was heated at 65° C. in a sealed tube for 30 minutes. After cooling to room temperature, to the resulting mixture was added 1.0 M sodium cyanoborohyride in tetrahydrofuran (2.8 mL, 2.8 mmol). The reaction was heated at 65° C. overnight, then cooled to room temperature and quenched with sat. NaHCO$_3$ solution and extracted with dichloromethane. The combined extracts were dried over MgSO$_4$ and evaporated to dryness. The residue was used directly in the next step. LCMS calculated for $C_{17}H_{15}F_2N_2$ (M+H)$^+$: m/z=285.1; Found: 285.1.

Step 3. N-{1-[5-Fluoro-8-(3-fluorophenyl)quinolin-7-yl]ethyl}-9H-purin-6-amine

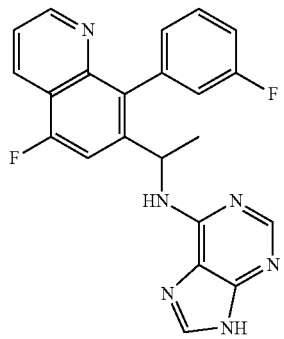 [SMILES: CC(Nc1ncnc2[nH]cnc12)c1cc(F)c2cccnc2c1-c1cccc(F)c1]

A mixture of 1-[5-fluoro-8-(3-fluorophenyl)quinolin-7-yl]ethanamine (0.39 g, 1.4 mmol, 6-chloropurine (0.27 g, 1.8 mmol) and sodium hydrogenecarbonate (0.17 g, 2.0 mmol) in 1-butanol (4 mL) was heated at 110° C. overnight. The mixture was filtered and purified on a preparative LCMS (XBridge C18 column, eluting with a gradient of acetonitrile in water with 0.2% ammonium hydroxide, at a flow rate of 30 mL/min) to give the desired product. LCMS calculated for $C_{22}H_{17}F_2N_6$ (M+H)$^+$: m/z=403.1; Found: 403.1. The racemic N-{1-[5-fluoro-8-(3-fluorophenyl)quinolin-7-yl]ethyl}-9H-purin-6-amine (70 mg, 0.2 mmol) was submitted for chiral resolution (column: ChiralPak IA, 20×250 mm, 5 µm; mobile phase: 15% ethanol/85% hexanes; flow rate: 15 mL/min) to give two enantiomers. retention times: 8.7 and 13.5 minutes, respectively.

Example 103

N-[1-(5-Fluoro-8-{4-[(1-methyl-1H-pyrazol-4-yl)carbonyl]piperazin-1-yl}quinolin-7-yl)ethyl]-9H-purin-6-amine bis(trifluoroacetate)

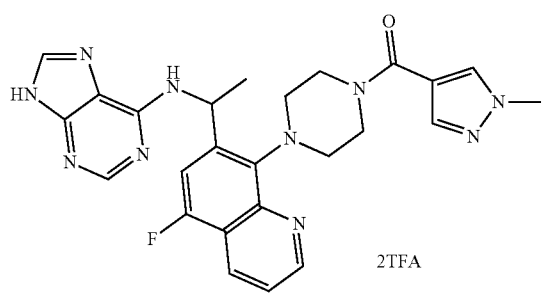 [SMILES: CC(Nc1ncnc2[nH]cnc12)c1cc(F)c2cccnc2c1N1CCN(C(=O)c2cnn(C)c2)CC1]

Step 1.
1-(5-Fluoro-8-piperazin-1-ylquinolin-7-yl)ethanone

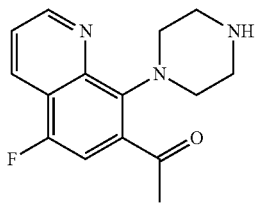

A stirred mixture of 7-acetyl-5-fluoroquinolin-8-yltrifluoromethanesulfonate (1.00 g, 2.96 mmol, from Example 53, Step 2), piperazine (0.511 g, 5.93 mmol), and cesium carbonate (2.90 g, 8.90 mmol) in tetrahydrofuran (30 mL) was heated at 65° C. overnight. The mixture was cooled, diluted with dichloromethane and filtered. The filtrate was washed with brine, dried over sodium sulfate and evaporated to dryness. The resulting residue was purified on silica gel, eluting with 0 to 20% methanol in dichloromethane, to give the desired product (82 mg, 10%). LCMS calculated for $C_{15}H_{17}FN_3O$ (M+H)$^+$: m/z=274.1; Found: 274.1.

Step 2. 1-(5-Fluoro-8-{4-[(1-methyl-1H-pyrazol-4-yl)carbonyl]piperazin-1-yl}quinolin-7-yl)ethanone

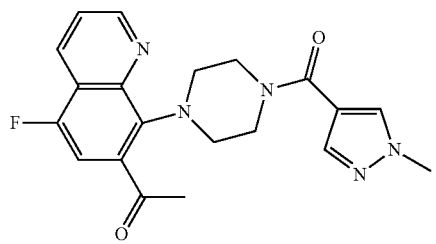 [SMILES: CC(=O)c1cc(F)c2cccnc2c1N1CCN(C(=O)c2cnn(C)c2)CC1]

1-(5-Fluoro-8-piperazin-1-ylquinolin-7-yl)ethanone (0.038 g, 0.14 mmol) was combined with 1-methyl-1H-pyrazole-4-carbonyl chloride (0.030 g, 0.21 mmol) and triethylamine (0.058 mL, 0.42 mmol) in methylene chloride (1.0 mL, 16 mmol) at room temperature and stirred for 2 hrs. The reaction was diluted with dichloromethane, washed with water, dried over MgSO$_4$, concentrated and purified on silica gel (eluting with 0 to 5% methanol in dichloromethane) to give the desired product (45 mg, 85%). LCMS calculated for $C_{20}H_{21}FN_5O_2$ (M+H)$^+$: m/z=382.2; Found: 382.1.

Step 3. 1-(5-Fluoro-8-{4-[(1-methyl-1H-pyrazol-4-yl)carbonyl]piperazin-1-yl}quinolin-7-yl)ethanamine

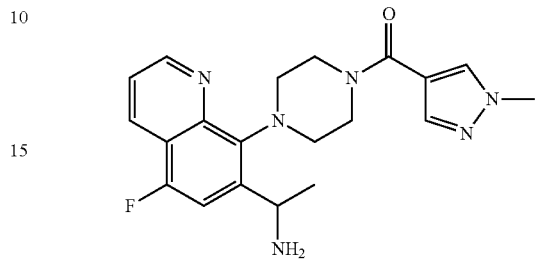

A mixture of 1-(5-fluoro-8-{4-[(1-methyl-1H-pyrazol-4-yl)carbonyl]piperazin-1-yl}quinolin-7-yl)ethanone (0.045 g, 0.12 mmol) and ammonium acetate (0.0909 g, 1.18 mmol) in methanol (0.5 mL) and acetonitrile (0.5 mL) was heated at 65° C. in a sealed tube for 1 hour. After cooling to room temperature, to the resulting mixture was added 1.0 M sodium cyanoborohydride in tetrahydrofuran (0.30 mL, 0.30 mmol). The reaction was heated at 65° C. overnight. The mixture was cooled to room temperature, quenched with sat. NaHCO$_3$ solution, extracted with dichloromethane, dried over MgSO$_4$ and concentrated to give the desired product. LCMS calculated for $C_{20}H_{24}FN_6O$ (M+H)$^+$: m/z=383.2; Found: 383.2.

Step 4. N-[1-(5-Fluoro-8-{4-[(1-methyl-1H-pyrazol-4-yl)carbonyl]piperazin-1-yl}quinolin-7-yl)ethyl]-9H-purin-6-amine bis(trifluoroacetate)

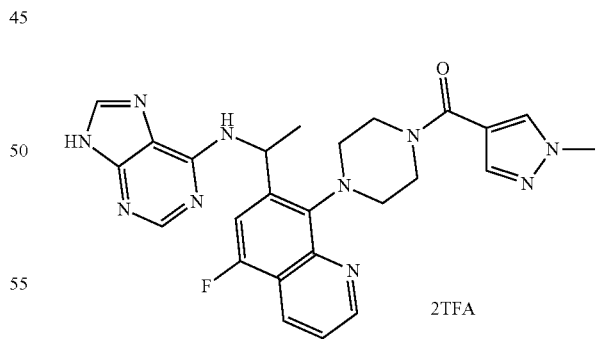

A mixture of 1-(5-fluoro-8-{4-[(1-methyl-1H-pyrazol-4-yl)carbonyl]piperazin-1-yl}quinolin-7-yl)ethanamine (0.058 g, 0.15 mmol), 6-bromo-9H-purine (0.060 g, 0.30 mmol) and N,N-diisopropylethylamine (0.079 mL, 0.45 mmol) in ethanol (0.5 mL) was heated at 110° C. overnight. The mixture was purified on a preparative LCMS (XBridge C18 column, eluting with a gradient of acetonitrile in water with 0.05% trifluoroacetic acid, at a flow rate of 30 mL/min)

to give the desired product as a TFA salt. LCMS calculated for C$_{25}$H$_{26}$FN$_{10}$O (M+H)$^+$: m/z=501.2; Found: 501.2.

Example 104

N-{1-[4-Chloro-7-(3-fluorophenyl)-2,1-benzisoxazol-6-yl]ethyl}-9H-purin-6-amine

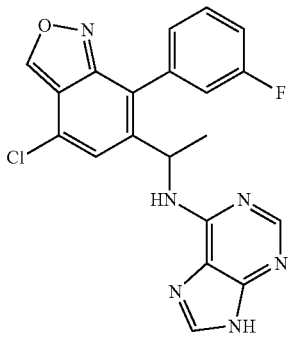 [SMILES: CC(Nc1ncnc2[nH]cnc12)c1cc(Cl)c2conc2c1-c1cccc(F)c1]

Step 1. Methyl 5-chloro-2-hydroxy-4-iodobenzoate

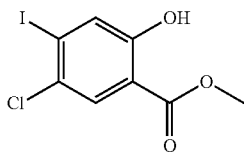

A mixture of methyl 2-hydroxy-4-iodobenzoate (10.0 g, 36.0 mmol, from Aldrich) and N-chlorosuccinimide (5.76 g, 43.2 mmol) in acetic acid (40 mL) was heated at 100° C. for 1 hour and then cooled to room temperature overnight. The precipitate was collected by filtration and washed with ethyl acetate and then air dried to give the desired product. In addition, the filtrate was concentrated to dryness and partitioned between water and ethyl acetate. The organic phase was separated, washed with brine, dried over sodium sulfate and concentrated to dryness. The residue was purified on silica gel, eluting with 0 to 20% ethyl acetate in hexane, to give additional desired product (total 9.03 g, 82%). LCMS calculated for C$_8$H$_7$ClIO$_3$ (M+H)$^+$: m/z=312.9; Found: 313.0.

Step 2. Methyl 5-chloro-2-hydroxy-4-iodo-3-nitrobenzoate

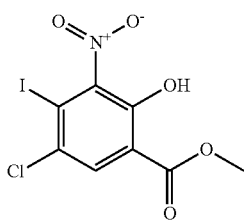 [SMILES: COC(=O)c1cc(Cl)c(I)c([N+](=O)[O-])c1O]

To a mixture of methyl 5-chloro-2-hydroxy-4-iodobenzoate (5.1 g, 16 mmol) in acetic acid (50 mL) was added nitric acid (6.8 mL) at room temperature. The reaction was stirred at 60° C. for 90 min and then cooled and poured into ice water. The precipitate was collected by filtration, washed with water and air dried to give the desired product (5.15 g, 88%).

Step 3. Methyl 5-chloro-4-cyano-2-hydroxy-3-nitrobenzoate

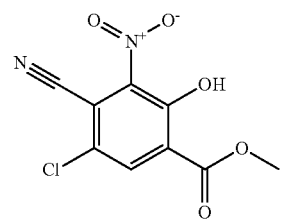 [SMILES: COC(=O)c1cc(Cl)c(C#N)c([N+](=O)[O-])c1O]

A mixture of methyl 5-chloro-2-hydroxy-4-iodo-3-nitrobenzoate (5.00 g, 14.0 mmol) and copper cyanide (1.9 g, 21 mmol) in N,N-dimethylformamide (25 mL) was heated at 110° C. for 2 hours. After cooling to room temperature, the mixture was quenched with 1 N HCl and extracted with ethyl acetate. The combined organic layers were washed with water, brine, dried over magnesium sulfate and then evaporated to dryness under reduced pressure. The residue was used directly in the next step (3.6 g, 100%).

Step 4. Methyl 5-chloro-4-cyano-3-nitro-2-{[(trifluoromethyl)sulfonyl]oxy}benzoate

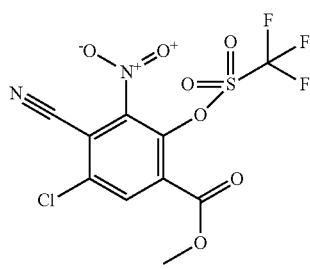

To a mixture of methyl 5-chloro-4-cyano-2-hydroxy-3-nitrobenzoate (3.60 g, 14.0 mmol) in methylene chloride (60 mL) was added triethylamine (5.9 mL, 42 mmol) followed by trifluoromethanesulfonic anhydride (3.5 mL, 21 mmol) at −78° C. The reaction was allowed to warm to room temperature and stirred at room temperature for 30 minutes. After quenching with water, the mixture was extracted with dichloromethane. The combined organic layers were washed with brine, dried over sodium sulfate and concentrated to dryness. The residue was purified on silica gel, eluting with 0 to 30% ethyl acetate in hexane, to give the desired product (3.8 g, 70%). LCMS calculated for $C_{10}H_5ClF_3N_2O_7S$ (M+H)$^+$: m/z=388.9; Found: 388.9.

Step 5. Methyl 4-chloro-5-cyano-3'-fluoro-6-nitrobiphenyl-2-carboxylate

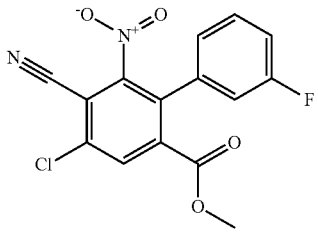

To a biphasic solution of methyl 5-chloro-4-cyano-3-nitro-2-{[(trifluoromethyl)sulfonyl]oxy}benzoate (3.60 g, 9.26 mmol) and (3-fluorophenyl)boronic acid (1.42 g, 10.2 mmol) in toluene (80 mL) was added saturated NaHCO$_3$ (80 mL) and then the reaction was bubbled with N$_2$ to degas. Tetrakis(triphenylphosphine)palladium(0) (0.535 g, 0.463 mmol) was added. The resulting mixture was bubbled with N$_2$ for 5 minutes and then heated at 80° C. for 2 hours. After cooling to room temperature, the mixture was diluted with ethyl acetate. The layers were separated and the aq. layer was extracted with ethyl acetate. The combined extracts were washed with brine, dried over Na$_2$SO$_4$, filtered, and concentrated. The resulting residue was purified on silica gel column, eluting with ethyl acetate/hexane, 0-30%, to give the desired product (1.23 g, 40%). LCMS calculated for $C_{15}H_9ClFN_2O_4$ (M+H)$^+$: m/z=335.0; Found: 335.1. $^1$H NMR (CDCl$_3$, 400 MHz) δ 8.14 (1H, s), 7.40 (1H, m), 7.20 (1H, m), 6.97 (1H, m), 6.93 (1H, m), 3.66 (3H, s) ppm.

Step 6. 4-Chloro-3'-fluoro-6-(hydroxymethyl)-2-nitrobiphenyl-3-carbaldehyde

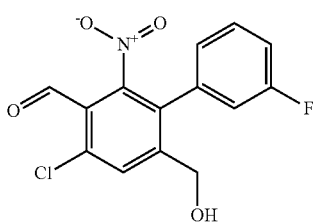

To a mixture of methyl 4-chloro-5-cyano-3'-fluoro-6-nitrobiphenyl-2-carboxylate (1.02 g, 3.05 mmol) in methylene chloride (20 mL) was added 1.0 M diisobutylaluminum hydride in hexane (7.6 mL, 7.6 mmol) at −78° C. The reaction was warmed to room temperature over 2 hours with stirring. 5.0 M Hydrogen chloride in water (30 mL, 100 mmol) was slowly added with stirring for 1 hour. The resulting mixture was extracted with ethyl acetate. The combined organic layers were washed with brine, dried over sodium sulfate and then concentrated to dryness. The residue was purified on silica gel, eluting with 0 to 50% ethyl acetate in hexane, to give the desired product (0.50 g, 53%). LCMS calculated for $C_{14}H_{10}ClFNO_4$ (M+H)$^+$: m/z=310.0; Found: 310.0.

Step 7. [4-Chloro-7-(3-fluorophenyl)-2,1-benzisoxazol-6-yl]methanol

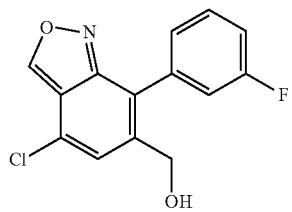 [SMILES: OCc1cc(Cl)c2conc2c1-c1cccc(F)c1]

To a mixture of 4-chloro-3'-fluoro-6-(hydroxymethyl)-2-nitrobiphenyl-3-carbaldehyde (0.50 g, 1.6 mmol), acetic acid (4 mL), and conc. HCl (4 mL) was added stannous chloride, dihydrate (1.4 g, 6.4 mmol). After stirring at room temperature for 2 hours, the resulting mixture was diluted with ethyl acetate, washed with water, brine, and then dried with sodium sulfate and concentrated to dryness. The residue was purified on silica gel, eluting with 0 to 50% ethyl acetate in hexane, to give the desired product (0.104 g, 23%). LCMS calculated for $C_{14}H_{10}ClFNO_2$ (M+H)$^+$: m/z=278.0; Found: 278.0.

Step 8. 4-Chloro-7-(3-fluorophenyl)-2,1-benzisoxazole-6-carbaldehyde

Dimethyl sulfoxide (0.064 mL, 0.90 mmol) was added to oxalyl chloride (0.048 mL, 0.56 mmol) in methylene chloride (2.1 mL) at −78° C. After 10 minutes, [4-chloro-7-(3-fluorophenyl)-2,1-benzisoxazol-6-yl]methanol (0.104 g, 0.374 mmol) in methylene chloride (4.2 mL) was added and the resulting mixture was stirred at −78° C. for 30 minutes. Triethylamine (0.261 mL, 1.87 mmol) was then added and the mixture was stirred for 5 hours at room temperature. After quenching with water, the mixture was extracted with methylene chloride. The organic layers were combined, washed with brine, dried over magnesium sulfate and evaporated to dryness. The resulting mixture was purified on silica gel, eluting with 0 to 30% ethyl acetate in hexane, to give the desired product (88 mg, 85%). LCMS calculated for C₁₄H₈ClFNO₂ (M+H)⁺: m/z=276.0; Found: 276.1.

Step 9. 1-[4-Chloro-7-(3-fluorophenyl)-2,1-benzisaxazol-6-yl]ethanol

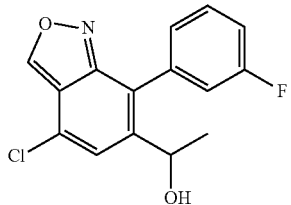 [SMILES: CC(O)c1cc(Cl)c2conc2c1-c1cccc(F)c1]

To a mixture of 4-chloro-7-(3-fluorophenyl)-2,1-benzisoxazole-6-carbaldehyde (88 mg, 0.32 mmol) in tetrahydrofuran (2 mL) was added 3.0 M methylmagnesium bromide in ether (0.16 mL, 0.48 mmol) dropwise at −78° C. The reaction was allowed to warm up to 0° C. and quenched with water and then extracted with ethyl acetate. The combined organic layers were washed with brine, dried over sodium sulfate and evaporated to dryness. The resulting residue was used directly in the next step (93 mg, 100%). LCMS calculated for C₁₅H₁₂ClFNO₂ (M+H)⁺: m/z=292.1; Found: 292.1.

Step 10. 6-(1-Azidoethyl)-4-chloro-7-(3-fluorophenyl)-2,1-benzisoxazole

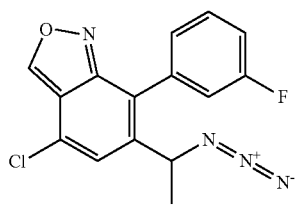 [SMILES: CC(N=[N+]=[N-])c1cc(Cl)c2conc2c1-c1cccc(F)c1]

To a mixture of 1-[4-chloro-7-(3-fluorophenyl)-2,1-benzisoxazol-6-yl]ethanol (0.094 g, 0.32 mmol) in methylene chloride (2 mL) was added triethylamine (0.067 mL, 0.48 mmol), followed by methanesulfonyl chloride (0.031 mL, 0.40 mmol). After stirring at room temperature for 30 minutes, the resulting mixture was diluted with dichloromethane, washed with sat. sodium bicarbonate, brine, dried over magnesium sulfate, and then concentrated to dryness under reduced pressure. The resulting 1-[4-chloro-7-(3-fluorophenyl)-2,1-benzisoxazol-6-yl]ethyl methanesulfonate was used directly in the next step. LCMS calculated for C₁₆H₁₄ClFNO₄S (M+H)⁺: m/z=370.0; Found: 370.1. The crude mesylate was dissolved in N,N-dimethylformamide (1 mL) and treated with sodium azide (0.105 g, 1.61 mmol) at room temperature overnight. After diluted with ethyl acetate, the mixture was washed with water, brine and then dried over magnesium sulfate and evaporated to dryness. The crude product was used in the next step (90 mg, 88%). LCMS calculated for C₁₅H₁₁ClFN₄O (M+H)⁺: m/z=317.1; Found: 317.0.

Step 11. 1-[4-Chloro-7-(3-fluorophenyl)-2,1-benzisoxazol-6-yl]ethanamine

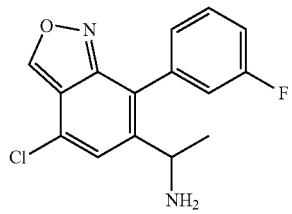 [SMILES: CC(N)c1cc(Cl)c2conc2c1-c1cccc(F)c1]

To a stirred mixture of 6-(1-azidoethyl)-4-chloro-7-(3-fluorophenyl)-2,1-benzisoxazole (90. mg, 0.28 mmol) in tetrahydrofuran (2 mL) and water (0.3 mL) was added 1.0 M trimethylphosphine in THF (0.35 mL, 0.35 mmol). The mixture was stirred at room temperature for 1 hour. After degassing with nitrogen, the reaction mixture was extracted with dichloromethane. The extracts were washed with brine, dried over magnesium sulfate and evaporated to dryness. The crude residue was used directly in the next step (68 mg, 82%). LCMS calculated for C₁₅H₁₀ClFNO (M−NH₂)⁺: m/z=274.1; Found: 274.0.

Step 12. N-{1-[4-chloro-7-(3-fluorophenyl)-2,1-benzisoxazol-6-yl]ethyl}-9H H-purin-6-amine

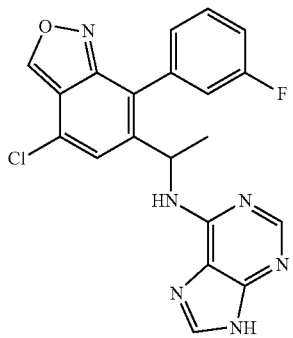 [SMILES: CC(Nc1ncnc2[nH]cnc12)c1cc(Cl)c2conc2c1-c1cccc(F)c1]

A mixture of 6-bromo-9H-purine (51 mg, 0.26 mmol), 1-[4-chloro-7-(3-fluorophenyl)-2,1-benzisoxazol-6-yl]ethanamine (68 mg, 0.23 mmol), and N,N-diisopropylethylamine (0.081 mL, 0.47 mmol) in isopropyl alcohol (0.9 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for C₂₀H₁₅ClFN₆O (M+H)⁺: m/z=409.1; Found: 409.0. ¹H NMR (DMSO-d₆, 400 MHz) δ 9.97 (1H, s), 8.26 (1H, d, J=7.6 Hz), 8.11 (1H, s), 8.04 (1H, s), 7.64 (1H, s), 7.58 (1H, m), 7.51 (1H, m), 7.49 (1H, m), 7.32 (1H, td, J=9.2 and 2.8 Hz), 5.33 (1H, br s), 3.23 (1H, br s), 1.45 (3H, d, J=6.8 Hz) ppm. $^{19}$F NMR (DMSO-d$_6$, 376 MHz) δ −114 ppm.

Example 105

N-{1-[4-Chloro-7-(3-fluorophenyl)-1H-indazol-6-yl]ethyl}-9H-purin-6-amine

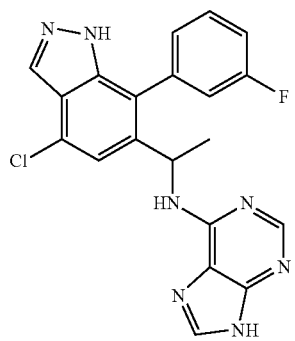 [SMILES: CC(Nc1ncnc2[nH]cnc12)c1cc(Cl)c2cn[nH]c2c1-c1cccc(F)c1]

Step 1. 6-Acetyl-4-chloro-3-methyl-2-nitrophenyl trifluoromethanesulfonate

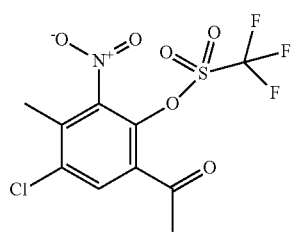

To a mixture of 1-(5-chloro-2-hydroxy-4-methyl-3-nitrophenyl)ethanone (8.59 g, 37.4 mmol) in methylene chloride (200 mL) was added triethylamine (16 mL, 110 mmol) followed by trifluoromethanesulfonic anhydride (9.4 mL, 56 mmol) at −78° C. The reaction was allowed to warm to room temperature gradually and stirred at room temperature for 30 minutes. After quenching with water, the mixture was extracted with dichloromethane. The combined organic layers were washed with brine, dried over sodium sulfate and concentrated to dryness. The residue was purified on silica gel, eluting with 0 to 30% ethyl acetate in hexane, to give the desired product (10.56 g, 78%). LCMS calculated for $C_{10}H_8ClF_3NO_6S$ (M+H)$^+$: m/z=362.0; Found: 362.1.

Step 2. 1-(4-chloro-3'-fluoro-5-methyl-6-nitrobiphenyl-2-yl)ethanone

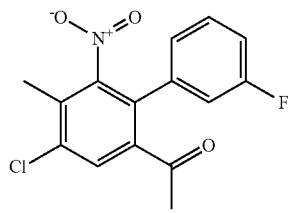

A biphasic solution of 6-acetyl-4-chloro-3-methyl-2-nitrophenyl trifluoromethanesulfonate (3.00 g, 8.29 mmol) and (3-fluorophenyl)boronic acid (1.74 g, 12.4 mmol) in toluene (80 mL) and saturated NaHCO$_3$ (80 mL) was bubbled with N$_2$ to degas. Tetrakis(triphenylphosphine)palladium(0) (0.479 g, 0.415 mmol) was added The reaction mixture was bubbled with N$_2$ for 5 minutes more and heated at 80° C. for 2 hours. After cooling to room temperature, the mixture was diluted with ethyl acetate. The layers were separated and the aq. layer was extracted with ethyl acetate. The combined extracts were washed with brine, dried over Na$_2$SO$_4$, filtered and concentrated. The resulting material was purified on silica gel column, eluting with ethyl acetate/hexane, 0-30%, to give the desired product (2.35 g, 92%). LCMS calculated for $C_{15}H_{12}ClFNO_3$ (M+H)$^+$: m/z=308.0; Found: 308.1.

Step 3. 1-(6-Amino-4-chloro-3'-fluoro-5-methylbiphenyl-2-yl)ethanone

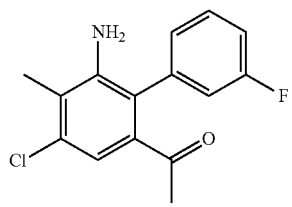 [SMILES: CC(=O)c1cc(Cl)c(C)c(N)c1-c1cccc(F)c1]

A mixture of 1-(4-chloro-3'-fluoro-5-methyl-6-nitrobiphenyl-2-yl)ethanone (4.43 g, 14.4 mmol) in 80 mL of methanol was hydrogenated in the presence of 443 mg of 5% Pt/C, under ballon pressure of hydrogen, overnight. After filtered off catalyst, the filtrate was concentrated under reduced pressure to give the desired product (4.00 g, 100%). LCMS calculated for $C_{15}H_{14}ClFNO$ (M+H)⁺: m/z=278.1; Found: 278.1.

Step 4. 1-[4-chloro-7-(3-fluorophenyl)-1H-indazol-6-yl]ethanone

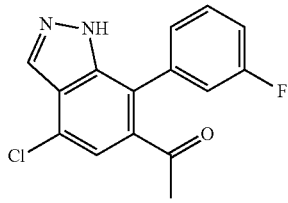 [SMILES: CC(=O)c1cc(Cl)c2cn[nH]c2c1-c1cccc(F)c1]

To a solution of 1-(6-amino-4-chloro-3'-fluoro-5-methylbiphenyl-2-yl)ethanone (4.00 g, 14.4 mmol) in acetic acid (90 mL) was added i-amyl nitrite (1.86 g, 15.8 mmol). The mixture was stirred at room temperature for 30 min before being heated at reflux for 1 hour. Upon cooling, the mixture was concentrated and purified by flash chromatography on silica gel, eluting with 0 to 50% ethyl acetate in hexane, to give the desired product (2.37 g, 57%). LCMS calculated for $C_{15}H_{11}ClFN_2O$ (M+H)⁺: m/z=289.1; Found: 289.1.

Step 5. 1-[4-chloro-7-(3-fluorophenyl)-1H-indazol-6-yl]ethanamine

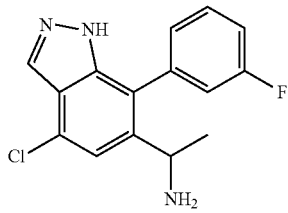 [SMILES: CC(N)c1cc(Cl)c2cn[nH]c2c1-c1cccc(F)c1]

A mixture of 1-[4-chloro-7-(3-fluorophenyl)-1H-indazol-6-yl]ethanone (2.365 g, 8.192 mmol), ammonium acetate (6.31 g, 81.9 mmol) and sodium cyanoborohydride (1.03 g, 16.4 mmol) in methanol (30 mL) and acetonitrile (30 mL) was heated at 65° C. overnight, in a sealed tube. The mixture was then cooled to room temperature and quenched with sat. sodium bicarbonate and then extracted with dichloromethane. The combined extracts were dried over magnesium sulfate and evaporated to dryness to give the crude product (2.37 g). LCMS calculated for $C_{15}H_{11}ClFN_2$ (M−NH₂)⁺: m/z=273.1; Found: 273.0.

Step 6. N-{1-[4-Chloro-7-(3-fluorophenyl)-1H-indazol-6-yl]ethyl}-9H-purin-6-amine

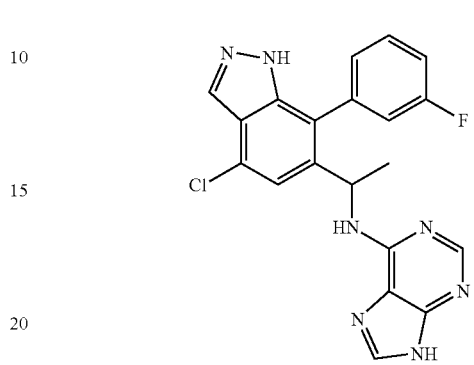

A mixture of 6-bromo-9H-purine (2.4 g, 12 mmol), 1-[4-chloro-7-(3-fluorophenyl)-1H-indazol-6-yl]ethanamine (2.37 g, 8.18 mmol), and N,N-diisopropylethylamine (2.8 mL, 16 mmol) in isopropyl alcohol (30 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min). The fractions were collected and acetonitrile removed in vacuo. The aqueous mixture was then extracted with ethyl acetate. The combined organic layers were washed with brine and dried over magnesium sulfate and concentrated to dryness under reduced pressure to give the desired product (400 mg). LCMS calculated for $C_{20}H_{16}ClFN_7$ (M+H)⁺: m/z=408.1; Found: 408.1. ¹H NMR (DMSO-d₆, 400 MHz) δ 13.02 (1H, s), 12.88 (1H, br s), 8.25 (1H, m), 8.10 (1H, s), 8.07 (1H, s), 8.03 (1H, m), 7.58 (2H, m), 7.33 (1H, m), 7.25 (1H, m), 5.34 (1H, m), 3.32 (1H, br s), 1.40 (3H, d, J=6.4 Hz) ppm.

Example 106

N-{1-[4-Chloro-7-(3,5-difluorophenyl)-1H-indazol-6-yl]ethyl}-9H-purin-6-amine

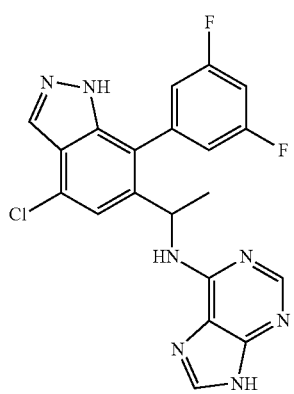 [SMILES: CC(Nc1ncnc2[nH]cnc12)c1cc(Cl)c2cn[nH]c2c1-c1cc(F)cc(F)c1]

Step 1. 1-(4-Chloro-3',5'-difluoro-5-methyl-6-nitro-biphenyl-2-yl)ethanone

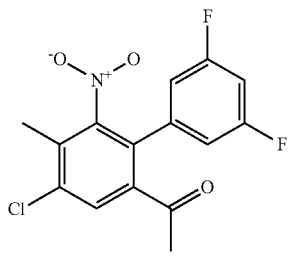

A biphasic solution of 6-acetyl-4-chloro-3-methyl-2-nitrophenyl trifluoromethanesulfonate (9.56 g, 26.4 mmol) and (3,5-difluorophenyl)boronic acid (5.00 g, 31.7 mmol) in toluene (100 mL) and saturated NaHCO$_3$ (80 mL) was bubbled with N$_2$ to degas. Tetrakis(triphenylphosphine)palladium(0) (1.22 g, 1.06 mmol) was added. The reaction mixture was bubbled with N$_2$ for an additional 5 minutes and then heated at 80° C. for 2 hrs. After cooling to room temperature, the mixture was diluted with ethyl acetate. The layers were separated and the aqueous layer was extracted with ethyl acetate. The combined extracts were washed with brine, dried over Na2SO$_4$, filtered and concentrated. The resulting material was purified on silica gel column, eluting with ethyl acetate/hexane, 0-30%, to give the desired product (8.65 g, 100%). LCMS calculated for C$_{15}$H$_{11}$ClFF$_2$NO$_3$ (M+H)$^+$: m/z=326.0; Found: 326.0.

Step 2. 1-(6-Amino-4-chloro-3',5'-difluoro-5-methyl-biphenyl-2-yl)ethanone

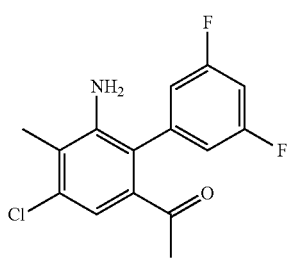 [SMILES: CC(=O)c1cc(Cl)c(C)c(N)c1-c1cc(F)cc(F)c1]

A mixture of 1-(4-chloro-3',5'-difluoro-5-methyl-6-nitro-biphenyl-2-yl)ethanone (8.61 g 26.4 mmol) in 160 mL of methanol was hydrogenated in the presence of 0.86 of 5% Pt/C, under ballon pressure of hydrogen, overnight. After filtering off catalyst, the filtrate was concentrated under reduced pressure to give the desired product. LCMS calculated for C$_{15}$H$_{13}$ClF$_2$NO (M+H)$^+$: m/z=296.1; Found: 296.1.

Step 3. 1-[4-Chloro-7-(3,5-difluorophenyl)-1H-indazol-6-yl]ethanone

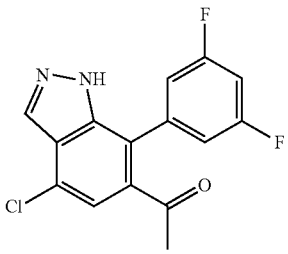 [SMILES: CC(=O)c1cc(Cl)c2cn[nH]c2c1-c1cc(F)cc(F)c1]

To a solution of 1-(6-amino-4-chloro-3',5'-difluoro-5-methylbiphenyl-2-yl) ethanone (7.82 g, 26.4 mmol) in acetic acid (200 mL) was added i-amyl nitrite (3.41 g, 29.1 mmol). The mixture was stirred at room temperature for 30 minutes before being heated at reflux for 1 hour. Upon cooling, the mixture was concentrated and purified by flash chromatography on silica gel, eluting with 0 to 50% ethyl acetate in hexane, to give the desired product (3.3 g, 41%). LCMS calculated for C$_{15}$H$_{10}$ClF$_2$N$_2$O (M+H)$^+$: m/z=307.0; Found: 306.8.

Step 4. 1-[4-Chloro-7-(3,5-difluorophenyl)-1H-indazol-6-yl]ethanamine

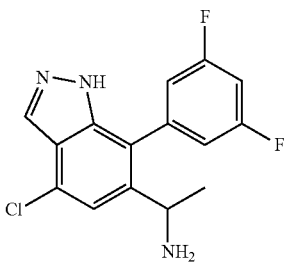 [SMILES: CC(N)c1cc(Cl)c2cn[nH]c2c1-c1cc(F)cc(F)c1]

A mixture of 1-[4-chloro-7-(3,5-difluorophenyl)-1H-indazol-6-yl]ethanone (0.20 g, 0.65 mmol) and ammonium acetate (0.50 g, 6.5 mmol) and sodium cyanoborohydride (0.082 g, 1.3 mmol) in methanol (2 mL) and acetonitrile (2 mL) was heated at 65° C. overnight in a sealed tube. The mixture was then cooled to room temperature and quenched with sat. sodium bicarbonate and then extracted with dichloromethane. The combined extracts were dried over magnesium sulfate and evaporated to dryness to give the crude amine which was used directly in the next step. LCMS calculated for $C_{15}H_{10}ClF_2N_2$ $(M-NH_2)^+$: m/z=291.0; Found: 291.0.

Step 5. N-{1-[4-Chloro-7-(3,5-difluorophenyl)-1H-indazol-6-yl]ethyl}-9H-purin-6-amine

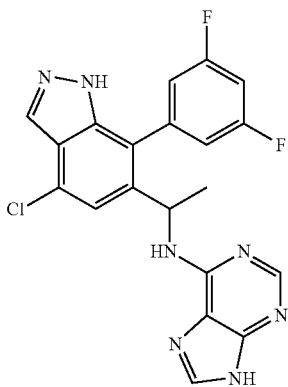

A mixture of 6-bromo-9H-purine (0.19 g, 0.97 mmol), 1 44-chloro-7-(3,5-difluorophenyl)-1H-indazol-6-yl]ethanamine (0.20 g, 0.65 mmol), and N,N-diisopropylethylamine (0.23 mL, 1.3 mmol) in isopropyl alcohol (2 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for $C_{20}H_{15}ClF_2N_7$ $(M+H)^+$: m/z=426.1; Found: 426.1.

Example 107

N-{1-4-Chloro-7-(3,5-difluorophenyl)-1-methyl-1H-indazol-6-yl]ethyl}-9H-purin-6-amine

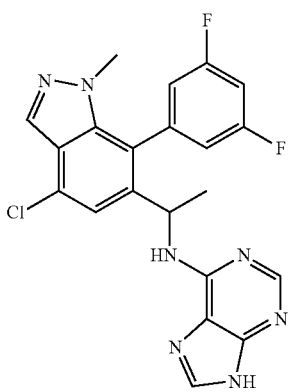 [SMILES: CC(Nc1ncnc2[nH]cnc12)c1cc(Cl)c2cnn(C)c2c1-c1cc(F)cc(F)c1]

Step 1. 1-[4-Chloro-7-(3,5-difluorophenyl)-1-methyl-1H-indazol-6-yl]ethanone

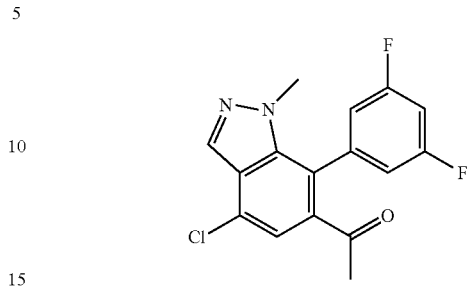

To a mixture of 1-[4-chloro-7-(3,5-difluorophenyl)-1H-indazol-6-yl]ethanone (1.0 g, 3.3 mmol) in N,N-dimethylformamide (20 mL) was added sodium hydride (200 mg, 4.9 mmol). After being stirred at room temperature for 30 minutes, to the resulting mixture was added methyl iodide (0.30 mL, 4.9 mmol). The reaction was stirred at room temperature for another 30 minutes, then quenched with sat. ammonium chloride and extracted with Ethyl acetate. The combined organic layers were washed with water, brine and dried over sodium sulfate, then concentrated to dryness under reduced pressure. The residue was purified on silica gel, eluting with 0 to 30% ethyl acetate in hexane, to give the desired product (0.438 g, 42%). LCMS calculated for $C_{16}H_{12}ClF_2N_2O$ $(M+H)^+$: m/x=321.1; Found: 321.0. The other isomer, 1-[4-chloro-7-(3,5-difluorophenyl)-2-methyl-2H-indazol-6-yl]ethanone, was also isolated in a yield of 47%.

Step 2. 1-[4-Chloro-7-(3,5-difluorophenyl)-1-methyl-1H-indazol-6-yl]ethanamine

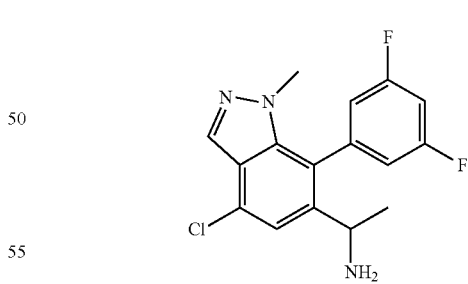

A mixture of 1-[4-chloro-7-(3,5-difluorophenyl)-1-methyl-1H-indazol-6-yl]ethanone (0.438 g, 1.36 mmol), ammonium acetate (1.05 g, 13.6 mmol) and sodium cyanoborohydride (0.172 g, 2.73 mmol) in methanol (5 mL) and acetonitrile (5 mL) was heated at 65° C. overnight, in a sealed tube. The mixture was then cooled to room temperature and quenched with sat. sodium bicarbonate, extracted with dichloromethane. The combined extracts were dried over magnesium sulfate and evaporated to dryness to give the desired product. LCMS calculated for C$_{16}$H$_{12}$ClF$_2$N$_2$ (M−NH$_2$)$^+$: m/z=305.1; Found: 305.0.

Step 3. N-{1-[4-chloro-7-(3,5-difluorophenyl)-1-methyl-1H-indazol-6-yl]ethyl}-9H-purin-6-amine

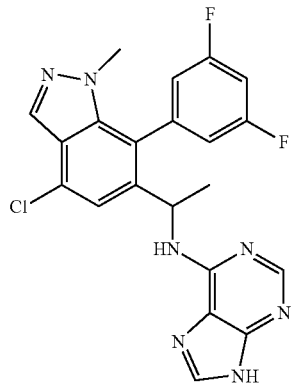 [SMILES: CC(Nc1ncnc2[nH]cnc12)c1cc(Cl)c2cnn(C)c2c1-c1cc(F)cc(F)c1]

A mixture of 6-bromo-9H-purine (0.30 g, 1.5 mmol), 1-[4-chloro-7-(3,5-difluorophenyl)-1-methyl-1H-indazol-6-yl]ethanamine (0.439 g, 1.36 mmol), and N,N-diisopropylethylamine (0.48 mL, 2.7 mmol) in isopropyl alcohol (5 mL) was heated at 90° C. under nitrogen overnight. The mixture was evaporated and the resulting mixture was purified on a RP-HPLC (XBridge C18 column, eluting with a gradient of acetonitrile in water with 0.2% ammonium hydroxide, at a flow rate of 30 mL/min) to give the desired product. LCMS calculated for C$_{21}$H$_{17}$ClF$_2$N$_7$ (M+H)$^+$: m/z=440.1; Found: 440.1. $^1$H NMR (DMSO-d$_6$, 400 MHz) δ 8.29 (1H, br s), 8.10 (1H, s), 8.05 (1H, s), 8.04 (1H, s), 7.62 (1H, s), 7.52 (1H, d, J=8.8 Hz), 7.43 (1H, m), 7.31 (1H, d, J=8.8 Hz), 5.10(1H, br s), 3.41 (3H, s), 3.35 (1H, m), 1.41 (3H, d, J=6.8 Hz) ppm. $^{19}$F NMR (DMSO-d$_6$, 376 MHz) δ −110 ppm.

Example 108

N-{(1S)-1-[5-Chloro-8-(3-fluorophenyl)cinnolin-7-yl]ethyl}-9H-purin-6-amine adipic acid salt (1:1)

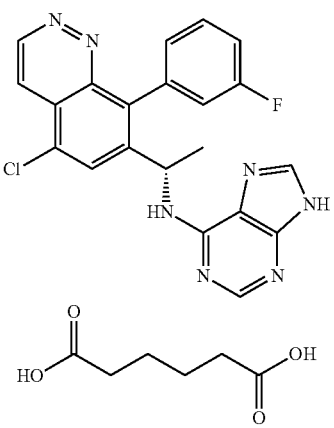

Step A: Methyl 5-chloro-2-hydroxy-4-iodobenzoate

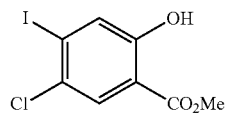

A solution of methyl 2-hydroxy-4-iodobenzoate (470 g, 1.7 mol) in acetic acid (1.9 L) was treated with N-chlorosuccinimide (250 g, 1.9 mol) and heated at 100-110° C. for 1 h. The reaction mixture was cooled to room temperature and the solid that precipitated was filtered, rinsed with acetic acid (250 mL) and water (2×500 mL), and dried on the filter under vacuum overnight to give the desired product (370 g, 70%) as a yellow powder. HPLC 95.8% pure @ 220 nm. LCMS for C$_8$H$_7$ClIO$_3$ (M+H)$^+$: m/z=312.9; Found: 313.0; $^1$H NMR (300 MHz, DMSO-d6): δ 10.5 (s, 1 H), 7.75 (s, 1 H), 7.57 (s, 1 H), 3.83 (s, 3 H).

Step B: Methyl 5-chloro-2-hydroxy-4-[(trimethylsilyl)ethynyl]benzoate

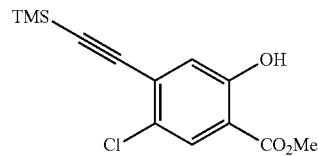 [SMILES: COC(=O)c1cc(Cl)c(C#C[Si](C)(C)C)cc1O]

A solution of methyl 5-chloro-2-hydroxy-4-iodobenzoate (690 g, 2.2 mol), copper (I) iodide (4.2 g, 22 mmol) in triethylamine (5.6 L) was degassed with nitrogen for 5-10 minutes, treated with bis(triphenylphosphine)palladium(II) chloride (16 g, 22 mmol) and (trimethylsilyl)acetylene (470 mL, 3.3 mol), degassed with nitrogen for 2 minutes, and heated at 65° C. The heat was removed and the reaction temperature increased from 65 to 85° C. by itself. The temperature was dropped to 75° C. after 30 minutes with stirring. The reaction was cooled to room temperature, filtered over a pad of celite and rinsed with ethyl acetate (3 L). The filtrate was concentrated and dried on a high vacuum pump for 72 hours to give the desired product (650 g, quantitative) as a yellow solid. HPLC 91.3% pure @ 220 nm. LCMS for C$_{13}$H$_{16}$ClO$_3$Si (M+H)$^+$: m/z=283.1; Found: 282.8; $^1$H NMR (400 MHz, DMSO-d$_6$): δ 10.5 (br s, 1 H), 7.76 (s, 1 H), 7.13 (s, 1 H), 3.85 (s, 3 H), 0.24 (s, 9 H).

Step C: Methyl 5-chloro-2-hydroxy-3-nitro-4-[(trimethylsilyl)ethynyl]benzoate

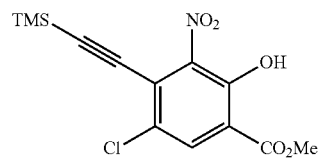 [SMILES: COC(=O)c1cc(Cl)c(C#C[Si](C)(C)C)c([N+](=O)[O-])c1O]

A solution of methyl 5-chloro-2-hydroxy-4-[(trimethylsilyl)ethynyl]benzoate (540 g, 1.9 mol) in acetic acid (3.7 L) was heated at 55-59° C. The heating was discontinued and the reaction mixture was flushed with nitrogen and treated with a solution of nitric acid (120 mL, 2.9 mol) in acetic acid (200 mL, 3.6 mol) over 30 minutes. The reaction temperature reached 98.9° C. The resulting solution was stirred for 30 minutes at which time the temperature went from 98.9 to 87.5° C. The reaction was cooled to room temperature and treated with crushed ice (3.5 kg) in one portion. The reaction mixture temperature dropped to −12° C. The reaction mixture was treated with water (3.5 kg) and and stirred at room temperature for 1 hour. The product was filtered, rinsed with water (2 L), and dried on the filter under vacuum overnight to give the desired product (450 g, 72%) as a yellow solid. HPLC 92.9% pure @ 220 nm. LCMS for $C_{13}H_{15}ClNO_5Si$ (M+H)$^+$: m/z=328.0; Found: 327.9; $^1$H NMR (300 MHz, DMSO-d$_6$): δ 11.2 (br s, 1 H), 8.00 (s, 1 H), 3.89 (s, 3 H), 0.23 (s, 9 H).

Step D: Methyl 4-chloro-3'-fluoro-6-nitro-5-[(trimethylsilyl)ethynyl]biphenyl-2-carboxylate

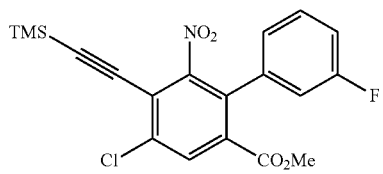

A solution of methyl 5-chloro-2-hydroxy-3-nitro-4-[(trimethylsilyl)ethynyl]benzoate (380 g, 1.2 mol) in toluene (3.7 L) at −12° C. was treated with triethylamine (320 mL, 2.3 mol), followed by trifluoromethanesulfonic anhydride (270 mL, 1.6 mol) dropwise over a 15 minute period (temperature was −3° C. at the end of the addition). The dry ice/isopropanol bath was removed. The reaction mixture was kept at −15 to 20° C. for 3 hours. The reaction mixture was treated with water (3.2 L) and stirred for 20 minutes. The organic layer was separated and rinsed with water (2×1.6 L). The organic layer containing the triflate intermediate was used immediately without further purification. The triflate solution was treated with water (1.9 L), sodium bicarbonate (390 g, 4.6 mol), (3-fluorophenyl)boronic acid (210 g, 1.5 mol) and the mixture was degassed with nitrogen for approximately 10 minutes. The reaction mixture was treated with tetrakis(triphenylphosphine)palladium(0) (27 g, 23 mmol), degassed with nitrogen for an additional 10 minutes, and heated to 80° C. for 3 hours. The reaction mixture was cooled to room temperature, diluted with ethyl acetate (2 L) and water (2 L), and stirred. The organic layer was separated and washed with water (2×2 L) and brine. Celite (150 g) was added to the organic layer and the mixture was stirred for 30 minutes. The organic layer was filtered through a pad of celite, rinsed with ethyl acetate (1 L), and concentrated to give a dark green solid. The solid was diluted with isopropanol (3 L) and heated to 70° C. which gave a dark green solution. The solution was stirred at room temperature for 2 hours and at 0° C. for 30 minutes. The solid was collected by filtration, rinsed with isopropanol (800 mL), and dried to give the desired product (330 g, 71%) as a green solid. HPLC 98.9% pure @ 220 nm. LCMS for $C_{19}H_{18}ClFNO_4Si$ (M+H)$^+$: m/z=406.1; Found: 405.9; $^1$H NMR (300 MHz, DMSO-d6): δ 8.27 (s, 1 H), 7.52-7.41 (m, 1 H), 7.35-7.23 (m, 1 H), 7.19-7.11 (m, 1 H), 7.09-7.02 (m, 1 H), 3.58 (s, 3 H), 0.22 (s, 9 H).

Step E: Methyl 6-amino-4-chloro-3'-fluoro-5-[(trimethylsilyl)ethynyl]biphenyl-2-carboxylate

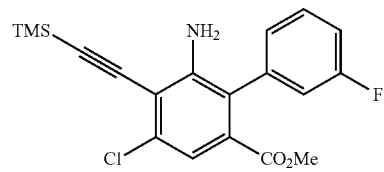

A solution of methyl 4-chloro-3'-fluoro-6-nitro-5-[(trimethylsilyl)ethynyl]biphenyl-2-carboxylate (330 g, 780 mmol) in ethyl acetate (1 L) was treated with methanol (1 L) and saturated aqueous ammonium chloride solution (670 mL, 10 mol). The mixture was cooled with an ice-water bath and treated with <10 micron zinc dust (310 g, 4.7 mol) in portions with internal temperature at 15 to 45° C. After addition, the ice bath was removed and the reaction mixture was stirred for 3 hours. The reaction mixture was filtered over a pad of celite and rinsed with ethyl acetate (2×1 L). The combined filtrate was diluted with brine (500 mL) and stirred for 10 minutes. The brine layer was separated and extracted with ethyl acetate (300 mL). The combined organic layers were dried over sodium sulfate, filtered, and concentrated to give a green oil which contained approximately 12% water. This material was dried with azeotropic drying with toluene to give the desired product (300 g, quantitative) as a green semi-solid. HPLC 90.5% pure @ 220 nm. LCMS for $C_{19}H_{20}ClFNO_2Si$ (M+H)$^+$: m/z=376.1; Found: 376.0; $^1$H NMR (300 MHz, DMSO-d6): δ 7.56-7.42 (m, 1H), 7.28-7.16 (m, 7.28-7.16 (m, 1 H), 7.07 (s, 1 H), 7.06-6.94 (m, 2 H), 5.06 (s, 2 H), 3.47 (s, 3 H), 0.25 (s, 9 H).

Step F: Methyl 4-chloro-3'-fluoro-6-[(E)-pyrrolidin-1-yldiazenyl]-5-[(trimethylsilyl)ethynyl]biphenyl-2-carboxylate

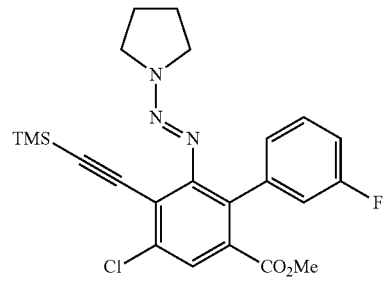 [SMILES: COC(=O)c1cc(Cl)c(C#C[Si](C)(C)C)c(/N=N/N2CCCC2)c1-c1cccc(F)c1]

A solution of methyl 6-amino-4-chloro-3'-fluoro-5-[(trimethylsilyl)ethynyl]biphenyl-2-carboxylate (840 g, 2.2 mol) in tetrahydrofuran (12 L) was cooled with an ice-water bath under nitrogen and treated with boron trifluoride etherate (600 mL, 4.7 mol) dropwise [internal temperature changed from 1.4° C. to 4.4° C.] followed by tert-butyl nitrite (800 mL, 6.7 mol) dropwise over 20 minutes [internal temperature rose from 3.1° C. to 8.9° C.]. After the addition was complete a solid formed to give a suspension which was stirred at 0-5° C. for 3 hours. The reaction mixture was treated with pyrrolidine (650 mL, 7.8 mol) in portions over 10 minutes [internal temperature changed from 1° C. to 14° C. gradually] and the reaction mixture was stirred for additional 10 minutes. The reaction mixture was treated with 7.0 M ammonium chloride in water (2.5 L, 17 mol). The organic layer was separated and the aqueous layer was extracted with ethyl acetate (1 L). The tetrahydrofuran layer was stirred with pre-mixed 2.0 M hydrogen chloride in water (1 L, 2.0 mol) and brine (2 L) for 10 minutes. The tetrahydrofuran layer was separated and stirred with 0.5 M sodium carbonate in water (4 L) and brine (1.0 L), and concentrated to give the crude desired product (theoretical yield 1.1 kg) as a brown oil. This material was used in the next step without further purification. A small sample was purified for spectroscopic analysis. LCMS for $C_{23}H_{26}ClFN_3O_2Si$ (M+H)$^+$: m/z=458.1; Found: 458.0; $^1$H NMR (400 MHz, DMSO-$d_6$): δ 7.64 (s, 1H), 7.36-7.30 (m, 1 H), 7.13-7.10 (m, 1 H), 6.91-6.84 (m, 2 H), 3.70 (br s, 2 H), 3.52 (s, 3 H), 3.18 (br s, 2 H), 1.85 (br s, 4 H), 0.18 (s, 9 H).

Step G: 4-Chloro-5-ethynyl-3'-fluoro-6-[(E)-pyrrolidin-1-yldiazenyl]biphenyl-2-carboxylic acid

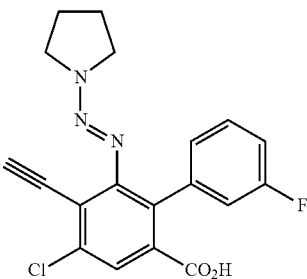 [SMILES: C#Cc1c(Cl)cc(C(=O)O)c(-c2cccc(F)c2)c1/N=N/N1CCCC1]

A solution of methyl 4-chloro-3'-fluoro-6-[(E)-pyrrolidin-1-yldiazenyl]-5-[(trimethylsilyl)ethynyl]biphenyl-2-carboxylate (1.0 kg, 2.2 mol) in tetrahydrofuran (3 L) and methanol (0.86 L) was treated with 2.0 M sodium hydroxide in water (3.4 L, 6.7 mol) and heated to 60° C. in 30 minutes and kept at an internal temperature of 60-63° C. for 90 minutes. The reaction mixture was cooled to 1 to 5° C. with an ice bath, treated with 3.0 M hydrogen chloride in water (2.8 L, 8.3 mol) in portions (temperature reached 16° C.) until the pH reached 1-2. The reaction mixture was diluted with ethyl acetate (2 L) and stirred for 20 minutes. The aqueous layer was separated and extracted with ethyl acetate (1 L). The combined organic layers were washed with water (2×3 L) and brine (300 mL), dried over sodium sulfate, filtered, and concentrated to give the desired product as an oil. This material was azeotroped with toluene (1 L) to give the desired product (theoretical yield 830 g) as a dark syrup. This material was used in the next step without further purification.

Step H: 4-Chloro-5-ethynyl-3'-fluoro-N-methoxy-N-methyl-6-[(E)-pyrrolidin-1-yldiazenyl]biphenyl-2-carboxamide

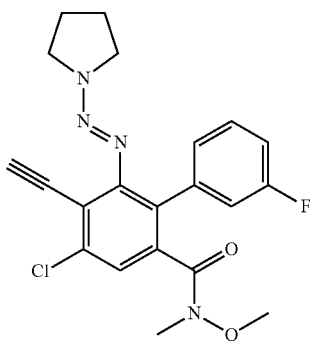 [SMILES: C#Cc1c(Cl)cc(C(=O)N(C)OC)c(-c2cccc(F)c2)c1/N=N/N1CCCC1]

A solution of 4-chloro-5-ethynyl-3'-fluoro-6-[(E)-pyrrolidin-1-yldiazenyl]biphenyl-2-carboxylic acid (830 g, 2.2 mol), N,O-dimethylhydroxylamine hydrochloride (280 g, 2.9 mol), 1-hydroxybenzotriazole hydrate (360 g, 2.4 mol), and N,N-diisopropylethylamine (1.4 L, 7.8 mol) in tetrahydrofuran (5 L) was treated with EDCI HCl (520 g, 2.7 mol) and stirred at room temperature for 36 hours. The reaction mixture was cooled to approximately 5° C. and treated with 2.0 M hydrogen chloride in water (3.4 L, 6.7 mol) in portions while maintaining the internal temperature lower than 10° C. The organic layer was separated and the aqueous layer was extracted with tetrahydrofuran (2 L). The combined organic layers (~6 L, pH ~5) were washed with 2.0 M hydrogen chloride in water (2 L), 0.5 M sodium carbonate in water (2 L), and brine, dried over sodium sulfate, filtered, and concentrated to give a crude oil. This material was azeotroped with toluene to give the desired product (theoretical yield 930 g) as a brown oil. This material was used in the next step without further purification. A small sample was purified for spectroscopic analysis. LCMS for $C_{21}H_{21}ClFN_4O_2$ (M+H)$^+$: m/z=415.1; Found: 415.0; $^1$H NMR (400 MHz, DMSO-d6): δ 7.44 (s, 1H), 7.35-7.29 (m, 1H), 7.12-7.06 (m, 1H), 6.93-

6.84 (m, 2H), 4.48 (s, 1H), 3.62-3.58 (m, 2H), 3.29 (s, 3H), 3.25-3.17 (m, 2H), 2.93 (s, 15 H), 2.85 (s, 1.5H), 1.89-1.77 (m, 4H).

Step I: 1-{4-Chloro-5-ethynyl-3'-fluoro-6-[(E)-pyrrolidin-1-yldiazenyl]biphenyl-2-yl}ethanone

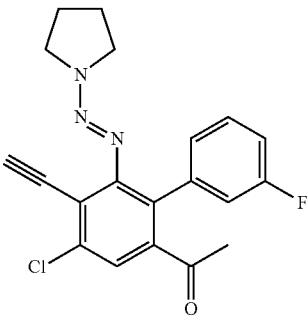 [SMILES: C#Cc1c(Cl)cc(C(C)=O)c(-c2cccc(F)c2)c1/N=N/N1CCCC1]

A solution of 4-chloro-5-ethynyl-3'-fluoro-N-methoxy-N-methyl-6-[(E)-pyrrolidin-1-yldiazenyl]biphenyl-2-carboxamide (930 g, 2.2 mol) in tetrahydrofuran (4.3 L) at 0° C. under nitrogen was treated with 3.0 M methylmagnesium chloride in tetrahydrofuran (2.2 L, 6.7 mol) dropwise over 45 minutes. Gas formation was observed and the internal temperature ranged from 1-8° C. The ice bath was removed and the reaction mixture was stirred at room temperature for 70 minutes. The reaction mixture was cooled to 0-5° C. and treated with 2.0 M hydrogen chloride in water (4.1 L, 8.3 mol) dropwise with gas formation observed. The solution was diluted with ethyl acetate (2 L) and stirred for 10 min. The aqueous layer was separated and extracted with ethyl acetate (1 L). The combined organic layers were washed with brine (0.7 L, 4 mol), dried over sodium sulfate, filtered, and concentrated to an oil. This material was azeotroped with toluene (1 L) to give the desired product. A small sample was purified by silica gel column for spectroscopic analysis. LCMS for $C_{20}H_{18}ClFN_3O$ $(M+H)^+$: m/z=370.1; Found: 370.0; $^1H$ NMR (400 MHz, DMSO-$d_6$): δ 7.54 (s, 1H), 7.37-7.31 (m, 1H), 7.14-7.09 (m, 1H), 6.94-6.86 (m, 2H), 4.54 (s, 1H), 3.68-3.59 (m, 2H), 3.22-3.13 (m, 2H), 2.11 (s, 3H), 1.89-1.78 (m, 4H).

Step J: (1R)-1-{4-Chloro-5-ethynyl-3'-fluoro-6-[(E)-pyrrolidin-1-yldiazenyl]biphenyl-2-yl)ethanol

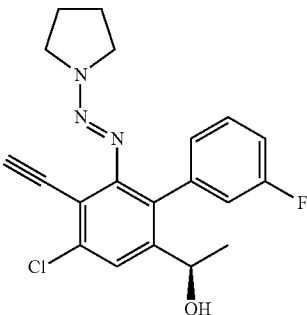 [SMILES: C#Cc1c(Cl)cc([C@@H](C)O)c(-c2cccc(F)c2)c1/N=N/N1CCCC1]

A solution of (3aS)-1-methyl-3,3-diphenyltetrahydro-3H-pyrrolo[1,2-c][1,3,2]oxazaborole (280 g, 1.0 mol) in tetrahydrofuran (2.8 L) at room temperature under an atmosphere of nitrogen was treated with 1.0 M borane-THF complex in THF (1.2 L, 1.2 mol) in small portions, stirred for 15 minutes, and then cooled to −20° C. The reaction mixture was treated with a solution of 1-{4-chloro-5-ethynyl-3'-fluoro-6-[(E)-pyrrolidin-1-yldiazenyl]biphenyl-2-yl}ethanone (380 g, 1.0 mol) in anhydrous tetrahydrofuran (3.0 L) dropwise over 60 min with the internal temperature rising from −20 to −12° C. The flask that contained the ketone was rinsed with tetrahydrofuran (500 mL) and added dropwise to the reaction mixture. The reaction mixture was stirred at −12 to −10° C. for 30 minutes. The reaction mixture was quenched with water (440 mL, 24 mol) at −10° C. over 10 minutes (temperature rose to 0° C.), warmed to room temperature, treated with 10% potassium carbonate in water (3.0 L, 2.1 mol), and stirred for 20 minutes. The organic layer was separated, diluted with ethyl acetate (2 L) and hexanes (0.5 L) and washed with 0.5 M citric acid in water (3.0 L, 1.5 mol), 1.0 M hydrogen chloride in water (3.0 L, 3.0 mol), and 0.5 M citric acid in water (3.0 L, 1.5 mol). The organic layer was washed with brine, dried over sodium sulfate, filtered, and concentrated to give the desired product (470 g, theoretical 380 g). The main impurities were the alcohol with triazene moiety removed and the hydrolyzed ligand. The product had ~91 ee %. This material was used directly in the next step without further purification.

Step K: (1R)-1-[5-Chloro-8-(3-fluorophenyl)cinnolin-7-yl]ethanol

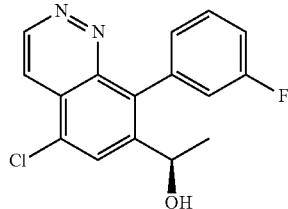 [SMILES: C[C@@H](O)c1cc(Cl)c2ccnnc2c1-c1cccc(F)c1]

A solution of (1R)-1-(4-chloro-5-ethynyl-3'-fluoro-6-[(E)-pyrrolidin-1-yldiazenyl]biphenyl-2-yl}ethanol (20 g, 54 mmol, ~70% pure by HPLC) [CAUTION: this material was shown to exhibit a large energy release in its solid state during DSC analysis. Care should be taken in heating up this material in solution as an mild exotherm was observed in the initial heating of this reaction] in 1,2-dichlorobenzene (500 mL) was degassed with nitrogen for 10-15 minutes. The reaction mixture was heated in an oil bath that was pre-heated to 154-155° C. After 80-90 minutes, the heating was discontinued and the reaction mixture was cooled to room temperature, diluted with hexanes (500 mL), and stirred. Solid precipitated and settled at the bottom of the flask. The upper clear solution was filtered under vacuum through a pad of silica gel (30 g) packed in a filter funnel. The solid was rinsed with hexanes (100-200 mL) and the solution was filtered. The silica gel was mixed with the solid, diluted with dichloromethane (250 mL), and concentrated to dryness for solid loading flash column purification. The crude material adsorbed on silica gel was purified by flash column chromatography using ethyl acetate in hexanes (0 to 40% in 12 column volumes and then at 40% for 8 column volumes) to give the desired product (yields ranged from 5.6 to 7 g) as a brown foam. LCMS for $C_{16}H_{13}ClFN_2O$ $(M+H)^+$: m/z=303.1; Found: 303.0; $^1H$ NMR (300 MHz, CDCl$_3$): δ 9.41 (d, J=6.2 Hz, 1H), 8.22-8.19

(m, 2H), 7.50-7.42 (m, 1H), 7.21-6.99 (m, 3H), 5.07-4.99 (m, 1H), 2.14-2.08 (m, 1H), 1.46-1.42 (m, 3H).

Step L: 7-[(1S)-1-Azidoethyl]-5-chloro-8-(3-fluorophenyl)cinnoline

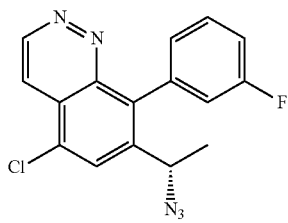

A solution of (1R)-1-[5-chloro-8-(3-fluorophenyl)cinnolin-7-yl]ethanol (58 g, 190 mmol) in methylene chloride (580 mL) was treated with N,N-diisopropylethylamine (53 mL, 300 mmol), cooled to 0-5° C., treated with methanesulfonyl chloride (22 mL, 290 mmol) dropwise, and stirred at 0-5° C. for 1 hour. The reaction mixture was treated with water (200 mL) and stirred for 5 min. The organic layer was separated and washed with brine (200 mL), dried over sodium sulfate, filtered, and concentrated to a crude solid. This material was azeotroped with toluene (200 mL) to give 82 g of the mesylate intermediate. A solution of the mesylate in N,N-dimethylformamide (580 mL) was treated with sodium azide (37 g, 570 mmol) and stirred at room temperature overnight. The reaction mixture was diluted with 5% sodium bicarbonate (1.5 L) over 15 minutes and stirred at room temperature for 1 hour at which time a solid precipitated. The product was collected by filtration, rinsed with water (500 mL), and dried on the filter under vacuum for 17 hours to give the desired product (48 g, 77%) as an off-white solid. LCMS for $C_{16}H_{12}ClFN_5$ (M+H)$^+$: m/z=328.1; Found: 328.0; $^1$H NMR (300 MHz, DMSO-d6): δ 9.54 (d, J=5.9 Hz, 1H), 8.36 (d, J=5.9 Hz, 1H), 8.24 (d, J=1.2 Hz, 1H), 7.64-7.53 (m, 1H), 7.40-7.28 (m, 1H), 7.26-7.16 (m, 2H), 4.86-4.78 (m, 1H), 1.50 (d, J=6.8 Hz, 3H).

Step M: (1S)-1-[5-Chloro-8-(3-fluorophenyl)cinnolin-7-yl]ethanamine

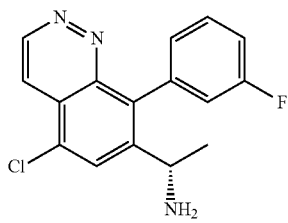

A solution of 7-[(1S)-1-azidoethyl]-5-chloro-8-(3-fluorophenyl)cinnoline (48 g, 150 mmol) in methanol (430 mL) was treated with sodium iodide (130 g, 880 mmol) and stirred at room temperature for 10 minutes. The reaction mixture was cooled with a water bath. The reaction mixture was treated with chlorotrimethylsilane (110 mL, 880 mmol) dropwise over 20 minutes while maintaining the internal temperature at 28-35° C. The reaction mixture turned dark red and the stirring was continued for 26 min. After 42 min, the reaction mixture was treated with a solution of sodium sulfite (130 g, 1.0 mol) in water (430 mL). The dark red color of the solution faded and gave a yellow suspension. The reaction mixture was stirred for 30 minutes and then concentrated under reduced pressure to remove the methanol. The mixture was adjusted to pH>11 with 3 N NaOH solution and extracted with dichloromethane. The pH of the solution changed during the work-up, potentially due to the slow hydrolysis of TMSCl. The pH needed to be checked regularly and basified to pH>11 by addition of 3 N NaOH. The combined organic extracts were washed with brine (50 mL), dried over sodium sulfate, filtered, and concentrated to give the desired product (43 g, 96%) as a solid. LCMS for $C_{16}H_{14}ClFN_3$ (M+H)$^+$: m/z=302.1; Found: 302.0; $^1$H NMR (300 MHz, DMSO-d$_6$): δ 9.47 (d, J=5.9 Hz, 1H), 8.41 (d, J=1.9 Hz, 1H), 8.29 (d, J=5.9 Hz, 1H), 7.59-7.49 (m, 1H), 7.34-7.14 (m, 3H), 4.04-3.95 (m, 1H), 2.22 (br s, 2H), 1.21-1.16 (m, 3H).

Step N: (2R,3R)-2,3-Dihydroxysuccinic acid-(1S)-1-[5-chloro-8-(3-fluorophenyl)cinnolin-7-yl]ethanamine (0.75:1)

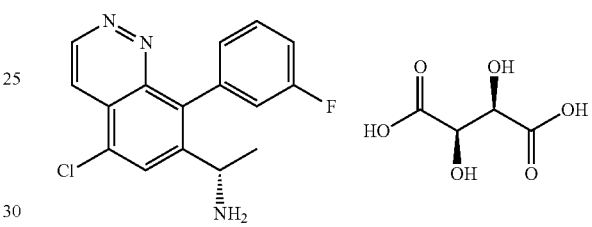

A solution of (1S)-1-[5-chloro-8-(3-fluorophenyl)cinnolin-7-yl]ethanamine (43 g, 140 mmol, 80-90% ee) in ethanol (640 mL) at 60° C. was treated with a solution of L-tartaric acid (20 g, 130 mmol) in ethanol (430 mL). The flask containing the acid was rinsed with ethanol (12 ml) and the rinse solution was added to the reaction mixture at 60° C. The reaction mixture was stirred at 60° C. for 15 minutes and at room temperature for 18 hours. The solid that precipitated was collected by filtration and rinsed with ice-cold ethanol (9 mL) followed by 2-methoxy-2-methylpropane (3×18 ml) to give the desired product (43 g, 73%) as an off-white solid with 99.4% ee. $^1$H NMR determined that the amine to acid ratio was 1:0.75. LCMS for the free amine $C_{16}H_{14}ClFN_3$ (M+H)$^+$: m/z=302.1; Found: 302.0; $^1$H NMR (400 MHz, DMSO-d$_6$): δ 9.53 (d, J=6.0 Hz, 1H), 8.47 (d, J=0.6 Hz, 1H), 8.35 (d, J=6.0 Hz, 1H), 7.62-7.54 (m, 1H), 7.37-7.19 (m, 3H), 4.18-4.13 (m, 1H), 3.92 (s, 1.5H, tartaric acid), 1.38-1.34 (m, 3H).

Step O: (1S)-1-[5-Chloro-8-(3-fluorophenyl)cinnolin-7-yl]ethanamine

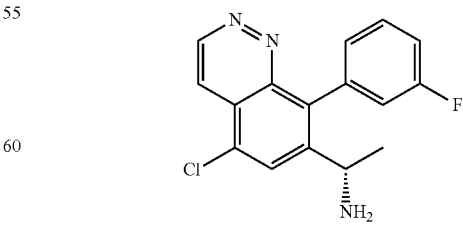

A solution of (2R,3R)-2,3-dihydroxysuccinic acid-(1S)-1-[5-chloro-8-(3-fluorophenyl)cinnolin-7-yl]ethanamine (0.75:1) (43 g, 103 mmol) in methylene chloride (570 mL)

was treated with 2.0 M sodium carbonate in water (400 mL, 800 mmol) was added. The reaction mixture was treated with additional methylene chloride (400 mL) to dissolve the solid that had formed a ball. The methylene chloride solution was separated and concentrated to give the desired product (29 g, 94%) as an off-white solid. This material was used directly in the next step without further purification.

Step P: N-{(1S)-1-[5-Chloro-8-(3-fluorophenyl)cinnolin-7-yl]ethyl}-9H-purin-6-amine

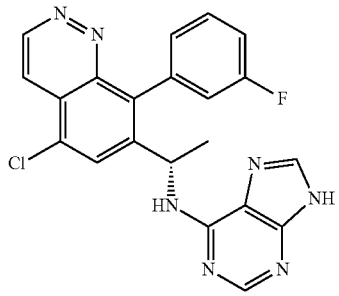

A solution of (1S)-1-[5-chloro-8-(3-fluorophenyl)cinnolin-7-yl]ethanamine (29 g, 96 mmol), 6-chloropurine (19 g, 130 mmol), sodium bicarbonate (8.1 g, 96 mmol) in 1-butanol (580 mL) was degassed with nitrogen for 5 min and heated at 105° C. under nitrogen for 6 hours, 20 minutes. The reaction mixture was treated with N,N-diisopropylethylamine (1.8 mL, 10 mmol), heated for an additional 10 h and 40 min, and allowed to cool to room temperature in 5 hours. The reaction mixture was cooled to 4-5° C. for 20 minutes and the solid that precipitated was filtered. The solid and filtrate were processed separately.

The solid (~55 g, contained inorganic salt) was dissolved in dichloromethane (500 mL) and the solution was rinsed with 10% acetic acid (3×200 mL). The organic layer was washed with 10% sodium carbonate (200 mL). The solid that precipitated was diluted with water (200 mL) and dichloromethane (400 mL) and filtered. The organic layer in the filtrate was separated. The solid was washed with water and dissolved in dichloromethane and methanol The combined organic layer was washed with brine (100 mL) and dried with sodium sulfate, filtered, and concentrated to give 30.8 g of an off-white solid. The 30.8 g of product was diluted with dichloromethane (800 mL) and methanol (20 mL) and heated to 40° C. Ethyl acetate (300 mL) was added portion by portion while distilling off the dichloromethane. The ending distilling temperature was 58° C. The mixture was cooled to 22° C. The product was collected by filtration, rinsed with ethyl acetate (50 mL), dried on the filter under vacuum for 2 hours to give 40 g of partially dried desired product.

Separately, the above filtrate from the first filtration was concentrated. The concentrated residue was dissolved in dichloromethane (500 mL) and washed with 2.5% sodium carbonate (2×250 mL), 10% acetic acid (2×250 mL), and 10% sodium carbonate (500 mL). The organic layer was filtered and diluted with methanol (50 mL) and ethyl acetate (300 mL). The dichloromethane was distilled off until the internal temperature reached 61° C. The solution was cooled to 30° C. and the product was filtered and rinsed with ethyl acetate (50 mL). The solid was dried on the filter under vacuum for 16 hours to give and additional 7.8 g of the desired product. This material was combined with the partially dried material (40 g) and used directly in the salt formation.

Step Q: Hexanedioic acid-N-{(1S)-1-[5-chloro-8-(3-fluorophenyl)cinnolin-7-yl]ethyl}-9H-purin-6-amine (1:1)

A solution of N-{(1S)-1-[5-chloro-8-(3-fluorophenyl)cinnolin-7-yl]ethyl}-9H-purin-6-amine (10 g, 24 mmol) and hexanedioic acid (7.0 g, 48 mmol) in isopropyl alcohol (240 mL) was heated at 69° C. for 30 min which gave a milky solution. The reaction mixture was treated with heptane (120 mL) and heated for an additional 30 minUTES which gave a clear solution. The solution was cooled to 30° C. slowly and then to room temperature. The solid that precipitated was collected by filtration, rinsed with heptane (100 mL), and dried on the filter under vacuum for 2 d to give the desired product (12 g, 91%) as an off-white solid. LCMS for $C_{21}H_{16}ClFN_7$ (M+H)$^+$: m/z=420.1; Found: 420.3; $^1$H NMR (500 MHz, DMSO-d$_6$): δ 12.9 (br s, 1H), 12.0 (br s, 2H), 9.47 (d, J=6.0 Hz, 1H), 8.49-8.43 (m, 1H), 8.41-8.31 (m, 1H), 8.25 (d, J=6.0 Hz, 1H), 8.14-8.05 (m, 2H), 7.68-7.55 (m, 2H), 7.37-7.23 (m, 2H), 5.46-5.34 (m, 1H), 2.22-2.17 (m, 4H), 1.52-1.47 (m, 7H).

Alternatively, the adipic salt was formed by heating a solution of the free base product of Example 17 (10 g, 24 mmol) and hexanedioic acid (7.0 g, 48 mmol) in isopropyl alcohol (240 mL) was heated at 69° C. for 30 min which gave a milky solution. The reaction mixture was treated with heptane (120 mL) and heated for an additional 30 min which gave a clear solution. The solution was cooled to 30° C. slowly and then to room temperature. The solid that precipitated was collected by filtration, rinsed with heptane (100 mL), and dried on the filter under vacuum for 2 days to give the desired product (12 g, 91%) as an off-white solid.

The crystallinity of the salt was confirmed by X-ray powder diffraction (XRPD) (FIG. 1; Table 1) and further supported by differential scanning calorimetry (FIG. 2) and thermogravimetric analysis (TGA) (FIG. 3).

The DSC thermogram revealed one major endothermic event with an onset of the peak at 179° C. with a peak maximum at 182° C. (see FIG. 2). The DSC was scanned from an initial temperature of 30° C. to a final temperature of 350° C. using a heating rate of 10° C./min. The TGA thermogram was obtained when the sample was heated from room temperature to 300° C. at a heating rate of 20° C./min.

DSC parameters:_Mettler Toledo Differential Scanning calorimetry (DSC) instrument, Model No. 822; Aluminum sample pan (40 µL); general condition: 30-280° C. at 10° C./min.

TGA parameters: TA Instrument, Model No. Q500. The general starting method condition is: ramp at 20° C./min. to 600° C.

XRPD conditions: Rigaku MiniFlex X-ray Powder Diffractometer (XRPD) instrument; X-ray radiation is from Copper Cu at 1.054056 Å with K$_β$ filter; sample powder is dispersed on a zero-background sample holder; and general measurement conditions are:

Start Angle—3

Stop Angle—45

Sampling—0.02

Scan speed—2

TABLE 1

| 2-Theta | d(Å) | BG | Height | H % | Area | A % | FWHM |
|---|---|---|---|---|---|---|---|
| 4.013 | 21.9994 | 10 | 300 | 24.4 | 19287 | 100 | 1.092 |
| 7.127 | 12.3936 | 173 | 133 | 10.8 | 3191 | 16.5 | 0.407 |
| 8.489 | 10.4072 | 159 | 256 | 20.8 | 3609 | 18.7 | 0.239 |
| 10.101 | 8.7503 | 151 | 518 | 42 | 9162 | 47.5 | 0.301 |
| 11.635 | 7.5996 | 153 | 125 | 10.1 | 2360 | 12.2 | 0.322 |
| 12.328 | 7.174 | 157 | 205 | 16.6 | 4361 | 22.6 | 0.362 |
| 13.703 | 6.4569 | 164 | 65 | 5.3 | 1244 | 6.5 | 0.323 |
| 14.262 | 6.205 | 158 | 142 | 11.5 | 4451 | 23.1 | 0.534 |
| 14.867 | 5.9538 | 171 | 297 | 24.1 | 3939 | 20.4 | 0.225 |
| 16.467 | 5.3788 | 145 | 90 | 7.3 | 1360 | 7.1 | 0.258 |
| 17.52 | 5.0579 | 148 | 77 | 6.2 | 1448 | 7.5 | 0.322 |
| 19.316 | 4.5914 | 163 | 217 | 17.6 | 3067 | 15.9 | 0.24 |
| 20.221 | 4.3881 | 181 | 668 | 54.2 | 10782 | 55.9 | 0.275 |
| 20.571 | 4.314 | 183 | 88 | 7.2 | 1926 | 10 | 0.371 |
| 21.422 | 4.1446 | 194 | 595 | 48.3 | 8733 | 45.3 | 0.249 |
| 22.226 | 3.9964 | 216 | 103 | 8.3 | 1267 | 6.6 | 0.209 |
| 23.016 | 3.8611 | 246 | 250 | 20.3 | 3344 | 17.3 | 0.227 |
| 24.097 | 3.6902 | 259 | 1233 | 100 | 18856 | 97.8 | 0.26 |
| 24.818 | 3.5846 | 236 | 158 | 12.8 | 3774 | 19.6 | 0.406 |
| 25.164 | 3.5361 | 198 | 95 | 7.7 | 2914 | 15.1 | 0.524 |
| 26.198 | 3.3988 | 196 | 287 | 23.3 | 6411 | 33.2 | 0.38 |
| 28.418 | 3.1381 | 181 | 500 | 40.5 | 6143 | 31.9 | 0.209 |
| 29.33 | 3.0427 | 150 | 113 | 9.1 | 2324 | 12.1 | 0.35 |
| 30.398 | 2.9381 | 149 | 78 | 6.4 | 2437 | 12.6 | 0.529 |
| 30.746 | 2.9056 | 151 | 99 | 8 | 2437 | 12.6 | 0.418 |
| 31.364 | 2.8498 | 145 | 75 | 6.1 | 1318 | 6.8 | 0.3 |
| 32.436 | 2.758 | 145 | 112 | 9 | 1671 | 8.7 | 0.255 |
| 33.934 | 2.6396 | 156 | 55 | 4.5 | 1845 | 9.6 | 0.566 |
| 36.05 | 2.4894 | 131 | 40 | 3.2 | 1692 | 8.8 | 0.721 |
| 37.12 | 2.4201 | 120 | 60 | 4.9 | 2141 | 11.1 | 0.605 |
| 39.59 | 2.2746 | 149 | 59 | 4.8 | 1713 | 8.9 | 0.493 |
| 40.256 | 2.2384 | 153 | 57 | 4.7 | 1760 | 9.1 | 0.52 |
| 40.589 | 2.2209 | 147 | 274 | 22.2 | 5309 | 27.5 | 0.329 |

Example A

PI31Dδ Scintillation Proximity Assay

Materials: [γ-$^{33}$P]ATP (10 mCi/mL) was purchased from Perkin-Elmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, MgCl$_2$, DTT, EDTA, MOPS and CHAPS were purchased from Sigma-Aldrich (St. Louis, Mo.). Wheat Germ Agglutinin (WGA)YSi SPA Scintillation Beads was purchased from GE healthcare life sciences (Piscataway, N.J.).

Assay: The kinase reaction was conducted in polystyrene 384-well matrix white plate from Thermo Fisher Scientific in a final volume of 25 μL. Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM MgCl$_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P] ATP, 4 nM PI3Kδ. Reactions were incubated for 210 minutes and terminated by the addition of 40 μL SPA beads suspended in quench buffer: 150 mM potassium phosphate pH 8.0, 20% glycerol. 25 mM EDTA, 400 μM ATP. The final concentration of SPA beads is 1.0 mg/mL. After the plate sealing, plates were shaken overnight at room temperature and centrifuged at 1800 rpm for 10 minutes, the radioactivity of the product was determined by scintillation counting on Topcount (Perkin-Elmer). IC$_{50}$ determination was performed by fitting the curve of percent control activity versus the log of the inhibitor concentration using the GraphPad Prism® 3.0 software. Table 1 shows PI3K δ scintillation proximity assay data for certain compounds described herein.

TABLE 1

IC$_{50}$ data for PI3Kδ scintillation proximity assay

| Example | IC$_{50}$ (nM) |
|---|---|
| 1 | C |
| 2 | F |
| 3 | A |
| 4 | E/E$^a$ |
| 5 | A |
| 6 | E |
| 7 | F/E$^a$ |
| 8 | D |
| 9 | E |
| 10 | C/A$^a$ |
| 11 | A |
| 12 | F/A$^a$ |
| 13 | A |
| 14 | C |
| 15 | A |
| 16 | A |
| 17 | A |
| 18 | F |
| 19 | C |
| 20 | A |
| 21 | F |
| 22 | A |
| 23 | A |
| 24 | F |
| 25 | F |
| 26 | D |
| 27 | B |
| 28 | A |
| 29/30 | C/F |
| 31 | E |
| 32/33 | F/A |
| 34/35 | B/F |
| 36/37 | A/E |
| 38/39 | A/F |
| 40 | F |
| 41 | E |
| 42 | E |
| 43 | A |
| 44 | C |
| 45 | A |
| 46 | C |
| 47 | E |
| 48 | A/F$^a$ |
| 49 | F |
| 50 | C |
| 51 | B |
| 52 | B |
| 53 | F/C$^a$ |
| 54 | B |
| 55 | A |
| 56 | A |
| 57 | D |
| 58 | A |
| 59 | C |
| 60 | C |
| 61 | D |
| 62 | C |
| 63 | C/C$^a$ |
| 64 | C |
| 65 | B |
| 66 | A |
| 67 | C/D$^a$ |
| 68 | B/A |
| 69 | A |
| 70 | B |
| 71 | B |
| 72 | F |
| 73 | C |
| 74 | A |
| 75 | F |

TABLE 1-continued

IC$_{50}$ data for PI3Kδ scintillation proximity assay

| Example | IC$_{50}$ (nM) |
|---|---|
| 76 | D/D$^a$ |
| 77 | F/A$^a$ |
| 78 | F/A$^a$ |
| 79 | B/A$^a$ |
| 80 | D/A$^a$ |
| 81 | C |
| 82 | A |
| 83 | A |
| 84 | A |
| 85 | A |
| 86 | A |
| 87 | A |
| 88 | A |
| 89 | B |
| 90 | A |
| 91 | C |
| 92 | C |
| 93 | D |
| 94 | A |
| 95 | A |
| 96 | A |
| 97 | A |
| 98 | A |
| 99 | A |
| 100 | A |
| 101 | A |
| 102 | A/F$^a$ |
| 103 | A |
| 104 | A |
| 105 | A |
| 106 | A |
| 107 | A |
| 108 | A |

* "A" = <50 nM; "B" = 50 nM-100 nM; "C" = >100 nM to 250 nM; "D" = >250 nM to 500 nM; "E" = >500 nM to 1 μM; and "F" = >1 μM
$^a$where two diastereoisomers were separated, their IC$_{50}$ are shown as 1$^{st}$ peak/2$^{nd}$ peak

Example B

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs® (Miltenyi Biotech) according to the manufacture's instruction.

The purified B cells (2×10$^5$/well/200 μL) are cultured in 96-well ultra-low binding plates (Corning, Corning, N.Y.) in RPMI1640, 10% FBS and goat F(ab')2 anti-human IgM (10 ηg/ml) (Invitrogen, Carlsbad, Calif.) in the presence of different amount of test compounds for three days. [$^3$H]-thymidine (1 μCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount® (Packard Bioscience).

Example C

Pfeiffer Cell Proliferation Assay

Pfeiffer cell line (diffuse large B cell lymphoma) was purchased from ATCC (Manassas, Va.) and maintained in the culture medium recommended (RPMI and 10% FBS). To measure the anti-proliferation activity of the compounds, the Pfeiffer cells were plated with the culture medium (2×10$^3$ cells/well/per 200 μl) into 96-well ultra-low binding plates (Corning, Corning, N.Y.), in the presence or absence of a concentration range of test compounds. After 3-4 days, [$^3$H]-thymidine (1 μCi/well) (PerkinElmer, Boston, Mass.) in PBS was then added to the cell culture for an additional 12 hours before the incorporated radioactivity was separated by filtration with water through GF/B filters (Packard Bioscience, Meridenj, Conn.) and measured by liquid scintillation counting with a TopCount® (Packard Bioscience). Table 2 shows Pfeiffer cell proliferation data for certain compounds described herein.

TABLE 2

IC$_{50}$ data for Pfeiffer cell proliferation assay*

| Example | IC$_{50}$ (nM) |
|---|---|
| 16 | A |
| 17 | A |
| 18 | F |
| 19 | D |
| 20 | C |
| 22 | A |
| 23 | B |
| 29 | C |
| 33 | C |
| 34 | C |
| 36 | A |
| 37 | E |
| 38 | C |
| 43 | A |
| 44 | F |
| 45 | E |
| 46 | E |
| 47 | F |
| 48 | F/F$^a$ |
| 49 | F |
| 50 | D |
| 51 | C |
| 52 | B |
| 53 | nt/D$^a$ |
| 54 | E |
| 55 | B |
| 56 | A |
| 57 | F |
| 58 | D |
| 59 | E |
| 60 | E |
| 61 | F |
| 62 | D |
| 63 | F/F$^a$ |
| 64 | F |
| 65 | F |
| 66 | B |
| 67 | C/C$^a$ |
| 68 | C/B$^a$ |
| 69 | B |
| 70 | C |
| 71 | D |
| 72 | D |
| 75 | nt/D$^a$ |
| 78 | nt/E$^a$ |
| 79 | D/C$^a$ |
| 80 | nt/C$^a$ |
| 81 | D |
| 83 | C |
| 84 | B |
| 85 | A |
| 86 | A |
| 87 | A |
| 88 | C |
| 89 | B |
| 90 | B |
| 91 | D |
| 92 | E |

TABLE 2-continued

IC$_{50}$ data for Pfeiffer cell proliferation assay*

| Example | IC$_{50}$ (nM) |
|---|---|
| 93 | F |
| 94 | A |
| 95 | A |
| 96 | A |
| 97 | A |
| 98 | B |
| 99 | E |
| 100 | C |
| 101 | E |
| 102 | A |
| 103 | A |
| 104 | D |
| 105 | B |
| 106 | B |
| 107 | A |
| 108 | A |

*"A" = <50 nM; "B" = 50 nM-100 nM; "C" = >100 nM to 250 nM; "D" = >250 nM to 500 nM; "E" = >500 nM to 1 µM; and "F" = >1 µM
nt = not tested
$^a$two isomers were isolated in the corresponding experiments and they were tested respectively Example C Akt Phosphorylation Assay Ramos cells (B lymphocyte from Burkitts lymphoma) are obtained from ATCC (Manassas, Va.) and maintained in RPMI1640 and 10% FBS. The cells (3×10$^7$ cells /tube/3 mL in RPMI) are incubated with different amounts of test compounds for 2 hrs at 37° C. and then stimulated with goat F(ab')2 anti-human IgM (5 µg/mL) (Invitrogen) for 17 minutes in a 37° C. water bath. The stimulated cells are spun down at 4° C. with centrifugation and whole cell extracts are prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

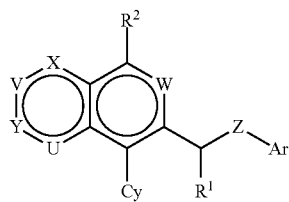

or a pharmaceutically acceptable salt thereof; wherein:
the symbol

indicates that the ring is aromatic;
Z is O, S, or NR$^A$;
Cy is cycloalkyl, heterocycloalkyl, aryl or heteroaryl, each optionally substituted with 1, 2, 3, 4, or 5 independently selected R$^C$ groups;
each R$^C$ is independently selected from halo, C$_{1-6}$ alkyl, C$_{2-6}$ alkenyl, C$_{2-6}$ alkynyl, C$_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, C$_{1-6}$ haloalkyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, Cy$^1$, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;
W is CR$^3$; V is CR$^4$ or N; X is CR$^5$; Y is CR$^6$ or N; and U is CR$^7$ or N; or
W is CR$^3$; V is CR$^4$ or N; X is O or S; Y is absent; and U is CR$^7$ or N; or
W is CR$^3$; V is N; X is CR$^5$; Y is absent; and U is NR$^{A1}$; or
W is CR$^3$; V is O or S; X is CR$^5$; Y is absent; and U is CR$^7$ or N;
provided that when Y is present, then at least one of V, Y, and U is other than N;
R$^1$ is independently selected from H, C$_{1-6}$ alkyl, C$_{1-6}$ haloalkyl, C$_{2-6}$ alkenyl, and C$_{2-6}$ alkynyl; wherein said C$_{1-6}$ alkyl, C$_{1-6}$ haloalkyl, C$_{2-6}$ alkenyl, and C$_{2-6}$ alkynyl are each optionally substituted with 1, 2, 3 or 4 substituents independently selected from halo, OH, CN, NR$^{1\dagger}$R$^{2\dagger}$, C$_{1-6}$ alkoxy, C$_{1-6}$ haloalkoxy, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, and C$_{1-6}$ alkylcarbonylamino;
each R$^{1\dagger}$ and R$^{2\dagger}$ is independently selected from H and C$_{1-6}$ alkyl;
or any R$^{1\dagger}$ and R$^{2\dagger}$ together with the N atom to which they are attached form a 3-, 4-, 5-, 6-, or 7-membered heterocycloalkyl group, which is optionally substituted with 1, 2, 3, or 4 substituents independently selected from C$_{1-6}$ alkyl;
R$^2$, R$^3$, R$^4$, R$^5$, R$^6$ and R$^7$ are each independently selected from H, OH, NO$_2$, CN, halo, C$_{1-6}$ alkyl, C$_{2-6}$ alkynyl, C$_{3-7}$ cycloalkyl, C$_{1-6}$ haloalkyl, C$_{1-6}$ alkoxy, C$_{1-6}$ haloalkoxy, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, and C$_{1-6}$ alkoxycarbonyl;

Ar is

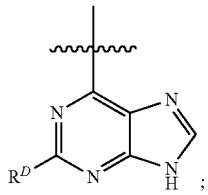

$R^D$ is selected from H, —$(C_{1-4}$ alkyl)$_r$-Cy$^1$, halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

$R^A$ is selected from H, $C_{1-6}$ alkyl, $C_{2-6}$ alkenyl, and $C_{2-6}$ alkynyl;

$R^{A1}$ is selected from H, $C_{1-6}$ alkyl, $C_{2-6}$ alkenyl, and $C_{2-6}$ alkynyl;

each Cy$^1$ is, independently, aryl, heteroaryl, cycloalkyl, or heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^e$)NR$^{c1}$R$^{d1}$, NR$^{c1}$C(=NR$^e$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

each $R^a$, $R^b$, $R^c$, and $R^d$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any $R^c$ and $R^d$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each $R^e$ and $R^f$ is independently selected from H, $C_{1-6}$ alkyl, CN, OR$^{a5}$, SR$^{b5}$, S(O)$_2$R$^{b5}$, C(O)R$^{b5}$, S(O)$_2$NR$^{c5}$R$^{d5}$, and C(O)NR$^{c5}$R$^{d5}$;

each $R^{a1}$, $R^{b1}$, $R^{c1}$, and $R^{d1}$ is independently selected from H, $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, 3, 4, or 5 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any $R^{c1}$ and $R^{d1}$ together with the N atom to which they are attached form a 3-, 4-, 5-, 6-, or 7-membered heterocycloalkyl group or a heteroaryl group, each optionally substituted with 1, 2, or 3 substituents independently selected from $C_{1-6}$ alkyl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^f$)NR$^{c5}$R$^{d5}$, NR$^{c5}$C(=NR$^f$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each $R^{a5}$, $R^{b5}$, $R^{c5}$, and $R^{d5}$ is independently selected from H, $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, and heterocycloalkylalkyl, wherein said $C_{1-6}$ alkyl, $C_{1-6}$ haloalkyl, $C_{2-6}$ alkenyl, $C_{2-6}$ alkynyl, aryl, cycloalkyl, heteroaryl, heterocycloalkyl, arylalkyl, heteroarylalkyl, cycloalkylalkyl, or heterocycloalkylalkyl is optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy;

or any $R^{c5}$ and $R^{d5}$ together with the N atom to which they are attached form a 3-, 4-, 5-, 6-, or 7-membered heterocycloalkyl group or heteroaryl group, each optionally substituted with 1, 2, or 3 substituents independently selected from OH, CN, amino, halo, $C_{1-6}$ alkyl, $C_{1-6}$ alkoxy, $C_{1-6}$ alkylthio, $C_{1-6}$ alkylamino, di($C_{1-6}$ alkyl)amino, $C_{1-6}$ haloalkyl, and $C_{1-6}$ haloalkoxy; and r is 0 or 1;

or a pharmaceutically acceptable salt thereof.

2. The compound of claim 1, or a pharmaceutically acceptable salt thereof, wherein:

W is CR$^3$;

V is CR$^4$ or N;

X is CR$^5$; and Y is CR$^6$ or N; or

X is O or S; and Y is absent;

U is CR$^7$ or N; and each R$^c$ is independently selected from halo, $C_{1-6}$ alkyl, $C_{2-6}$ alkenyl, $C_{2-6}$ alkynyl, $C_{1-6}$ haloalkyl, halosulfanyl, aryl, cycloalkyl, heteroaryl, heterocycloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, $C_{1-6}$ haloalkyl, aryl, cycloalkyl, heteroaryl, and heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C (O)R$^b$, NR$^c$C(O)OR$^a$, NR$^c$C(O)NR$^c$R$^d$, NR$^b$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$.

3. The compound of claim 2, or a pharmaceutically acceptable salt thereof, wherein Z is NR$^A$.

4. The compound of claim 1, or a pharmaceutically acceptable salt thereof, wherein Cy is heterocycloalkyl, aryl or heteroaryl, each optionally substituted with 1, 2, 3, 4, or 5 independently selected R$^C$ groups.

5. The compound of claim 1, or a pharmaceutically acceptable salt thereof, wherein Cy is a phenyl ring, a pyrrolidine ring, a piperidine ring, a piperazine ring, or a pyridine ring, each of which is optionally substituted with 1, 2, 3, 4, or 5 independently selected R$^C$ groups.

6. The compound of claim 1, or a pharmaceutically acceptable salt thereof, wherein each R$^C$ is independently selected from C$_{1-6}$ alkyl, halo, OR$^a$, and NR$^c$C(O)R$^b$, wherein said C$_{1-6}$ alkyl is optionally substituted with hydroxyl or C$_{1-4}$ alkoxy.

7. The compound of claim 1, or a pharmaceutically acceptable salt thereof, wherein each R$^C$ is independently halo.

8. The compound of claim 1, or a pharmaceutically acceptable salt thereof, wherein each R$^C$ is independently selected from halo, C$_{1-6}$ alkyl, aryl, cycloalkyl, heteroaryl, heterocycloalkyl, CN, OR$^a$, C(O)R$^b$, C(O)NR$^c$R$^d$, C(O)OR$^a$, NR$^c$C(O)R$^b$, NR$^c$C(O)OR$^a$, or NR$^c$S(O)$_2$R$^b$; wherein said C$_{1-6}$ alkyl, aryl, cycloalkyl, heteroaryl, and heterocycloalkyl are each optionally substituted with 1, 2, 3, 4, or 5 substituents independently selected from halo, C$_{1-6}$ alkyl, CN, OR$^a$, and NR$^c$C(O)R$^b$.

9. The compound of claim 1, or a pharmaceutically acceptable salt thereof, wherein R$^D$ is H.

10. The compound of claim 1, or a pharmaceutically acceptable salt thereof, wherein R$^1$ is selected from H and C$_{1-6}$ alkyl.

11. The compound of claim 1, or a pharmaceutically acceptable salt thereof, wherein R$^2$, R$^3$, R$^4$, R$^5$, R$^6$, and R$^7$ are independently selected from H, CN, halo, C$_{1-6}$ alkyl, and C$_{1-6}$ haloalkyl.

12. The compound of claim 1, or a pharmaceutically acceptable salt thereof, wherein R$^2$ is H, CN, halo, C$_{1-3}$ alkyl, or C$_{1-3}$ haloalkyl; and R$^3$, R$^4$, R$^5$, R$^6$, and R$^7$ are each independently H or C$_{1-3}$ alkyl.

13. The compound of claim 1, or a pharmaceutically acceptable salt thereof, wherein R$^4$ is H.

14. A compound of claim 1, or a pharmaceutically acceptable salt thereof, wherein:
Z is NR$^A$;
Cy is heterocycloalkyl, aryl or heteroaryl, each optionally substituted with 1, 2, 3, 4, or 5 independently selected R$^C$ groups;
each R$^C$ is independently selected from C$_{1-6}$ alkyl, halo, OR$^a$, and NR$^c$C(O)R$^b$, wherein said C$_{1-6}$ alkyl is optionally substituted with hydroxyl or C$_{1-4}$ alkoxy;
each R$^a$, R$^b$, and R$^c$ is independently selected from H and C$_{1-4}$ alkyl;

Ar is a moiety of formula:

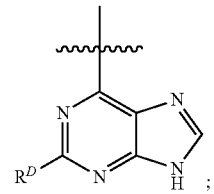

R$^D$ is selected from H, methyl and amino,
R$^1$ is methyl;
R$^A$ is H;
R$^2$ is H or halo; and
R$^3$, R$^4$, R$^5$, R$^6$, and R$^7$ are each independently H or methyl.

15. A compound of claim 1, or a pharmaceutically acceptable salt thereof, wherein:
Z is NR$^A$;
Cy is heterocycloalkyl, aryl or heteroaryl, each optionally substituted with 1, 2, 3, 4, or 5 independently selected R$^C$ groups;
each R$^C$ is independently selected from halo, C$_{1-6}$ alkyl, aryl, cycloalkyl, heteroaryl, heterocycloalkyl, CN, OR$^a$, C(O)R$^b$, C(O)NR$^c$R$^d$, C(O)OR$^a$, NR$^c$C(O)R$^b$, NR$^c$C(O)OR$^a$, or NR$^c$S(O)$_2$R$^b$; wherein said C$_{1-6}$ alkyl, aryl, cycloalkyl, heteroaryl, and heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, halosulfanyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

Ar is a moiety of formula:

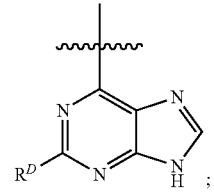

R$^1$ is independently selected from H and C$_{1-6}$ alkyl;
R$^A$ is selected from H and C$_{1-6}$ alkyl; and
R$^2$, R$^3$, R$^4$, R$^5$, R$^6$, and R$^7$ are each independently selected from H, halo, CN, C$_{1-6}$ alkyl, and C$_{1-6}$ haloalkyl.

16. A compound of claim 1, or a pharmaceutically acceptable salt thereof, wherein:
Z is NR$^A$;
Cy is heterocycloalkyl, aryl or heteroaryl, each optionally substituted with 1, 2, 3, 4, or 5 independently selected R$^C$ groups;
each R$^C$ is independently selected from halo, C$_{1-6}$ alkyl, aryl, cycloalkyl, heteroaryl, heterocycloalkyl, CN, OR$^a$, C(O)R$^b$, C(O)NR$^c$R$^d$, C(O)OR$^a$, NR$^c$C(O)R$^b$, NR$^c$C(O)OR$^a$, or NR$^c$S(O)$_2$R$^b$; wherein said C$_{1-6}$ alkyl, aryl, cycloalkyl, heteroaryl, and heterocycloalkyl are each optionally substituted with 1, 2, 3, 4, or 5 substituents independently selected from halo, C$_{1-6}$ alkyl, CN, OR$^a$, and NR$^c$C(O)R$^b$;

Ar is a moiety of formula:

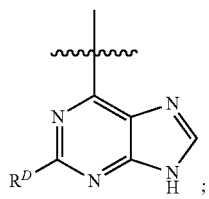

R¹ is independently selected from H and $C_{1-6}$ alkyl;
$R^A$ is selected from H and $C_{1-6}$ alkyl; and
R², R³, R⁴, R⁵, R⁶, and R⁷ are each independently selected from H, halo, CN, $C_{1-6}$ alkyl, and $C_{1-6}$ haloalkyl.

17. The compound of claim 1 having Formula Ia, Ib, Ic, or Id:

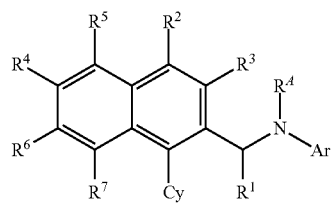

Ia

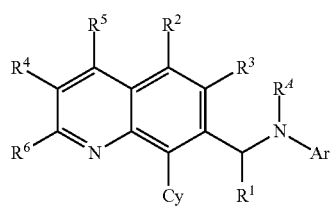

Ib

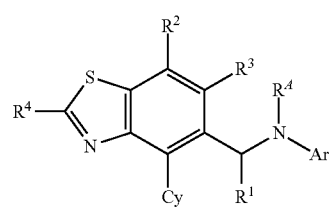

Ic

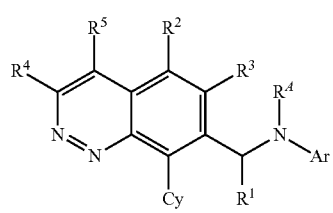

Id or a pharmaceutically acceptable salt thereof.

18. The compound according to claim 1, having Formula IIa, IIb, IIc, or IId:

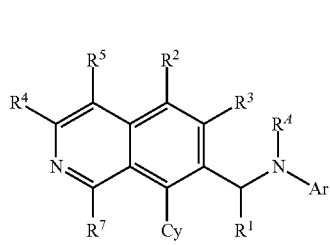

IIa

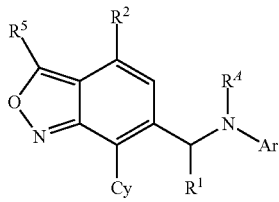

IIc

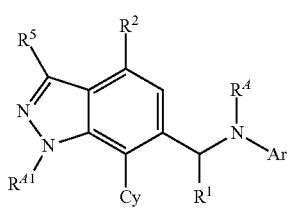

IId or a pharmaceutically acceptable salt thereof.

19. The compound according to claim 2, selected from:
N-{1-[1-(3-fluorophenyl)-2-naphthyl]ethyl}-9H-purin-6-amine;
N-{1-[4-(3-fluorophenyl)-2-methyl-1,3-benzothiazol-5-yl]ethyl}-9H-purin-6-amine;
N(6)-{1-[1-(5-fluoropyridin-3-yl)-2-naphthyl]ethyl}-9H-purine-2,6-diamine;
N(6)-{1-[1-(3-fluorophenyl)-2-naphthyl]ethyl}-9H-purine-2,6-diamine;
N-{1-[1-(5-fluoropyridin-3-yl)-2-naphthyl]ethyl}-9H-purin-6-amine;
N-{1-[8-(3,5-difluorophenyl)quinolin-7-yl]ethyl}-9H-purin-6-amine;
N-{1-[8-(2-fluorophenyl)quinolin-7-yl]ethyl}-9H-purin-6-amine;
N-{1-[8-(3-fluorophenyl)quinolin-7-yl]ethyl}-9H-purin-6-amine;
N-{1-[8-(5-fluoropyridin-3-yl)quinolin-7-yl]ethyl}-9H-purin-6-amine;
N-{1-[5-chloro-8-(2-fluorophenyl)quinolin-7-yl]ethyl}-9H-purin-6-amine;
N-(1-{5-chloro-8-[4-(2-methoxyethyl)piperazin-1-yl]quinolin-7-yl}ethyl)-9H-purin-6-amine;
(3R)-1-{5-chloro-7-[1-(9H-purin-6-ylamino)ethyl]quinolin-8-yl}pyrrolidin-3-ol;
N-((3S)-1-{5-chloro-7-[1-(9H-purin-6-ylamino)ethyl]quinolin-8-yl}pyrrolidin-3-yl)acetamide;
N-(1-{5-chloro-8-[(2R)-2-(methoxymethyl)pyrrolidin-1-yl]quinolin-7-yl}ethyl)-9H-purin-6-amine;
N-{1-[5-chloro-8-(3-fluorophenyl)quinolin-7-yl]ethyl}-9H-purin-6-amine;
or a pharmaceutically acceptable salt thereof.

20. The compound according to claim 2, selected from:
N-{1-[5-Chloro-8-(3-fluorophenyl)cinnolin-7-yl]ethyl}-9H-purin-6-amine;
N-{1-[5-Fluoro-8-(3-fluorophenyl)cinnolin-7-yl]ethyl}-9H-purin-6-amine;

N(6)-{1-[5-Fluoro-8-(3-fluorophenyl)cinnolin-7-yl]ethyl}-9H-purine-2,6-diamine;
N-{1-[5-Chloro-8-(3,5-difluorophenyl)cinnolin-7-yl]ethyl}-9H-purin-6-amine; and
N-{1-[5-Chloro-8-(2-fluorophenyl)cinnolin-7-yl]ethyl}-9H-purin-6-amine;
or a pharmaceutically acceptable salt thereof.

21. The compound according to claim 1, selected from:
N-{1-[8-(3,5-difluorophenyl)-5-fluorocinnolin-7-yl]ethyl}-9H-purin-6-amine;
N-{[5-Chloro-8-(3-fluorophenyl)cinnolin-7-yl]methyl}-9H-purin-6-amine;
N-{1-[5-chloro-8-(3-fluorophenyl)cinnolin-7-yl]propyl}-9H-purin-6-amine;
N-{1-[5-chloro-8-(5-fluoropyridin-3-yl)cinnolin-7-yl]ethyl}-9H-purin-6-amine;
N-{1-[8-(3-fluorophenyl)-5-methylcinnolin-7-yl]ethyl}-9H-purin-6-amine;
N-{1-[8-(3,5-difluorophenyl)-5-methylcinnolin-7-yl]ethyl}-9H-purin-6-amine;
3-{5-Chloro-7-[1-(9H-purin-6-ylamino)ethyl]cinnolin-8-yl}-5-fluoro-N-methylbenzamide;
N-{1-[5-Chloro-8-(3-fluoro-4-methoxyphenyl)cinnolin-7-yl]ethyl}-9H-purin-6-amine;
N-{1-[5-Chloro-8-(2-fluoropyridin-4-yl)cinnolin-7-yl]ethyl}-9H-purin-6-amine;
1-{5-Chloro-7-[1-(9H-purin-6-ylamino)ethyl]quinolin-8-yl}piperidin-4-ol;
1-{4-Chloro-2-[1-(9H-purin-6-ylamino)ethyl]-1-naphthyl}piperidin-4-ol;
N-{1-[4-Chloro-1-(3-fluorophenyl)-2-naphthyl]ethyl}-9H-purin-6-amine;
N-{1-[5-Chloro-8-(4,4-difluoropiperidin-1-yl)quinolin-7-yl]ethyl}-9H-purin-6-amine;
(3S)-1-{5-Chloro-7-[1-(9H-purin-6-ylamino)ethyl]quinolin-8-yl}piperidin-3-ol;
1-{5-Chloro-7-[1-(9H-purin-6-ylamino)ethyl]quinolin-8-yl}-4-phenylpiperidin-4-ol;
N-{1-[8-(3-Fluorophenyl)-5-methylquinolin-7-yl]ethyl}-9H-purin-6-amine;
N-{1-[5-Ethyl-8-(3-fluorophenyl)quinolin-7-yl]ethyl}-9H-purin-6-amine;
8-(3-fluorophenyl)-7-[1-(9H-purin-6-ylamino)ethyl]quinoline-5-carbonitrile;
(3R)-1-{5-fluoro-7-[1-(9H-purin-6-ylamino)ethyl]quinolin-8-yl}pyrrolidin-3-ol;
N-{1-[8-(4-Cyclobutylpiperazin-1-yl)-5-fluoroquinolin-7-yl]ethyl}-9H-purin-6-amine;
N-{1-[5-Chloro-8-(3-fluorophenyl)isoquinolin-7-yl]ethyl}-9H-purin-6-amine;
N-(1-{5-Chloro-8-[(3S)-3-fluoropyrrolidin-1-yl]quinolin-7-yl}ethyl)-9H-purin-6-amine;
2-(4-{5-Chloro-7-[1-(9H-purin-6-ylamino)ethyl]quinolin-8-yl}piperazin-1-yl)ethanol;
1-{5-Chloro-7-[1-(9H-purin-6-ylamino)ethyl]quinolin-8-yl}piperidine-4-carbonitrile;
1-{5-Chloro-7-[1-(9H-purin-6-ylamino)ethyl]quinolin-8-yl}pyrrolidine-3-carbonitrile;
N-{1-[5-Chloro-8-(3-fluoropiperidin-1-yl)quinolin-7-yl]ethyl}-9H-purin-6-amine;
N-{1-[5-Chloro-8-(4-fluoropiperidin-1-yl)quinolin-7-yl]ethyl}-9H-purin-6-amine;
(1-{5-Chloro-7-[1-(9H-purin-6-ylamino)ethyl]quinolin-8-yl}piperidin-3-yl)methanol;
(1-{5-Chloro-7-[1-(9H-purin-6-ylamino)ethyl]quinolin-8-yl}piperidin-4-yl)methanol;
N-{1-[5-Chloro-8-(4-cyclohexylpiperazin-1-yl)quinolin-7-yl]ethyl}-9H-purin-6-amine;
N-{1-[5-Chloro-8-(4-cyclopropylpiperazin-1-yl)quinolin-7-yl]ethyl}-9H-purin-6-amine;
N-{1-[5-Chloro-8-(3-methoxypiperidin-1-yl)quinolin-7-yl]ethyl}-9H-purin-6-amine;
N-{1-[5-Chloro-8-(3-methoxypyrrolidin-1-yl)quinolin-7-yl]ethyl}-9H-purin-6-amine;
N-{1-[5-Chloro-8-(4-cyclobutylpiperazin-1-yl)quinolin-7-yl]ethyl}-9H-purin-6-amine;
N-{1-[8-(1,4'-Bipiperidin-1'-yl)-5-chloroquinolin-7-yl]ethyl}-9H-purin-6-amine;
N-{1-[5-Chloro-8-(4-methoxypiperidin-1-yl)quinolin-7-yl]ethyl}-9H-purin-6-amine;
N-{1-[5-Chloro-8-(4-phenylpiperidin-1-yl)quinolin-7-yl]ethyl}-9H-purin-6-amine;
2-(1-{5-Chloro-7-[1-(9H-purin-6-ylamino)ethyl]quinolin-8-yl}piperidin-4-yl)ethanol;
N-(1-{5-Chloro-8-[4-(pyridin-4-ylmethyl)piperazin-1-yl]quinolin-7-yl}ethyl)-9H-purin-6-amine;
N-{1-[5-Chloro-8-(4-phenoxypiperidin-1-yl)quinolin-7-yl]ethyl}-9H-purin-6-amine;
N-{1-[5-Chloro-8-(3-phenylpyrrolidin-1-yl)quinolin-7-yl]ethyl}-9H-purin-6-amine;
N-((3S)-1-{5-Chloro-7-[1-(9H-purin-6-ylamino)ethyl]quinolin-8-yl}pyrrolidin-3-yl)propanamide;
N-((3S)-1-{5-Chloro-7-[1-(9H-purin-6-ylamino)ethyl]quinolin-8-yl}pyrrolidin-3-yl)-2-methylpropanamide;
Methyl ((3S)-1-{5-Chloro-7-[1-(9H-purin-6-ylamino)ethyl]quinolin-8-yl}pyrrolidin-3-yl)carbamate;
N-((3S)-1-{5-Chloro-7-[1-(9H-purin-6-ylamino)ethyl]quinolin-8-yl}pyrrolidin-3-yl)methanesulfonamide;
N-(1-{5-Chloro-7-[1-(9H-purin-6-ylamino)ethyl]quinolin-8-yl}piperidin-4-yl)methanesulfonamide;
N-(1-{5-Chloro-7-[1-(9H-purin-6-ylamino)ethyl]quinolin-8-yl}piperidin-4-yl)acetamide;
Methyl (1-{5-Chloro-7-[1-(9H-purin-6-ylamino)ethyl]quinolin-8-yl}piperidin-4-yl)carbamate;
N-(1-{5-Chloro-8-[4-(cyclopropylcarbonyl)piperazin-1-yl]quinolin-7-yl}ethyl)-9H-purin-6-amine;
Methyl 4-{5-Chloro-7-[1-(9H-purin-6-ylamino)ethyl]quinolin-8-yl}piperazine-1-carboxylate;
N-(1-{5-Chloro-8-[4-(cyclobutylcarbonyl)piperazin-1-yl]quinolin-7-yl}ethyl)-9H-purin-6-amine;
N-(1-{5-Chloro-8-[4-(methoxyacetyl)piperazin-1-yl]quinolin-7-yl}ethyl)-9H-purin-6-amine;
4-{5-Chloro-7-[1-(9H-purin-6-ylamino)ethyl]quinolin-8-yl}-N,N-dimethylpiperazine-1-carboxamide;
N-{1-[8-(4-Benzoylpiperazin-1-yl)-5-chloroquinolin-7-yl]ethyl}-9H-purin-6-amine;
2-(4-{5-Chloro-7-[1-(9H-purin-6-ylamino)ethyl]quinolin-8-yl}piperazin-1-yl)-N,N-dimethylacetamide;
N-(1-{5-Chloro-8-[4-(4-fluorobenzoyl)piperazin-1-yl]quinolin-7-yl}ethyl)-9H-purin-6-amine;
N-(1-{5-Chloro-8-[4-(3-fluorobenzoyl)piperazin-1-yl]quinolin-7-yl}ethyl)-9H-purin-6-amine;
N-(1-{5-Chloro-8-[4-(2-fluorobenzoyl)piperazin-1-yl]quinolin-7-yl}ethyl)-9H-purin-6-amine;
N-[1-(8-{4-[(1-Acetylpiperidin-4-yl)carbonyl]piperazin-1-yl}-5-chloroquinolin-7-yl)ethyl]-9H-purin-6-amine;
N-(1-{5-Chloro-8-[4-(pyridin-2-ylcarbonyl)piperazin-1-yl]quinolin-7-yl}ethyl)-9H-purin-6-amine;
N-(1-{5-Chloro-8-[4-(pyridin-3-ylcarbonyl)piperazin-1-yl]quinolin-7-yl}ethyl)-9H-purin-6-amine;
N-(1-{5-Chloro-8-[4-(pyrazin-2-ylcarbonyl)piperazin-1-yl]quinolin-7-yl}ethyl)-9H-purin-6-amine;

N-{1-[5-Chloro-8-(4-isonicotinoylpiperazin-1-yl)quinolin-7-yl]ethyl}-9H-purin-6-amine;

N-[1-(5-Chloro-8-{4-[(5-methylisoxazol-3-yl)carbonyl]piperazin-1-yl}quinolin-7-yl)ethyl]-9H-purin-6-amine;

N-[1-(5-Chloro-8-{4-[(3,5-dimethylisoxazol-4-yl)carbonyl]piperazin-1-yl}quinolin-7-yl)ethyl]-9H-purin-6-amine;

N-[1-(5-Chloro-8-{4-[(1-methyl-1H-pyrazol-3-yl)carbonyl]piperazin-1-yl}quinolin-7-yl)ethyl]-9H-purin-6-amine;

N-{1-[5-fluoro-8-(3-fluorophenyl)quinolin-7-yl]ethyl}-9H-purin-6-amine;

N-[1-(5-Fluoro-8-{4-[(1-methyl-1H-pyrazol-4-yl)carbonyl]piperazin-1-yl}quinolin-7-yl)ethyl]-9H-purin-6-amine;

N-{1-[4-Chloro-7-(3-fluorophenyl)-2,1-benzisoxazol-6-yl]ethyl}-9H-purin-6-amine;

N-{1-[4-Chloro-7-(3-fluorophenyl)-1H-indazol-6-yl]ethyl}-9H-purin-6-amine;

N-{1-[4-Chloro-7-(3,5-difluorophenyl)-1H-indazol-6-yl]ethyl}-9H-purin-6-amine;

N-{1-[4-Chloro-7-(3,5-difluorophenyl)-1-methyl-1H-indazol-6-yl]ethyl}-9H-purin-6-amine;

or a pharmaceutically acceptable salt of any of the aforementioned.

22. A compound of claim 1, which is N-{1-[5-chloro-8-(3-fluorophenyl)cinnolin-7-yl]ethyl}-9H-purin-6-amine, or a pharmaceutically acceptable salt thereof.

23. A compound of claim 1, which is N-{(1S)-1-[5-chloro-8-(3-fluorophenyl)cinnolin-7-yl]ethyl}-9H-purin-6-amine, or a pharmaceutically acceptable salt thereof.

24. A compound of claim 1, which is N-{(1S)-1-[5-chloro-8-(3-fluorophenyl)cinnolin-7-yl]ethyl}-9H-purin-6-amine adipic acid salt.

25. A composition comprising a compound according to claim 1, or a pharmaceutically acceptable salt thereof, and at least one pharmaceutically acceptable carrier.

26. A method of inhibiting an activity of a PI3K kinase, comprising contacting the kinase with a compound of claim 1, or a pharmaceutically acceptable salt thereof, wherein said PI3K kinase is PI3Kδ.

27. A method of treating B cell lymphoma in a patient, comprising administering to said patient a therapeutically effective amount of a compound of claim 1, or a pharmaceutically acceptable salt thereof.

28. A method of treating diffuse large B-cell lymphoma in a patient, comprising administering to said patient a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 8,680,108 B2
APPLICATION NO. : 12/972155
DATED : March 25, 2014
INVENTOR(S) : Yun-Long Li et al.

Page 1 of 1

It is certified that error appears in the above-identified patent and that said Letters Patent is hereby corrected as shown below:

On the Title Page

Item 56 Other Publications

Page 4, Col. 1, Line 14-15, delete "Sinhibitors,"" and insert -- S inhibitors," --

Page 5, Col. 1, Line 59, delete "Sebell," and insert -- Schell, --

Page 6, Col. 2, Line 35, delete "P13K,"" and insert -- PI3K," --

Page 6, Col. 2, Line 36, delete "Actived" and insert -- Activated --

Page 6, Col. 2, Line 38, delete "associate" and insert -- association --

Page 6, Col. 2, Line 43, delete "Phosphatidinylinositol" and insert -- Phosphatidylinositol --

In the Claims

Col. 284, Line 11, in Claim 1, delete "S(O)NR$^{c5}$,R$^{d5}$," and insert -- S(O)NR$^{c5}$R$^{d5}$," --

Col. 285, Line 1, in Claim 2, delete "NR$^{b}$S(O)R$^{b}$," and insert -- NR$^{c}$S(O)R$^{b}$, --

Col. 286, Line 33, in Claim 15, delete "OC(O)NR $^{c}$R$^{d}$," and insert -- OC(O)NR$^{c}$R$^{d}$, --

Signed and Sealed this
Sixteenth Day of February, 2016

Michelle K. Lee
*Director of the United States Patent and Trademark Office*